(12) United States Patent
Sugawara

(10) Patent No.: US 11,548,910 B2
(45) Date of Patent: Jan. 10, 2023

(54) OLIGONUCLEOTIDE PRODUCTION METHOD

(71) Applicant: NISSAN CHEMICAL CORPORATION, Tokyo (JP)

(72) Inventor: Yudai Sugawara, Funabashi (JP)

(73) Assignee: NISSAN CHEMICAL CORPORATION, Tokyo (JP)

(*) Notice: Subject to any disclaimer, the term of this patent is extended or adjusted under 35 U.S.C. 154(b) by 588 days.

(21) Appl. No.: 15/776,709

(22) PCT Filed: Nov. 17, 2016

(86) PCT No.: PCT/JP2016/084150
§ 371 (c)(1),
(2) Date: Aug. 10, 2018

(87) PCT Pub. No.: WO2017/086397
PCT Pub. Date: May 26, 2017

(65) Prior Publication Data
US 2019/0169223 A1 Jun. 6, 2019

(30) Foreign Application Priority Data
Nov. 17, 2015 (JP) .............................. JP2015-224617

(51) Int. Cl.
*C07H 21/04* (2006.01)
*C07H 21/02* (2006.01)
*C07H 19/10* (2006.01)
*C07H 19/20* (2006.01)
*C07H 1/00* (2006.01)
*C07D 405/06* (2006.01)

(52) U.S. Cl.
CPC ............ *C07H 21/04* (2013.01); *C07D 405/06* (2013.01); *C07H 1/00* (2013.01); *C07H 19/10* (2013.01); *C07H 19/20* (2013.01); *C07H 21/02* (2013.01); *Y02P 20/55* (2015.11)

(58) Field of Classification Search
None
See application file for complete search history.

(56) References Cited

U.S. PATENT DOCUMENTS

| 3,739,015 | A | 6/1973 | Wattanabe et al. |
| 3,860,722 | A | 1/1975 | Grisar et al. |
| 2004/0116685 | A1 | 6/2004 | Picken et al. |
| 2004/0215010 | A1 | 10/2004 | Kumarev |
| 2012/0296074 | A1 | 11/2012 | Hirai et al. |
| 2015/0210731 | A1 | 7/2015 | Kataoka |
| 2015/0315229 | A1 | 11/2015 | Nonogawa |

FOREIGN PATENT DOCUMENTS

| CN | 102139203 | B | 1/2013 | |
| EP | 2711370 | A1 | 3/2014 | |
| EP | 2816053 | A1 | 12/2014 | |
| EP | 2857412 | A1 | 4/2015 | |
| EP | 2921499 | A1 | 9/2015 | |
| EP | 3263579 | A1 | 1/2018 | |
| EP | 3398955 | A1 | 11/2018 | |
| JP | S60-174797 | A | 9/1985 | |
| JP | 2000-500740 | A | 1/2000 | |
| JP | 2004-503560 | A | 2/2004 | |
| JP | 2004-262809 | A | 9/2004 | |
| JP | 2010-275254 | A | 12/2010 | |
| WO | WO 2004/089925 | A1 | 10/2004 | |
| WO | WO2005/028494 | | * 3/2005 | ............ C07H 19/10 |
| WO | WO 2005/028494 | A1 | 3/2005 | |
| WO | WO 2012/157723 | A1 | 11/2012 | |
| WO | WO 2013/122236 | A1 | 8/2013 | |
| WO | WO 2014/017615 | A1 | 1/2014 | |
| WO | WO 2014/077292 | A1 | 5/2014 | |

OTHER PUBLICATIONS

English machine translation of JP H04-616175, downloaded from translationportal.epo.org, equivalent to WO2005/028494 (Year: 2005).*
Padiya et al., "Large Scale, Liquid Phase Oligonucleotide Synthesis by Alkyl H-phosphonate Approach" Bioorganic and Medicinal Chemistry Letters vol. 8 pp. 337-342 (Year: 2000).*
Azéma et al., "Efficient approach to acyloxymethyl esters of nalidixic acid and in vitro evaluation as intra-ocular prodrugs," *Bioorg. Med. Chem.*, 14(8): 2569-2580 (2006).
Baker et al., "Irreversible Enzyme Inhibitors. 195. Inhibitors of Thymidine Kinase from Walker 256 Carcinoma Derived from Thymidine 5'Aacetate," *J. Med. Chem.*, 15(9): 940-944 (1972).
Gopalakrishnan et al., "A Virtual Screening Approach for Thymidine Monophosphate Kinase Inhibitors as Antitubercular Agents Based on Docking and Pharmacophore Models," *J. Chem. Inf. Model*, 45(4): 1101-1108 and Supporting Information (2005).
Ringshaw et al., "Alkaline Hydrolysis of O-Acylglycollic Esters. Part I," *J. Chem. Soc.*, 1559-1562 (1964).
European Patent Office, Extended European Search Report in European Patent Application No. 16866398.7 (dated Aug. 19, 2019).
Agrawal (Editor), Protocols for Oligonucleotides and Analogs: Synthesis and Properties [from Methods in Molecular Biology, vol. 20], Humana Press Inc., Totowa, New Jersey (1993)—cover page, copyright page, and pp. 44-73.
Japanese Patent Office, International Search Report in International Patent Application No. PCT/JP2016/084150 (dated Jan. 24, 2017).

(Continued)

*Primary Examiner* — Eric Olson
(74) *Attorney, Agent, or Firm* — Leydig, Voit & Mayer, Ltd.

(57) ABSTRACT

The invention provides a novel method for producing an oligonucleotide using a nucleoside or oligonucleotide that is easy to isolate and has high storage stability. The oligonucleotide production method includes a step of subjecting a nucleoside or oligonucleotide having a pseudo solid phase-protecting group in at least one location selected from the group consisting of 2'-position, 3'-position, 5'-position and a nucleobase moiety and having a 5'-hydroxyl group or a 3'-hydroxyl group, to H-phosphonation to convert the 5'-hydroxyl group or the 3'-hydroxyl group into an H-phosphonated form.

17 Claims, 1 Drawing Sheet

(56) References Cited

OTHER PUBLICATIONS

Esipov et al., "Synthesis of 3'-Azido-3'-Deoxythymidine-Terminated Oligonucleotide," *Nucleosides & Nucleotides*, 17(9-11): 1697-1704 (1998).

Kim et al., "Liquid-Phase RNA Synthesis by Using Alkyl-Chain-Soluble Support," *Chem. Eur. J.*, 19(26): 8615-8620 (2013).

Kraszewski et al., "H-Phosphonates: Versatile synthetic precursors to biologically active phosphorus compounds," *Pure Appl. Chem.*, 79(12): 2217-2227 (2007).

Zaramella et al., "The Application of H-Phosphonate Chemistry in the Help Synthesis of Oligonucleotides," *Nucleosides & Nucleotides*, 14(3-5): 809-812 (1995).

Zlatev et al., "Phosphoramidate Dinucleosides as Hepatitis C Virus Polymerase Inhibitors," *J. Med. Chem.*, 51(58): 5745-5757 (2008).

Girotto et al., "Luminescent Columnar Liquid Crystals Based on 1,3,4-oxadiazole," *Tetrahedron*, 70(20): 3355-3360 (2014).

Guo et al., "Room Temperature Liquid Crystal of Symmetric Gallic Trimer Containing Cyanuric Core: Synthesis and Mesomorphism," *Liquid Crystals*, 42(12): 1808-1814 (2015).

Lai et al., "Discotic Metallomesogens: Mesophase Crossover of Columnar Rectangularto Hexagonal Arrangements in Bis(Hydrazinato)nickel(II) Complexes," *J. Mater. Chem.*, 8(6): 1355-1360 (1998).

Li et al., "Synthesis, Characterization, and the Photochromic, Luminescence, Metallogelation and Liquid-Crystalline Properties of Multifunctional Platinum(II) Bipyridine Complexes," *Chem. Eur. J..*, 17(29): 8048-8059 (2011).

Singh et al., "Synthesis, Characterisation and Mesomorphic Properties of Ester Containing Aroylhydrazones and Their Nickel(II) Complexes," *Liquid Crystals*, 38(9): 1117-1129 (2011).

Taillemite et al., "Synthesis of the First Tetracene-[60]fullerene Dyad," *Eur. J. Org. Chem.*, 2004(24): 4981-4984 (2004).

European Patent Office, Communication Pursuant to Article 94(3) EPC in European Patent Application No. 16866398.7 (dated May 4, 2022).

\* cited by examiner

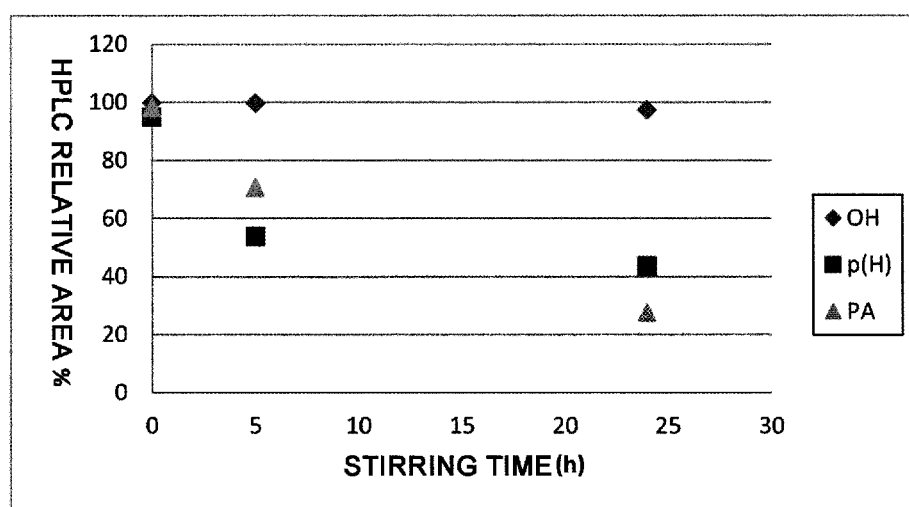

OLIGONUCLEOTIDE PRODUCTION METHOD

CROSS-REFERENCE TO RELATED APPLICATIONS

This patent application is the U.S. national phase of International Patent Application No. PCT/JP2016/084150, filed Nov. 17, 2016, which claims the benefit of Japanese Patent Application No. 2015-224617, filed on Nov. 17, 2015, which are incorporated by reference in their entireties herein.

TECHNICAL FIELD

The present invention relates to a novel method for producing oligonucleotides.

BACKGROUND ART

The forefront biotechnological researches such as genome-based drug discovery, and gene diagnosis and treatment have undergone rapid progress and development. Associated with that, oligonucleotides such as DNA probes, siRNA, antisense DNA and antisense RNA have been actively used recently. Some known chemical methods for the synthesis of oligonucleotides are phosphoramidite method and H-phosphonate method.

In the phosphoramidite method, a typical amidite reagent such as 2-cyanoethyl chloro(diisopropylamino)phosphinite or 2-cyanoethyl bis(diisopropylamino)phosphinite is used. These reagents are very expensive, and the isolation of an amidite compound entails complicated operations such as column purification and reprecipitation at an ultralow temperature. Further, amidite compounds are instable and need to be stored at −20° C.

On the other hand, the H-phosphonate method uses, among others, diphenyl phosphite or phosphorous acid that is a typical H-phosphonate reagent. These reagents are inexpensive, but complicated operations such as column purification are indispensable to the isolation of H-phosphonate compounds. H-phosphonate compounds need to be stored at 0° C. because of their stability (see, for example, Non Patent Literature 1).

Currently, a solid-phase synthesis process by phosphoramidite method has been increasingly optimized and automated. Thus, the solid-phase synthesis process by phosphoramidite method is advantageous in speed and is used most widely. However, the solid-phase synthesis process has drawbacks in that the scaling up of the process is limited for facility reasons, that the process involves excessive amounts of reagents and raw materials, and that it is difficult, for example, to know the status of the progress of the reaction in midstream and to analyze the structure of an intermediate.

In recent years, a liquid-phase synthesis process by H-phosphonate method using a pseudo solid phase-protecting group has been studied. Specifically, synthesis processes have been reported which use polyethylene glycol (MPEG) (see, for example, Patent Literature 1) or a long-chain hydrocarbon-containing group (see, for example, Patent Literature 2) as a pseudo solid phase-protecting group.

CITATION LIST

Patent Literature

Patent Literature 1: WO 2014/017615
Patent Literature 2: WO 2014/077292

Non Patent Literature

Non Patent Literature 1: Protocols for Oligonucleotides and Analogs, Humana Press (1993), pp. 44-73

SUMMARY OF INVENTION

Technical Problem

In the synthesis processes using polyethylene glycol (MPEG), examples of synthesis of up to 21-mer oligonucleotides have been presented, but GPC column purification is necessary for every elongation cycles. In the production processes using a long-chain hydrocarbon-containing group, examples of synthesis of 5-mer oligonucleotides have been presented, but a deprotection step results in a low yield.

As described above, the chemical processes for the synthesis of oligonucleotides using amidite compounds or H-phosphonate compounds have drawbacks in isolation operability and compound stability. There has been a demand for a novel oligonucleotide production method which is adaptable to mass synthesis.

An object of the present invention is to provide a novel method for producing an oligonucleotide using a nucleoside or oligonucleotide that is easy to isolate and has high storage stability.

Solution to Problem

To solve the problems discussed above, the present inventors carried out extensive studies. As a result, the present inventors have found that the problems can be solved by a production method which differs from a usual production method including a coupling step, a phosphorus atom modification step (such as oxidation reaction or sulfurization reaction) and a deprotection step, and which includes a step of subjecting to H-phosphonation a 5'-hydroxyl group or a 3'-hydroxyl group of a nucleoside or oligonucleotide having a pseudo solid phase-protecting group. The present invention has been completed based on the finding.

Aspects of the present invention include the following.

[1] A production method of an oligonucleotide including a step of subjecting a nucleoside or oligonucleotide having a pseudo solid phase-protecting group in at least one location selected from the group consisting of 2'-position, 3'-position, 5'-position and a nucleobase moiety and having a 5'-hydroxyl group or a 3'-hydroxyl group, to H-phosphonation to convert the 5'-hydroxyl group or the 3'-hydroxyl group into an H-phosphonated form.

[2] The production method described in [1], which includes at least one elongation reaction cycle including a step of subjecting a nucleoside or oligonucleotide having a pseudo solid phase-protecting group in at least one location selected from the group consisting of 2'-position, 3'-position, 5'-position and a nucleobase moiety and having a 5'-hydroxyl group or a 3'-hydroxyl group, to H-phosphonation to convert the 5'-hydroxyl group or the 3'-hydroxyl group into an H-phosphonated form.

[3] The production method described in [2], wherein the elongation reaction cycle includes:
a first step including deprotecting a first nucleoside or first oligonucleotide having a pseudo solid phase-protecting group in at least one location selected from the group consisting of 2'-position, 3'-position and a nucleobase moiety, having a 3'-hydroxyl group protected with a basic protecting group or a pseudo solid phase-protecting group, and having a 5'-hydroxyl group protected with a temporary protecting group, to remove the temporary protecting group to form a 5'-hydroxyl group, a second step including converting the resultant 5'-hydroxyl group into an H-phosphonated form using an H-phosphonate reagent, and a third step of forming an oligomer of the first nucleoside or first oligonucleotide with a second nucleoside or second oligonucleotide having a 3'-hydroxyl group and having a 5'-hydroxyl group protected with a temporary protecting group, by forming a phosphite diester bond from the 5'-hydroxyl group, now converted to the H-phosphonated form, of the first nucleoside or first oligonucleotide and the 3'-hydroxyl group of the second nucleoside or second oligonucleotide.

[4] The production method described in [3], further including a fourth step including converting the phosphite diester bond of the oligomer into a phosphodiester bond, a thiophosphodiester bond, a boranophosphodiester bond, an aminophosphodiester bond, a phosphodiester bond protected with a basic protecting group, or a thiophosphodiester bond protected with a basic protecting group.

[5] The production method described in [3], further including a fourth step including converting the phosphite diester bond of the oligomer into a phosphodiester bond, a thiophosphodiester bond, a boranophosphodiester bond or an aminophosphodiester bond.

[6] The production method described in [4] or [5], further including a fifth step of adding a polar solvent to a reaction mixture obtained from at least one step selected from the group consisting of the first step to the fourth step to form a precipitate, and collecting the precipitate by solid liquid separation.

[7] The production method described in [6], wherein the polar solvent is an alcohol solvent with 1 to 6 carbon atoms or a nitrile solvent with 1 to 6 carbon atoms.

[8] The production method described in any one of [3] to [7], further including a sixth step of removing all of the basic protecting group, the temporary protecting group and the pseudo solid phase-protecting group.

[9] The production method described in any one of [3] to [8], wherein the first nucleoside or the first oligonucleotide has a hydroxyl group protected with a pseudo solid phase-protecting group at 3'-position.

[10] The production method described in any one of [3] to [9], wherein the third step uses the second nucleoside.

[11] The production method described in [2], wherein the elongation reaction cycle includes:

a seventh step including deprotecting a third nucleoside or third oligonucleotide having a pseudo solid phase-protecting group in at least one location selected from the group consisting of 2'-position, 5'-position and a nucleobase moiety, having a 5'-hydroxyl group protected with a basic protecting group or a pseudo solid phase-protecting group, and having a 3'-hydroxyl group protected with a temporary protecting group, to remove the temporary protecting group to form a 3'-hydroxyl group, an eighth step including converting the resultant 3'-hydroxyl group into an H-phosphonated form using an H-phosphonate reagent, and a ninth step of forming an oligomer of the third nucleoside or third oligonucleotide with a fourth nucleoside or fourth oligonucleotide having a 5'-hydroxyl group and having a 3'-hydroxyl group protected with a temporary protecting group, by forming a phosphite diester bond from the 3'-hydroxyl group, now converted to the H-phosphonated form, of the third nucleoside or third oligonucleotide and the 5'-hydroxyl group of the fourth nucleoside or fourth oligonucleotide.

[12] The production method described in [11], further including a tenth step including converting the phosphite diester bond of the oligomer into a phosphodiester bond, a thiophosphodiester bond, a boranophosphodiester bond, an aminophosphodiester bond, a phosphodiester bond protected with a basic protecting group, or a thiophosphodiester bond protected with a basic protecting group.

[13] The production method described in [11], further including a tenth step including converting the phosphite diester bond of the oligomer into a phosphodiester bond, a thiophosphodiester bond, a boranophosphodiester bond or an aminophosphodiester bond.

[14] The production method described in [12] or [13], further including an eleventh step of adding a polar solvent to a reaction mixture obtained from any of the seventh step to the tenth step to form a precipitate, and collecting the precipitate by solid liquid separation.

[15] The production method described in [14], wherein the polar solvent is an alcohol solvent with 1 to 6 carbon atoms or a nitrile solvent with 1 to 6 carbon atoms.

[16] The production method described in any one of [11] to [15], further including a twelfth step of removing all of the basic protecting group, the temporary protecting group and the pseudo solid phase-protecting group.

[17] The production method described in any one of [11] to [16], wherein the third nucleoside or the third oligonucleotide has a hydroxyl group protected with a pseudo solid phase-protecting group at 5'-position.

[18] The production method described in any one of [11] to [17], wherein the ninth step uses the fourth nucleoside.

[19] The production method described in any one of [1] to [18], wherein the pseudo solid phase-protecting group is represented by the following formula (I):

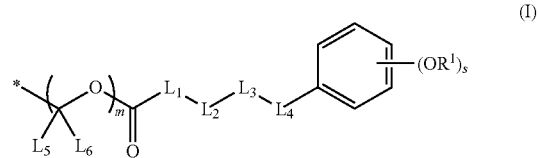

(I)

wherein * indicates a bond to a group protected by the pseudo solid phase-protecting group, $R^1$ is a C1-40 alkyl group, a C2-40 alkenyl group or a C2-40 alkynyl group, s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^5$ is a hydrogen atom, a C1-6 alkyl group, a C1-6 haloalkyl group, a C2-6 alkenyl group or a C2-6 haloalkenyl group, $L^6$ is a hydrogen atom, a C1-6 alkyl group, a C1-6 haloalkyl group, a C2-6 alkenyl group or a C2-6 haloalkenyl group, m is 0 or 1, and when the pseudo solid phase-protecting group is present in the nucleobase moiety and when m in the pseudo solid phase-protecting group is 0, the number of single bonds represented by $L^1$, $L^2$, $L^3$ and $L^4$ in the pseudo solid phase-protecting group is 0 to 3.

[20] The production method described in any one of [1] to [18], wherein the pseudo solid phase-protecting group is represented by the following formula (II):

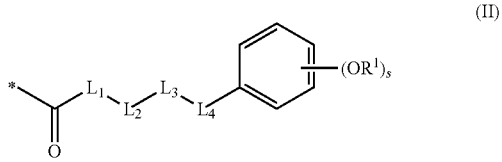

(II)

wherein * indicates a bond to a group protected by the pseudo solid phase-protecting group, $R^1$ is a C1-40 alkyl group, a C2-40 alkenyl group or a C2-40 alkynyl group, s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group) or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group) or —O—, and when the pseudo solid phase-protecting group is present in the nucleobase moiety, the number of single bonds represented by $L^1$, $L^2$, $L^3$ and $L^4$ in the pseudo solid phase-protecting group is 0 to 3.

[21] The production method described in any one of [3] to [20], wherein the temporary protecting group is a tert-butyldimethylsilyl group, a 4,4'-dimethoxytrityl group or a levulinyl group.

[22] The production method described in any one of [1] to [21], wherein the H-phosphonation step uses at least one H-phosphonate reagent selected from the group consisting of phosphorous acid, diphenyl phosphite, phenyl-H-phosphonate triethylammonium salt, p-toluyl-H-phosphonate triethylammonium salt, 2-chloro-4H-1,3,2-benzodioxaphosphorin-4-one and phosphorus trichloride.

[23] The production method described in any one of [1] to [22], wherein the nucleobases present in the nucleoside(s) and the oligonucleotide(s) are each independently at least one selected from the group consisting of 6-aminopurin-9-yl group (adenine residue), 2-amino-6-hydroxypurin-9-yl group (guanine residue), 2-oxo-4-amino-1,2-dihydropyrimidin-1-yl group (cytosine residue), 2-oxo-4-amino-5-methyl-1,2-dihydropyrimidin-1-yl group (5-methylcytosine residue), 2-oxo-4-hydroxy-1,2-dihydropyrimidin-1-yl group (uracil residue) and 2-oxo-4-hydroxy-5-methyl-1,2-dihydropyrimidin-1-yl group (thymine residue).

[24] A compound represented by the following formula (XI), or a salt thereof:

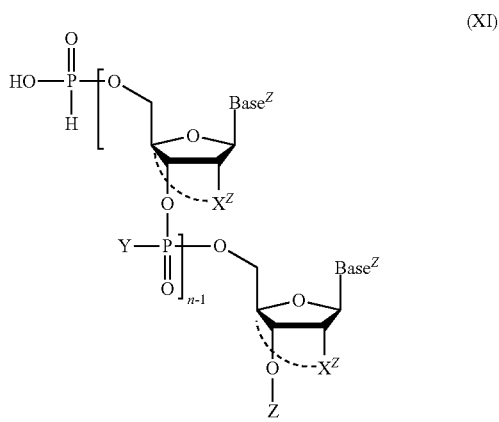

(XI)

wherein n is an integer of 1 or greater, $Base^Z$ independently at each occurrence is a nucleobase, a nucleobase protected with a basic protecting group, or a nucleobase protected with a pseudo solid phase-protecting group, $X^Z$ independently at each occurrence is a hydrogen atom, a halogen atom, a hydroxyl group, a hydroxyl group protected with a basic protecting group, an organic group bridged to the 4-carbon atom, or a hydroxyl group protected with a pseudo solid phase-protecting group, Y independently at each occurrence is a hydrogen atom, a hydroxyl group, a hydroxyl group protected with a basic protecting group, a thiol group, a thiol group protected with a basic protecting group, a borohydride group, a mono-C1-6 alkylamino group or a di-C1-6 alkylamino group, Z is a hydrogen atom, a basic protecting group, a temporary protecting group or a pseudo solid phase-protecting group, and the compound or salt thereof satisfies at least one of that at least one $Base^Z$ is a nucleobase protected with a pseudo solid phase-protecting group, that at least one $X^Z$ is a hydroxyl group protected with a pseudo solid phase-protecting group, and that Z is a pseudo solid phase-protecting group.

[25] The compound or salt thereof described in [24], wherein the pseudo solid phase-protecting group is represented by the following formula (II):

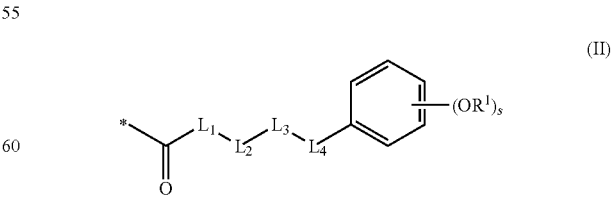

(II)

wherein * indicates a bond to a group protected by the pseudo solid phase-protecting group, $R^1$ is a C1-40 alkyl group, a C2-40 alkenyl group or a C2-40 alkynyl group, s is an integer of 1 to 5, L¹ is a single bond, a C1-6 alkylene group, a C2-6 alkenylene group or a C2-6 alkynylene group, L² is a single bond, —COO—, —CON(R²)— (wherein R² is a hydrogen atom, a C1-6 alkyl group, a C1-6 haloalkyl group, a C2-6 alkenyl group or a C2-6 haloalkenyl group), —OCO—, —N(R²)CO— (wherein R² is a hydrogen atom, a C1-6 alkyl group, a C1-6 haloalkyl group, a C2-6 alkenyl group or a C2-6 haloalkenyl group) or —O—, L³ is a single bond, a C1-6 alkylene group, a C2-6 alkenylene group or a C2-6 alkynylene group, L⁴ is a single bond, —COO—, —CON(R²)— (wherein R² is a hydrogen atom, a C1-6 alkyl group, a C1-6 haloalkyl group, a C2-6 alkenyl group or a C2-6 haloalkenyl group), —OCO—, —N(R²)CO— (wherein R² is a hydrogen atom, a C1-6 alkyl group, a C1-6 haloalkyl group, a C2-6 alkenyl group or a C2-6 haloalkenyl group) or —O—, and when the pseudo solid phase-protecting group is present in the nucleobase moiety, the number of single bonds represented by $L^1$, $L^2$, $L^3$ and $L^4$ in the pseudo solid phase-protecting group is 0 to 3.

[26] The compound or salt thereof described in [24] or [25], which satisfies at least one of that at least one $Base^Z$ in the formula (XI) is a nucleobase protected with a pseudo solid phase-protecting group, and that Z is a pseudo solid phase-protecting group.

[27] The compound or salt thereof described in any one of [24] to [26], wherein Z in the formula (XI) is a pseudo solid phase-protecting group.

[28] The compound or salt thereof described in any one of [24] to [27], wherein n in the formula (XI) is 1 to 30.

[29] A compound represented by the following formula (XII), or a salt thereof:

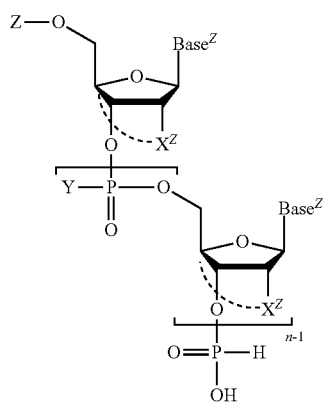

(XII)

wherein n is an integer of 1 or greater, $Base^Z$ independently at each occurrence is a nucleobase, a nucleobase protected with a basic protecting group, or a nucleobase protected with a pseudo solid phase-protecting group, $X^Z$ independently at each occurrence is a hydrogen atom, a halogen atom, a hydroxyl group, a hydroxyl group protected with a basic protecting group, an organic group bridged to the 4-carbon atom, or a hydroxyl group protected with a pseudo solid phase-protecting group, Y independently at each occurrence is a hydrogen atom, a hydroxyl group, a hydroxyl group protected with a basic protecting group, a thiol group, a thiol group protected with a basic protecting group, a borohydride group, a mono-C1-6 alkylamino group or a di-C1-6 alkylamino group, Z is a hydrogen atom, a basic protecting group, a temporary protecting group or a pseudo solid phase-protecting group, and the compound or salt thereof satisfies at least one of that at least one $Base^Z$ is a nucleobase protected with a pseudo solid phase-protecting group, that at least one $X^Z$ is a hydroxyl group protected with a pseudo solid phase-protecting group, and that Z is a pseudo solid phase-protecting group.

[30] The compound or salt thereof described in [29], wherein the pseudo solid phase-protecting group is represented by the following formula (II):

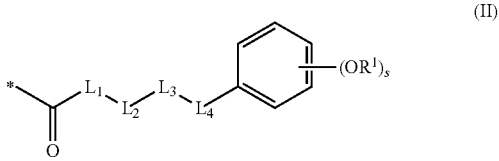

(II)

wherein * indicates a bond to a group protected by the pseudo solid phase-protecting group, $R^1$ is a C1-40 alkyl group, a C2-40 alkenyl group or a C2-40 alkynyl group, s is an integer of 1 to 5, $L^1$ is a single bond, a C1-6 alkylene group, a C2-6 alkenylene group or a C2-6 alkynylene group, $L^2$ is a single bond, —COO—, —CON(R²)— (wherein R² is a hydrogen atom, a C1-6 alkyl group, a C1-6 haloalkyl group, a C2-6 alkenyl group or a C2-6 haloalkenyl group), —OCO—, —N(R²)CO— (wherein R² is a hydrogen atom, a C1-6 alkyl group, a C1-6 haloalkyl group, a C2-6 alkenyl group or a C2-6 haloalkenyl group) or —O—, $L^3$ is a single bond, a C1-6 alkylene group, a C2-6 alkenylene group or a C2-6 alkynylene group, $L^4$ is a single bond, —COO—, —CON(R²)— (wherein R² is a hydrogen atom, a C1-6 alkyl group, a C1-6 haloalkyl group, a C2-6 alkenyl group or a C2-6 haloalkenyl group), —OCO—, —N(R²)CO— (wherein R² is a hydrogen atom, a C1-6 alkyl group, a C1-6 haloalkyl group, a C2-6 alkenyl group or a C2-6 haloalkenyl group) or —O—, and when the pseudo solid phase-protecting group is present in the nucleobase moiety, the number of single bonds represented by $L^1$, $L^2$, $L^3$ and $L^4$ in the pseudo solid phase-protecting group is 0 to 3.

[31] The compound or salt thereof described in [29] or [30], which satisfies at least one of that at least one $Base^Z$ in the formula (XII) is a nucleobase protected with a pseudo solid phase-protecting group, and that Z is a pseudo solid phase-protecting group.

[32] The compound or salt thereof described in any one of [29] to [31], wherein Z in the formula (XII) is a pseudo solid phase-protecting group.

[33] The compound or salt thereof described in any one of [29] to [32], wherein n in the formula (XII) is 1 to 30.

[34] A compound represented by the following formula (XIII), or a salt thereof:

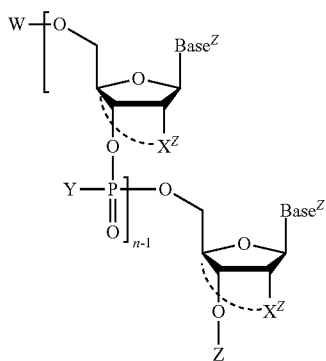

(XIII)

wherein n is an integer of 1 or greater,

Base$^Z$ independently at each occurrence is a nucleobase, a nucleobase protected with a basic protecting group, or a nucleobase protected with a pseudo solid phase-protecting group, X$^Z$ independently at each occurrence is a hydrogen atom, a halogen atom, a hydroxyl group, a hydroxyl group protected with a basic protecting group, an organic group bridged to the 4-carbon atom, or a hydroxyl group protected with a pseudo solid phase-protecting group, W is a hydrogen atom or a temporary protecting group, Y independently at each occurrence is a hydrogen atom, a hydroxyl group, a hydroxyl group protected with a basic protecting group, a thiol group, a thiol group protected with a basic protecting group, a borohydride group, a mono-C1-6 alkylamino group or a di-C1-6 alkylamino group, Z is a hydrogen atom, a basic protecting group, a temporary protecting group or a pseudo solid phase-protecting group, the compound or salt thereof satisfies at least one of that at least one Base$^Z$ is a nucleobase protected with a pseudo solid phase-protecting group, that at least one X$^Z$ is a hydroxyl group protected with a pseudo solid phase-protecting group, and that Z is a pseudo solid phase-protecting group, and at least one of the pseudo solid phase-protecting groups is represented by the formula (I):

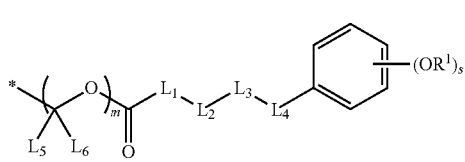

(I)

wherein * indicates a bond to a group protected by the pseudo solid phase-protecting group, R$^1$ is a C1-40 alkyl group, a C2-40 alkenyl group or a C2-40 alkynyl group, s is an integer of 1 to 5, L$^1$ is a single bond, a C1-6 alkylene group, a C2-6 alkenylene group or a C2-6 alkynylene group, L$^2$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^3$ is a single bond, a C1-6 alkylene group, a C2-6 alkenylene group or a C2-6 alkynylene group, L$^4$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^5$ is a hydrogen atom, a C1-6 alkyl group, a C1-6 haloalkyl group, a C2-6 alkenyl group or a C2-6 haloalkenyl group, L$^6$ is a hydrogen atom, a C1-6 alkyl group, a C1-6 haloalkyl group, a C2-6 alkenyl group or a C2-6 haloalkenyl group, and m is 0 or 1 with the proviso that when m is 0, L$^4$ is not a single bond.

[35] A compound represented by the following formula (XIV), or a salt thereof:

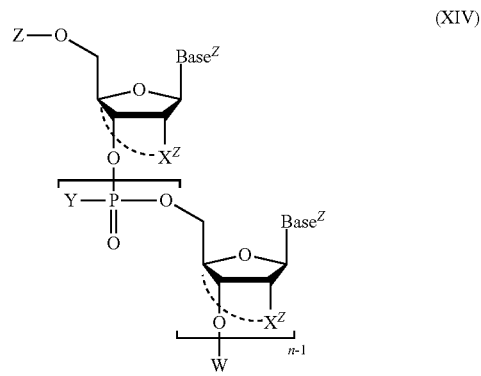

(XIV)

wherein n is an integer of 1 or greater,

Base$^Z$ independently at each occurrence is a nucleobase, a nucleobase protected with a basic protecting group, or a nucleobase protected with a pseudo solid phase-protecting group, X$^Z$ independently at each occurrence is a hydrogen atom, a halogen atom, a hydroxyl group, a hydroxyl group protected with a basic protecting group, an organic group bridged to the 4-carbon atom, or a hydroxyl group protected with a pseudo solid phase-protecting group, W is a hydrogen atom or a temporary protecting group, Y independently at each occurrence is a hydrogen atom, a hydroxyl group, a hydroxyl group protected with a basic protecting group, a thiol group, a thiol group protected with a basic protecting group, a borohydride group, a mono-C1-6 alkylamino group or a di-C1-6 alkylamino group, Z is a hydrogen atom, a basic protecting group, a temporary protecting group or a pseudo solid phase-protecting group, the compound or salt thereof satisfies at least one of that at least one Base$^Z$ is a nucleobase protected with a pseudo solid phase-protecting group, that at least one X$^Z$ is a hydroxyl group protected with a pseudo solid phase-protecting group, and that Z is a pseudo solid phase-protecting group, and at least one of the pseudo solid phase-protecting groups is represented by the formula (I):

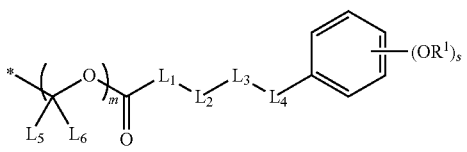

wherein * indicates a bond to a group protected by the pseudo solid phase-protecting group, R$^1$ is a C1-40 alkyl group, a C2-40 alkenyl group or a C2-40 alkynyl group, s is an integer of 1 to 5, L$^1$ is a single bond, a C1-6 alkylene group, a C2-6 alkenylene group or a C2-6 alkynylene group, L$^2$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^3$ is a single bond, a C1-6 alkylene group, a C2-6 alkenylene group or a C2-6 alkynylene group, L$^4$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^5$ is a hydrogen atom, a C1-6 alkyl group, a C1-6 haloalkyl group, a C2-6 alkenyl group or a C2-6 haloalkenyl group, L$^6$ is a hydrogen atom, a C1-6 alkyl group, a C1-6 haloalkyl group, a C2-6 alkenyl group or a C2-6 haloalkenyl group, and m is 0 or 1 with the proviso that when m is 0, L$^4$ is not a single bond.

[36] A pseudo solid phase-protecting group represented by the following formula (I):

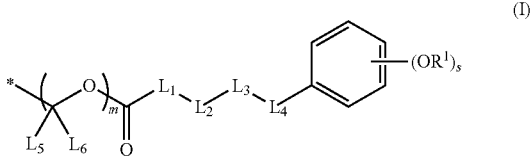

wherein * indicates a bond to at least one selected from the group consisting of 2'-, 3'- and 5'-hydroxyl groups and a nucleobase moiety of a nucleoside or oligonucleotide, R$^1$ is a C1-40 alkyl group, a C2-40 alkenyl group or a C2-40 alkynyl group, s is an integer of 1 to 5, L$^1$ is a single bond, a C1-6 alkylene group, a C2-6 alkenylene group or a C2-6 alkynylene group, L$^2$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^3$ is a single bond, a C1-6 alkylene group, a C2-6 alkenylene group or a C2-6 alkynylene group, L$^4$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^5$ is a hydrogen atom, a C1-6 alkyl group, a C1-6 haloalkyl group, a C2-6 alkenyl group or a C2-6 haloalkenyl group, L$^6$ is a hydrogen atom, a C1-6 alkyl group, a C1-6 haloalkyl group, a C2-6 alkenyl group or a C2-6 haloalkenyl group, and m is 0 or 1 with the proviso that when m is 0, L$^4$ is not a single bond.

[37] A method for producing a nucleoside or oligonucleotide, including reacting a nucleoside or oligonucleotide having:

a hydroxyl group or a protected hydroxyl group independently at 3'-position and 5'-position, and a hydroxyl group in at least one location selected from the group consisting of 2'-position, 3'-position, 5'-position and a nucleobase moiety, or a hydroxyl or amino group in at least one location of 2'-position and a nucleobase moiety, with a carboxyl compound represented by the following formula (X-1):

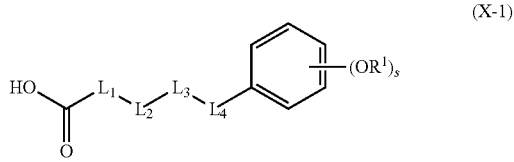

wherein R$^1$ is a C1-40 alkyl group, a C2-40 alkenyl group or a C2-40 alkynyl group, s is an integer of 1 to 5, L$^1$ is a single bond, a C1-6 alkylene group, a C2-6 alkenylene group or a C2-6 alkynylene group, L$^2$ is a single bond, —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, L$^3$ is a single bond, a C1-6 alkylene group, a C2-6 alkenylene group or a C2-6 alkynylene group, L$^4$ is —COO—, —CON(R$^2$)— (wherein R$^2$ is a hydrogen atom, a C1-6 alkyl group, a C1-6 haloalkyl group, a C2-6 alkenyl group or a C2-6 haloalkenyl group), —OCO—, —N(R$^2$)CO— (wherein R$^2$ is a hydrogen atom, a C1-6 alkyl group, a C1-6 haloalkyl group, a C2-6 alkenyl group or a C2-6 haloalkenyl group), —C(O)— or —O—, or with an acid halide represented by the following formula (X-2):

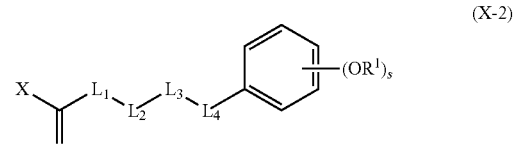

wherein X is a halogen atom, and R$^1$, L$^1$, L$^2$, L$^3$ and L$^4$ are the same as defined in the formula (X-1), or with an alkyl halide compound represented by the following formula (X-3):

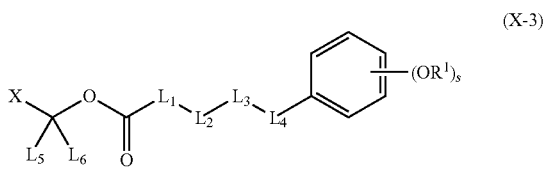

(X-3)

wherein X is a halogen atom, $R^1$, $L^1$, $L^2$ and $L^3$ are the same as defined in the formula (X-1), $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^5$ is a hydrogen atom, a C1-6 alkyl group, a C1-6 haloalkyl group, a C2-6 alkenyl group or a C2-6 haloalkenyl group, and $L^6$ is a hydrogen atom, a C1-6 alkyl group, a C1-6 haloalkyl group, a C2-6 alkenyl group or a C2-6 haloalkenyl group; thereby producing a nucleoside or oligonucleotide having, in at least one location selected from the group consisting of 2'-position, 3'-position, 5'-position and a nucleobase moiety, a pseudo solid phase-protecting group represented by the following formula (I):

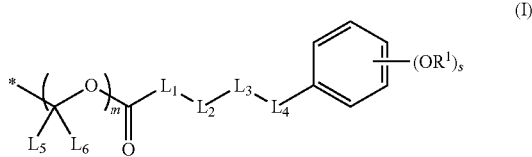

(I)

wherein * indicates a bond to at least one selected from the group consisting of the 2'-position, the 3'-position, the 5'-position and the nucleobase moiety, $R^1$ is a C1-40 alkyl group, a C2-40 alkenyl group or a C2-40 alkynyl group, s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^5$ is a hydrogen atom, a C1-6 alkyl group, a C1-6 haloalkyl group, a C2-6 alkenyl group or a C2-6 haloalkenyl group, $L^6$ is a hydrogen atom, a C1-6 alkyl group, a C1-6 haloalkyl group, a C2-6 alkenyl group or a C2-6 haloalkenyl group, and m is 0 or 1 with the proviso that when m is 0, $L^4$ is not a single bond.

Advantageous Effects of Invention

The novel method provided by the present invention can produce an oligonucleotide using a nucleoside or oligonucleotide that is easy to isolate and has high storage stability. The novel production method is adaptable to mass synthesis of oligonucleotides.

BRIEF DESCRIPTION OF DRAWING

FIG. 1 is a diagram illustrating the stability of nucleic acid monomers used for synthesis of oligonucleotides.

DESCRIPTION OF EMBODIMENTS

The present invention will be described in detail hereinbelow.

As long as otherwise mentioned, all the technical terms and scientific terms used in the present specification have the same meanings as generally understood by skilled artisans in the technical field to which the present invention pertains. Some preferred methods and materials are given below, but any methods and materials that are similar or equivalent to those described in the present specification may be used in the implementation or testing of the present invention.

The term "step" comprehends not only an independent step but also a combination of steps which are not distinct from one another as long as such combined steps fulfill the desired purpose. The numerical ranges indicated with "to" include the values before and after the "to" as the minimum and the maximum, respectively.

In the present specification, "n-" means normal, "i-" iso, "t-" and "tert-" tertiary, "Ph" phenyl, "Py" pyridyl or pyridine, "Me" methyl, "Et" ethyl, "Pr" propyl, "Bu" butyl, "Bn" benzyl, "Boc" tertiary-butoxycarbonyl, "TBS" tertiary-butyldimethylsilyl, "TIPS" triisopropylsilyl, "TBDPS" tertiary-butyldiphenylsilyl, and "DMTr" 4,4'-dimethoxytrityl.

"$L^1$" and "$L_1$" are synonymous, and the same applies to "$L^2$" and "$L_2$", "$L^3$" and "$L_3$", "$L^4$" and "$L_4$", "$L^5$" and "$L_5$", and "$L^6$" and "$L_6$".

In the specification, "halogen atom" indicates a fluorine atom, a chlorine atom, a bromine atom or an iodine atom.

"C1-6 alkyl group" means a linear or branched, saturated hydrocarbon group with 1 to 6 carbon atoms, with examples including methyl group, ethyl group, n-propyl group, isopropyl group, n-butyl group, isobutyl group, sec-butyl group, tert-butyl group, n-pentyl group, isopentyl group, neopentyl group, n-hexyl group and isohexyl group.

"C2-6 alkenyl group" means a linear or branched hydrocarbon group with 2 to 6 carbon atoms which has one or more double bonds at any positions, with examples including ethenyl group (vinyl group), 1-propenyl group, 2-propenyl group (allyl group), isopropenyl group, 1-butenyl group, 2-butenyl group, 3-butenyl group (homoallyl group), 4-pentenyl group and 5-hexenyl group.

"C2-6 alkynyl group" means a linear or branched hydrocarbon group with 2 to 6 carbon atoms which has one or more triple bonds at any positions, with examples including ethynyl group, 1-propynyl group, 2-propynyl group, 1-butynyl group, 2-butynyl group, 3-butynyl group, 4-pentynyl group and 5-hexynyl group.

"C1-40 alkyl group" means a linear or branched, saturated hydrocarbon group with 1 to 40 carbon atoms, with examples including methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, decyl group, octadecyl group, icosyl group, triacontyl group and tetracontyl group.

"C2-40 alkenyl group" means a linear or branched hydrocarbon group with 2 to 40 carbon atoms which has one or more double bonds at any positions, with examples including ethenyl group (vinyl group), 1-propenyl group, 2-propenyl group (allyl group), isopropenyl group, 1-butenyl group, 2-butenyl group, 3-butenyl group (homoallyl group), 4-pentenyl group, 5-hexenyl group, 10-decenyl group, 18-octadecenyl group, 20-icosenyl group, 30-triacontenyl group and 40-tetracontenyl group.

"C2-40 alkynyl group" means a linear or branched hydrocarbon group with 2 to 40 carbon atoms which has one or more triple bonds at any positions, with examples including ethynyl group, 1-propynyl group, 2-propynyl group, 1-butynyl group, 2-butynyl group, 3-butynyl group, 4-pentynyl group, 5-hexynyl group, 10-decynyl group, 18-octadecynyl group, 20-icosynyl group, 30-triacontynyl group and 40-tetracontynyl group.

"C10-30 alkyl group" means a linear or branched, saturated hydrocarbon group with 10 to 30 carbon atoms, with examples including decyl group, octadecyl group, icosyl group and triacontyl group.

"C15-25 alkyl group" means a linear or branched, saturated hydrocarbon group with 15 to 25 carbon atoms, with examples including pentadecyl group, hexadecyl group, heptadecyl group, octadecyl group, nonadecyl group, icosyl group and docosyl group.

"C15-20 alkyl group" means a linear or branched, saturated hydrocarbon group with 15 to 20 carbon atoms, with examples including pentadecyl group, hexadecyl group, heptadecyl group, octadecyl group, nonadecyl group and icosyl group.

"C10-30 alkenyl group" means a linear or branched hydrocarbon group with 10 to 30 carbon atoms which has one or more double bonds at any positions, with examples including 2-decenyl group, 10-decenyl group, 18-octadecenyl group, 20-icosenyl group and 30-triacontenyl group.

"C1-6 alkylene group" means a divalent substituent resulting from the removal of one hydrogen atom from any position of the "C1-6 alkyl group", with examples including methylene group, ethylene group (ethanediyl group), propane-1,3-diyl group, propane-2,2-diyl group, 2,2-dimethylpropane-1,3-diyl group, hexane-1,6-diyl group and 3-methylbutane-1,2-diyl group.

"C2-6 alkylene group" means a linear or branched divalent substituent with 2 to 6 carbon atoms which is among the "C1-6 alkylene groups" mentioned above, with examples including ethylene group (ethanediyl group), propane-1,3-diyl group, propane-2,2-diyl group, hexane-1,6-diyl group and 3-methylbutane-1,2-diyl group.

"C2-6 alkenylene group" means a divalent substituent resulting from the removal of one hydrogen atom from any position of the "C2-6 alkenyl group", with examples including ethene-1,1-diyl group, ethene-1,2-diyl group, propene-1,1-diyl group, propene-1,2-diyl group, propene-1,3-diyl group, but-1-ene-1,4-diyl group, but-1-ene-1,3-diyl group, but-2-ene-1,4-diyl group, buta-1,3-diene-1,4-diyl group, pent-2-ene-1,5-diyl group, hex-3-ene-1,6-diyl group and hexa-2,4-diene-1,6-diyl group.

"C2-6 alkynylene group" means a divalent substituent resulting from the removal of one hydrogen atom from any position of the "C2-6 alkynyl group", with examples including ethyne-1,2-diyl group, propyne-1,3-diyl group, but-1-yne-1,4-diyl group, but-1-yne-1,3-diyl group, but-2-yne-1,4-diyl group, pent-2-yne-1,5-diyl group, pent-2-yne-1,4-diyl group and hex-3-yne-1,6-diyl group.

"C1-6 haloalkyl group" means a group resulting from the substitution of the "C1-6 alkyl group" with one or more "halogen atoms" in place of a hydrogen atom at any position, with examples including monofluoromethyl group, monofluoroethyl group, monofluoropropyl group, 2,2,3,3,3-pentafluoropropyl group, monochloromethyl group, trifluoromethyl group, trichloromethyl group, 2,2,2-trifluoroethyl group, 2,2,2-trichloroethyl group, 1,2-dibromoethyl group and 1,1,1-trifluoropropan-2-yl group.

"C2-6 haloalkenyl group" means a group resulting from the substitution of the "C2-6 alkenyl group" with one or more "halogen atoms" in place of a hydrogen atom at any position.

"C3-6 cycloalkyl group" means a monovalent substituent resulting from the removal of one hydrogen atom from any position of a monocyclic, condensed cyclic, bridged cyclic or spirocyclic, aliphatic hydrocarbon ring in which the ring is composed of 3 to 6 carbon atoms, with specific examples including cyclopropyl group, cyclobutyl group, cyclopentyl group and cyclohexyl group.

"C1-6 alkoxy group" means a group formed by combination of the "C1-6 alkyl group" with an oxy group (—O—).

"Mono-C1-6 alkylamino group" means a group formed by combination of one C1-6 alkyl group with an amino group, with examples including methylamino group, ethylamino group, n-propylamino group, isopropylamino group, n-butylamino group, isobutylamino group, sec-butylamino group, tert-butylamino group, n-pentylamino group, isopentylamino group, neopentylamino group, n-hexylamino group and isohexylamino group.

"Di-C1-6 alkylamino group" means a group formed by combination of two identical or different "C1-6 alkyl groups" with an amino group, with examples including dimethylamino group, diethylamino group, di-n-propylamino group, diisopropylamino group, di-n-butylamino group, diisobutylamino group, di-t-butylamino group, di-n-pentylamino group, di-n-hexylamino group, N-ethyl-N-methylamino group, N-methyl-N-n-propylamino group, N-isopropyl-N-methylamino group, N-n-butyl-N-methylamino group, N-isobutyl-N-methylamino group, N-t-butyl-N-methylamino group, N-methyl-N-n-pentylamino group, N-n-hexyl-N-methylamino group, N-ethyl-N-n-propylamino group, N-ethyl-N-isopropylamino group, N-n-butyl-N-ethylamino group, N-ethyl-N-isobutylamino group, N-t-butyl-N-ethylamino group, N-ethyl-N-n-pentylamino group and N-ethyl-N-n-hexylamino group.

"C1-6 alkoxycarbonyl group", "mono-C1-6 alkylaminocarbonyl group", "di-C1-6 alkylaminocarbonyl group" and the like mean groups formed by combinations of the "C1-6 alkoxy group", the "mono-C1-6 alkylamino group" and the "di-C1-6 alkylamino group" with a carbonyl group (—C(O)—), respectively.

"C6-10 aryl group" means a monovalent substituent resulting from the removal of one hydrogen atom from any position of a monocyclic or bicyclic, aromatic hydrocarbon ring in which the ring is exclusively formed of carbon atoms and the number of carbon atoms is 6 to 10, with specific examples including phenyl group and naphthyl group.

"5-10 Membered heteroaryl group" means a monovalent substituent resulting from the removal of one hydrogen atom from any position of a monocyclic or condensed cyclic, aromatic heterocycle in which the ring is composed of 5 to 10 atoms including 1 to 5 heteroatoms (the heteroatom is a nitrogen atom, an oxygen atom or a sulfur atom and, when two or more of such atoms are present, may be the same as or different from one another).

Examples of the "5-10 membered heteroaryl groups" which are monocyclic include 2-thienyl group, 3-thienyl group, 2-furyl group, 3-furyl group, 2-pyranyl group, 3-pyranyl group, 4-pyranyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 1,2,4-triazol-1-yl group, 1,2,4-triazol-3-yl group, 1,2,4-triazol-5-yl group, 1,2,3-triazol-1-yl group, 1,2,3-triazol-4-yl group, 1,2,3-triazol-5-yl group, 2-oxazolyl group, 4-oxazolyl group, 5-oxazolyl group, 3-isoxazolyl group, 4-isoxazolyl group, 5-isoxazolyl group, 2-pyridyl group, 3-pyridyl group, 4-pyridyl group, 2-pyrazinyl group, 2-pyrimidinyl group, 4-pyrimidinyl group, 5-pyrimidinyl group, 3-pyridazinyl group, 4-pyridazinyl group, 1,3,4-oxadiazol-2-yl group, 1,3,4-thiadiazol-2-yl group, 1,2,4-oxadiazol-3-yl group, 1,2,4-oxadiazol-5-yl group, 1,2,4-thiadiazol-3-yl group, 1,2,4-thiadiazol-5-yl group, 1,2,5-oxadiazol-3-yl group and 1,2,5-thiadiazol-3-yl group.

Examples of the "5-10 membered heteroaryl groups" which are condensed rings include 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-benzothiazolyl group, 4 benzothiazolyl group, 5-benzothiazolyl group, 6-benzothiazolyl group, 7-benzothiazolyl group, 2-chromenyl group, 3-chromenyl group, 4-chromenyl group, 5-chromenyl group, 6-chromenyl group, 7-chromenyl group, 8-chromenyl group, 1-indolizinyl group, 2-indolizinyl group, 3-indolizinyl group, 5-indolizinyl group, 6-indolizinyl group, 7-indolizinyl group, 8-indolizinyl group, 1-isoindolyl group, 2-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 3 indazolyl group, 4-indazolyl group, 5-indazolyl group, 6-indazolyl group, 7-indazolyl group, 2 purinyl group, 6 purinyl group, 7-purinyl group, 8-purinyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthalazinyl group, 5-phthalazinyl group, 6-phthalazinyl group, 2,7-naphthyridin-1-yl group, 2,7-naphthyridin-3-yl group, 2,7-naphthyridin-4-yl group, 2,6-naphthyridin-1-yl group, 2,6-naphthyridin-3-yl group, 2,6-naphthyridin-4-yl group, 1,8-naphthyridin-2-yl group, 1,8-naphthyridin-3-yl group, 1,8-naphthyridin-4-yl group, 1,7-naphthyridin-2-yl group, 1,7-naphthyridin-3-yl group, 1,7-naphthyridin-4-yl group, 1,7-naphthyridin-5-yl group, 1,7-naphthyridin-6-yl group, 1,7-naphthyridin-8-yl group, 1,6-naphthyridin-2-yl group, 1,6-naphthyridin-3-yl group, 1,6-naphthyridin-4-yl group, 1,6-naphthyridin-5-yl group, 1,6-naphthyridin-7-yl group, 1,6-naphthyridin-8-yl group, 1,5-naphthyridin-2-yl group, 1,5-naphthyridin-3-yl group, 1,5-naphthyridin-4-yl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, 8-cinnolinyl group, 2-pteridinyl group, 4-pteridinyl group, 6-pteridinyl group and 7-pteridinyl group.

"Aralkyl group" means a monovalent substituent resulting from the substitution of the "C1-6 alkyl group" with the "C6-10 aryl group" in place of a hydrogen atom at any position.

"Heteroaralkyl group" means a monovalent substituent resulting from the substitution of the "C1-6 alkyl group" with the "5-10 membered heteroaryl group" in place of a hydrogen atom at any position.

"3-11 Membered nitrogen-containing nonaromatic heterocyclic group" means a monovalent substituent resulting from the removal of one hydrogen atom from any position of a monocyclic, condensed cyclic (the condensed ring may be composed of a nonaromatic ring with a nonaromatic ring or with an aromatic ring), bridged cyclic or spirocyclic, nonaromatic heterocycle which contains at least one or more nitrogen atoms and in which the ring is composed of 3 to 11 atoms, with examples including azetidinyl group, pyrrolidinyl group, 2-oxopyrrolidinyl group, piperidinyl group, 3-oxopiperidinyl group, piperazinyl group, morpholino group, thiomorpholino group, homomorpholino group and homopiperazino group.

"C1-40 alkylthio group", "C3-6 cycloalkylthio group", "C6-10 arylthio group", "5-10 membered heteroarylthio group", "aralkylthio group", "heteroarylthio group" and the like mean groups formed by combinations of the "C1-40 alkyl group", the "C3-6 cycloalkyl group", the "C6-10 aryl group", the "5-10 membered heteroaryl group", the "aralkyl group" and the "heteroaryl group" with a thio group (—S—), respectively.

In the present specification, "nucleoside" that is a structural unit of an oligonucleotide means a compound in which a nucleobase is linked to 1'-position of a sugar (for example, ribose, 2'-deoxyribose or 2'-4' bridged ribose) by N-glycosidation.

Here, the ribose and the 2'-deoxyribose are unsubstituted, or are substituted with one or more substituents selected from the group consisting of C1-6 alkyl groups, halogen atoms, hydroxyl groups, amino groups, hydroxy groups protected with a basic protecting group, and protected amino groups. The C1-6 alkyl groups are unsubstituted, or are substituted with one or more substituents selected independently from halogen atoms, C1-6 alkoxycarbonyl groups, mono-C1-6 alkylaminocarbonyl groups, di-C1-6 alkylaminocarbonyl groups and the like. The C1-6 alkoxycarbonyl groups, the mono-C1-6 alkylaminocarbonyl groups, the di-C1-6 alkylaminocarbonyl groups and the like are unsubstituted, or are substituted with a C6-10 aryl group, a 5-10 membered heteroaryl group or a 3-11 membered nitrogen-containing nonaromatic heterocyclic group.

The 2'-4' bridged ribose is not particularly limited as long as the 2'-position and the 4'-position of the nucleoside are bridged through a bridging group. Examples of such riboses include those in which the 2'-position and the 4'-position are bridged via a C2-6 alkylene group (the alkylene group is unsubstituted or is substituted with a C1-6 alkyl group, and one or two methylene groups in the alkylene group may be replaced by a group selected from —O—, —NR$^{11}$— (R$^{11}$ is a hydrogen atom or a C1-6 alkyl group), —S—, —CO—, —CS—, —COO—, —OCONR$^{12}$— (R$^{12}$ is a hydrogen atom or a C1-6 alkyl group), —CONR$^{13}$— (R$^{13}$ is a hydrogen atom or a C1-6 alkyl group) and —CSNR$^{14}$— (R$^{14}$ is a hydrogen atom or a C1-6 alkyl group). Specific examples thereof include compounds of the following formulae. The sugar in the nucleoside is preferably ribose or 2'-deoxyribose.

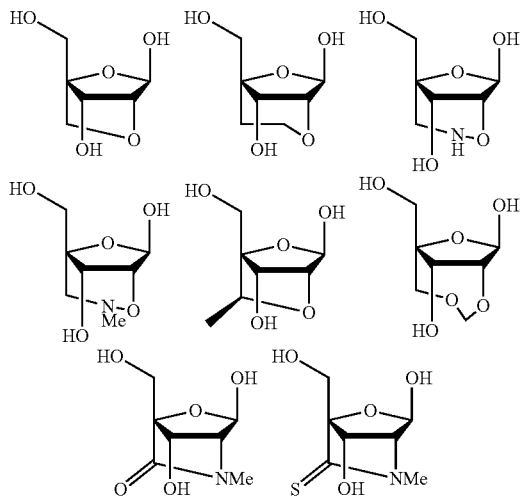

In the present specification, "nucleobase" is not particularly limited as long as it is used for the synthesis of a nucleic acid. Examples thereof include pyrimidine bases such as cytosyl group, uracil group, thyminyl group and 5-methylcytosyl group, and purine bases such as adenyl group and guanyl group. "Protected nucleobase" means, for example, that an amino group is protected when the nucleobase having an amino group is an adenyl, guanyl or cytosyl group, that a hydroxyl group is protected when the nucleobase has a hydroxyl group, that a thiol group is protected when the nucleobase has a thiol group, or that the nucleobase has a carbonyl group, and the carbonyl group is protected in the form of a hydroxyl group by being conjugated with an amino group or a hydroxyl group substituted on the ring. Preferably, the protected nucleobase is a nucleobase protected with a protecting group which can withstand conditions under which the temporary protecting group at 3'-position or 5'-position will be removed.

"Amino-protecting group" in the nucleobase is not particularly limited, and examples thereof include those protecting groups described in literature such as PROTECTIVE GROUPS IN ORGANIC SYNTHESIS, Third Edition, JOHN WILLY & SONS (1999). Specific examples of the "amino-protecting groups" include pivaloyl group, pivaloyloxymethyl group, trifluoroacetyl group, phenoxyacetyl group, 4-isopropylphenoxyacetyl group, 4-tert-butylphenoxyacetyl group, acetyl group, benzoyl group, isobutyryl group, dimethylformamidinyl group and 9-fluorenylmethyloxycarbonyl group. Of these, phenoxyacetyl group, 4-isopropylphenoxyacetyl group, acetyl group, benzoyl group, isobutyryl group and dimethylformamidinyl group are preferable.

"Hydroxyl-protecting group" in the nucleobase is not particularly limited, and examples thereof include any protecting groups described in literature such as PROTECTIVE GROUPS IN ORGANIC SYNTHESIS, Third Edition, JOHN WILLY & SONS (1999). Specific examples include alkyl groups (such as methyl group and tert-butyl group), arylmethyl groups (such as benzyl group and p-methoxybenzyl group), alkoxyalkyl groups (such as methoxymethyl group, methoxyethyl group, cyanoethoxymethyl group and ethoxyethyl group), 2-tetrahydropyranyl group, cyanoethyl group, carbamoyl groups (such as phenylcarbamoyl group and 1,1-dioxothiomorpholine-4-thiocarbamoyl group), acyl groups (such as acetyl group, pivaloyl group, isobutyryl group, benzoyl group, phenoxyacetyl group, levulinyl group and 3-benzoylpropionyl group), silyl groups (such as trimethylsilyl group, triethylsilyl group, triisopropylsilyl group, tert-butyldimethylsilyl group and tert-butyldiphenylsilyl group), [(triisopropylsilyl)oxy]methyl group (Tom group) and 1-(4-chlorophenyl)-4-ethoxypiperidin-4-yl group (Cpep group). Of these, acetyl group, benzoyl group, benzyl group or p-methoxybenzyl group is preferable.

Examples of the "thiol-protecting group" in the nucleobase include the protecting groups mentioned above as the "hydroxyl-protecting groups", and protecting groups which form a disulfide bond.

When a carbonyl group of the nucleobase is protected in the form of a hydroxyl group by being conjugated, such a protection of a carbonyl group may be attained by, for example, reacting the nucleobase with phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride or the like.

Besides the groups described above, the "nucleobases" include modified nucleobases substituted at any positions with 1 to 3 substituents (such as, for example, halogen atoms, alkyl groups, aralkyl groups, alkoxy groups, acyl groups, alkoxyalkyl groups, hydroxyl groups, amino groups, monoalkylaminos, dialkylaminos, carboxy, cyano and nitro) (with examples including 8-bromoadenyl group, 8-bromoguanyl group, 5-bromocytosyl group, 5-iodocytosyl group, 5-bromouracil group, 5-iodouracil group, 5-fluorouracil group, 5-methylcytosyl group, 8-oxoguanyl group and hypoxanthinyl group).

[Elongation Reaction Cycles]

In the specification, "elongation reaction cycle" means a reaction cycle in which a nucleoside or oligonucleotide having a pseudo solid phase-protecting group is converted into H-phosphonated form and is thereafter reacted with a nucleoside or oligonucleotide having a hydroxyl group to form an oligomer in which the nucleoside or oligonucleotide having a pseudo solid phase-protecting group is coupled to the nucleoside or oligonucleotide having a hydroxyl group through the phosphorus-containing group.

For example, the elongation reaction cycle includes a step including deprotecting a nucleoside or oligonucleotide that has a pseudo solid phase-protecting group and a 3'- or 5'-hydroxyl group protected with a temporary protecting group to remove the temporary protecting group to form the hydroxyl group, a step including converting the resultant hydroxyl group into an H-phosphonated form to form an H-phosphonate compound, and a step of reacting the H-phosphonate compound with a nucleoside or oligonucleotide having a hydroxyl group to form an oligonucleotide in which these compounds are coupled through a phosphite diester bond.

[Pseudo Solid Phase-Protecting Groups]

The pseudo solid phase-protecting group used in the present invention is a protecting group which, when possessed by a reaction substrate, renders the reaction substrate and a reaction product soluble in a low-polarity solvent, thereby allowing the reaction to take place in a liquid phase, and, after the addition of an amount of a polar solvent, causes the reaction product or the reaction substrate to be precipitated, thereby allowing solid liquid separation, and which is stable under conditions under which a temporary protecting group described later on the 5'-hydroxyl group or the 3'-hydroxyl group can be removed. By using a reaction substrate having such a pseudo solid phase-protecting group, reactivity and easy post-treatment can be attained at the same time.

Examples of the pseudo solid phase-protecting groups include groups represented by the following formula (I):

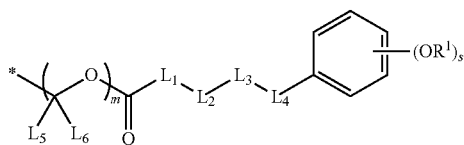

(I)

In the formula, * indicates a bond to a group protected by the pseudo solid phase-protecting group, $R^1$ is a C1-40 alkyl group, a C2-40 alkenyl group or a C2-40 alkynyl group, s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^5$ is a hydrogen atom, a C1-6 alkyl group, a C1-6 haloalkyl group, a C2-6 alkenyl group or a C2-6 haloalkenyl group, $L^6$ is a hydrogen atom, a C1-6 alkyl group, a C1-6 haloalkyl group, a C2-6 alkenyl group or a C2-6 haloalkenyl group, and m is 0 or 1.

When $L^2$ is —COO— or —O— and $L^4$ is —OCO— or —O—, it is preferable that $L^3$ be a C1-6 alkylene group, a C2-6 alkenylene group or a C2-6 alkynylene group.

Typical examples of the pseudo solid phase-protecting groups include 3,4,5-tris(octadecyloxy)benzyloxysuccinyl group (3-{3,4,5-tris(octadecyloxy)benzyloxycarbonyl}propanoyl group), 3,4,5-tris(octadecyloxy)benzoyl group, 4-oxo-4-(2,4,6-tris(octadecyloxy)phenyl)butyryl group, 2-(3,4,5-tris(octadecyloxy)benzamido)ethoxysuccinyl group (3-[2-{3,4,5-tris(octadecyloxy)benzamido}ethoxycarbonyl]propanoyl group), 2-(N-methyl-3,4,5-tris(octadecyloxy)benzamido)ethoxysuccinyl group (3-[2-{N-methyl-3,4,5-tris(octadecyloxy)benzamido}ethoxycarbonyl]propanoyl group), (N-methyl-3,4,5-tris(octadecyloxy)benzamido)acetyl group, ((3,4,5-tris(octadecyloxy)benzoyl)oxy)methyl group, and 2-(N-methyl-3,4,5-tris(octadecyloxy)benzamido)ethoxysuccinyloxymethyl group ({(3-[2-{N-methyl-3,4,5-tris(octadecyloxy)benzamido}ethoxycarbonyl]propanoyl)oxy} methyl group).

Specific examples of the pseudo solid phase-protecting groups also include groups disclosed in literature such as WO 2014/077292.

The pseudo solid phase-protecting group is preferably a group represented by the following formula (II):

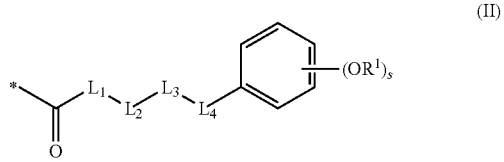

(II)

In the formula, * indicates a bond to a group protected by the pseudo solid phase-protecting group, $R^1$ is a C1-40 alkyl group, a C2-40 alkenyl group or a C2-40 alkynyl group, s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group) or —O—, $L^3$ is a single bond, a C1-6 alkylene group, a C2-6 alkenylene group or a C2-6 alkynylene group, and $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group) or —O—.

When $L^2$ is —COO— or —O— and $L^4$ is —OCO— or —O—, it is more preferable that $L^3$ be a C1-6 alkylene group, a C2-6 alkenylene group or a C2-6 alkynylene group.

The pseudo solid phase-protecting group is more preferably a group represented by the following formula (III):

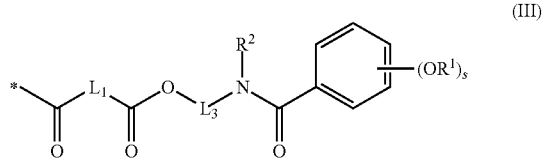

(III)

In the formula, * indicates a bond to a group protected by the pseudo solid phase-protecting group, $R^1$ is a C1-40 alkyl group, a C2-40 alkenyl group or a C2-40 alkynyl group, s is an integer of 1 to 5, $L^1$ is a C1-6 alkylene group or a C2-6 alkenylene group, $L^3$ is a C1-6 alkylene group or a C2-6 alkenylene group, and $R^2$ is a hydrogen atom, a C1-6 alkyl group, a C1-6 haloalkyl group or a C2-6 alkenyl group.

The pseudo solid phase-protecting group is more preferably a group represented by the following formula (IV):

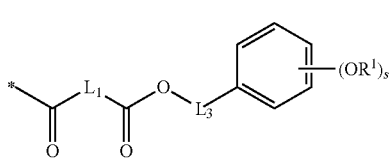

(IV)

In the formula, * indicates a bond to a group protected by the pseudo solid phase-protecting group,
$R^1$ is a C1-40 alkyl group, a C2-40 alkenyl group or a C2-40 alkynyl group, s is an integer of 1 to 5,
$L^1$ is a C1-6 alkylene group or a C2-6 alkenylene group, and
$L^3$ is a C1-6 alkylene group or a C2-6 alkenylene group.

The pseudo solid phase-protecting group is more preferably a group represented by the following formula (IV-2):

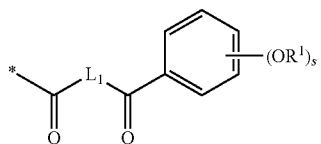

(IV-2)

In the formula, * indicates a bond to a group protected by the pseudo solid phase-protecting group,
$R^1$ is a C1-40 alkyl group, a C2-40 alkenyl group or a C2-40 alkynyl group, s is an integer of 1 to 5, and
$L^1$ is a C1-6 alkylene group or a C2-6 alkenylene group.

The pseudo solid phase-protecting group is more preferably a group represented by the following formula (IV-3):

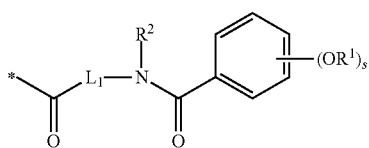

(IV-3)

In the formula, * indicates a bond to a group protected by the pseudo solid phase-protecting group,
$R^1$ is a C1-40 alkyl group, a C2-40 alkenyl group or a C2-40 alkynyl group, s is an integer of 1 to 5,
$L^1$ is a C1-6 alkylene group or a C2-6 alkenylene group, and
$R^2$ is a hydrogen atom, a C1-6 alkyl group, a C1-6 haloalkyl group or a C2-6 alkenyl group.

In the formula (II) to the formula (IV-2), $L^1$ is preferably a C1-6 alkylene group, and is particularly preferably an ethylene group.

In the formula (IV-3), $L^1$ is preferably a C1-6 alkylene group, and is particularly preferably a methylene group.

In the formula (II) to the formula (IV), $L^3$ is preferably a C1-6 alkylene group, and is particularly preferably a methylene group or an ethylene group.

In the formula (II), the formula (III) and the formula (IV-3), $R^2$ is preferably a hydrogen atom or a C1-6 alkyl group, and is particularly preferably a hydrogen atom or a methyl group.

In another embodiment, the pseudo solid phase-protecting group is preferably a group represented by the following formula (V):

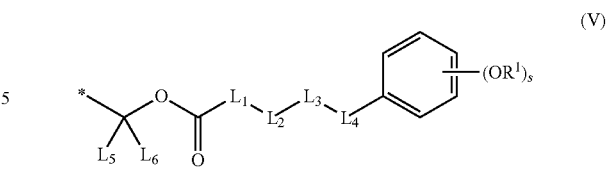

(V)

In the formula, * indicates a bond to a group protected by the pseudo solid phase-protecting group,
$R^1$ is a C1-40 alkyl group, a C2-40 alkenyl group or a C2-40 alkynyl group, s is an integer of 1 to 5,
$L^1$ is a single bond, a C1-6 alkylene group, a C2-6 alkenylene group or a C2-6 alkynylene group,
$L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—,
$L^3$ is a single bond, a C1-6 alkylene group, a C2-6 alkenylene group or a C2-6 alkynylene group,
$L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—,
$L^5$ is a hydrogen atom, a C1-6 alkyl group, a C1-6 haloalkyl group, a C2-6 alkenyl group or a C2-6 haloalkenyl group, and
$L^6$ is a hydrogen atom, a C1-6 alkyl group, a C1-6 haloalkyl group, a C2-6 alkenyl group or a C2-6 haloalkenyl group.

When $L^2$ is —COO— or —O— and $L^4$ is —OCO— or —O—, it is more preferable that $L^3$ be a C1-6 alkylene group, a C2-6 alkenylene group or a C2-6 alkynylene group.

The pseudo solid phase-protecting group is more preferably: a group represented by the following formula (VI):

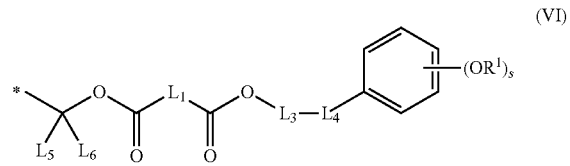

(VI)

wherein * indicates a bond to a group protected by the pseudo solid phase-protecting group,
$R^1$ is a C1-40 alkyl group, a C2-40 alkenyl group or a C2-40 alkynyl group, s is an integer of 1 to 5,
$L^1$ is a C1-6 alkylene group or a C2-6 alkenylene group,
$L^3$ is a C1-6 alkylene group or a C2-6 alkenylene group,
$L^4$ is a single bond or —N($R^2$)CO— (wherein $R^2$ is a hydrogen atom, a C1-6 alkyl group, a C1-6 haloalkyl group or a C2-6 alkenyl group),
$L^5$ is a hydrogen atom or a C1-6 alkyl group, and
$L^6$ is a hydrogen atom or a C1-6 alkyl group; or a group represented by the following formula (VII):

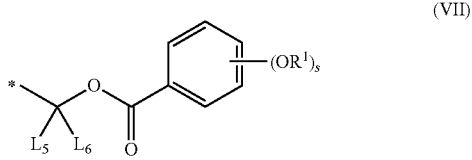

(VII)

wherein * indicates a bond to a group protected by the pseudo solid phase-protecting group, $L^5$ is a hydrogen atom or a C1-6 alkyl group, and $L^6$ is a hydrogen atom or a C1-6 alkyl group.

The pseudo solid phase-protecting group is still more preferably a group represented by the above formula (VII).

In the formula (I), the formula (V) and the formula (VI), $L^1$ is preferably a C1-6 alkylene group, and is particularly preferably a methylene group or an ethylene group.

In the formula (I), the formula (V) and the formula (VI), $L^3$ is preferably a C1-6 alkylene group, and is particularly preferably a methylene group or an ethylene group.

In the formula (I) and the formula (V) to the formula (VII), $L^5$ and $L^6$ are particularly preferably each a hydrogen atom.

In the pseudo solid phase-protecting groups represented by the formula (I) to the formula (VII), $R^1$ is preferably a C10-30 alkyl group or a C10-30 alkenyl group, more preferably a C10-30 alkyl group, still more preferably a C15-25 alkyl group, even more preferably a C15-20 alkyl group, and particularly preferably an octadecyl group.

In the pseudo solid phase-protecting groups represented by the formula (I) to the formula (VII), s is preferably an integer of 2 to 4, and more preferably 3.

When s in the formula (I) to the formula (VII) is 2 to 5, the groups $R^1$ may be the same as or different from one another.

[Temporary Protecting Groups]

The temporary protecting group used in the present invention is a protecting group which protects the 5'-hydroxyl group or the 3'-hydroxyl group and is removed in the "elongation reaction cycle" described hereinabove. The 5'-hydroxyl group or the 3'-hydroxyl group resulting from the deprotection is converted into an H-phosphonated form during the elongation reaction cycle, and the H-phosphonated form is used to form a bond with other nucleoside or oligonucleotide. Examples of the temporary protecting groups include protecting groups described in the following literature:

Protective Groups in Organic Synthesis, Greene T. W. and Wuts P. G. M., published by Wiley Interscience, 1999, and Protecting Groups, Kocienski P. J., 1994, Georg Thieme Verlag.

[Basic Protecting Groups]

The basic protecting group used in the present invention is a general protecting group which protects an amino group, a carbonyl group, a hydroxyl group or a thiol group in the nucleobase, or protects a 2'-hydroxyl group, a 3'-hydroxyl group or a 5'-hydroxyl group, or protects a hydroxyl group of a phosphodiester bond or a thiol group of a thiophosphodiester bond, and which is not removed in the "elongation reaction cycle" described hereinabove and does not have the function of the "pseudo solid phase-protecting group". Examples of the basic protecting groups include protecting groups described in the following literature:

Protective Groups in Organic Synthesis, Greene T. W. and Wuts P. G. M., published by Wiley Interscience, 1999, and Protecting Groups, Kocienski P. J., 1994, Georg Thieme Verlag.

The basic protecting groups used for an amino group, a hydroxyl group or a thiol group in the nucleobase are as described in the "amino-protecting groups" in the nucleobase, the "hydroxyl-protecting groups" in the nucleobase, and the "thiol-protecting groups" in the nucleobase.

Examples of the basic protecting groups used for a carbonyl group in the nucleobase include phenoxy group, 2,5-dichlorophenyl group, 3-chlorophenyl group, 3,5-dichlorophenyl group, 2-formylphenyl group, 2-naphthyl group, 4-methoxyphenyl group, 4-chlorophenyl group, 2-nitrophenyl group, 4-nitrophenyl group, 4-acetylaminophenyl group, pentafluorophenyl, 4-pivaloyloxybenzylalkyl group, 4-nitrophenethylalkyl group, 2-(methylsulfonyl)ethyl group, 2-(phenylsulfonyl)ethyl group, 2-cyanoethyl group, 2-(trimethylsilyl)ethyl group, dimethylaminocarbonyl group, diethylaminocarbonyl group, N-methyl-N-phenylcarbamoyl group, 1-pyrrolidinocarbonyl group, 4-morpholinocarbonyl group and N,N-diphenylaminocarbonyl group. A nucleoside or oligonucleotide having the protected carbonyl group can be obtained in accordance with the method described hereinabove.

The basic protecting groups for a 2'-hydroxyl group will be described later as the basic protecting groups in "hydroxyl groups protected with a basic protecting group" represented by $X^Z$. The basic protecting groups for a 3'-hydroxyl group and a 5'-hydroxyl group will be described later as the basic protecting groups in "hydroxyl groups protected with a basic protecting group" represented by Z.

The basic protecting groups for a hydroxyl group of a phosphodiester bond or a thiol group of a thiophosphodiester bond will be described later.

The phrase that the functional groups are protected with the protecting groups (for example, the hydroxyl groups and nucleobases protected with the pseudo solid phase-protecting groups, the hydroxyl groups protected with the temporary protecting groups, and the hydroxyl groups, amino groups, thiol groups and the like protected with the basic protecting groups) means that the functional groups are substituted with the protecting group in place of a hydrogen atom.

In the present specification, the "organic group bridged to the 4-carbon atom" means an organic group that bridges the 2'-position and the 4'-position of the sugar. For example, this bridging group is, although not particularly limited, a C2-6 alkylene group (the alkylene group is unsubstituted or is substituted with a C1-6 alkyl group wherein one or two methylene groups in the alkylene group may be replaced by groups selected from —O—, —NR$^{11}$— (R$^{11}$ is a hydrogen atom or a C1-6 alkyl group), —S—, —CO—, —CS—, —COO—, —OCONR$^{12}$— (R$^{12}$ is a hydrogen atom or a C1-6 alkyl group), —CONR$^{13}$— (R$^{13}$ is a hydrogen atom or a C1-6 alkyl group) and —CSNR$^{14}$— (R$^{14}$ is a hydrogen atom or a C1-6 alkyl group).

[Oligonucleotide Production Methods]

Next, an oligonucleotide production method according to the present invention (hereinafter, also written as the "production method of the invention") will be described. Specifically, there will be described a method in which a nucleoside or oligonucleotide (hereinafter, also written as the "n-mer oligonucleotide") protected with a pseudo solid phase-protecting group is elongated with a nucleoside or oligonucleotide (hereinafter, also written as the "p-mer oligonucleotide") to produce an oligonucleotide (hereinafter, also written as the "(n+p)-mer oligonucleotide") protected with a pseudo solid phase-protecting group. The n-mer oligonucleotide means an oligonucleotide in which n nucleoside units are linked together via a phosphorus-containing group. When n is 1, the n-mer oligonucleotide is understood as a nucleoside. The same applies to the p-mer oligonucleotide.

In the case where the n-mer oligonucleotide has two or more nucleobase moieties, the nucleobase moieties may be the same as or different from one another. When the n-mer oligonucleotide has two or more pseudo solid phase-protecting groups, the pseudo solid phase-protecting groups may be the same as or different from one another. When the n-mer oligonucleotide has two or more basic protecting groups, the basic protecting groups may be the same as or different from one another. When the n-mer oligonucleotide has two or more organic groups bridged to the 4-carbon atom, the organic groups bridged to the 4-carbon atom may be the same as or different from one another.

The same applies to the p-mer oligonucleotide.

The oligonucleotide production method includes a step of subjecting a nucleoside or oligonucleotide having a pseudo solid phase-protecting group in at least one location selected from the group consisting of 2'-position, 3'-position, 5'-position and a nucleobase moiety and having a 5'-hydroxyl group or a 3'-hydroxyl group, to H-phosphonation to convert the 5'-hydroxyl group or the 3'-hydroxyl group into an H-phosphonated form.

Further, the oligonucleotide production method includes at least one elongation reaction cycle including the above H-phosphonation step.

The oligonucleotide production method is characterized in that the elongation reaction cycle includes the step of subjecting a nucleoside or oligonucleotide having a pseudo solid phase-protecting group to H-phosphonation to introduce an H-phosphonated form in place of the 5'-hydroxyl group or the 3'-hydroxyl group. The oligonucleotide production method preferably includes the following Step a to Step d in the elongation reaction cycle. Step a to Step d are performed in the order of Step a, Step b, Step c and Step d, or in the order of Step a, Step d, Step b and Step c, and are preferably performed in the order of Step a, Step b, Step c and Step d.

(Step a)

Step a is a temporary protecting group removal step including deprotecting a nucleoside or oligonucleotide which has a pseudo solid phase-protecting group on at least one of a hydroxyl group that is not the elongation terminal, a nucleobase moiety and 2'-position and which has at the elongation terminal a hydroxyl group protected with a temporary protecting group, to remove the temporary protecting group to form a hydroxyl group.

(Step b)

Step b is a phosphonation step including converting the hydroxyl group resulting from the removal of the temporary protecting group into an H-phosphonated form using an H-phosphonate reagent.

(Step c)

Step c is a coupling step including adding a nucleoside or oligonucleotide having a hydroxyl group to the H-phosphonated nucleoside or oligonucleotide obtained in Step b, and condensing the compounds by forming a phosphite diester bond via the hydroxyl group.

(Step d)

Step d is a conversion step including converting the phosphite diester bond into a phosphodiester bond, a thiophosphodiester bond, an aminophosphodiester bond, a boranophosphodiester bond, a phosphodiester bond protected with a basic protecting group (a phosphotriester bond), a thiophosphodiester bond protected with a basic protecting group (a thiophosphate-O, O, S-triester bond) or the like.

Here, the amino group in the aminophosphodiester bond is unsubstituted or is substituted with one or two C1-6 alkyl groups.

The phosphodiester bond protected with a basic protecting group is a bond formed by substituting a phosphodiester bond with, for example, a C1-40 alkyl group, a C3-6 cycloalkyl group, a C6-10 aryl group, a 5-10 membered heteroaryl group, an aralkyl group or a heteroaralkyl group in place of the hydrogen atom of the single hydroxyl group. Here, the C1-6 alkyl group is unsubstituted, or is substituted with a substituent such as a halogen atom or a cyano group. The C3-6 cycloalkyl group, the C6-10 aryl group, the 5-10 membered heteroaryl group, the aralkyl group and the heteroaralkyl group are unsubstituted, or are substituted with a substituent such as a C1-6 alkyl group, a halogen atom or a cyano group.

The thiophosphodiester bond protected with a basic protecting group is a bond formed by substituting a thiophosphodiester bond with, for example, a C1-40 alkyl group, a C3-6 cycloalkyl group, a C6-10 aryl group, a 5-10 membered heteroaryl group, an aralkyl group or a heteroaralkyl group in place of the hydrogen atom of the single thiol group. Here, the C1-40 alkyl group is unsubstituted, or is substituted with a substituent such as a halogen atom or a cyano group. The C3-6 cycloalkyl group, the C6-10 aryl group, the 5-10 membered heteroaryl group, the aralkyl group and the heteroaralkyl group are unsubstituted, or are substituted with a substituent such as a C1-6 alkyl group, a halogen atom or a cyano group.

In the nucleoside or oligonucleotide with a pseudo solid phase-protecting group that is used in Step a, the number n of the nucleoside units is not particularly limited as long as it is an integer of 1 or greater, but is preferably 1 to 50, more preferably 1 to 30, still more preferably 1 to 20, even more preferably 1 to 10, and particularly preferably 1 to 5.

In the nucleoside or oligonucleotide with a hydroxyl group that is used in Step c, the number p of the nucleoside units is not particularly limited as long as it is an integer of 1 or greater, but is preferably 1 to 50, more preferably 1 to 30, still more preferably 1 to 20, even more preferably 1 to 5, further preferably 1 to 3, and particularly preferably 1. That is, it is particularly preferable to use a nucleoside.

The reaction mixture obtained in Step d may be directly used in Step a. Treatment such as heating may be performed appropriately after the completion of Step d, and thereby Step a may be performed concurrently.

The oligonucleotide production method may further include the following Step e, in which case the nucleoside or oligonucleotide may be purified simply and effectively by removing the excess of raw materials and byproducts.

(Step e)

Step e is a separation step of adding a polar solvent to the reaction mixture obtained from any of Step a to Step d to precipitate the nucleoside or oligonucleotide having a pseudo solid phase-protecting group, and collecting the precipitate by solid liquid separation.

Step e is specific to the liquid phase synthesis method using a pseudo solid phase-protecting group, and cannot be present in a usual liquid phase synthesis method using no pseudo solid phase-protecting groups or in a solid phase synthesis method.

The number of Steps e present in the elongation reaction cycle is not particularly limited. Step e may be performed after any of Step a to Step d.

For example, Step e may be performed 0 to 5 times, preferably 0 to 3 times, more preferably 0 to 2 times, and still more preferably 0 or 1 time independently after each of Step a to Step d. Here, one or more Steps e are present after at least one of Steps a to d.

The elongation reaction cycle preferably includes one to four Steps e. To manage and control the generation of byproducts strictly and to lead the compounds to a high-purity oligonucleotide, it is preferable that Step e be performed one time after at least one of Step a, Step b and Step d during the elongation reaction cycle. More preferably, Step e is performed one time after Step b, one time after Step d, or one time after each of Step b and Step d during the elongation reaction cycle.

In another embodiment, it is more preferable that Step e be performed one time after Step a, one time after Step b, or one time after each of Step a and Step b, and it is still more preferable that Step e be performed one time after each of Step a and Step b during the elongation reaction cycle.

If the circumstances permit the amount of byproducts to be controlled by controlling the equivalents of the raw materials and by controlling the reaction, it is preferable that Step e be performed after Step a to Step d as a basic unit are repeated.

The oligonucleotide production method may further include Step f, in which case the desired oligonucleotide can be isolated and produced.

(Step f)

Step f is a deprotection step of removing all of the basic protecting group, the temporary protecting group and the pseudo solid phase-protecting group in the oligonucleotide obtained by Step a through Step e.

The oligonucleotide production method is mainly classified into Method A and Method B depending on the direction in which the oligonucleotide is elongated. In Method A, the 5'-hydroxyl group is converted in Step a to Step c and the nucleoside or oligonucleotide is added to the 5'-position. In Method B, the 3'-hydroxyl group is converted in Step a to Step c and the nucleoside or oligonucleotide is added to the 3'-position.

Method A is an oligonucleotide production method including:

a first step (Step a) including deprotecting a first nucleoside or first oligonucleotide having a pseudo solid phase-protecting group in at least one location selected from the group consisting of 2'-position, 3'-position and a nucleobase moiety, having a 3'-hydroxyl group protected with a basic protecting group or a pseudo solid phase-protecting group, and having a 5'-hydroxyl group protected with a temporary protecting group, to remove the temporary protecting group to form a 5'-hydroxyl group, a second step (Step b) including converting the resultant 5'-hydroxyl group into an H-phosphonated form using an H-phosphonate reagent, a third step (Step c) of forming an oligomer of the first nucleoside or first oligonucleotide with a second nucleoside or second oligonucleotide having a 3'-hydroxyl group and having a 5'-hydroxyl group protected with a temporary protecting group, by forming a phosphite diester bond from the 5'-hydroxyl group, now converted to the H-phosphonated form, of the first nucleoside or first oligonucleotide and the 3'-hydroxyl group of the second nucleoside or second oligonucleotide, and a fourth step (Step d) including converting the phosphite diester bond of the oligomer into a phosphodiester bond, a thiophosphodiester bond, a boranophosphodiester bond, an aminophosphodiester bond, a phosphodiester bond protected with a basic protecting group, or a thiophosphodiester bond protected with a basic protecting group.

Method B is an oligonucleotide production method including:

a seventh step (Step a) including deprotecting a third nucleoside or third oligonucleotide having a pseudo solid phase-protecting group in at least one location selected from the group consisting of 2'-position, 5'-position and a nucleobase moiety, having a 5'-hydroxyl group protected with a basic protecting group or a pseudo solid phase-protecting group, and having a 3'-hydroxyl group protected with a temporary protecting group, to remove the temporary protecting group to form a 3'-hydroxyl group, an eighth step (Step b) including converting the resultant 3'-hydroxyl group into an H-phosphonated form using an H-phosphonate reagent, a ninth step (Step c) of forming an oligomer of the third nucleoside or third oligonucleotide with a fourth nucleoside or fourth oligonucleotide having a 5'-hydroxyl group and having a 3'-hydroxyl group protected with a temporary protecting group, by forming a phosphite diester bond from the 3'-hydroxyl group, now converted to the H-phosphonated form, of the third nucleoside or third oligonucleotide and the 5'-hydroxyl group of the fourth nucleoside or fourth oligonucleotide, and a tenth step (Step d) including converting the phosphite diester bond of the oligomer into a phosphodiester bond, a thiophosphodiester bond, a boranophosphodiester bond, an aminophosphodiester bond, a phosphodiester bond protected with a basic protecting group, or a thiophosphodiester bond protected with a basic protecting group.

Step a to Step f will be described in detail sequentially hereinbelow.

(Step a) (Temporary Protecting Group Removal Step)

Step a in Method A or Method B is illustrated in Scheme 1 or Scheme 2, respectively.

In Method A, Step a is a step (a temporary protecting group removal step) in which an n-mer oligonucleotide (ia) having a 5'-hydroxyl group protected with a temporary protecting group R that is removable with a fluorine reagent, an acid or a base (in the formula, n is an integer of 1 or greater, and the compound is a nucleoside when n=1) is deprotected in a low-polarity solvent to remove the temporary protecting group R by the addition of a fluorine reagent, an acid or a base (Scheme 1).

Scheme 1

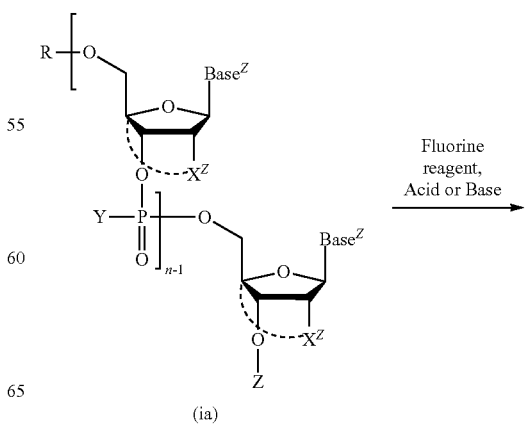

(ia)

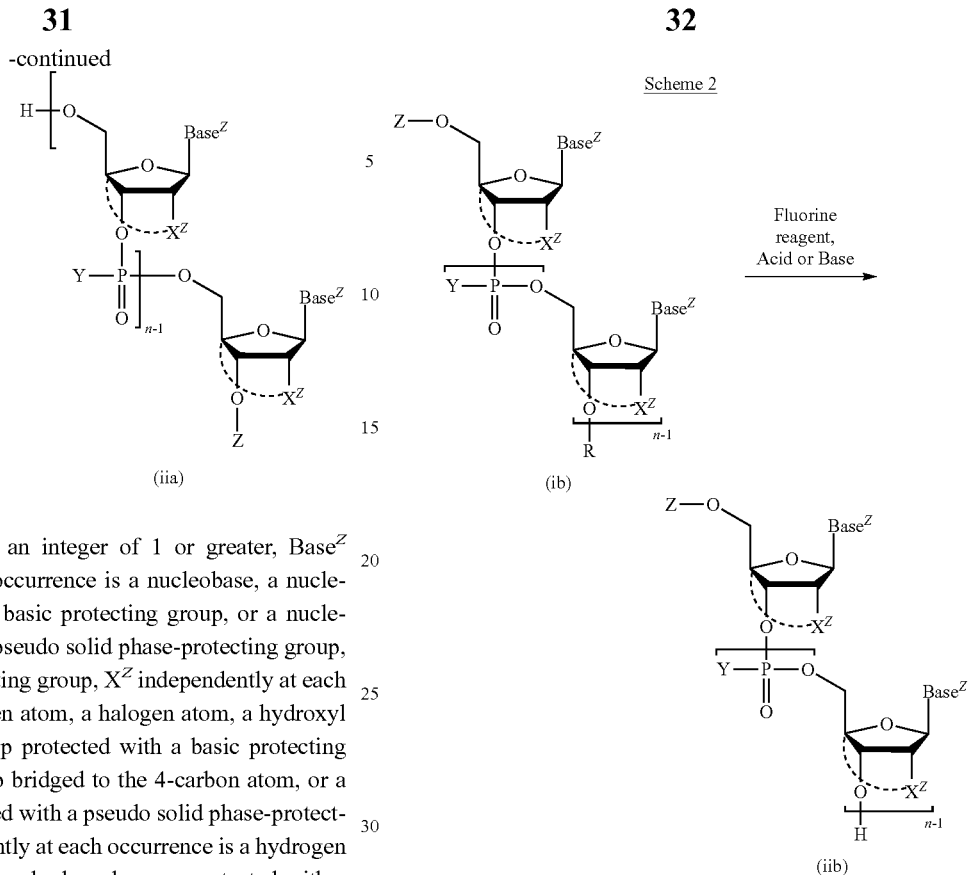

Scheme 2

(iia)

(ib)

(iib)

In the scheme, n is an integer of 1 or greater, $Base^Z$ independently at each occurrence is a nucleobase, a nucleobase protected with a basic protecting group, or a nucleobase protected with a pseudo solid phase-protecting group, R is a temporary protecting group, $X^Z$ independently at each occurrence is a hydrogen atom, a halogen atom, a hydroxyl group, a hydroxyl group protected with a basic protecting group, an organic group bridged to the 4-carbon atom, or a hydroxyl group protected with a pseudo solid phase-protecting group, Y independently at each occurrence is a hydrogen atom, a hydroxyl group, a hydroxyl group protected with a basic protecting group, a thiol group, a thiol group protected with a basic protecting group, a borohydride group, a mono-C1-6 alkylamino group or a di-C1-6 alkylamino group, and Z is a basic protecting group, a temporary protecting group or a pseudo solid phase-protecting group. Here, at least one of $Base^Z$, $X^Z$ and Z includes a pseudo solid phase-protecting group.

In the case where the compound (ia) or (iia) in Scheme 1 has two or more nucleobase moieties, the nucleobase moieties may be the same as or different from one another. When the compound (ia) or (iia) has two or more pseudo solid phase-protecting groups, the pseudo solid phase-protecting groups may be the same as or different from one another. When the compound (ia) or (iia) has two or more basic protecting groups, the basic protecting groups may be the same as or different from one another. When the n-mer oligonucleotide has two or more organic groups bridged to the 4-carbon atom, the organic groups bridged to the 4-carbon atom may be the same as or different from one another.

In Method B, (Step a) is a step (a temporary protecting group removal step) in which an n-mer oligonucleotide (ib) having a 3'-hydroxyl group protected with a temporary protecting group R that is removable with a fluorine reagent, an acid or a base (in the formula, n is an integer of 1 or greater, and the compound is a nucleoside when n=1) is deprotected in a low-polarity solvent to remove the temporary protecting group R by the addition of a fluorine reagent, an acid or a base (Scheme 2). In the scheme, n, $Base^Z$, R, $X^Z$, Y and Z are the same as defined in Scheme 1.

It is preferable that at least one of $Base^Z$ and Z include a pseudo solid phase-protecting group, and it is more preferable that Z include a pseudo solid phase-protecting group.

Z is preferably a basic protecting group or a pseudo solid phase-protecting group, and more preferably a pseudo solid phase-protecting group.

The pseudo solid phase-protecting group contained in $X^Z$ or Z is preferably a group represented by any of the formulae (I) to (VII) described hereinabove, and preferred embodiments thereof are similar as described above.

The pseudo solid phase-protecting group contained in $Base^Z$ is preferably a group represented by the formula (I) below in which m is 1 or in which m is 0 and the number of single bonds represented by $L^1$, $L^2$, $L^3$ and $L^4$ is 0 to 3.

(I)

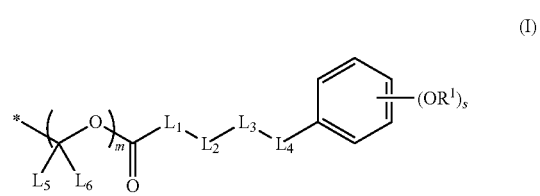

In the formula, * indicates a bond to the nucleobase moiety, and the definitions and preferred embodiments of the other symbols are the same as in the formula (I) described hereinabove.

The pseudo solid phase-protecting group contained in $Base^Z$ is more preferably a group represented by the formula (II) below in which the number of single bonds represented by $L^1$, $L^2$, $L^3$ and $L^4$ is 0 to 3.

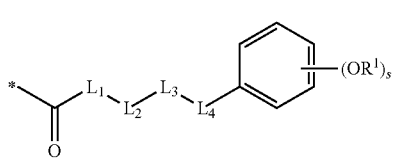
(II)

In the formula, * indicates a bond to the nucleobase moiety, and the definitions and preferred embodiments of the other symbols are the same as in the formula (II) described hereinabove.

The pseudo solid phase-protecting group contained in $Base^Z$ is still more preferably a group represented by the formula (III) below.

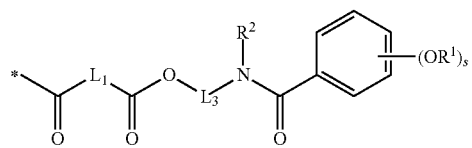
(III)

In the formula, * indicates a bond to the nucleobase moiety, and the other symbols are the same as defined in the formula (III) described hereinabove.

The pseudo solid phase-protecting group contained in $Base^Z$ is still more preferably a group represented by the formula (IV) below.

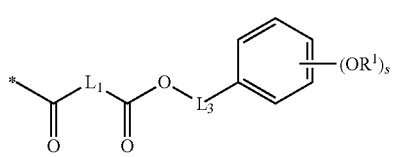
(IV)

In the formula, * indicates a bond to the nucleobase moiety, and the other symbols are the same as defined in the formula (IV) described hereinabove.

The pseudo solid phase-protecting group contained in $X^Z$ or Z is more preferably a group represented by the formula (IV-2) below.

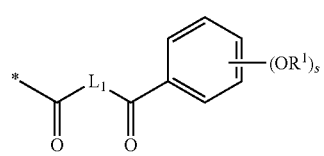
(IV-2)

In the formula, * indicates a bond to the nucleobase moiety, and the other symbols are the same as defined in the formula (IV-2) described hereinabove.

The pseudo solid phase-protecting group contained in $X^Z$ or Z is still more preferably a group represented by the formula (IV-3) below.

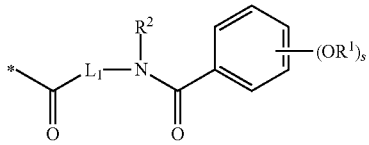
(IV-3)

In the formula, * indicates a bond to the nucleobase moiety, and the other symbols are the same as defined in the formula (IV-3) described hereinabove.

$L^1$ in the pseudo solid phase-protecting group contained in $Base^Z$, represented by any of the formula (II) to the formula (IV-3), is preferably a C1-6 alkylene group, and particularly preferably an ethylene group.

$L^3$ in the pseudo solid phase-protecting group contained in $Base^Z$, represented by any of the formula (II) to the formula (IV), is preferably a C1-6 alkylene group, and particularly preferably a methylene group or an ethylene group.

In another embodiment, the pseudo solid phase-protecting group contained in $Base^Z$ is preferably a group represented by the formula (V) below.

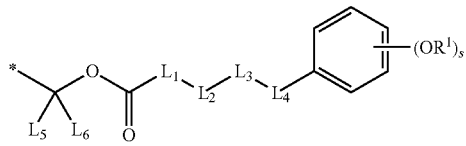
(V)

In the formula, * indicates a bond to the nucleobase moiety, and the definitions and preferred embodiments of the other symbols are the same as in the formula (V) described hereinabove.

The pseudo solid phase-protecting group contained in $Base^Z$ is more preferably a group represented by the formula (VI) below:

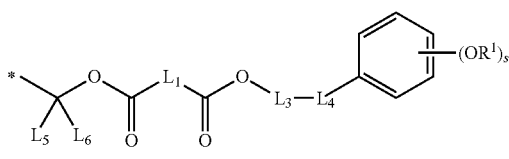
(VI)

wherein * indicates a bond to the nucleobase moiety, and the other symbols are the same as defined in the formula (VI) described hereinabove; or a group represented by the formula (VII) below:

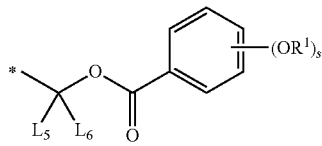
(VII)

wherein * indicates a bond to the nucleobase moiety, and the other symbols are the same as defined in the formula (VII) described hereinabove.

The pseudo solid phase-protecting group contained in $Base^Z$ is even more preferably a group represented by the above formula (VII).

$L^1$ in the pseudo solid phase-protecting group contained in $Base^Z$, represented by the formula (I), the formula (V) or the formula (VI), is preferably a C1-6 alkylene group, and particularly preferably a methylene group or an ethylene group.

$L^3$ in the pseudo solid phase-protecting group contained in $Base^Z$, represented by the formula (I), the formula (V) or the formula (VI), is preferably a C1-6 alkylene group, and particularly preferably a methylene group or an ethylene group.

$L^5$ and $L^6$ in the pseudo solid phase-protecting group contained in $Base^Z$, represented by any of the formula (I) and the formula (V) to the formula (VII), are particularly preferably hydrogen atoms.

$R^1$ in the pseudo solid phase-protecting group contained in $Base^z$, represented by any of the formula (I) to the formula (VII), is preferably a C10-30 alkyl group or a C10-30 alkenyl group, and more preferably a C10-30 alkyl group.

The letter s in the pseudo solid phase-protecting group contained in $Base^Z$, represented by any of the formula (I) to the formula (VII), is preferably an integer of 2 to 4, and more preferably 3.

When s in any of the formula (I) to the formula (VII) is 2 to 5, the groups $R^1$ may be the same as or different from one another.

The pseudo solid phase-protecting group represented by any of the formula (V) to the formula (VII) that correspond to the formula (I) in which m=1 is particularly useful when introduced into thymine or uracil.

The temporary protecting group R which may be used for the hydroxyl group at the elongation terminal of the oligonucleotide is not particularly limited as long as it is removable with a fluorine reagent, an acid or a base and is used as a hydroxyl-protecting group. Examples of the temporary protecting groups R removable with a fluorine reagent include silyl groups (such as tert-butyldimethylsilyl group, triethylsilyl group and trimethylsilyl group). Examples of the temporary protecting groups R removable with an acid include xanthenyl groups (such as 9-(9-phenyl)xanthenyl group and 9-phenylthioxanthenyl group), alkoxyalkyl groups (such as 1-methoxy-1-methylethyl group, 1,3-dioxolan-2-yl group and 1,3-benzodioxol-2-yl group), alkylthioalkyl groups (such as 1,3-dithiolan-2-yl group and 1,3-benzodithiol-2-yl group), alkoxycarbonyl groups (such as tert-butyloxycarbonyl group), and triarylmethyl groups (such as trityl group, dimethoxytrityl group and monomethoxytrityl group). Examples of the temporary protecting groups R removable with a base include levulinyl group and 3-benzoylpropionyl group. Preferred are tert-butyldimethylsilyl group, trityl group, 9-(9-phenyl)xanthenyl group, 9-phenylthioxanthenyl group, 1,1-bis(4-methoxyphenyl)-1-phenylmethyl group (dimethoxytrityl group) and 1-(4-methoxyphenyl)-1,1-diphenylmethyl group (monomethoxytrityl group). Of these, from the points of view of easy deprotection and availability, tert-butyldimethylsilyl group, monomethoxytrityl group and dimethoxytrityl group are preferable, tert-butyldimethylsilyl group and dimethoxytrityl group are more preferable, and dimethoxytrityl group is particularly preferable. Tert-butyldimethylsilyl group is also particularly preferable.

In the "hydroxyl group protected with a basic protecting group" represented by $X^Z$, examples of the basic protecting groups include protecting groups described in literature such as PROTECTIVE GROUPS IN ORGANIC SYNTHESIS, Third Edition, JOHN WILLY & SONS (1999). Specific examples include alkyl groups (such as methyl group and tert-butyl group), arylmethyl groups (such as benzyl group and p-methoxybenzyl group), diarylmethyl groups (such as diphenylmethyl group), alkoxyalkyl groups (such as methoxymethyl group, methoxyethyl group, ethoxyethyl group and cyanoethoxymethyl group), 2-tetrahydropyranyl group, cyanoethyl group, carbamoyl groups (such as phenylcarbamoyl group and 1,1-dioxothiomorpholine-4-thiocarbamoyl group), acyl groups (such as acetyl group, pivaloyl group, benzoyl group, levulinyl group and 3-benzoylpropionyl group), silyl groups (such as triisopropylsilyl group, tert-butyldimethylsilyl group and tert-butyldiphenylsilyl group), [(triisopropylsilyl)oxy] methyl (Tom) Group, and 1-(4-chlorophenyl)-4-ethoxypiperidin-4-yl (Cpep) group. Of these, tert-butyldimethylsilyl group, triisopropylsilyl group or tert-butyldiphenylsilyl group is preferable, and tert-butyldimethylsilyl group or triisopropylsilyl group is more preferable. In another embodiment, levulinyl group or 3-benzoylpropionyl group is preferable, and levulinyl group is more preferable.

$X^Z$ is preferably a hydrogen atom, a hydroxyl group, a hydroxyl group protected with a basic protecting group, or an organic group bridged to the 4-carbon atom, more preferably a hydrogen atom, a hydroxyl group or a hydroxyl group protected with a C1-6 alkyl group, a tert-butyldimethylsilyl group, a triisopropylsilyl group or a tert-butyldiphenylsilyl group, and more preferably a hydrogen atom or a hydroxyl group protected with a triisopropylsilyl group. Here, the C1-6 alkyl group is unsubstituted, or is substituted with a group selected from the group consisting of C1-6 alkoxycarbonyl groups, mono-C1-6 alkylaminocarbonyl groups and di-C1-6 alkylaminocarbonyl groups.

In another embodiment, $X^z$ is more preferably an organic group bridged to the 4-carbon atom which is represented by a C2-6 alkylene group (wherein the alkylene group is unsubstituted or is substituted with a methyl group, and one or two methylene groups in the alkylene group may be replaced by a group selected from —O—, —$NR^{11}$— ($R^{11}$ is a hydrogen atom or a methyl group), —CO—, —CS—, —COO—, —$OCONR^{12}$— ($R^{12}$ is a hydrogen atom or a methyl group), —$CONR^{13}$— ($R^{13}$ is a hydrogen atom or a methyl group) and —$CSNR^{14}$ ($R^{14}$ is a hydrogen atom or a methyl group). $X^Z$ is still more preferably an organic group bridged to the 4-carbon atom which is represented by an ethylene group (wherein one or two methylene groups in the ethylene group may be replaced by a group selected from —O—, —$CONR^{13}$— ($R^{13}$ is a hydrogen atom or a methyl group) and —$CSNR^{14}$— ($R^{14}$ is a hydrogen atom or a methyl group).

Examples of the basic protecting groups represented by Z include those protecting groups mentioned as the basic protecting groups in the "hydroxyl group protected with a basic protecting group" represented by $X^Z$.

In particular, tert-butyldimethylsilyl group, triisopropylsilyl group, tert-butyldiphenylsilyl group, levulinyl group or 3-benzoylpropionyl group is preferable, levulinyl group or 3-benzoylpropionyl group is more preferable, and levulinyl group is still more preferable.

The basic protecting group in $X^Z$ or Z may be a protecting group that is not removed under conditions under which the temporary protecting group is removed. When, for example, an acid-labile temporary protecting group is used, the basic protecting group may be a protecting group that belongs to the aforementioned temporary protecting groups and is not removed with an acid but is removed with a base or a fluorine reagent. When a base-labile temporary protecting group is used, the basic protecting group may be a protecting group that belongs to the aforementioned temporary protecting groups and is not removed with a base but is removed with an acid or a fluorine reagent. When a fluorine reagent-labile temporary protecting group is used, the basic protecting group may be a protecting group that belongs to the aforementioned temporary protecting groups and is not removed with a fluorine reagent but is removed with an acid or a base.

When, for example, the basic protecting group in $X^Z$ or Z is such a group as a levulinyl group or a 3-benzoylpropionyl group, the temporary protecting group is preferably a silyl group such as tert-butyldimethylsilyl group or triethylsilyl group, or a triarylmethyl group such as trityl group, dimethoxytrityl group or monomethoxytrityl group.

When the temporary protecting group is such a group as a levulinyl group or a 3-benzoylpropionyl group, the basic protecting group in $X^Z$ or Z is preferably a silyl group such as tert-butyldimethylsilyl group or triethylsilyl group, or a triarylmethyl group such as trityl group, dimethoxytrityl group or monomethoxytrityl group. Such a group as a levulinyl group or a 3-benzoylpropionyl group may be used as the temporary protecting group particularly in the case of Method B.

Y independently at each occurrence is a hydrogen atom, a hydroxyl group, a protected hydroxyl group, a thiol group, a protected thiol group, a borohydride group, a mono-C1-6 alkylamino group or a di-C1-6 alkylamino group. The protected hydroxyl group is the same as a group that replaces the hydroxyl group in the "phosphodiester bond protected with a basic protecting group" converted in Step d described later. The protected thiol group is the same as a group that replaces the thiol group in the "thiophosphodiester bond protected with a basic protecting group" converted in Step d described later.

Preferably, Y independently at each occurrence is a hydrogen atom, a hydroxyl group, a thiol group or a 2-cyanoethoxy group, and more preferably a hydroxyl group or a thiol group. The phosphorus functional group including Y has, for example, any of the following structures (or salts of the following structures).

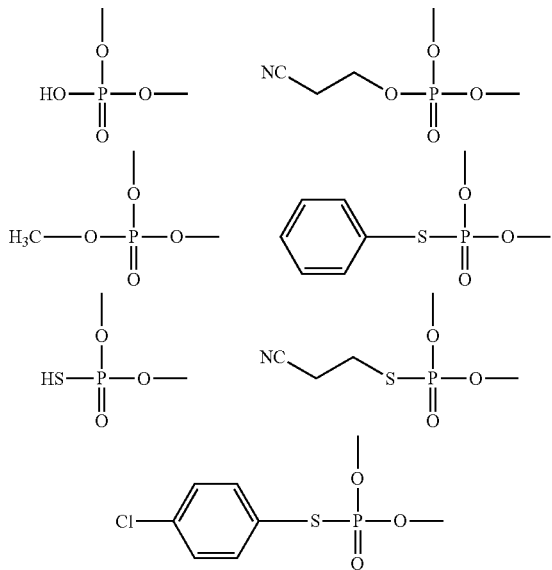

-continued

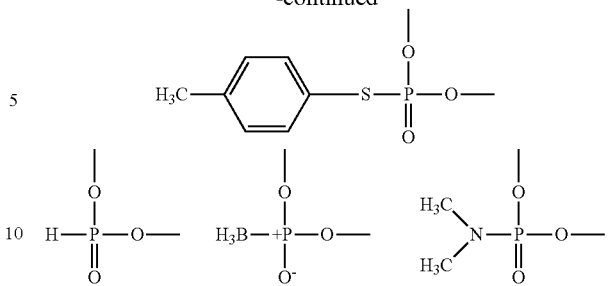

Step a is performed in a solvent that does not affect the reaction. Because higher reactivity is expected with increasing solubility in the solvent, it is preferable to select a low-polarity solvent that has high solubility for the target compound. Specific examples include halogenated solvents such as chloroform, dichloromethane and 1,2-dichloroethane; aromatic solvents such as benzene, toluene, xylene and mesitylene; ester solvents such as ethyl acetate and isopropyl acetate; aliphatic solvents such as hexane, pentane, heptane, octane, nonane and cyclohexane; and ether solvents such as tetrahydrofuran, diethyl ether, cyclopentyl methyl ether and tert-butyl methyl ether. Two or more of these solvents may be used as a mixture at any ratio. As long as the n-mer oligonucleotide can be dissolved, the low-polarity solvent may be mixed in any ratio with a polar solvent, for example, a nitrogen-containing aromatic solvent such as pyridine, a nitrile solvent such as acetonitrile or propionitrile, or an amide solvent such as N,N-dimethylformamide, N,N-dimethylacetamide or N-methylpyrrolidone. In particular, the solvent used in Step a is preferably dichloromethane, chloroform, 1,2-dichloroethane, benzene, toluene, xylene, mesitylene, hexane, pentane, heptane, nonane, cyclohexane, ethyl acetate, isopropyl acetate, tetrahydrofuran, tert-butyl methyl ether, cyclopentyl methyl ether, or a combination of these solvents, and is particularly preferably dichloromethane or tetrahydrofuran.

In Step a, the concentration of the n-mer oligonucleotide in the solvent is not particularly limited as long as the compound is dissolved, but is preferably 1 to 30 wt %.

The fluorine reagent, the acid or the base used in Step a is not particularly limited as long as the temporary protecting group can be removed satisfactorily.

The fluorine reagent is preferably hydrogen fluoride pyridine salt, tetrabutylammonium fluoride, hydrogen fluoride triethylamine salt, hydrofluoric acid, ammonium fluoride, adduct of ammonium fluoride with hydrogen fluoride, potassium fluoride or adduct of potassium fluoride with hydrogen fluoride. In particular, hydrogen fluoride pyridine salt or tetrabutylammonium fluoride is more preferable, and hydrogen fluoride pyridine salt is particularly preferable.

The acid is preferably trifluoroacetic acid, dichloroacetic acid, trifluoromethanesulfonic acid, trichloroacetic acid, methanesulfonic acid, p-toluenesulfonic acid, hydrochloric acid, acetic acid, ammonium cerium nitrate, phosphonic acid or phosphoric acid. In particular, trifluoroacetic acid, dichloroacetic acid, trifluoromethanesulfonic acid, trichloroacetic acid, methanesulfonic acid, p-toluenesulfonic acid, hydrochloric acid, acetic acid or ammonium cerium nitrate is more preferable, trifluoroacetic acid, dichloroacetic acid, trifluoromethanesulfonic acid, trichloroacetic acid, methanesulfonic acid or p-toluenesulfonic acid is still more preferable, and dichloroacetic acid or phosphonic acid is particularly preferable. Trifluoroacetic acid or p-toluenesulfonic acid is also particularly preferable.

Examples of the bases include hydrazine derivatives (such as hydrazine monohydrate, hydrazine acetate salt, hydrazinium sulfate, acetohydrazide, methyl carbazate, phenylhydrazine and p-toluenesulfonylhydrazine), ethylenediamine derivatives (such as ethylenediamine) and inorganic bases (such as potassium carbonate). The base is preferably a hydrazine derivative, and more preferably hydrazine monohydrate.

These fluorine reagents, acids and bases may be used as dilute solutions in the low-polarity solvents described above. Besides the fluorine reagents, the acids and the bases, deprotection can be accomplished with enzymes such as Chirazyme L-2 and Chirazyme L-5.

The amount of the fluorine reagent, the acid or the base in Step a may be 1 to 100 mol per 1 mol of the n-mer oligonucleotide, and is preferably 1 to 40 mol, more preferably 1 to 30 mol, and still more preferably 5 to 30 mol.

The reaction temperature in Step a is not particularly limited as long as the reaction proceeds, but is preferably −10° C. to 60° C., more preferably 0° C. to 50° C., and still more preferably 0° C. to 30° C. The reaction time varies depending on conditions such as the type of the n-mer oligonucleotide used, the type of the fluorine reagent, the acid or the base, the type of the solvent and the reaction temperature, but is preferably 5 minutes to 50 hours, more preferably 5 minutes to 12 hours, and still more preferably 30 minutes to 6 hours.

If the fluorine reagent, the acid or the base used as the deprotecting agent is present in the coupling reaction in Step c described later, the temporary protecting group R on the 5'- or 3'-hydroxyl group of the p-mer oligonucleotide (iv) is removed. It is therefore necessary that the residual deprotecting agent be removed by quenching treatment. The quenching treatment is performed using a silicon reagent or an organic base when the deprotecting agent is the fluorine reagent or the acid, and is performed with a ketone compound when the deprotecting agent is the base.

The silicon reagent used in the quenching treatment is not particularly limited as long as it can quench the fluorine reagent. Some preferred reagents are hexamethyldisiloxane [TMS$_2$O], trimethylsilyl chloride [TMSCl], hexamethyldisilazane, trimethylsilyl bromide, trimethylsilyl iodide, trimethylsilyl trifluoromethanesulfonate, triethylsilyl chloride, triisopropylsilyl chloride, tert-butyldimethylsilyl chloride, tert-butyldiphenylsilyl chloride, phenyldimethylsilyl chloride, diphenylmethylsilyl chloride and triphenylsilyl chloride. TMS$_2$O and TMSCl are more preferable, and TMS$_2$O is particularly preferable.

The organic base used in the quenching treatment is not particularly limited as long as it can neutralize the acid. Some preferred bases are pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole and 5-nitrobenzimidazole. Pyridine, 2,4,6-trimethylpyridine, benzimidazole, 1,2,4-triazole, N-phenylimidazole, N-methylimidazole, 2-amino-4,6-dimethylpyrimidine and 1,10-phenanthroline are more preferable, and pyridine is particularly preferable.

The ketone compound used in the quenching treatment is not particularly limited as long as it can consume the base. Examples include acetylacetone and acetone, with acetylacetone being preferable.

The amount of the silicon reagent, the organic base or the ketone compound used in the quenching treatment in Step a is, for example, 0.01 to 100 mol per 1 mol of the fluorine reagent, the acid or the base, and is preferably 0.1 to 50 mol, more preferably 1 to 20 mol, and still more preferably 1 to 3 mol.

To perform Step a and subsequent Step b continuously in the liquid phase, it is preferable to add a cation scavenger during the deprotection reaction of the temporary protecting group R in Step a or after the deprotection reaction. The cation scavenger may be added or may not be added when Step a and Step b are not continuous.

The cation scavenger is not particularly limited as long as the compound is not re-protected with the protecting group R that has been removed (the protecting group does not return) or the deprotected functional group does not undergo side reaction. Examples include pyrrole derivatives such as pyrrole, 2-methylpyrrole, 3-methylpyrrole, 2,3-dimethylpyrrole and 2,4-dimethylpyrrole; and indole derivatives such as indole, 4-methylindole, 5-methylindole, 6-methylindole, 7-methylindole, 5,6-dimethylindole and 6,7-dimethylindole. For the reason that a good cation scavenging effect is obtained, pyrrole, 3-methylpyrrole, 2,4-dimethylpyrrole, indole, 4-methylindole, 5-methylindole, 6-methylindole, 7-methylindole, 5,6-dimethylindole and 6,7-dimethylindole are preferable, pyrrole, 3-methylpyrrole and indole are more preferable, pyrrole and indole are still more preferable, and pyrrole is particularly preferable.

The amount of the cation scavenger is, for example, 1 to 50 mol per 1 mol of the n-mer oligonucleotide (ia or ib), and is preferably 1 to 15 mol, and more preferably 1 to 3 mol.

Step a is followed by Step b or Step d. As required, Step b or Step d may be preceded by liquid separation treatment and distillation to replace the solvent by a solvent used in Step b or Step d, or may be preceded by Step e to isolate the n-mer oligonucleotide having the deprotected 5'-hydroxyl group (iia) or deprotected 3'-hydroxyl group (iib).

(Step b) (Phosphonation Step)

Step b in Method A or Method B is illustrated in Scheme 3 or 4, respectively.

In Method A, Step b is a step in which the n-mer oligonucleotide (iia), having the deprotected 5'-hydroxyl group, that is obtained by Step a described above or Step d described later in Method A, is phosphonated to convert the 5'-hydroxyl group into an H-phosphonated form (Scheme 3 below). In Scheme 3, the symbols are the same as defined hereinabove.

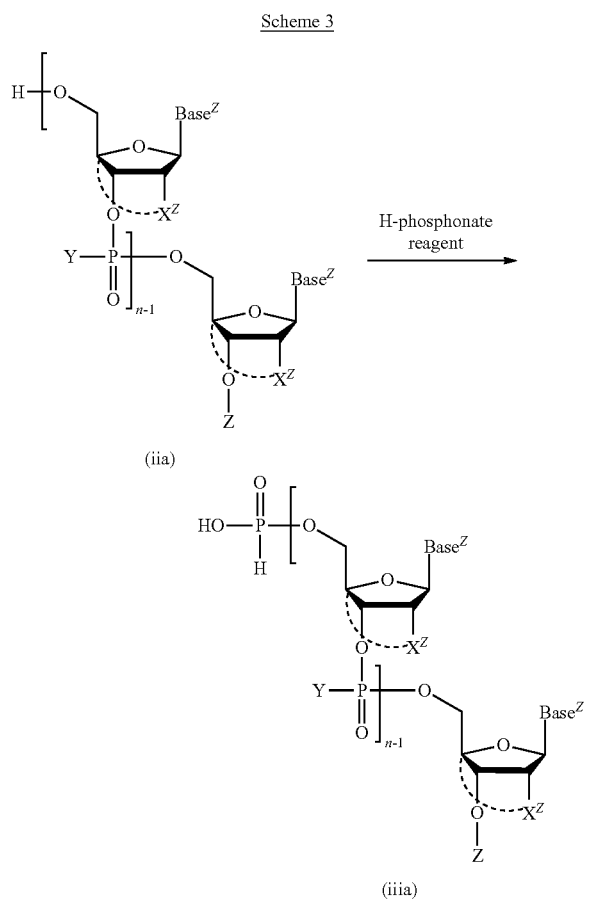

In Method B, Step b is a step in which the n-mer oligonucleotide (iib), having the deprotected 3'-hydroxyl group, that is obtained by Step a described above or Step d described later in Method B, is phosphonated to convert the 3'-hydroxyl group into an H-phosphonated form (Scheme 4 below). In Scheme 4, the symbols are the same as defined hereinabove.

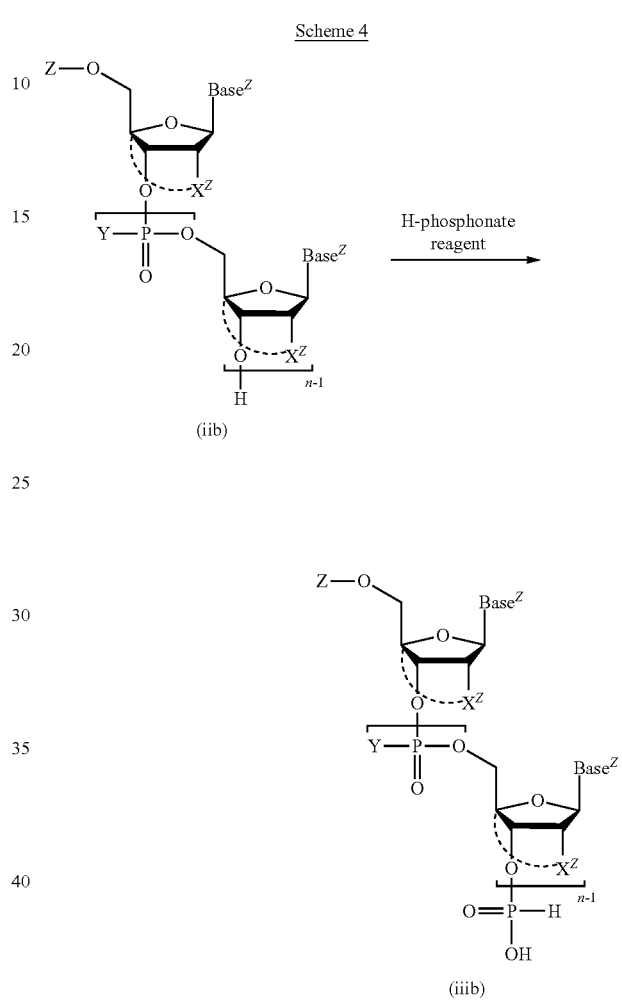

Specific examples of the solvents used in Step b include those solvents mentioned in Step a. In particular, dichloromethane, chloroform, 1,2-dichloroethane, benzene, toluene, xylene, mesitylene, hexane, pentane, heptane, nonane, cyclohexane, ethyl acetate, isopropyl acetate, tetrahydrofuran, tert-butyl methyl ether, cyclopentyl methyl ether, or a combination of these solvents is preferable. Pyridine or dichloromethane is more preferable, and pyridine is particularly preferable.

When Step b involves a solvent other than nitrogen-containing aromatic solvents such as pyridine, it is preferable to add a nucleophile such as pyridine. The nucleophile is not particularly limited as long as the H-phosphonation can be achieved satisfactorily. Specific examples include pyridine nucleophiles such as pyridine, 2,6-di-tert-butylpyridine, 2-picoline, 3-picoline, 4-picoline, 3,4-lutidine, 2,6-lutidine, 2,4-lutidine, 3,5-lutidine, 2,4,6-collidine, 4-acetylpyridine, N,N-dimethylaminopyridine, 2-cyanopyridine, 3-cyanopyridine, 4-cyanopyridine, 2-chloropyridine, 3-chloropyridine, 4-chloropyridine, 2-methoxypyridine, 3-methoxypyridine, 4-methoxypyridine, ethyl picolinate, ethyl nicotinate and ethyl isonicotinate; Pybox nucleophiles such as (S,S)-2,6-bis(4-isopropyl-2-oxazolin-2-yl)pyridine and (R,R)-2,6-bis(4-phenyl-2-oxazolin-2-yl) pyridine; quinoline nucleophiles such as quinoline, quinine, quinidine and cinchonine; nitrogen-containing aromatic nucleophiles such as N-methylimidazole, pyrimidine, 2-methylpyrazine, 3-methylpyridazine and 1,10-phenanthroline; N-oxide nucleophiles such as 4-methoxypyridine-N-oxide; aniline nucleophiles such as N,N-dimethylaniline; N-heterocyclic carbene nucleophiles such as 1,3-di-tert-butylimidazol-2-ylidene and 1,3-dimesitylimidazol-2-ylidene; phosphorus nucleophiles such as triphenylphosphine and trimethyl phosphite; and aliphatic amine nucleophiles such as triethylamine and 1,4-diazabicyclo[2.2.2]octane. In particular, preferable are pyridine, 2-picoline, 4-picoline, 3,4-lutidine, 2,6-lutidine, 2,4,6-collidine, N,N-dimethylaminopyridine, 3-methoxypyridine, 4-methoxypyridine, (S,S)-2,6-bis(4-isopropyl-2-oxazolin-2-yl)pyridine, (R,R)-2,6-bis(4-phenyl-2-oxazolin-2-yl)pyridine, quinoline, quinidine, N-methylimidazole, 3-methylpyridazine and 4-methoxypyridine-N-oxide. Pyridine is particularly preferable.

The amount of the nucleophile used in Step b is not particularly limited, but is, for example, 1 to 300 mol per 1 mol of the n-mer oligonucleotide (iia or iib), and is preferably 1 to 100 mol, and more preferably 1 to 40 mol.

The H-phosphonate reagent used in Step b is not particularly limited as long as the H-phosphonation can be achieved satisfactorily. Examples include phosphorous acid, diaryl phosphites (such as diphenyl phosphite), aryl-H-phosphonate ammonium salts (such as phenyl-H-phosphonate triethylammonium salt and p-toluyl-H-phosphonate triethylammonium salt) and phosphorus halides (such as 2-chloro-4H-1,3,2-benzodioxaphosphorin-4-on and phosphorus trichloride). In particular, phosphorous acid, diphenyl phosphite, phenyl-H-phosphonate triethylammonium salt, p-toluyl-H-phosphonate triethylammonium salt, 2-chloro-4H-1,3,2-benzodioxaphosphorin-4-one and phosphorus trichloride are preferable, and phosphorous acid and diphenyl phosphite are more preferable.

When phosphorous acid or an aryl-H-phosphonate ammonium salt is used as the H-phosphonate reagent, it is preferable to add a condensing agent. The condensing agent may be any of condensing agents that are usually used in the H-phosphonate method. Specific examples include 2,2-dimethylbutyryl chloride, isobutyryl chloride, pivaloyl chloride, acetyl chloride, 1-adamantyl chloride, diphenyl chlorophosphate, 2,4,6-triisopropylbenzenesulfonyl chloride, 2-(benzotriazol-1-yloxy)-1,3-dimethyl-2-pyrrolidin-1-yl-1, 3,2-diazaphospholidinium hexafluorophosphate [BUMP], N,N-bis(2-oxazolidinyl)phosphonic chloride [BopCl], benzoyl chloride, benzoic anhydride, and diaryl carbonates such as diphenyl carbonate, di-p-nitrophenyl carbonate and bispentafluorophenyl carbonate. In particular, 2,2-dimethylbutyryl chloride, isobutyryl chloride, 1-adamantyl chloride, diphenyl chlorophosphate, 2,4,6-triisopropylbenzenesulfonyl chloride and BopCl are preferable, and 2,2-dimethylbutyryl chloride is more preferable.

When a diaryl phosphite or an aryl-H-phosphonate ammonium salt is used as the H-phosphonate reagent, the conversion to the H-phosphonate group can be accomplished by performing treatment with water and a tertiary amine such as triethylamine after the completion of the reaction.

The amount of the H-phosphonate reagent used in Step b is preferably 1 to 100 mol per 1 mol of the n-mer oligonucleotide (iia or iib), and is more preferably 1 to 40 mol, and still more preferably 10 to 40 mol.

The amount of the condensing agent used in Step b is preferably 1 to 100 mol per 1 mol of the n-mer oligonucleotide (iia or iib), and is more preferably 1 to 40 mol, and still more preferably 10 to 30 mol.

The reaction temperature in Step b is not particularly limited as long as the reaction proceeds, but is preferably −10° C. to 60° C., and more preferably 20° C. to 50° C. The reaction time varies depending on conditions such as the type of the n-mer oligonucleotide used, the type of the solvent, the type of the nucleophile, the type of the H-phosphonate reagent, the type of the condensing agent and the reaction temperature, but is preferably 5 minutes to 24 hours, more preferably 10 minutes to 12 hours, and still more preferably 30 minutes to 6 hours.

Step b is followed by Step c. As required, Step c may be preceded by liquid separation treatment and distillation to replace the solvent by a solvent used in Step c, or may be preceded by Step e to isolate the n-mer oligonucleotide having the 5'-phosphonate group (iiia) or 3'-phosphonate group (iiib).

(Step c) (Coupling Step)

(Step c) in Method A or Method B is illustrated in Scheme 5 or 6, respectively.

In Method A, (Step c) is a step in which the n-mer oligonucleotide (iiia), having the 5'-H-phosphonated form converted from the hydroxyl group, that is obtained in (Step b) in Method A is condensed with a p-mer oligonucleotide (iva) having a 5'-hydroxyl group protected with a temporary protecting group R and having a 3'-hydroxyl group (in the formula, p is an integer of 1 or greater, and the compound is a nucleoside when p=1) (Scheme 5).

Scheme 5

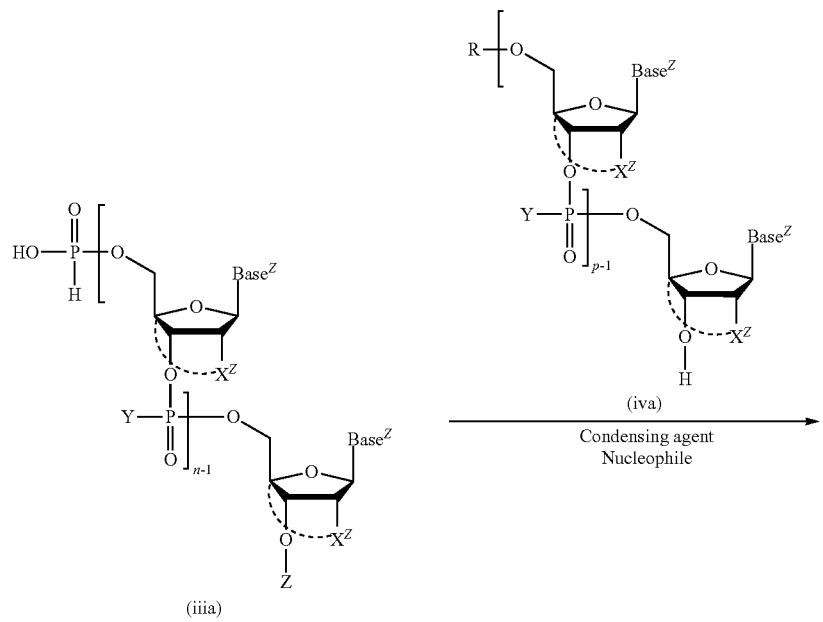

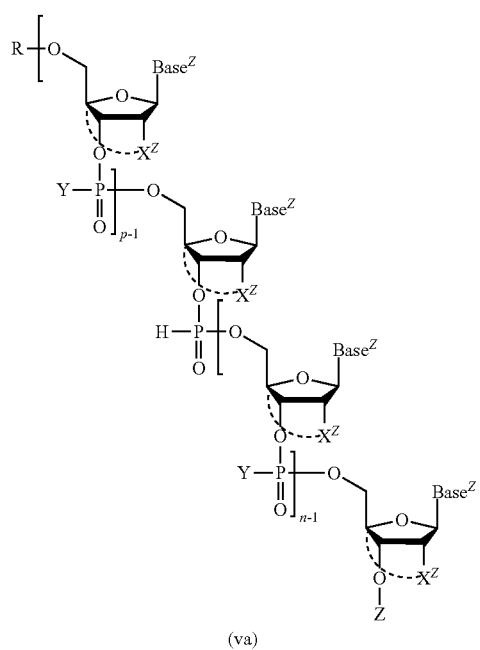

In the formula, p is an integer of 1 or greater, and the other symbols are the same as defined hereinabove. At least one of Base$^Z$ and X$^Z$ in the compound (iva) may include or may not include a pseudo solid phase-protecting group. The definition described hereinabove also applies when two or more nucleobase moieties are present, two or more pseudo solid phase-protecting groups are present, and two or more basic protecting groups are present.

In Method B, Step c is a step in which the n-mer oligonucleotide (iiib), having the 3'-H-phosphonated form converted from the hydroxyl group, that is obtained in Step b in Method B is condensed with a p-mer oligonucleotide (ivb) having a 3'-hydroxyl group protected with a temporary protecting group R and having a 5'-hydroxyl group (in the formula, p is an integer of 1 or greater, and the compound is a nucleoside when p=1) (Scheme 6). In Scheme 6, the symbols are the same as defined hereinabove. At least one of Base$^Z$ and X$^Z$ in the compound (ivb) may include or may not include a pseudo solid phase-protecting group.

Scheme 6

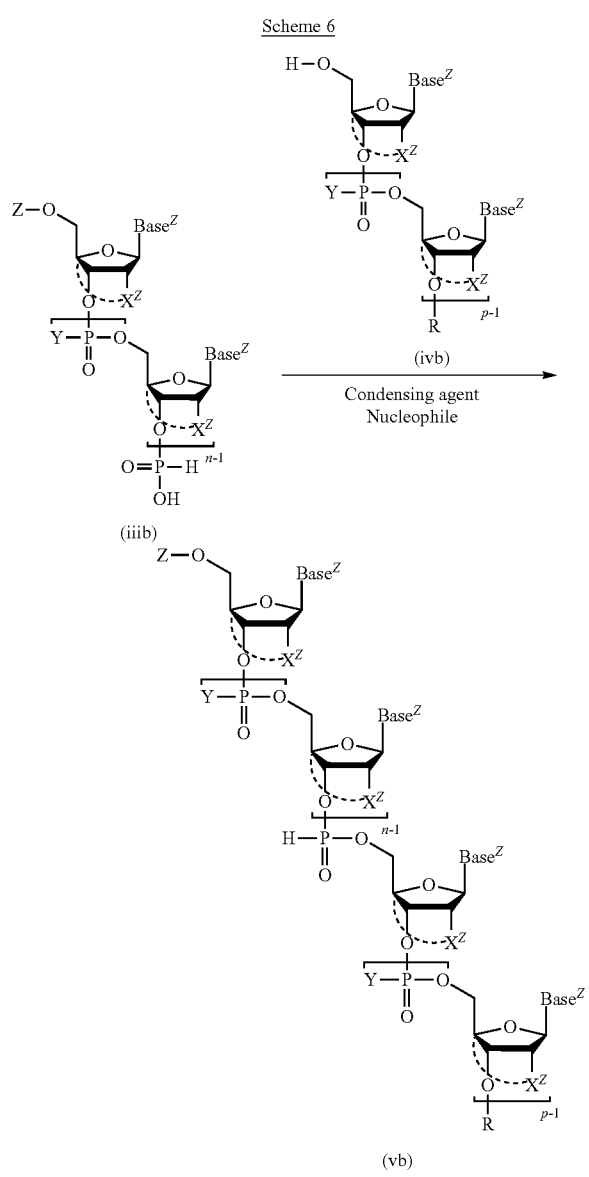

Specific examples of the solvents used in Step c include those solvents mentioned in Step a. In particular, among others, pyridine, dichloromethane, tetrahydrofuran and toluene are preferable, and pyridine is particularly preferable.

When Step c involves a solvent other than nitrogen-containing aromatic solvents such as pyridine, it is preferable to add a nucleophile such as pyridine. The nucleophile is not particularly limited as long as the coupling reaction takes place satisfactorily. Specific examples include those nucleophiles mentioned in Step b. Pyridine is particularly preferable.

The amount of the nucleophile used in Step c is, for example, 1 to 100 mol per 1 mol of the H-phosphonated n-mer oligonucleotide (iiia or iiib) obtained in Step b, and is preferably 1 to 20 mol, and more preferably 1 to 10 mol.

The amount of the p-mer oligonucleotide (iva or ivb) used in Step c is preferably 1 to 10 mol per 1 mol of the H-phosphonated n-mer oligonucleotide (iiia or iiib) obtained in Step b, and is more preferably 1 to 5 mol, still more preferably 1 to 3 mol, and particularly preferably 1 to 1.5 mol.

The condensing agent used in Step c is not particularly limited as long as the coupling reaction takes place satisfactorily. Specific examples include those condensing agents mentioned in Step b. In particular, among others, 2,2-dimethylbutyryl chloride, isobutyryl chloride, 1-adamantyl chloride, diphenyl chlorophosphate, 2,4,6-triisopropylbenzenesulfonyl chloride, bis(2-oxo-3-oxazolidinyl)phosphinic chloride and bispentafluorophenyl carbonate are preferable, and 2,2-dimethylbutyryl chloride or bispentafluorophenyl carbonate is particularly preferable.

The amount of the condensing agent used in Step c is, for example, 1 to 200 mol per 1 mol of the H-phosphonated n-mer oligonucleotide (iiia or iiib) obtained in Step b, and is preferably 1 to 100 mol, and more preferably 1 to 50 mol.

The reaction temperature in Step c is not particularly limited as long as the reaction proceeds, but is preferably −10° C. to 60° C., more preferably 0° C. to 50° C., and still more preferably 0° C. to 30° C. The reaction time varies depending on conditions such as the type of the n-mer oligonucleotide used, the type of the solvent, the type of the nucleophile, the type of the condensing agent and the reaction temperature, but is preferably 1 minute to 12 hours, more preferably 2 minutes to 6 hours, and still more preferably 5 minutes to 3 hours.

If the compound represented by the formula (iva or ivb) in Scheme 5 or 6, or a salt thereof, or the compound represented by the formula (iia or iib) in Scheme 3 or 4, or a salt thereof remains after the reaction in Step c, the solution obtained may be subjected to capping reaction as required. The capping reaction may be performed by a usual method using an acid anhydride such as acetic anhydride or benzoic anhydride, or using, in addition to the condensing agent, an alkyl-H-phosphonate ammonium salt such as methyl-H-phosphonate triethylammonium salt, ethyl-H-phosphonate triethylammonium salt, isopropyl-H-phosphonate triethylammonium salt or 2-cyanoethyl-H-phosphonate triethylammonium salt.

The capping reaction is a reaction in which the compound which has a residual hydroxyl group after the coupling reaction or oxidation reaction is substituted, in place of the hydroxyl group, with a substituent to which no more nucleoside or oligonucleotide can be added.

The capping reaction may be performed after Step d described later. It is preferable that the capping reaction be performed after Step c or Step d.

Step c is followed by Step d or Step a. As required, Step d or Step a may be preceded by liquid separation treatment and distillation to replace the solvent by a solvent used in Step d or Step a, or may be preceded by Step e to isolate the (n+p)-mer oligonucleotide (va or vb). The reaction solution from Step c may be directly used in the next Step d or Step a.

(Step d) (Conversion Step)

In this step, the (n+p)-mer oligonucleotide (va or vb) obtained in Step c, or the n-mer oligonucleotide obtained in Step a is reacted with a reagent that modifies the phosphorus atom to convert the phosphite diester bond in the (n+p)-mer oligonucleotide (va or vb) into a phosphodiester bond, a thiophosphodiester bond, an aminophosphodiester bond, a boranophosphodiester bond, a phosphodiester bond protected with a basic protecting group, or a thiophosphodiester bond protected with a basic protecting group.

Step d in Method A is illustrated in Scheme 7 below. (In Scheme 7, the symbols are the same as defined hereinabove with the proviso that R is a hydrogen atom when the scheme takes place after Step a.)

Scheme 7

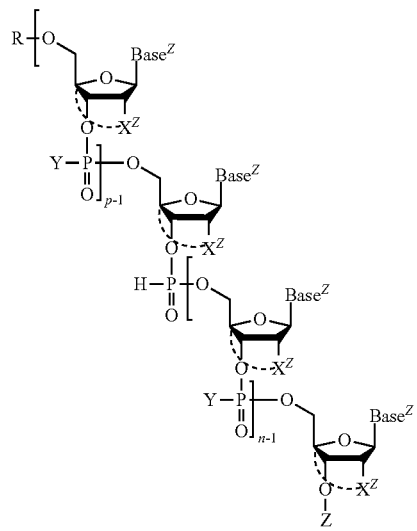

(va)

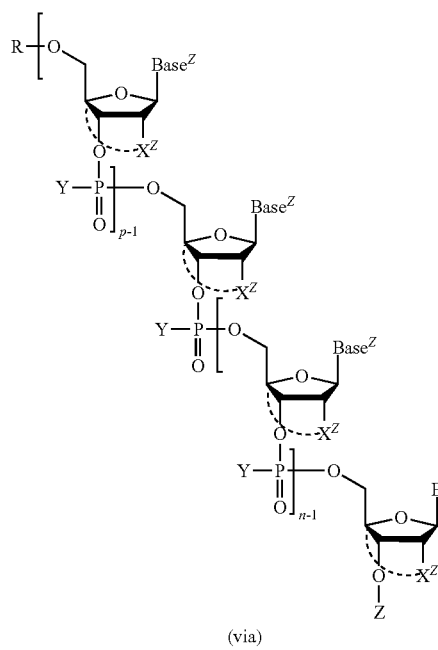

(via)

Step d in Method B is illustrated in Scheme 8 below. (In Scheme 8, the symbols are the same as defined hereinabove with the proviso that R is a hydrogen atom when the scheme takes place after Step a.)

Scheme 8

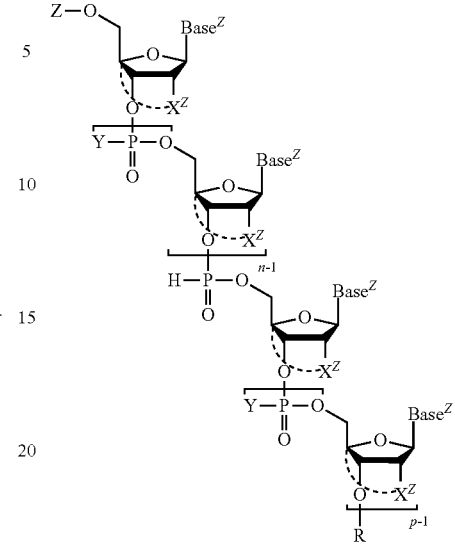

(vb)

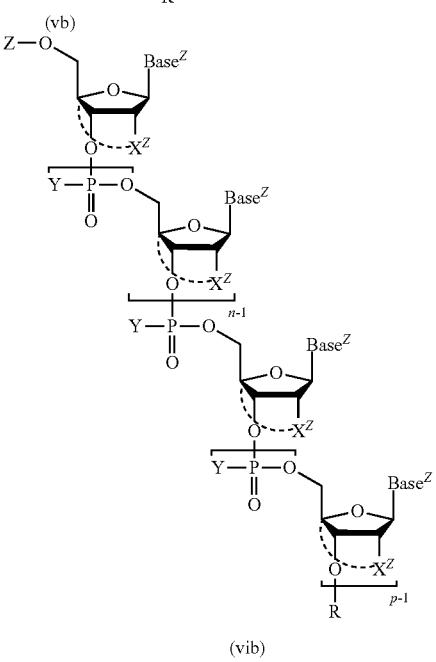

(vib)

Step d may be performed simply by adding directly a phosphorus-modifying reagent to the reaction mixture after Step c or Step a, without isolating the (n+p)-mer oligonucleotide (va or vb) obtained in Step c or the n-mer oligonucleotide (iia or iib) obtained in Step a. The phosphorus-modifying reagent is an oxidizing agent, a sulfurizing agent, an amidite-forming agent or a boronating agent. Preferably, with use of an oxidizing agent or a sulfurizing agent, the phosphite diester bond is converted into a phosphodiester bond, a thiophosphodiester bond, a phosphodiester bond protected with a basic protecting group, or a thiophosphodiester bond protected with a basic protecting group, and more preferably converted into a phosphodiester bond or a thiophosphodiester bond. Step d may be performed after the (n+p)-mer oligonucleotide (va or vb) obtained in Step c or the n-mer oligonucleotide (iia or iib) obtained in Step a is isolated.

Specific examples of the solvents used in Step d include those solvents mentioned in Step a. The solvent is selected appropriately in accordance with the oxidizing agent, the sulfurizing agent, the amidite-forming agent or the boronating agent that is used.

The "oxidizing agent" used in Step d is not particularly limited as long as the agent is capable of oxidizing the phosphite diester bond into a phosphodiester bond without oxidizing other moieties. Some preferred agents are iodine, (1S)-(+)-(10-camphanylsulfonyl)oxaziridine, tert-butyl hydroperoxide (TBHP), 2-butanone peroxide, 1,1-dihydroperoxycyclododecane, bis(trimethylsilyl)peroxide and m-chloroperbenzoic acid. For the reason that the oxidation reaction can be accomplished with good yield or reaction rate, iodine, tert-butyl hydroperoxide or 2-butanone peroxide is more preferable, and iodine is particularly preferable. The oxidizing agent may be diluted with an appropriate solvent so as to have a concentration of 0.05 to 2 M. The diluent solvent is not particularly limited as long as the solvent is inert in the reaction, with examples including pyridine, tetrahydrofuran [THF], dichloromethane, water and mixtures of these solvents. In particular, it is preferable to use, for example, iodine/water/pyridine mixed solvent or iodine/water/pyridine/THF mixed solvent.

When Step d involves the oxidizing agent, the reaction solvent in Step d is the same as described for the diluent solvent.

The "sulfurizing agent" used in Step d is not particularly limited as long as the agent is capable of converting the phosphite diester bond into a thiophosphodiester bond. Some preferred agents are elemental sulfur, 3-amino-1,2,4-dithiazole-5-thione (ADTT), 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD) and N-(benzoylthio)-succinimide. For the reason that the reaction can take place with good yield or reaction rate, elemental sulfur or ADTT is more preferable, and elemental sulfur is particularly preferable. The sulfurizing agent may be diluted with an appropriate solvent so as to have a concentration of 0.05 to 2 M. The diluent solvent is not particularly limited as long as the solvent is inert in the reaction, with examples including dichloromethane, acetonitrile, pyridine and mixtures of these solvents.

When Step d involves the sulfurizing agent, the reaction solvent in Step d is the same as described for the diluent solvent.

The reagent that converts the phosphite diester bond into a "phosphodiester bond protected with a basic protecting group" is not particularly limited as long as the reagent has such a conversion ability. Preferred reagents are corresponding alcohol compounds, and oxidizing agents such as carbon tetrachloride, iodine, carbon bromide trichloride, N-chlorosuccinimide, trichloroisocyanuric acid, sodium hypochlorite, 3,3-dichloro-5,5-dimethylhydantoin and N,N'-dichloro-bis(2,4,6-trichlorophenyl)urea. The solvent in the conversion reaction is not particularly limited as long as the solvent is inert in the reaction, with examples including dichloromethane, pyridine, and mixtures of these solvents. Dichloromethane or pyridine is preferable, and pyridine is more preferable.

The reagent that converts the phosphite diester bond into a "thiophosphodiester bond protected with a basic protecting group" is not particularly limited as long as the reagent has such a conversion ability. Examples include phthalimide sulfurizing agents, succinic acid-containing sulfurizing agents and morpholinedione sulfurizing agents. The solvent in the conversion reaction is not particularly limited as long as the solvent is inert in the reaction, with examples including dichloromethane, pyridine, and mixtures of these solvents. Dichloromethane or pyridine is preferable, and pyridine is more preferable.

Examples of the phthalimide sulfurizing agents include N—(C1-40 alkylthio)phthalimides, N—(C3-6 cycloalkylthio)phthalimides, N—(C6-10 arylthio)phthalimides, N-(5-10 membered heteroarylthio)phthalimides, N-(aralkylthio) phthalimides and N-(heteroarylthio)phthalimides that correspond to the target "thiophosphodiester bonds protected with a basic protecting group". When the target "thiophosphodiester bond protected with a basic protecting group" includes a substituent such as a halogen atom, a cyano group or a C1-6 alkyl group, use may be made of a sulfurizing agent having such a substituent at a corresponding position in the above N—(C1-40 alkylthio)phthalimide, N—(C3-6 cycloalkylthio)phthalimide, N—(C6-10 arylthio)phthalimide, N-(5-10 membered heteroarylthio)phthalimide, N-(aralkylthio)phthalimide or N-(heteroarylthio)phthalimide. Specific examples of the phthalimide sulfurizing agents include N-[(2-cyanoethyl)thio]phthalimide, N-(methylthio)phthalimide, N-(ethylthio)phthalimide, N-(propylthio)phthalimide, N-(isopropylthio)phthalimide, N-(butylthio)phthalimide, N-(tert-butylthio)phthalimide, N-(cyclohexylthio) phthalimide, N-(dodecylthio)phthalimide, N-(benzylthio) phthalimide, N-(phenylthio)phthalimide, N-{(p-chlorophenyl)thio}phthalimide, N-{(p-methylphenyl)thio] phthalimide and N-[(2-benzothiazolyl)thio]phthalimide.

Examples of the succinic acid sulfurizing agents include N—(C1-40 alkylthio)succinimides, N—(C3-6 cycloalkylthio)succinimides, N—(C6-10 arylthio)succinimides, N-(5-10 membered heteroarylthio)succinimides, N-(aralkylthio)succinimides and N-(heteroarylthio)succinimides that correspond to the target "thiophosphodiester bonds protected with a basic protecting group". When the target "thiophosphodiester bond protected with a basic protecting group" includes a substituent such as a halogen atom, a cyano group or a C1-6 alkyl group, use may be made of a sulfurizing agent having such a substituent at a corresponding position in the above N—(C1-40 alkylthio)succinimide, N—(C3-6 cycloalkylthio)succinimide, N—(C6-10 arylthio)succinimide, N-(5-10 membered heteroarylthio)succinimide, N-(aralkylthio)succinimide or N-(heteroarylthio)succinimide. Specific examples of the succinimide-containing sulfurizing agents include N-[(2-cyanoethyl)thio]succinimide, N-(methylthio)succinimide, N-(ethylthio)succinimide, N-(propylthio)succinimide, N-(isopropylthio)succinimide, N-(butylthio)succinimide, N-(tert-butylthio)succinimide, N-(cyclohexylthio) succinimide, N-(dodecylthio)succinimide, N-(benzylthio) succinimide, N-(phenylthio)succinimide, N-{(p-chlorophenyl)thio}succinimide, N-{(p-methylphenyl)thio] succinimide and N-[(2-benzothiazolyl)thio]succinimide.

Examples of the morpholinedione sulfurizing agents include N—(C1-40 alkylthio)morpholine-3,5-diones, N—(C3-6 cycloalkylthio)morpholine-3,5-diones, N—(C6-10 arylthio)morpholine-3,5-diones, N-(5-10 membered heteroarylthio)morpholine-3,5-diones, N-(aralkylthio)morpholine-3,5-diones and N-(heteroarylthio)morpholine-3,5-diones that correspond to the target "thiophosphodiester bonds protected with a basic protecting group". When the target "thiophosphodiester bond protected with a basic protecting group" includes a substituent such as a halogen atom, a cyano group or a C1-6 alkyl group, use may be made of a sulfurizing agent having such a substituent at a corresponding position in the above N—(C1-40 alkylthio)morpholine-3,5-dione, N—(C3-6 cycloalkylthio)morpholine-3,5-dione, N—(C6-10 arylthio)morpholine-3,5-dione, N-(5-10 membered heteroarylthio)morpholine-3,5-dione, N-(aralkylthio)morpholine-3,5-dione or N-(heteroarylthio)morpholine-3,5-dione. Specific examples of the morpholinedione sulfurizing agents include N-[(2-cyanoethyl)thio]morpholine-3,5-dione, N-(methylthio)morpholine-3,5-dione, N-(ethylthio)morpholine-3,5-dione, N-(propylthio)morpholine-3,5-dione, N-(isopropylthio)morpholine-3,5-dione, N-(butylthio)morpholine-3,5-dione, N-(tert-butylthio)morpholine-3,5-dione, N-(cyclohexylthio)morpholine-3,5-dione, N-(dodecylthio)morpholine-3,5-dione, N-(benzylthio)morpholine-3,5-dione, N-(phenylthio)morpholine-3,5-dione, N-{(p-chlorophenyl)thio}morpholine-3,5-dione, N-{(p-methylphenyl)thio]morpholine-3,5-dione and N-[(2-benzothiazolyl)thio]morpholine-3,5-dione.

The "amidite-forming agent" used in Step d is not particularly limited as long as the agent is capable of converting the phosphite diester bond into an aminophosphodiester bond. Preferred agents are corresponding amine compounds, and oxidizing agents such as carbon tetrachloride, iodine, carbon bromide trichloride, N-chlorosuccinimide, trichloroisocyanuric acid, sodium hypochlorite, 3,3-dichloro-5,5-dimethylhydantoin and N,N'-dichlorobis(2,4,6-trichlorophenyl)urea. The solvent in the conversion reaction is not particularly limited as long as the solvent is inert in the reaction, with examples including dichloromethane, pyridine, and mixtures of these solvents. Dichloromethane or pyridine is preferable, and pyridine is more preferable.

The "boronating agent" used in Step d is not particularly limited as long as the agent is capable of converting the phosphite diester bond into a boranophosphodiester bond. Some preferred agents are boron hydride ($BH_3$), $BH_3$-THF complex, $BH_3$-dimethyl sulfide complex and $BH_3$-pyridine complex. The solvent in the conversion reaction is not particularly limited as long as the solvent is inert in the reaction, with examples including dichloromethane, pyridine, and mixtures of these solvents. Dichloromethane or pyridine is preferable, and pyridine is more preferable.

The amount of the phosphorus-modifying reagent is preferably 1 to 50 mol per 1 mol of the (n+p)-mer oligonucleotide (va or vb) obtained in Step c or the n-mer oligonucleotide (iia or iib) obtained in Step a, and is more preferably 1 to 15 mol, still more preferably 1 to 10 mol, and even more preferably 1 to 7 mol.

The reaction temperature is not particularly limited as long as the reaction proceeds, but is preferably −10° C. to 60° C., and more preferably 20° C. to 50° C. The reaction time varies depending on conditions such as the type of the (n+p)-mer oligonucleotide (va or vb) obtained in Step c or the n-mer oligonucleotide (iia or iib) obtained in Step a, the type of the phosphorus-modifying reagent used, and the reaction temperature, but is preferably 1 minute to 24 hours, more preferably 10 minutes to 12 hours, and still more preferably 30 minutes to 6 hours.

When the oxidizing agent or the sulfurizing agent is used, there is a risk that the oxidizing agent or the sulfurizing agent may induce undesired side reactions after the completion of the reaction or during and after the next step. To suppress such side reactions, quenching treatment may be performed using a reducing agent after the completion of the reaction. Specific examples of the reducing agents include trivalent phosphorus reagents (for example, trialkyl phosphites such as trimethyl phosphite, triethyl phosphite and tris(2-carboxyethyl)phosphine, and dialkyl phosphites such as dimethyl phosphite and diethyl phosphate), and sodium thiosulfate. The quenching treatment may be omitted.

When Step d is performed after Step c, the solution obtained may be subjected to capping reaction as required if the compound represented by the formula (iva or ivb) in Scheme 5 or 6, or a salt thereof, or the compound represented by the formula (iia or iib) in Scheme 3 or 4, or a salt thereof remains after the reaction in Step d. The capping reaction may be performed by a usual method using an acid anhydride such as acetic anhydride or benzoic anhydride, or using, in addition to the condensing agent described hereinabove, an alkyl-H-phosphonate ammonium salt such as methyl-H-phosphonate triethylammonium salt, ethyl-H-phosphonate triethylammonium salt, isopropyl-H-phosphonate triethylammonium salt or 2-cyanoethyl-H-phosphonate triethylammonium salt.

The capping reaction may be performed after Step c described hereinabove.

In the case where Step d is performed after Step a, the capping reaction is not performed after Step d.

(Step e) (Precipitation and Solid Liquid Separation Step)

Step e is a step in which a polar solvent is added to the reaction solution obtained in any of Step a to Step d to precipitate the oligonucleotide, which is then collected by solid liquid separation.

Examples of the polar solvents in Step e include alcohol solvents such as methanol, ethanol, isopropanol and n-butanol; nitrile solvents such as acetonitrile and propionitrile; ketone solvents such as acetone and 2-butanone; amide solvents such as dimethylformamide, dimethylacetamide and N-methylpiperidone; sulfoxide solvents such as dimethyl sulfoxide; water; and mixtures of two or more kinds of these solvents. The polar solvent in Step e is preferably an alcohol solvent or a nitrile solvent, more preferably an alcohol solvent with 1 to 6 carbon atoms or a nitrile solvent with 1 to 6 carbon atoms, and particularly preferably methanol or acetonitrile.

When Step e is performed using the reaction solution from Step d, Step e may be conducted concurrently with the quenching treatment for the phosphorus-modifying reagent by using the reducing agent described hereinabove in the form of a solution in methanol or acetonitrile that is the precipitating solvent.

According to the oligonucleotide production method of the present invention, the target oligonucleotide can be obtained with high purity and high yield by repeating Step a to Step e as many times as desired.

(Step f) (Deprotection and Oligonucleotide Isolation Step)

In the oligonucleotide production method, deprotection may be performed after Step e in accordance with the types and properties of the basic protecting group, the temporary protecting group and the pseudo solid phase-protecting group, and the resultant oligonucleotide may be isolated. For example, the deprotection step may be performed by a deprotection method described in literature such as PROTECTIVE GROUPS IN ORGANIC SYNTHESIS, Third Edition, JOHN WILLY & SONS (1999), so as to remove all the protecting groups in the oligonucleotide. Specifically, the pseudo solid phase-protecting groups, the basic protecting groups such as benzoyl groups, isobutyryl groups, phenoxyacetyl groups, acetyl groups and levulinyl groups, and the basic protecting groups on the phosphodiester bonds or thiophosphodiester bonds such as 2-cyanoethyl groups may be all removed by treatment with ammonia water, ammonia water/ethanol solution, or a mixture of ammonia water and an aqueous methylamine solution. Further, the temporary protecting groups for the 5'- or 3'-hydroxyl groups may be removed by treatment with the fluorine reagent, the acid or the base used in Step a, or an appropriately diluted solution thereof. In accordance with the deprotection method described in Journal of the Chemical Society, Perkin Transactions 1, 2002, pp. 2619-2633, a method may be adopted in which treatment is performed using DBU [1,8-diazabicyclo [5.4.0]-7-undecene] and trimethylsilyl chloride to remove the protecting groups on the phosphodiester bonds or the thiophosphodiester bonds such as cyanoethyl groups, and thereafter the pseudo solid phase-protecting groups, and the basic protecting groups such as benzoyl groups, isobutyryl groups, phenoxyacetyl groups, acetyl groups and levulinyl groups are removed with ammonia water. Further, a method may be adopted in which the basic protecting groups such as benzoyl groups, isobutyryl groups, phenoxyacetyl groups, acetyl groups and levulinyl groups are removed with an inorganic base (such as potassium carbonate).

By, for example, the method described in Journal of the Chemical Society, Perkin Transactions 1, 1999, pp. 1477-1486 (in which treatment is performed using an oxime compound such as (E)-2-nitrobenzaldoxime or pyridine-2-aldoxime, and a base such as 1,1,3,3-tetramethylguanidine or DBU), the phosphodiester bonds protected with a basic protecting group may be deprotected into phosphodiester bonds. The thiophosphodiester bonds protected with a basic protecting group removable by β detachment, such as 2-cyanoethyl group, may be converted into thiophosphodiester bonds by deprotection under the aforementioned basic conditions. The thiophosphodiester bonds protected with other types of basic protecting groups may be converted into phosphodiester bonds by deprotection in accordance with, for example, the method described in Journal of the Chemical Society, Perkin Transactions 1, 1999, pp. 1477-1486 (in which treatment is performed using the oxime compound and the base).

Oligonucleotides having no protecting groups are prone to being decomposed by enzymes. It is therefore preferable that the oligonucleotide be isolated while controlling the air cleanliness.

In Step a to Step d and in Step f, the degree of the reaction may be determined by a method that is similar to the determination in general liquid-phase organic synthesis reactions. That is, the reaction may be tracked using a technique such as thin-layer silica gel chromatography or high-performance liquid chromatography.

The oligonucleotide obtained from Step e or Step f may be subjected to further organic synthesis reaction to form a desired oligonucleotide derivative. An oligonucleotide may be produced by Method A or Method B using an oligonucleotide produced by Method A and an oligonucleotide produced by Method B.

For example, an n-mer oligonucleotide (iiia), having an H-phosphonated form converted from the 5'-hydroxyl group, that is obtained by Step b in Method A may be condensed with an n-mer oligonucleotide (iib) that is obtained by Step a in Method B, under the same conditions as in Step c to form a phosphite diester bond. This step is illustrated in Scheme 9. In the scheme, the symbols are the same as defined hereinabove, the letter n in the formula (iiia) and the letter n in the formula (iib) may be the same as or different from each other, and Z in the formula (iiia) and Z in the formula (iib) may be the same as or different from each other.

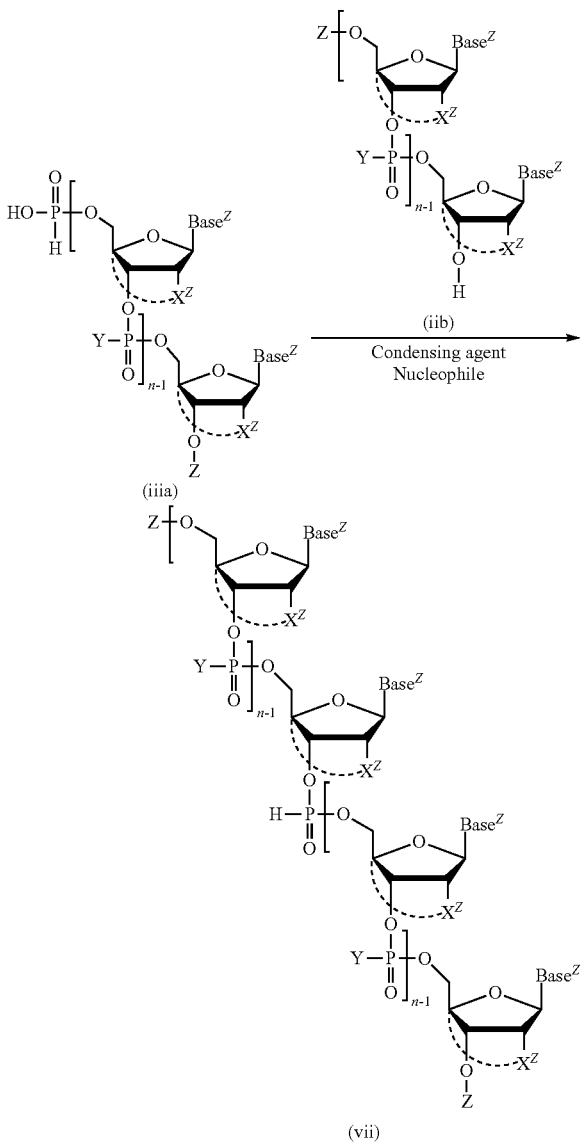

Scheme 9

Further, an n-mer oligonucleotide (iiib), having an H-phosphonated form converted from the 3'-hydroxyl group, that is obtained by Step b in Method B may be condensed with an n-mer oligonucleotide (iia) that is obtained by Step a in Method A, under the same conditions as in Step c to form a phosphite diester bond. This step is illustrated in Scheme 10. In the scheme, the symbols are the same as defined hereinabove, the letter n in the formula (iiib) and the letter n in the formula (iia) may be the same as or different from each other, and Z in the formula (iiib) and Z in the formula (iia) may be the same as or different from each other.

Scheme 10

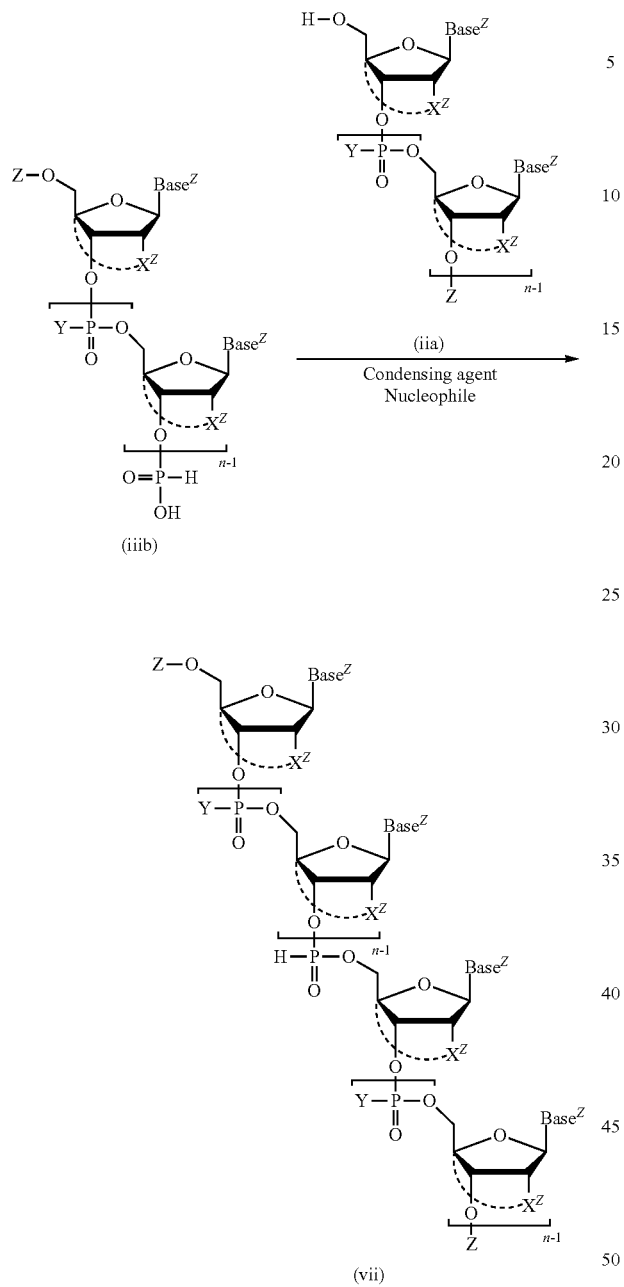

Scheme 11

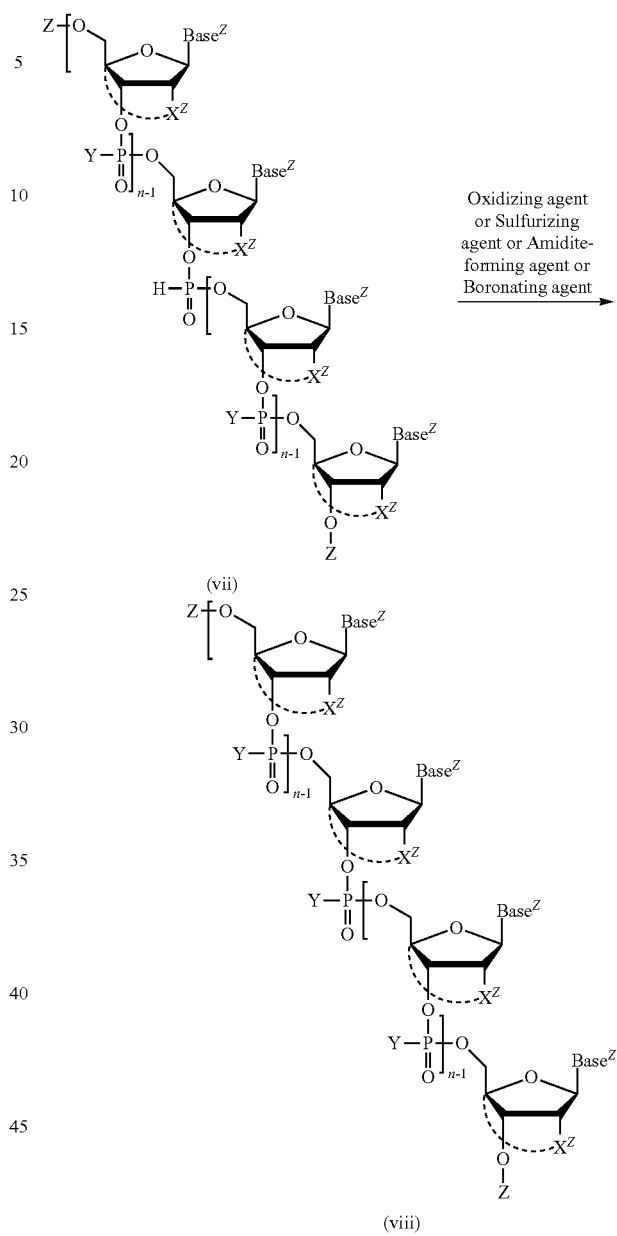

Under the same conditions as in Step d, the phosphite diester bond in the condensed oligonucleotide (vii) may be converted into a phosphodiester bond, a thiophosphodiester bond, an aminophosphodiester bond, a boranophosphodiester bond, a phosphodiester bond protected with a basic protecting group, or a thiophosphodiester bond protected with a basic protecting group. This step is illustrated in Scheme 11. In the scheme, the symbols are the same as defined hereinabove, the two letters n in the formula (vii) may be the same as or different from each other, and the two letters Z in the formula (vii) may be the same as or different from each other. The same applies to the formula (viii).

The reaction mixture obtained by the step in which the compounds are condensed via a phosphite diester bond may be subjected to a separation step in which the condensed nucleoside or oligonucleotide (vii) having a pseudo solid phase-protecting group is precipitated in the same manner as in Step e and is collected by solid liquid separation. Further, the reaction mixture obtained by the step of converting the phosphite diester bond may be subjected to a separation step in which the nucleoside or oligonucleotide (viii) having a pseudo solid phase-protecting group and a bond converted from the phosphite diester bond is precipitated in the same manner as in Step e and is collected by solid liquid separation.

After the above separation step, deprotection may be performed and the oligonucleotide may be isolated in the same manner as in Step f in accordance with the types and properties of the basic protecting group, the temporary protecting group and the pseudo solid phase-protecting group.

When the phosphite diester-bonded condensate (vii) or the condensate (viii) with a bond converted from the phosphite diester bond has a basic protecting group in at least one of the two groups Z and the basic protecting group is also usable as a temporary protecting group, Step a in Method A or Method B may be performed while using the phosphite diester-bonded condensate (vii) or the converted condensate (viii) as the compound represented by the formula (ia or ib) in Scheme 1 or 2

The oligonucleotides produced may be used in various applications such as various human or animal pharmaceuticals (such as RNA, DNA and oligonucleotide pharmaceuticals), functional foods, specified health foods, foods, chemicals, biological polymer materials and industrial polymer materials.

The starting materials in the oligonucleotide production method may be manufactured by generally known functional group transformation methods such as established oxidation, reduction, hydrolysis, esterification and amide condensation (see, for example, literature such as Comprehensive Organic Transformations, Second Edition, R. C. Larock, Wiley-VCH, (1999)).

For example, a nucleoside in which a nucleobase is linked to a ribose that has —CSNR$^{14}$— (R$^{14}$ is a hydrogen atom or a C1-6 alkyl group) bridging the 2'-position and the 4'-position may be synthesized from ingredients which include a nucleoside having a structure bridged by the corresponding —CONR$^{13}$— (R$^{13}$ is a hydrogen atom or a C1-6 alkyl group) using a thiocarbonylating reagent (for example, Lawesson's reagent) while performing protection reaction and deprotection reaction as required.

Nucleosides or oligonucleotides having a pseudo solid phase-protecting group may be produced by the methods described below. The production methods described below are some examples of the general production methods and do not intend to limit the methods by which nucleosides or the like having a pseudo solid phase-protecting group according to the present embodiment are produced.

A nucleoside or oligonucleotide having a pseudo solid phase-protecting group of the formula (I) in which m is 0 may be obtained by, for example, the reaction of a carboxylic acid represented by the formula (X-1) below or a carboxylic halide represented by the formula (X-2) below with a hydroxyl group or a nucleobase of a nucleoside or oligonucleotide.

When the carboxylic acid is used for the introduction of the pseudo solid phase-protecting group, the pseudo solid phase-protecting group may be introduced into the nucleoside or oligonucleotide in a solvent using a condensing agent such as dicyclohexylcarbodiimide, 1-ethyl-3-(3-dimethylaminopropyl)carbodiimide hydrochloride salt, N,N,N',N'-tetramethyl-O-(benzotriazol-1-yl)uronium hexafluorophosphate or carbonyldiimidazole. Where necessary, an additive such as 1-hydroxybenzotriazole may be used in combination with the condensing agent. When the carboxylic halide is used, the reaction may be performed in a solvent using a base such as triethylamine or diisopropylethylamine. Examples of the solvents include halogenated solvents such as chloroform, dichloromethane and 1,2-dichloroethane; aromatic solvents such as benzene, toluene, xylene and mesitylene; ester solvents such as ethyl acetate and isopropyl acetate; aliphatic solvents such as hexane, pentane, heptane, octane, nonane and cyclohexane; ether solvents such as tetrahydrofuran, diethyl ether, cyclopentyl methyl ether and tert-butyl methyl ether; and amide solvents such as N,N-dimethylformamide, N,N-dimethylacetamide and N-methylpyrrolidone.

The carboxylic acid or the carboxylic halide may be produced by generally known functional group transformation methods such as established oxidation, reduction and hydrolysis (see, for example, literature such as Comprehensive Organic Transformations, Second Edition, R. C. Larock, Wiley-VCH, (1999)).

Any of the L$^1$-L$^2$ bond, the L$^2$-L$^3$ bond and the L$^3$-L$^4$ bond may be formed by a method such as the aforementioned condensation or functional group transformation so as to introduce the pseudo solid phase-protecting group stepwise. When L$^2$ is —COO—, —CON(R$^2$)—, OCO— or —N(R$^2$)CO—, the ester bond or amide bond contained in L$^2$ may be formed by a method such as the aforementioned condensation or functional group transformation so as to introduce the pseudo solid phase-protecting group stepwise. The same applies to when L$^4$ is —COO—, —CON(R$^2$)—, OCO— or —N(R$^2$)CO—. Here, R$^2$ is the same as defined hereinabove.

For example, a nucleoside or oligonucleotide having a pseudo solid phase-protecting group of the formula (I) in which m is 0 and L$^2$ is —COO— or —CON(R$^2$)— may be produced by reacting a nucleoside or oligonucleotide with a dicarboxylic anhydride represented by the formula (X-4) (such as succinic anhydride) to form a nucleoside or oligonucleotide having a carboxyl-containing group represented by the formula (X-5) below, and thereafter condensing the nucleoside or oligonucleotide having a carboxyl-containing group represented by the formula (X-5) with an alcohol compound represented by the formula (X-6) below or an amine compound represented by the formula (X-7) below.

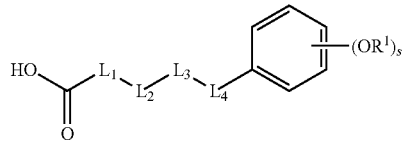
(X-1)

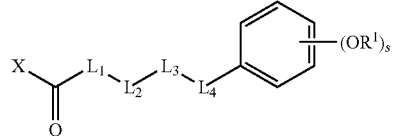
(X-2)

In the formulae, X is a halogen atom, and the other symbols are the same as defined hereinabove.

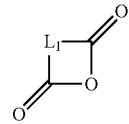
(X-4)

In the formula, L$^1$ is the same as defined hereinabove.

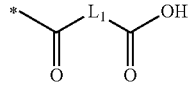
(X-5)

In the formula, the symbols are the same as defined hereinabove.

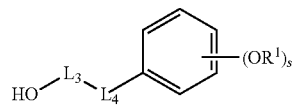  (X-6)

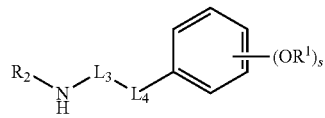  (X-7)

In the formulae, the symbols are the same as defined hereinabove.

The nucleoside or oligonucleotide having a carboxyl-containing group represented by the formula (X-5) may be usually condensed with the alcohol compound represented by the formula (X-6) or the amine compound represented by the formula (X-7) in a solvent using a condensing agent such as dicyclohexylcarbodiimide, 1-ethyl-3-(3-dimethylaminopropyl)carbodiimide hydrochloride salt, N,N,N',N'-tetramethyl-O-(benzotriazol-1-yl)uronium hexafluorophosphate or carbonyldiimidazole. Where necessary, an additive such as 1-hydroxybenzotriazole may be used in combination with the condensing agent. The solvent is the same as described for the reaction between the compound of the formula (X-1) or the formula (X-2) and the nucleoside or oligonucleotide.

For example, a nucleoside or oligonucleotide having a pseudo solid phase-protecting group of the formula (I) in which m is 0 and $L^4$ is —OCO— or —N(R$^2$)CO— may be produced by condensing a carboxylic acid represented by the formula (X-8) or (X-10) below or a carboxylic halide represented by the formula (X-9) or (X-11) below with a hydroxyl group or a nucleobase of a nucleoside or oligonucleotide under the same conditions as the aforementioned condensation reaction optionally followed by deprotection reaction to form an alcohol compound represented by the formula (X-12) below or an amino compound represented by the formula (X-13) below, and condensing the alcohol compound represented by the formula (X-12) or the amino compound represented by the formula (X-13) with a carboxyl compound represented by the formula (X-14) or an arylcarboxylic halide represented by the formula (X-15) under the same conditions as the aforementioned condensation reaction.

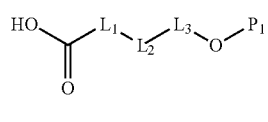  (X-8)

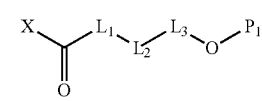  (X-9)

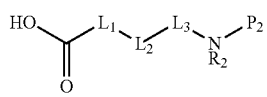  (X-10)

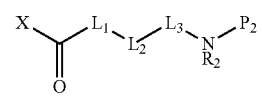  (X-11)

In the formulae, $P^1$ is a hydroxyl-protecting group, $P^2$ is an amino-protecting group, X is a halogen atom, and the other symbols are the same as defined hereinabove. $P^1$ may be selected from temporary protecting groups or basic protecting groups that protect the hydroxyl group. $P^2$ may be selected from basic protecting groups that protect the amino group.

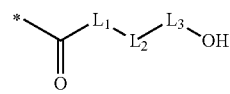  (X-12)

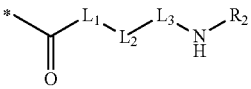  (X-13)

In the formulae, the symbols are the same as defined hereinabove.

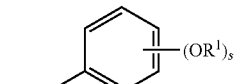  (X-14)

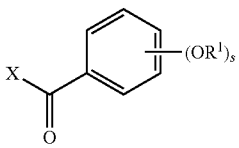  (X-15)

In the formulae, the symbols are the same as defined hereinabove, and X is a halogen atom.

For the conditions in the deprotection reaction, reference may be made to literature such as PROTECTIVE GROUPS IN ORGANIC SYNTHESIS, Third Edition, JOHN WILLY & SONS, (1999).

For example, a nucleoside or oligonucleotide having a pseudo solid phase-protecting group of the formula (I) in which m is 1 may be obtained by reacting an alkyl halide represented by the formula (X-3) below with a hydroxyl group or a nucleobase of a nucleoside or oligonucleotide in a solvent.

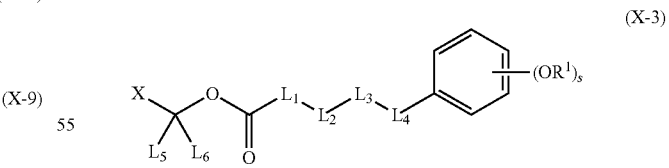  (X-3)

In the formula, X is a halogen atom, and the other symbols are the same as defined hereinabove.

A base (such as potassium carbonate or triethylamine) is used in the reaction of the alkyl halide represented by the formula (X-3) with the nucleoside or oligonucleotide. Examples of the solvents include the halogenated solvents, aromatic solvents, ester solvents, aliphatic solvents, ether solvents and amide solvents described hereinabove. In particular, an amide solvent is used.

The alkyl halide represented by the formula (X-3) may be produced by reacting a carboxylic acid represented by the aforementioned formula (X-1) with chloromethanesulfonyl chloride in a solvent (the method described in WO 2014/144285), or by reacting a carboxylic acid represented by the aforementioned formula (X-1) with paraformaldehyde and zinc chloride in a solvent (the method described in Journal of Medicinal Chemistry, 2009, Vol. 52, pp. 771-778).

Any of the $L^1$-$L^2$ bond, the $L^2$-$L^3$ bond and the $L^3$-$L^4$ bond may be formed by a method such as the aforementioned condensation or functional group transformation so as to introduce the pseudo solid phase-protecting group stepwise. When $L^2$ is —COO—, —CON($R^2$)—, OCO— or —N($R^2$)CO—, the ester bond or amide bond contained in $L^2$ may be formed by a method such as the aforementioned condensation or functional group transformation so as to introduce the pseudo solid phase-protecting group stepwise. The same applies to when $L^4$ is —COO—, —CON($R^2$)—, OCO— or —N($R^2$)CO—. Here, $R^2$ is the same as defined hereinabove.

EXAMPLES

Hereinbelow, the present invention will be described in detail based on Examples. However, it should be construed that the scope of the invention is in no way limited to such Examples. In Examples, NMR indicates nuclear magnetic resonance spectroscopy, and MS mass spectrometry.

$^1$H-NMR data are chemical shifts δ (unit: ppm) (splitting patterns, integrals) of signals measured at 300 MHz (JNM-ECP300 manufactured by JEOL Ltd., or JNM-ECX300 manufactured by JEOL Ltd.) with reference to tetramethylsilane as the internal standard. The letter "s" indicates singlet, "d" doublet, "t" triplet, "q" quartet, "quint" quintet, "dd" doublet of doublet, "m" multiplet, "brs" broad singlet, "CDCl$_3$" deuterated chloroform, and "C$_5$D$_5$N" deuterated pyridine.

$^{31}$P-NMR data are chemical shifts δ (unit: ppm) of signals measured with JNM-ECX300 manufactured by JEOL Ltd.

Unless otherwise mentioned, MS was performed by an ESI (electrospray ionization) method under Conditions 1 described below. "ESI$^+$" means ESI positive ion mode, and "ESI$^-$" ESI negative ion mode.

Conditions 1:
  Apparatus: AB SCIEX TripleTOF 5600
  Column: Kinetex PFP (2.6 μm 2.1×75 mm)
  Column temperature: 40° C.
  Eluent composition:
  Organic phase: tetrahydrofuran/acetonitrile=1/1 (by volume)
  Aqueous phase: 10 mM aqueous ammonium formate solution The measurement was started using an organic phase to aqueous phase mixing ratio of 50/50, which was thereafter changed linearly to 90/10 in 10 minutes. For the following 5 minutes, the organic phase to aqueous phase mixing ratio was fixed at 90/10.
  Flow rate: 0.50 mL/min
  Detection wavelength: 260 nm Unless otherwise mentioned, purification by silica gel column chromatography was performed using Hi-Flash Column manufactured by YAMAZEN CORPORATION.

Reference Example (Evaluation of Stability of Nucleic Acid Monomers Having 4,4'-dimethoxytrityl Group on 5'-hydroxyl Group)

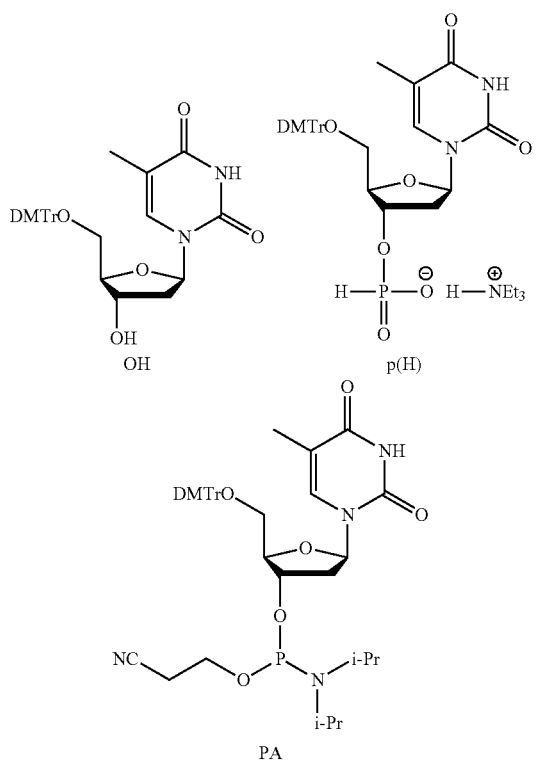

As nucleic acid monomers for use in oligonucleotide synthesis were selected 5'-O-(4,4'-dimethoxytrityl)thymidine [OH], 5'-O-(4,4'-dimethoxytrityl)-3'-O-hydroxyphosphynylthymidine triethylamine salt [p(H)], and 5'-O-(4,4'-dimethoxytrityl)-3'-O-cyanoethoxy(diisopropylamino) phosphinothymidine [PA]. These monomers in the form of solid were stirred at 100° C. and, after the lapse of a predetermined time, were analyzed by HPLC. The results are given in FIG. 1.

From FIG. 1, it has been shown that the nucleoside is more stable than the H-phosphonate compound and the amidite compound.

Reference Synthetic Example 1 (Synthesis of Nucleoside Having tert-butyldimethylsilyl Group on 5'-hydroxyl Group): Synthesis of Compound 1

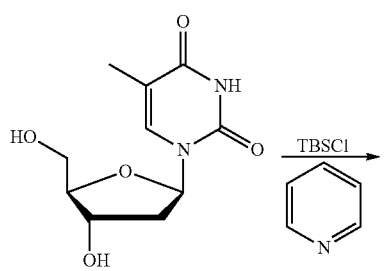

-continued

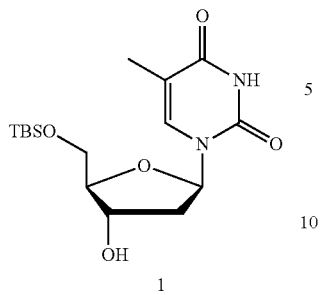

In a nitrogen atmosphere, tert-butyldimethylsilyl chloride (16.62 g, 110 mmol) was added to a pyridine (60 mL) suspension of thymidine (24.20 g, 100 mmol) at 0° C., and the mixture was stirred for 22 hours and 29 minutes. The solvent was distilled away under vacuum. Methylene chloride and water were added, and the liquids were separated. Methylene chloride was added to the aqueous phase, and the liquids were separated. The organic phases obtained were combined, and washed with a 5% aqueous sodium hydrogen carbonate solution and with water. The solvent was distilled away under vacuum. Toluene was added, and the resultant solid was recovered by filtration. Consequently, Compound 1 (29.77 g, yield 84%) was obtained as a white solid.

$^{1}$H-NMR: (300 MHz; CDCl$_{3}$) δ0.11 (s, 3H), 0.12 (s, 3H), 0.92 (s, 9H), 1.92 (d, 3H), 2.02-2.16 (m, 2H), 2.32-2.39 (m, 1H), 3.81-3.92 (m, 2H), 4.01-4.04 (m, 1H), 4.45-4.49 (m, 1H), 6.36 (q, 1H), 7.48 (d, 1H), 8.27 (brs, 1H).

Reference Synthetic Example 2 (Synthesis of Nucleoside Having tert-butyldimethylsilyl Group on 5'-hydroxyl Group and Triisopropylsilyl Group on 2'-hydroxyl Group): Synthesis of 5'-O-(tert-butyldimethylsilyl)-2'-O-triisopropylsilyluridine

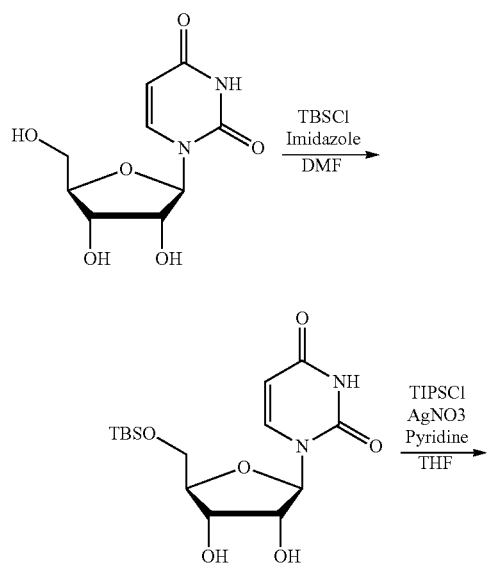

-continued

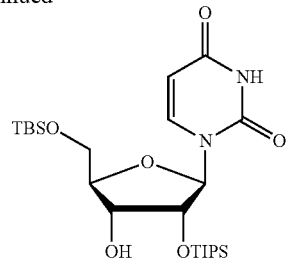

Step 1: Synthesis of 5'-O-(tert-butyldimethylsilyl)uridine

In a nitrogen atmosphere, tert-butyldimethylsilyl chloride (7.76 g, 51.5 mmol) was added to an N,N-dimethylformamide [DMF] (120 g) solution of uridine (12.03 g, 49.3 mmol) and imidazole (6.74 g, 99.0 mmol) at room temperature, and the mixture was stirred for 5 hours and 1 minute. This reaction mixture was dropped to water (240 g), and the resultant solid was recovered by filtration. Toluene was added to the crude product thus obtained, and the mixture was stirred for 30 minutes and was filtered to give 5'-O-(tert-butyldimethylsilyl)uridine (10.49 g, yield 59%) as a white solid.

$^{1}$H-NMR: (300 MHz; CDCl$_{3}$) δ0.11 (s, 6H), 0.92 (s, 9H), 3.82-3.87 (m, 1H), 4.00-4.05 (m, 1H), 4.14-4.15 (m, 1H), 4.21-4.26 (m, 2H), 5.67 (d, 1H), 5.90 (d, 1H), 8.06 (d, 1H).

Step 2: Synthesis of 5'-O-(tert-butyldimethylsilyl)-2'-O-triisopropylsilyluridine In a nitrogen atmosphere, triisopropylsilyl chloride (11.65 g, 60.4 mmol) was added to a THF (50 mL) suspension of 5'-O-(tert-butyldimethylsilyl)uridine (5.40 g, 15.1 mmol), silver nitrate [AgNO$_{3}$] (10.3 g, 60.6 mmol) and pyridine (6.1 mL, 75 mmol) at room temperature, and the mixture was stirred for 23 hours and 6 minutes. The reaction mixture was filtered through Celite. The solvent was distilled away under vacuum, and ethyl acetate was added. Water was added, and the liquids were separated. Ethyl acetate was added to the aqueous phase, and the liquids were separated. The organic phases obtained were combined, and washed with a 6% aqueous potassium hydrogen carbonate solution and with water. The solvent was distilled away under vacuum. Hexane was added to precipitate a solid, and the mixture was cooled to 0° C. and was filtered to give 5'-O-(tert-butyldimethylsilyl)-2'-O-triisopropylsilyluridine (5.24 g, yield 68%) as a white solid.

The filtrate was distilled under vacuum, and the residue was purified by silica gel chromatography (hexane-ethyl acetate) to give 5'-O-(tert-butyldimethylsilyl)-2'-O-triisopropylsilyluridine (1.72 g, yield 22%) as a white solid.

$^{1}$H-NMR: (300 MHz; CDCl$_{3}$) δ0.12 (s, 6H), 0.94 (s, 9H), 1.04-1.16 (m, 21H), 2.80 (d, 1H), 3.81 (d, 1H), 3.96 (d, 1H), 4.13-4.20 (m, 2H), 4.36 (t, 1H), 5.70 (d, 1H), 6.07 (d, 1H), 7.95 (dd, 1H), 8.17 (brs, 1H).

Example 1 (Synthesis of Nucleoside Having Pseudo Solid Phase-Protecting Group Bonded to 3'-hydroxyl Group): Synthesis of Compound 3

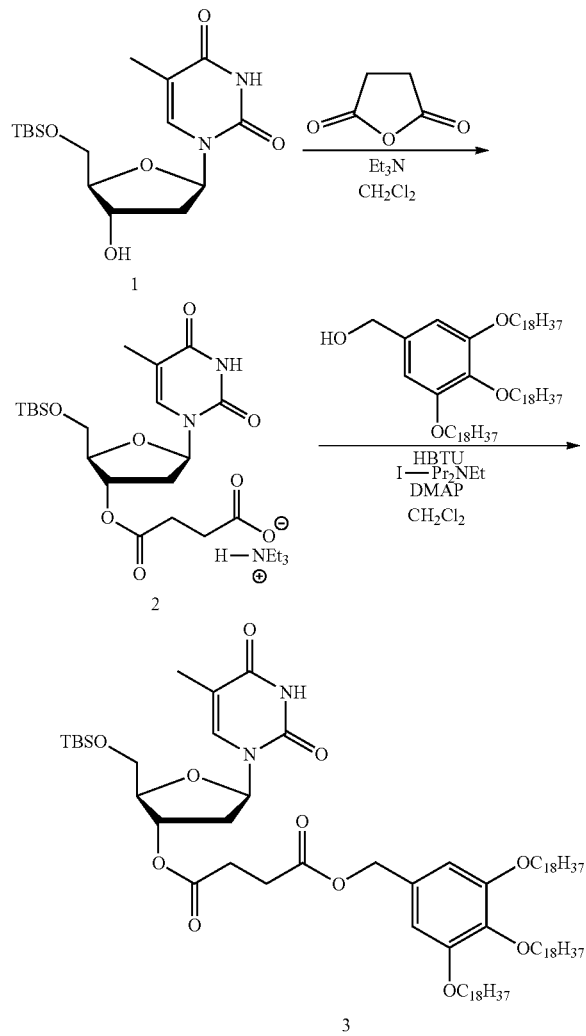

Step 1: Synthesis of Compound 2

In a nitrogen atmosphere, triethylamine (6.21 mL, 44.8 mmol) was added to a methylene chloride (80 g) solution of Compound 1 (8.02 g, 22.4 mmol) and succinic anhydride (3.35 g, 33.5 mmol) at room temperature, and the mixture was stirred for 4 hours and 3 minutes. A 2.0 M aqueous phosphoric acid-triethylamine solution was added to the reaction mixture, and the liquids were separated. The organic phase was washed by liquid separation with a 2 M aqueous phosphoric acid-triethylamine solution two times, and was dried with magnesium sulfate. The solvent was distilled away under vacuum. Consequently, Compound 2 was obtained as a light purple solid (11.37 g, yield 91%).

$^1$H-NMR: (300 MHz; CDCl$_3$) δ0.13 (s, 6H), 0.93 (s, 9H), 1.23 (t, 9H), 1.92 (d, 3H), 2.04-2.13 (m, 1H), 2.39-2.46 (m, 1H), 2.55-2.66 (m, 4H), 3.02 (q, 6H), 3.86-3.95 (m, 2H), 4.13 (d, 1H), 5.25 (d, 1H), 6.35 (q, 1H), 7.55 (d, 1H).

Step 2: Synthesis of Compound 3

In a nitrogen atmosphere, 2-(1H-benzotriazol-1-yl)-1,1,3,3-tetramethyluronium hexafluorophosphate [HBTU] (2.55 g, 6.7 mmol), diisopropylethylamine (1.2 mL, 7.1 mmol) and dimethylaminopyridine [DMAP] (847 mg, 6.9 mmol) were added to a methylene chloride (65 g) solution of Compound 2 (2.79 g, 5.0 mmol) and 3,4,5-tris(octadecyloxy)benzyl alcohol (synthesized in accordance with the method described in Tetrahedron, 2011, 67, 6633-6643) (3.13 g, 3.4 mmol) at room temperature, and the mixture was stirred for 1 hour and 8 minutes. Methanol was added to the reaction mixture, and the resultant solid was recovered by filtration. Consequently, Compound 3 (4.53 g, yield 98%) was obtained as a white solid.

$^1$H-NMR: (300 MHz; CDCl$_3$) δ0.130 (s, 3H), 0.133 (s, 3H), 0.88 (t, 9H), 0.94 (s, 9H), 1.14-1.83 (m, 96H), 1.93 (d, 3H), 2.05-2.15 (m, 1H), 2.37-2.44 (m, 1H), 2.68 (t, 4H), 3.89-3.97 (m, 8H), 4.07 (d, 1H), 5.02 (s, 2H), 5.27 (d, 1H), 6.34 (q, 1H), 6.53 (s, 2H), 7.54 (d, 1H), 8.11 (brs, 1H).

Example 2 (Deprotection of TBS Group): Synthesis of Compound 4

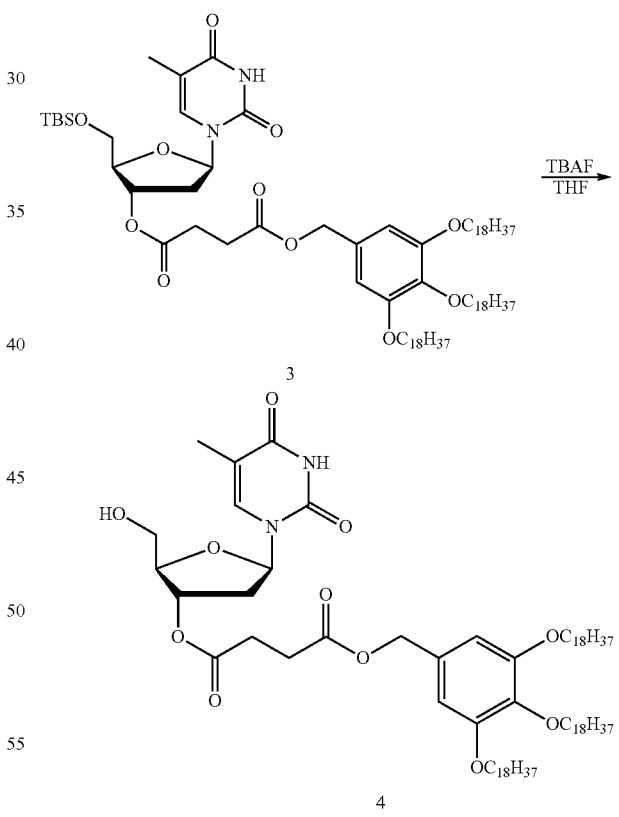

In a nitrogen atmosphere, a 1.0 M tetrabutylammonium fluoride [TBAF]/THF solution (2.4 mL, 2.4 mmol) was added to a tetrahydrofuran [THF] (65 g) solution of Compound 3 (2.97 g, 2.2 mmol) at room temperature, and the mixture was stirred for 2 hours and 10 minutes. Methanol was added to the reaction mixture, and the resultant solid was recovered by filtration. Consequently, Compound 4 (2.66 g, yield 98%) was obtained as a white solid.

$^1$H-NMR: (300 MHz; CDCl$_3$) δ0.88 (t, 9H), 1.09-1.84 (m, 96H), 1.93 (d, 3H), 2.30-2.45 (m, 2H), 2.62-2.73 (m, 4H), 3.82-4.04 (m, 9H), 5.02 (s, 2H) 5.25-5.29 (m, 1H), 6.19 (q, 1H), 6.53 (s, 2H), 7.49 (d, 1H), 8.07 (brs, 1H).

Example 3 (H-phosphonation): Synthesis of Compound 5a

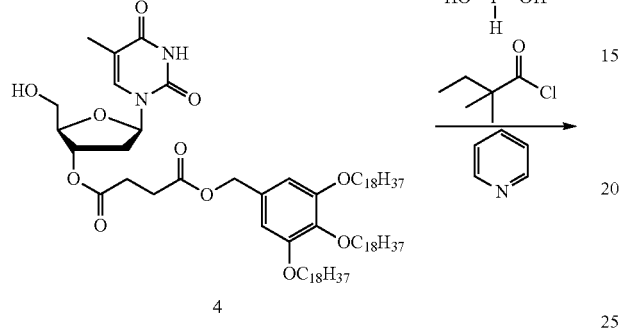

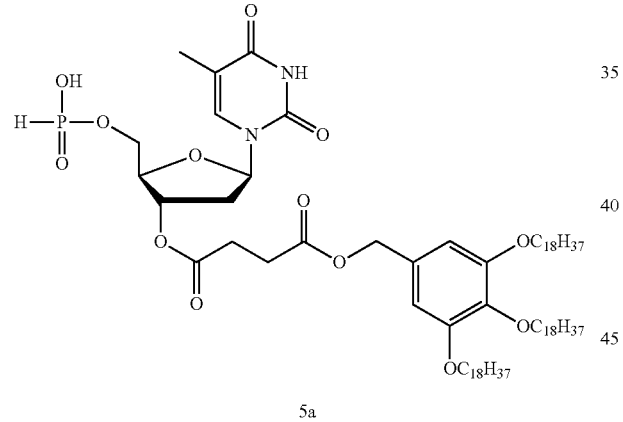

In a nitrogen atmosphere, 2,2-dimethylbutyryl chloride (0.33 mL, 2.4 mmol) was added to a pyridine (10 mL) solution of phosphorous acid (336 mg, 4.0 mmol) at 40° C., and the mixture was stirred for 39 minutes. Compound 4 (498 mg, 0.40 mmol) was added to the reaction mixture, and the mixture was stirred at 40° C. for 1 hour. 2,2-Dimethylbutyryl chloride (56 μL, 0.40 mmol) was added, and the mixture was stirred for 1 hour and 45 minutes. Acetonitrile was added to precipitate a solid, and the mixture was cooled with ice and filtered to give Compound 5a (562 mg) as a white solid.

$^1$H-NMR: (300 MHz; CDCl$_3$) δ0.88 (t, 9H), 1.16-1.83 (m, 96H), 1.92 (d, 3H), 2.31-2.35 (m, 2H), 2.68 (brs, 4H), 3.90-3.98 (m, 6H), 4.17-4.24 (m, 3H), 5.02 (s, 2H), 5.39 (d, 1H), 6.38 (q, 1H), 6.53 (s, 2H), 6.94 (d, 1H), 7.68 (d, 1H).

$^{31}$P-NMR: (300 MHz; CDCl$_3$) δ6.54.

Example 4 (H-phosphonation): Synthesis of Compound 5b (Triethylamine Salt)

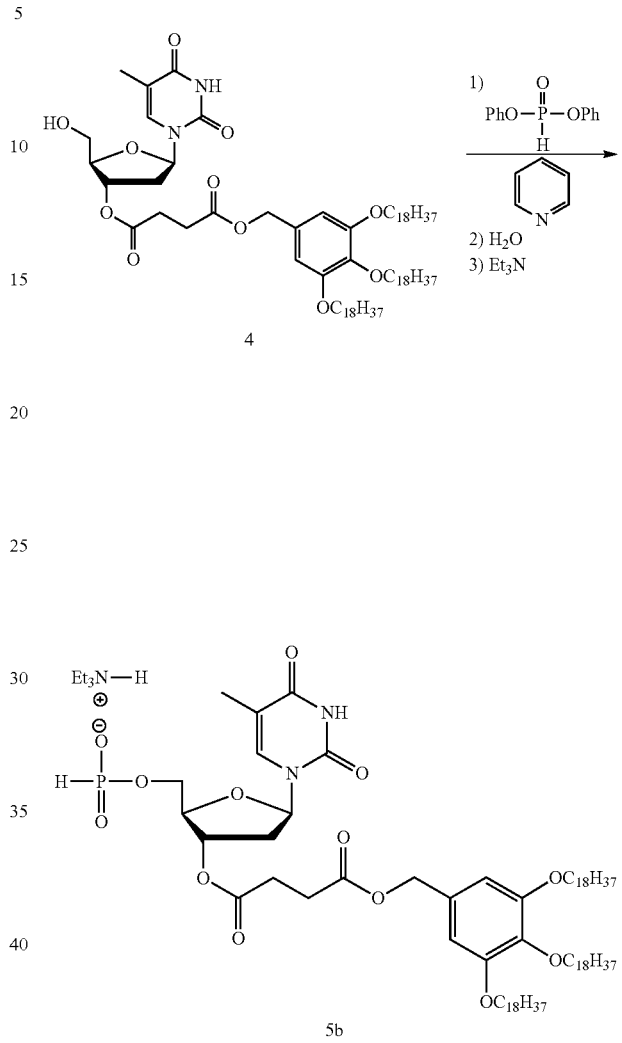

In a nitrogen atmosphere, a pyridine (5 g) solution of Compound 4 (0.5 g, 0.40 mmol) was added to a pyridine (7 g) solution of diphenyl phosphite (0.72 g, 3.1 mmol) at 35° C., and a wash was made with pyridine (3 g). The mixture was stirred at 35° C. for 1 hour and 55 minutes. Water (2.5 g) and triethylamine (1.9 g) were sequentially added, and the mixture was stirred for 26 minutes. Acetonitrile was added, and the resultant solid was recovered by filtration. Consequently, Compound 5b (507 mg) was obtained as a white solid.

$^1$H-NMR: (300 MHz; CDCl$_3$) δ0.88 (t, 9H), 1.20-1.81 (m, 105H), 1.98 (s, 3H), 2.32-2.35 (m, 2H), 2.67 (brs, 4H), 3.00-3.09 (m, 6H), 3.90-4.17 (m, 9H), 5.02 (s, 2H), 5.41 (t, 1H), 6.41 (t, 1H), 6.53 (s, 2H), 6.90 (d, 1H), 7.84 (s, 1H), 7.92 (brs, 1H), 12.67 (brs, 1H).

$^{31}$P-NMR: (300 MHz; CDCl$_3$) δ5.11.

Example 5 (Coupling and Oxidation): Synthesis of Compound 6

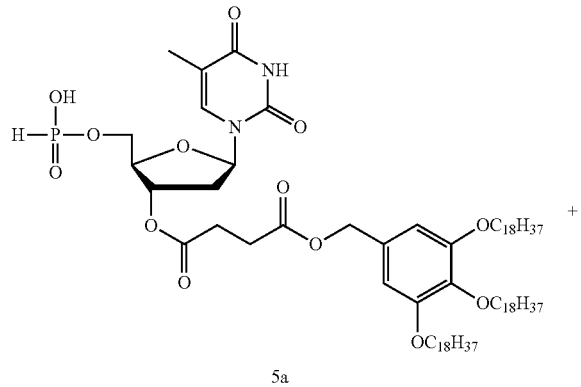

5a

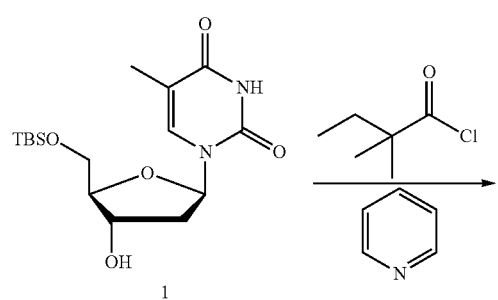

1

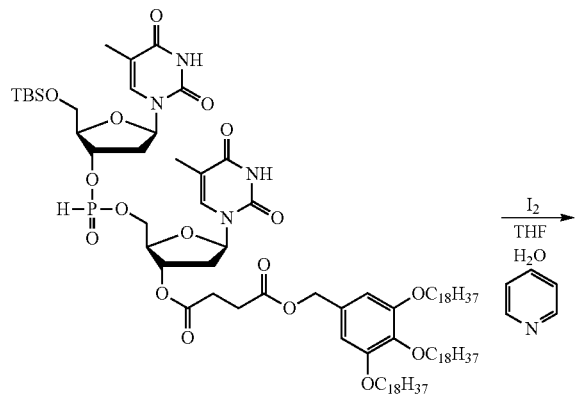

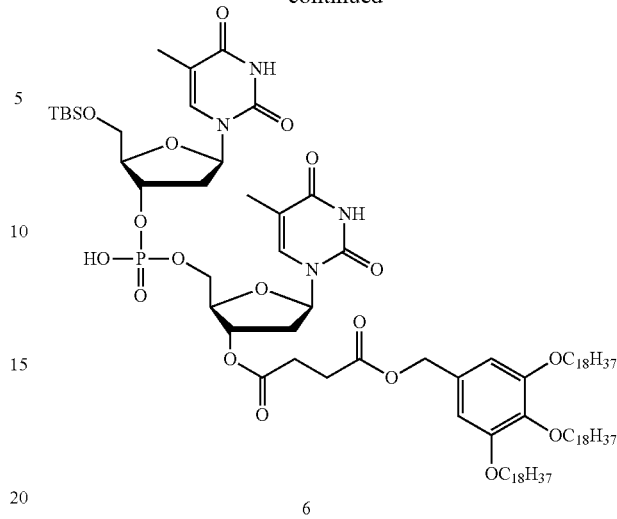

6

In a nitrogen atmosphere, 2,2-dimethylbutyl chloride (25 μL, 0.18 mmol) was added to a pyridine (1 mL) solution of Compound 5a (49 mg) and Compound 1 (20 mg, 0.056 mmol) at 25° C., and the mixture was stirred for 41 minutes. Thereafter, a 0.1 M iodine pyridine/THF/water solution (0.73 mL, 0.073 mmol) was added, and the mixture was stirred for 29 minutes. Trimethyl phosphite (4.3 μL, 0.036 mmol) was added. The reaction mixture was vacuum concentrated, and acetonitrile was added to precipitate a solid. The mixture was cooled with ice and was filtered to give Compound 6 (34 mg) as a skin color solid.

$^1$H-NMR: (300 MHz; CDCl$_3$) δ0.091-0.13 (m, 6H), 0.85-0.95 (m, 18H), 1.08-1.83 (m, 96H), 1.90 (s, 3H), 1.91 (s, 3H), 2.36 (brs, 2H), 2.57-2.67 (m, 6H), 3.81-4.29 (m, 12H), 4.91 (t, 1H), 5.01 (s, 2H), 5.42 (s, 1H), 6.28-6.37 (m, 2H), 6.53 (s, 2H), 7.51 (s, 1H), 7.72 (s, 1H).

$^{31}$P-NMR: (300 MHz; CDCl$_3$) δ0.70.

MS (ESI$^-$): [M−H]$^-$ 1654.1197.

Example 6 (Synthesis of 3-mer): Synthesis of Compound 9

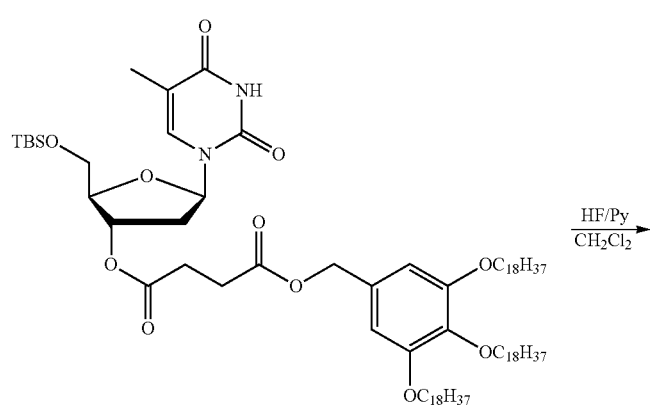

3

-continued
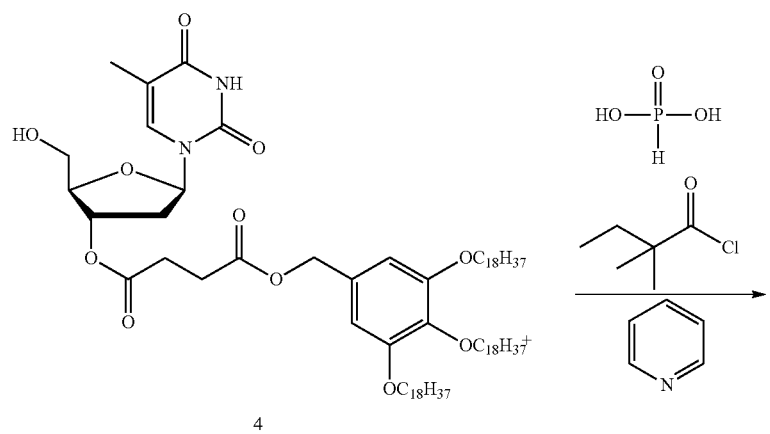
4
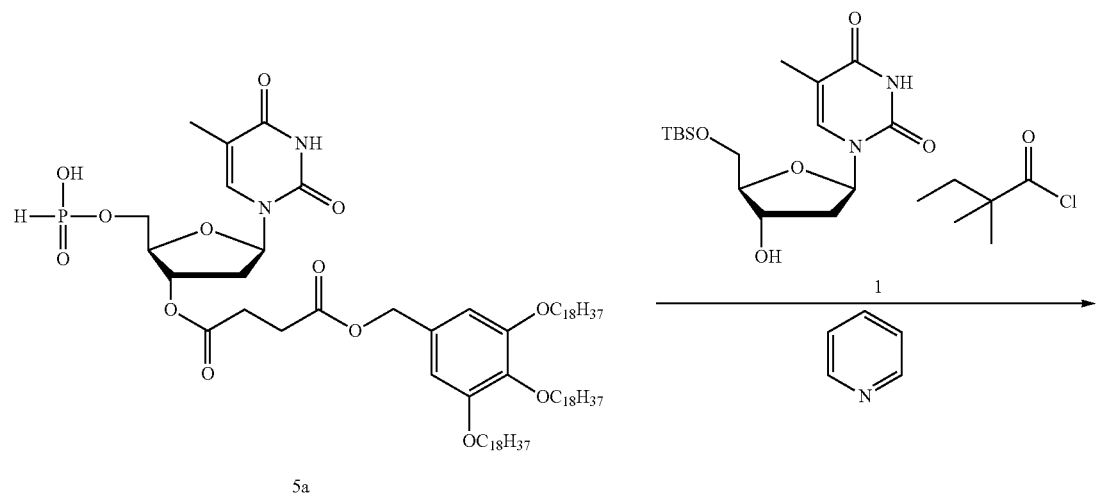
5a
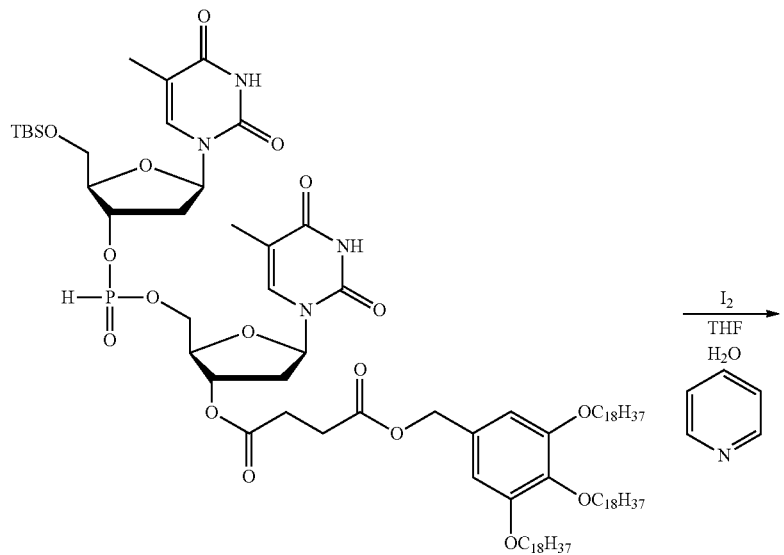

-continued
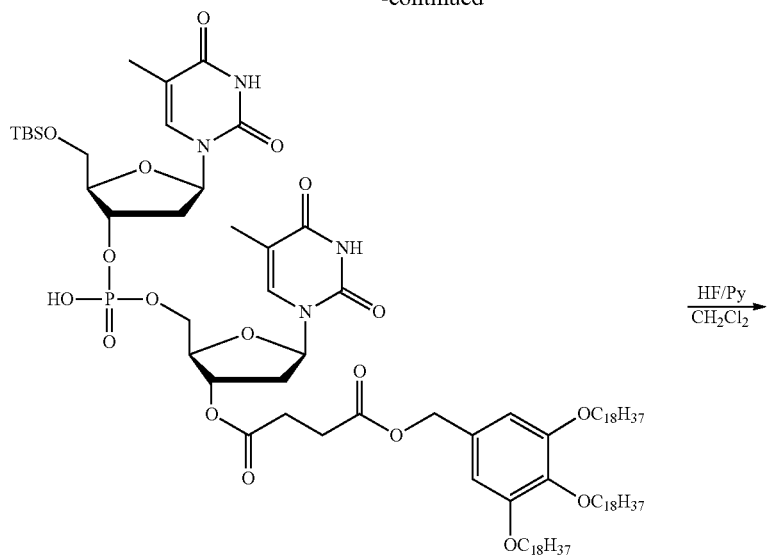
6
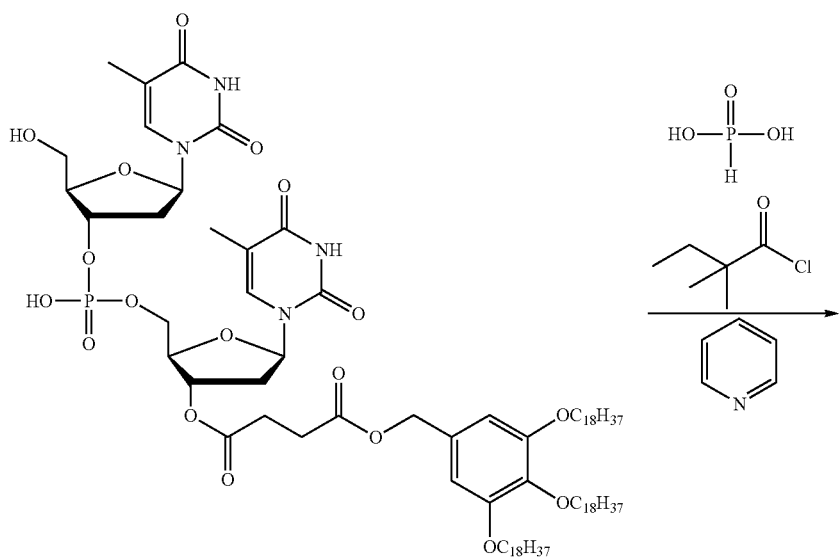
7

77 78
-continued
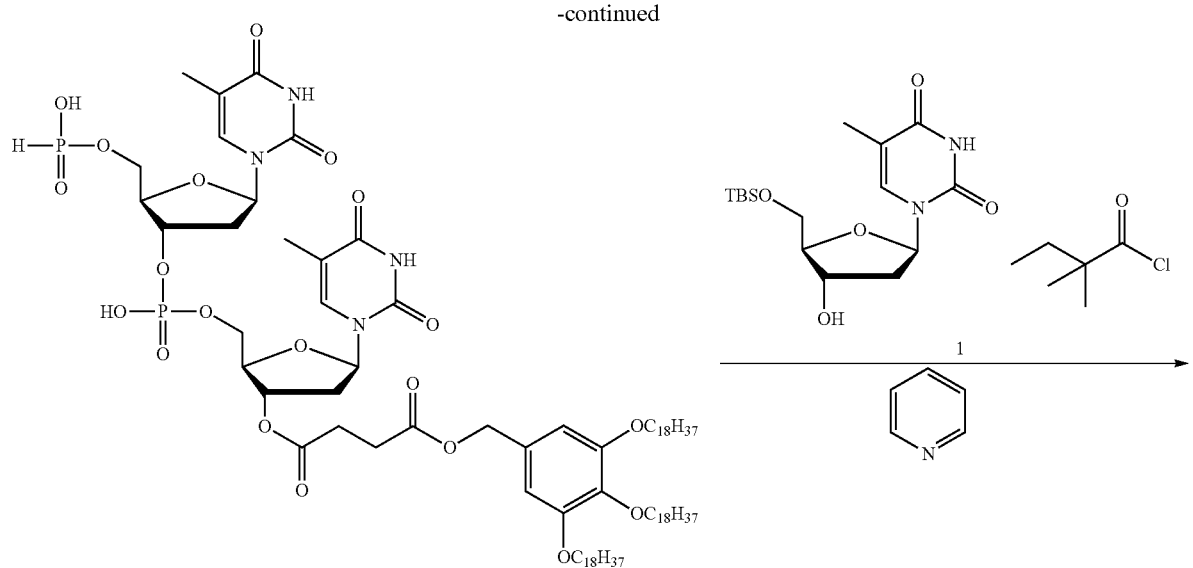
8
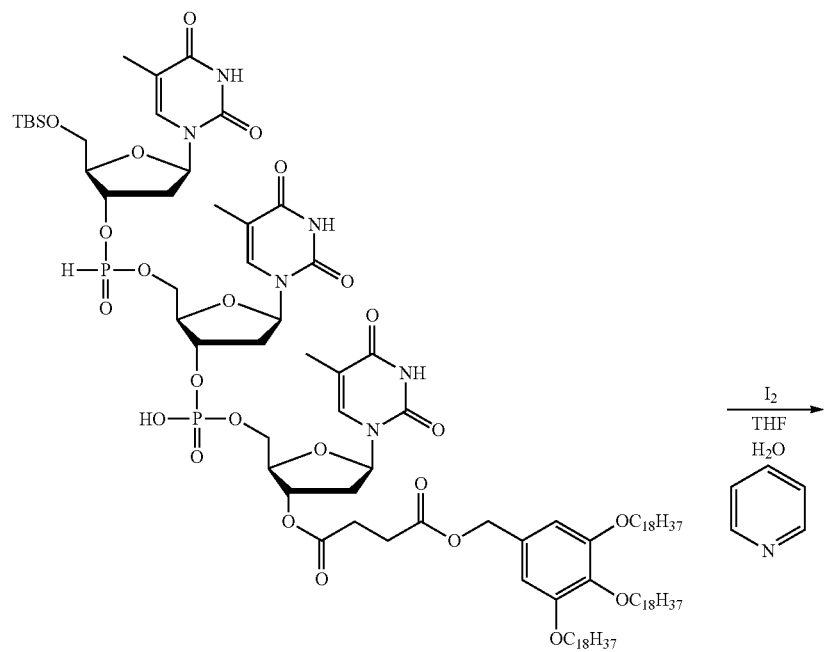

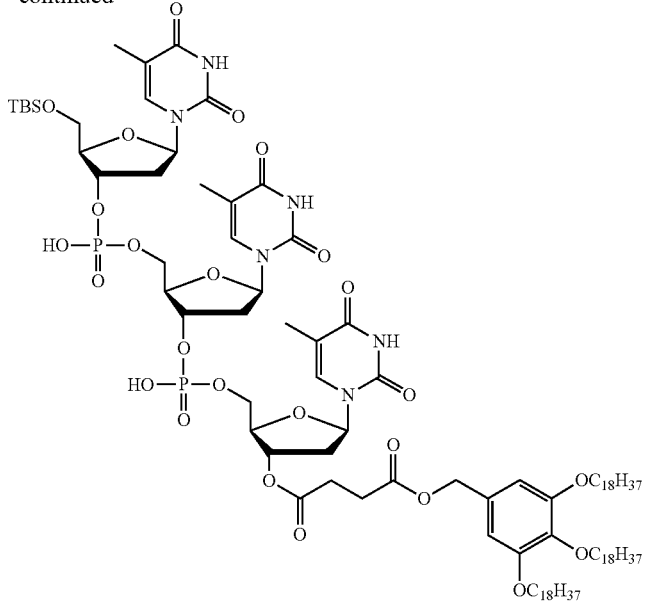

9

Step 1: Synthesis of Compound 6

In a nitrogen atmosphere, hydrogen fluoride-pyridine (86.5 μL, 3.3 mmol) was added to a methylene chloride (5 mL) solution of Compound 3 (1.00 g, 0.74 mmol) at 40° C., and the mixture was stirred for 4 hours and 42 minutes. Hexamethyldisiloxane [TMS$_2$O] (0.55 mL, 2.6 mmol) was added. Pyridine (8 mL) was added to a portion of the reaction mixture corresponding to 0.57 mmol of Compound 3, and the mixture was vacuum concentrated. Again, pyridine (8 mL) was added, and the mixture was vacuum concentrated. Pyridine (6 mL) was added to give a pyridine solution of Compound 4.

In a nitrogen atmosphere, 2,2-dimethylbutyryl chloride (0.41 mL, 3.0 mmol) was added to a pyridine (16 mL) solution of phosphorous acid (0.50 g, 6.1 mmol) at 40° C., and the mixture was stirred for 35 minutes. The pyridine solution of Compound 4 was added to this solution, and a wash was made with pyridine (1 mL). Stirring was performed at 40° C. for 6 hours and 35 minutes. 2,2-Dimethylbutyryl chloride (0.12 mL, 0.87 mmol) was added, and the mixture was stirred for 3 hours. Acetonitrile was added to precipitate a solid. The mixture was cooled with ice and was filtered to give Compound 5a (737 mg) as a white solid.

In a nitrogen atmosphere, 2,2-dimethylbutyl chloride (0.36 mL, 2.6 mmol) was added to a pyridine (14 mL) solution of Compound 5a (702 mg) and Compound 1 (279 mg, 0.78 mmol) at 25° C., and the mixture was stirred for 33 minutes. Thereafter, a 0.1 M solution of iodine in pyridine, THF and water (6.3 mL, 0.63 mmol) was added, and the mixture was stirred for 21 minutes. Trimethyl phosphite (12 μL, 0.11 mmol) was added. Acetonitrile was added to the reaction mixture to precipitate a solid, and the mixture was vacuum concentrated. Acetonitrile was added, and the mixture was cooled with ice and filtered to give Compound 6 (799 mg) as a light skin color solid.

$^1$H-NMR: (300 MHz; CDCl$_3$) δ0.096 (s, 3H), 0.11 (s, 3H), 0.85-0.95 (m, 18H), 1.10-1.83 (m, 96H), 1.90 (s, 3H), 1.91 (s, 3H), 2.35 (brs, 2H), 2.57-2.67 (m, 6H), 3.86-4.28 (m, 12H), 4.92 (t, 1H), 5.02 (s, 2H), 5.35 (s, 1H), 6.28-6.33 (m, 2H), 6.53 (s, 2H), 7.49 (s, 1H), 7.59 (s, 1H).

$^{31}$P-NMR: (300 MHz; CDCl$_3$) δ0.96.

Step 2: Synthesis of Compound 9

In a nitrogen atmosphere, hydrogen fluoride-pyridine (51.9 μL, 2.0 mmol) was added to a methylene chloride (4 mL) solution of Compound 6 (750 mg) at 40° C., and the mixture was stirred for 3 hours and 23 minutes. Hexamethyldisiloxane [TMS$_2$O] (0.33 mL, 1.6 mmol) was added. Pyridine (8 mL) was added, and the mixture was vacuum concentrated. Again, pyridine (8 mL) was added, and the mixture was vacuum concentrated. Pyridine (6 mL) was added to give a pyridine solution of Compound 7.

In a nitrogen atmosphere, 2,2-dimethylbutyryl chloride (0.37 mL, 2.7 mmol) was added to a pyridine (12 mL) solution of phosphorous acid (0.37 g, 4.4 mmol) at 40° C., and the mixture was stirred for 39 minutes. The pyridine solution of Compound 7 was added to this solution, and a wash was made with pyridine (1 mL). Stirring was performed at 40° C. for 1 hour and 43 minutes. 2,2-Dimethylbutyl chloride (61 μL, 0.44 mmol) was added. The mixture was stirred for 3 hours and 31 minutes. Acetonitrile was added to precipitate a solid, and the mixture was cooled with ice and was filtered to give Compound 8 (611 mg) as a white solid.

In a nitrogen atmosphere, 2,2-dimethylbutyryl chloride (0.25 mL, 1.8 mmol) was added to a pyridine (10 mL) solution of Compound 8 (600 mg) and Compound 1 (194 mg, 0.54 mmol) at 25° C., and the mixture was stirred for 34 minutes. Thereafter, a 0.1 M solution of iodine in pyridine, THF and water (4.3 mL, 0.43 mmol) was added, and the mixture was stirred for 58 minutes. Trimethyl phosphite (16 μL, 0.14 mmol) was added. Acetonitrile was added to the reaction mixture to precipitate a solid, and the mixture was vacuum concentrated. Acetonitrile was added. The mixture was cooled with ice and filtered to give Compound 9 (634 mg) as a light skin color solid.

81

¹H-NMR: (300 MHz; CDCl₃) δ0.093 (s, 3H), 0.10 (s, 3H), 0.85-0.92 (m, 18H), 1.09-1.89 (m, 105H), 2.01-2.52 (m, 6H), 2.67 (brs, 4H), 3.85-4.26 (m, 15H), 4.92 (s, 1H), 5.01 (s, 2H), 5.02 (s, 1H), 5.38 (s, 1H), 6.13 (s, 1H), 6.24-6.30 (m, 2H), 6.53 (s, 2H), 7.42 (s, 1H), 7.48 (s, 1H), 7.60 (s, 1H).

³¹P-NMR: (300 MHz; CDCl₃) δ−1.52, −1.33.

Example 7 (Coupling and Sulfurization): Synthesis of Compound 10

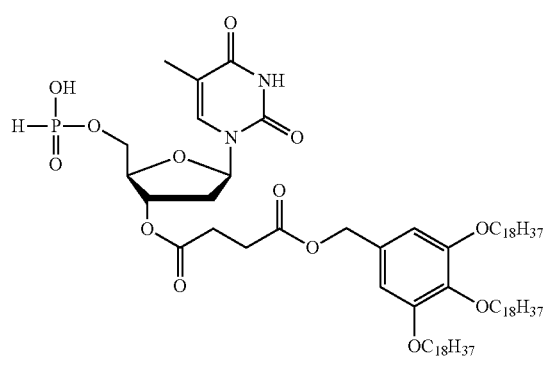

5a

+

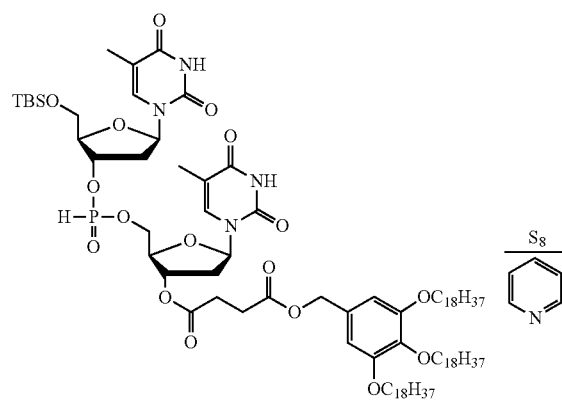

1

82

-continued

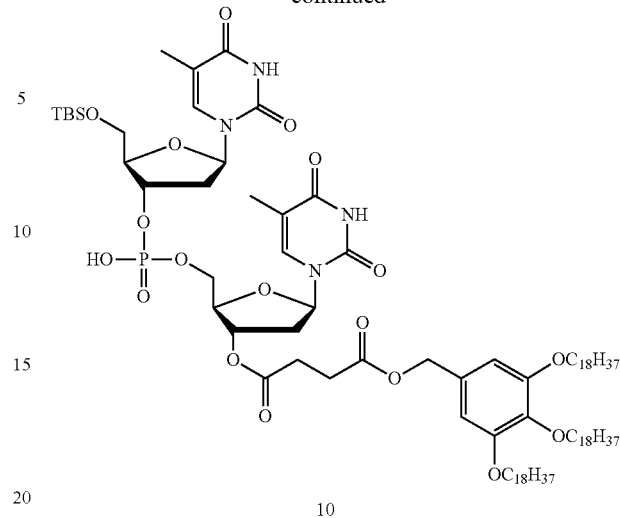

10

In a nitrogen atmosphere, 2,2-dimethylbutyl chloride (49 μL, 0.36 mmol) was added to a pyridine (2 mL) solution of Compound 5a (102 mg) and Compound 1 (38 mg, 0.11 mmol) at 25° C., and the mixture was stirred for 23 minutes. Thereafter, elemental sulfur (28 mg, 0.87 mmol) was added, and the mixture was stirred for 1 hour and 8 minutes. Acetonitrile was added to precipitate a solid. The mixture was cooled with ice and was filtered to give Compound 10 (121 mg) as a white solid.

³¹P-NMR: (300 MHz; CDCl₃) δ60.46, 61.07.

MS (ESI⁻): [M−H]⁻ 1670.0959.

Example 8 (Synthesis of 2-mer having Dimethoxytrityl group as Temporary Protecting Group): Synthesis of Compound 11

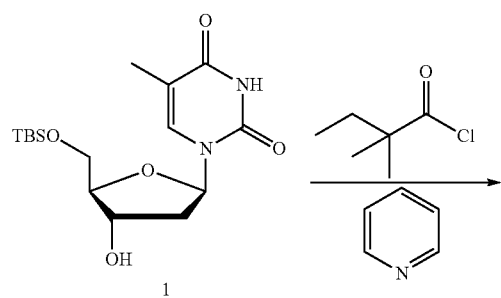

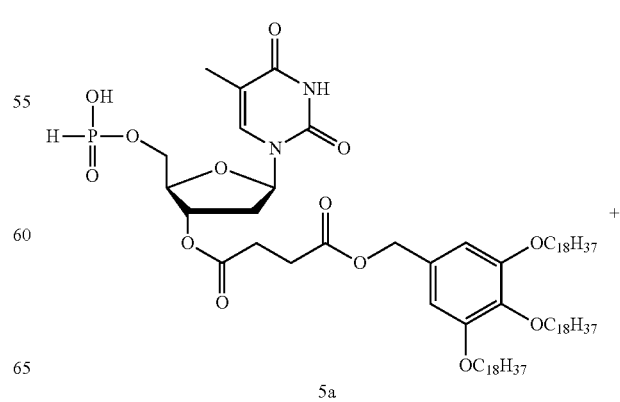

+

5a

83

-continued

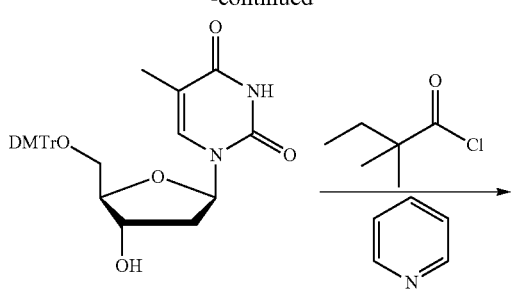

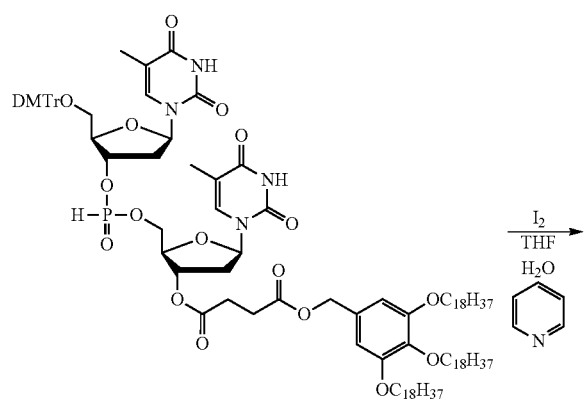

84

-continued

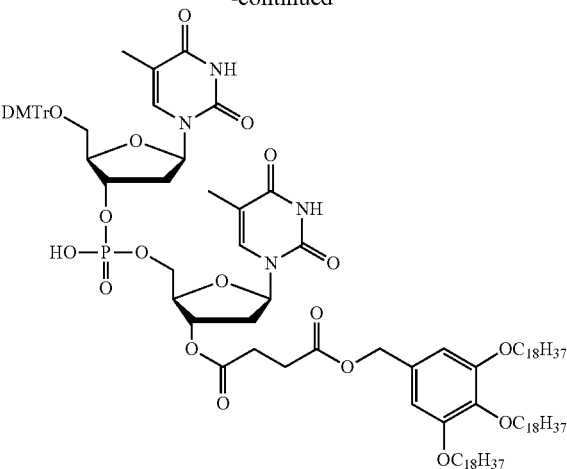

11

In a nitrogen atmosphere, 2,2-dimethylbutyryl chloride (50 μL, 0.36 mmol) was added to a pyridine (2 mL) solution of Compound 5a (103 mg) and 5'-O-(4,4'-dimethoxytrityl) thymidine (manufactured by Tokyo Chemical Industry Co., Ltd.) (61 mg, 0.11 mmol) at 25° C., and the mixture was stirred for 22 minutes. Thereafter, a 0.1 M solution of iodine in pyridine, THF and water (0.88 mL, 88 μmol) was added, and the mixture was stirred for 57 minutes. Trimethyl phosphite (1.7 μL, 14 μmol) was added. Acetonitrile was added. The reaction mixture was vacuum concentrated, and acetonitrile was added to precipitate a solid. The mixture was cooled with ice and was filtered to give Compound 11 (96 mg) as a light red solid.

$^1$H-NMR: (300 MHz; CDCl$_3$) δ0.88 (t, 9H), 1.09-2.01 (m, 102H), 2.37-2.69 (m, 8H), 3.67-4.22 (m, 18H), 4.91-5.02 (m, 3H), 5.38 (s, 1H), 6.09 (s, 1H), 6.25 (s, 1H), 6.54 (s, 2H), 6.81-7.36 (m, 13H), 7.51 (s, 1H), 7.56 (s, 1H).

Example 9 (Synthesis of 2-mer in 5'→3' Direction): Synthesis of Compound 16

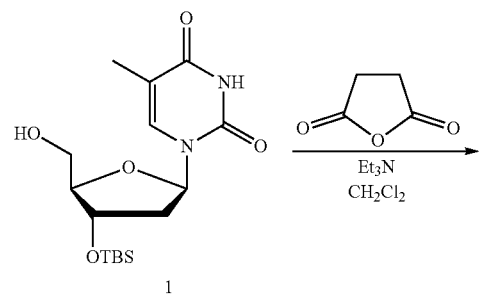

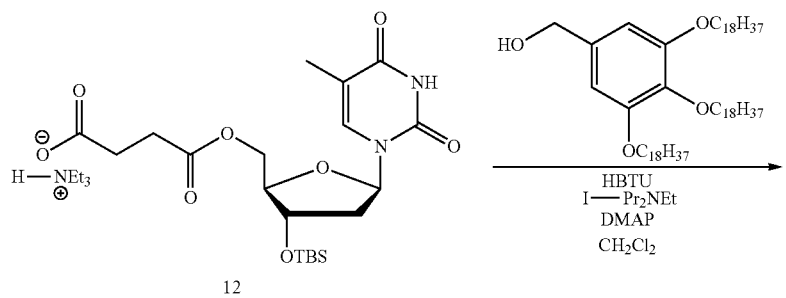

-continued
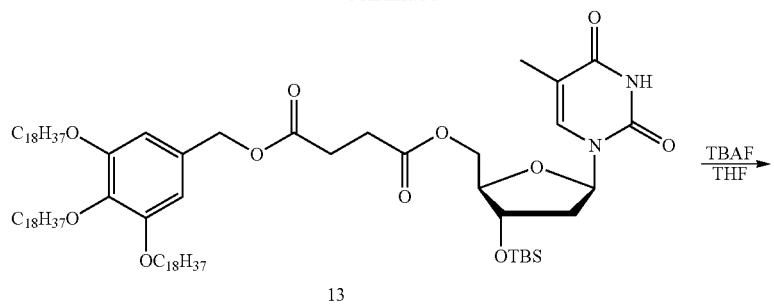
13
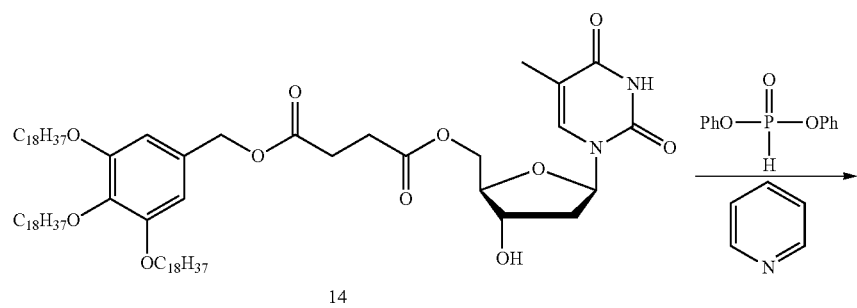
14
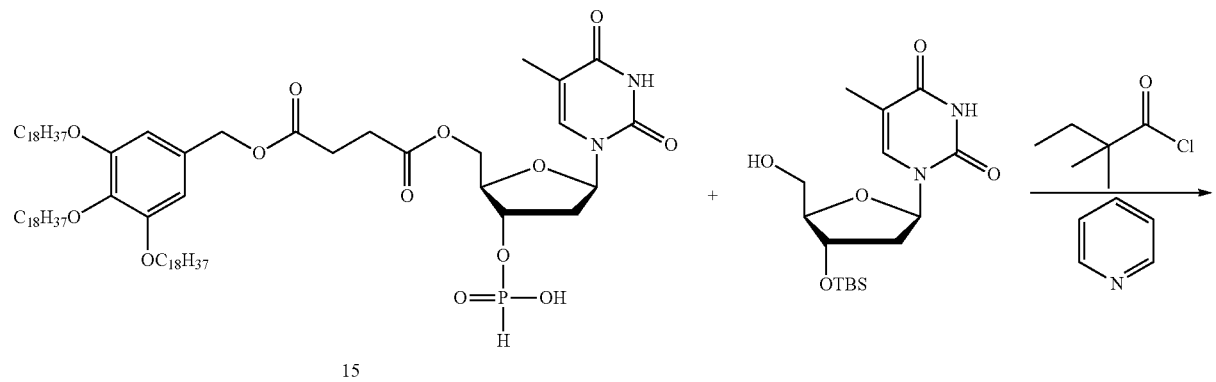
15
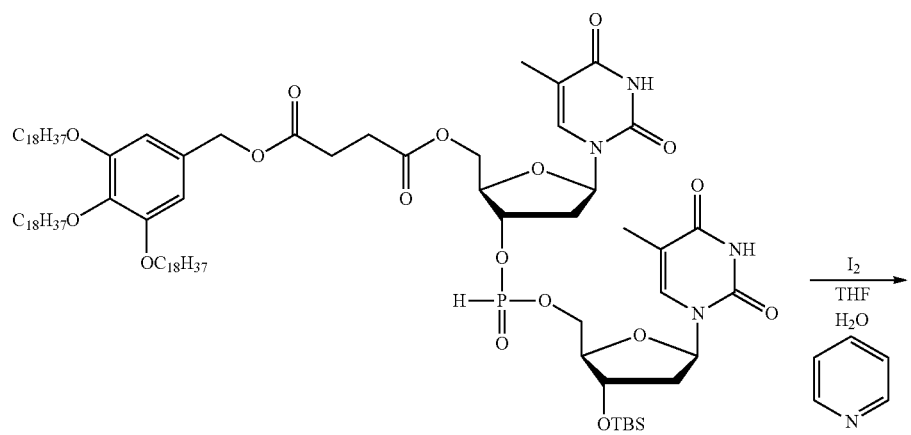

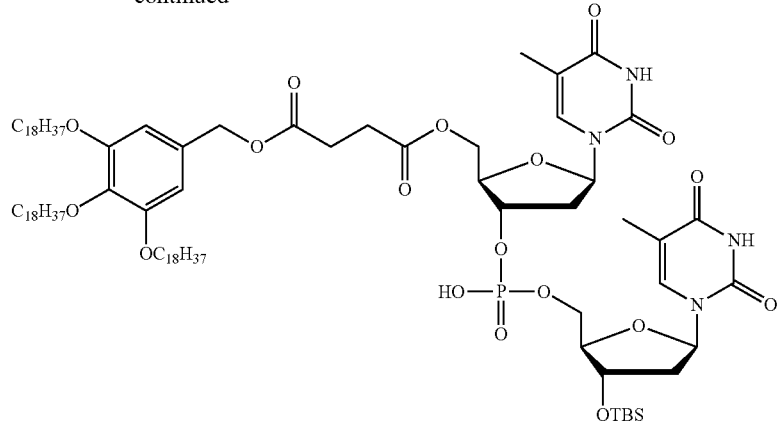

16

Step 1: Synthesis of Compound 12

In a nitrogen atmosphere, triethylamine (2.64 g, 26.1 mmol) was added to a methylene chloride (31 g) solution of 3'-O-(tert-butyldimethylsilyl)thymidine (manufactured by Berry) (3.07 g, 8.6 mmol) and succinic anhydride (1.29 g, 12.9 mmol) at room temperature, and the mixture was stirred for 2 hours and 33 minutes. A 2.0 M aqueous phosphoric acid-triethylamine solution was added to the reaction mixture, and the liquids were separated. The organic phase was washed by liquid separation with a 2 M aqueous phosphoric acid-triethylamine solution two times, and was dried with magnesium sulfate. The solvent was distilled away under vacuum. Consequently, Compound 12 was obtained as a white foamy solid (3.73 g).

$^1$H-NMR: (300 MHz; CDCl$_3$) δ0.10 (s, 3H), 0.12 (s, 3H), 0.90 (s, 9H), 1.23 (t, 9H), 1.90 (s, 3H), 2.05-2.14 (m, 1H), 2.36-2.43 (m, 1H), 2.51-2.86 (m, 4H), 3.00 (q, 6H), 4.10 (brs, 1H), 4.21-4.26 (m, 1H), 4.40-4.43 (m, 1H), 4.59-4.63 (m, 1H), 5.30 (s, 1H), 6.08 (q, 1H), 7.41 (d, 1H), 9.95 (brs, 1H).

Step 2: Synthesis of Compound 13

In a nitrogen atmosphere, 2-(1H-benzotriazol-1-yl)-1,1,3,3-tetramethyluronium hexafluorophosphate [HBTU] (4.13 g, 10.9 mmol), diisopropylethylamine (1.42 g, 11.0 mmol) and dimethylaminopyridine (1.37 g, 11.2 mmol) were added to a methylene chloride (224 g) solution of Compound 12 (3.73 g, 8.2 mmol) and 3,4,5-tris(octadecyloxy)benzyl alcohol (4.96 g, 5.4 mmol) at room temperature, and the mixture was stirred for 16 hours and 18 minutes. Methanol was added to the reaction mixture, and the resultant solid was recovered by filtration. Consequently, Compound 13 (7.18 g) was obtained as a white solid.

$^1$H-NMR: (300 MHz; CDCl$_3$) δ0.080-0.085 (m, 6H), 0.86-0.89 (m, 18H), 1.18-1.84 (m, 96H), 1.94 (d, 3H), 2.05-2.14 (m, 1H), 2.27-2.34 (m, 1H), 2.64-2.74 (m, 4H), 3.91-3.98 (m, 6H), 4.04-4.07 (m, 1H), 4.20-4.39 (m, 3H), 5.01 (s, 2H), 6.25 (t, 1H), 6.52 (s, 2H), 7.27 (d, 1H), 8.01 (brs, 1H).

Step 3 (Step a in Elongation Reaction Cycle: Deprotection): Synthesis of Compound 14

In a nitrogen atmosphere, a 1.0 M tetrabutylammonium fluoride [TBAF]/THF solution (4.5 mL, 4.9 mmol) was added to a tetrahydrofuran [THF] (60 g) solution of Compound 13 (6.06 g, 4.5 mmol) at room temperature, and the mixture was stirred for 1 hour and 23 minutes. Methanol was added to the reaction mixture, and the resultant solid was recovered by filtration. Consequently, Compound 14 (5.45 g) was obtained as a white solid.

$^1$H-NMR: (300 MHz; CDCl$_3$) δ0.88 (t, 9H), 1.08-1.84 (m, 96H), 1.93 (d, 3H), 2.07-2.16 (m, 1H), 2.32-2.40 (s, 1H), 2.62-2.79 (m, 4H), 3.91-4.00 (m, 7H), 4.16 (dd, 1H), 4.27 (quint, 1H), 4.39 (dd, 1H), 5.01 (q, 2H), 6.25 (t, 1H), 6.53 (s, 2H), 7.24 (d, 1H).

Step 4 (Step b in Elongation Reaction Cycle: H-phosphonation): Synthesis of Compound 15

In a nitrogen atmosphere, a pyridine (10 mL) solution of Compound 14 (1.05 g, 0.85 mmol) was added to a pyridine (15 mL) solution of diphenyl phosphite (1.36 g, 5.8 mmol) at room temperature, and a wash was made with pyridine (5 mL). Stirring was performed at 40° C. for 1 hour and 22 minutes, and water (5.13 g) and triethylamine (3.79 g) were sequentially added. The mixture was stirred for 14 minutes. Acetonitrile was added to the reaction mixture, and the resultant solid was recovered by filtration. Consequently, Compound 15 (1.09 g) was obtained as a white solid.

$^1$H-NMR: (300 MHz; CDCl$_3$) δ0.88 (t, 9H), 1.20-1.83 (m, 96H), 1.93 (d, 3H), 2.14-2.23 (m, 1H), 2.54-2.74 (m, 5H), 3.90-3.98 (m, 6H), 4.32-4.39 (m, 3H), 4.80-4.86 (m, 1H), 5.00 (s, 2H), 6.30 (t, 1H), 6.52 (s, 2H), 6.89 (d, 1H), 7.28 (d, 1H), 8.17 (brs, 1H), 12.32 (brs, 1H).

$^{31}$P-NMR: (300 MHz; CDCl$_3$) δ3.86.

Step 5 (Steps c and d in Elongation Reaction Cycle: Coupling and Oxidation): Synthesis of Compound 16

In a nitrogen atmosphere, 2,2-dimethylbutyryl chloride (0.12 mL, 0.90 mmol) was added to a pyridine (5 mL) solution of Compound 15 (250 mg) and 3'-O-(tert-butyldimethylsilyl)thymidine (97 mg, 0.27 mmol) at 25° C., and the mixture was stirred for 29 minutes. Thereafter, a 0.1 M solution of iodine in pyridine, THF and water (2.2 mL, 0.22 mmol) was added, and the mixture was stirred for 40 minutes. Trimethyl phosphite (4.3 μL, 36 μmol) was added. The reaction mixture was vacuum concentrated, and acetonitrile was added to precipitate a solid. The mixture was cooled with ice and was filtered to give Compound 16 (270 mg) as a light skin color solid.
$^1$H-NMR: (300 MHz; CDCl$_3$) δ0.076 (s, 6H), 0.83-0.96 (m, 18H), 1.06-1.83 (m, 96H), 1.89 (s, 3H), 1.92 (s, 3H), 2.11-2.67 (m, 8H), 3.90-4.47 (m, 13H), 4.92 (s, 1H), 4.99 (s, 2H), 6.19-6.28 (m, 2H), 6.52 (s, 2H), 7.26 (s, 1H), 7.55 (s, 1H).
$^{31}$P-NMR: (300 MHz; CDCl$_3$) δ−0.48.
MS(ESI$^−$): [M−H]$^−$ 1654.1123.
Example 10 (Synthesis of 2-mer): Synthesis of Compound 20
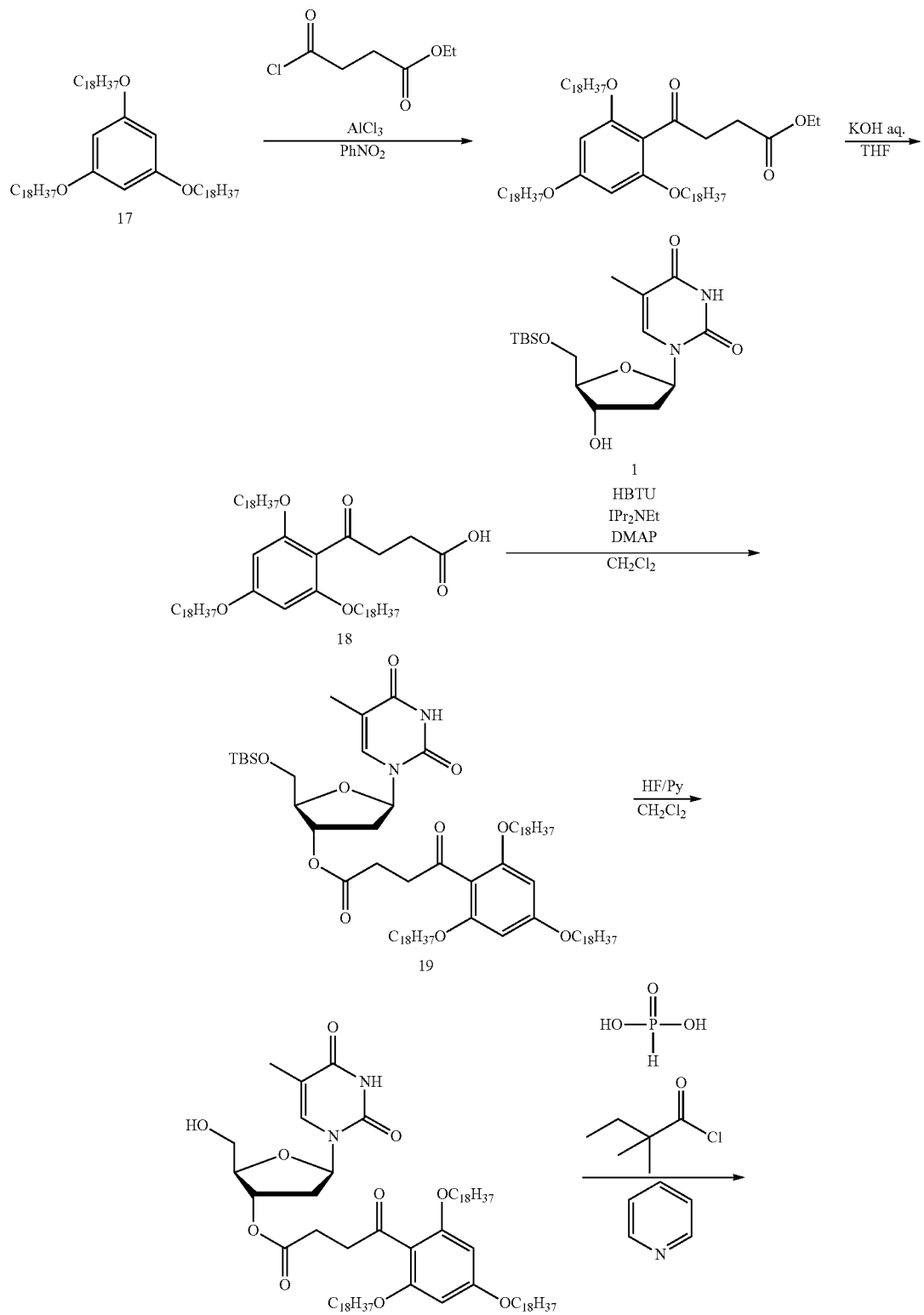

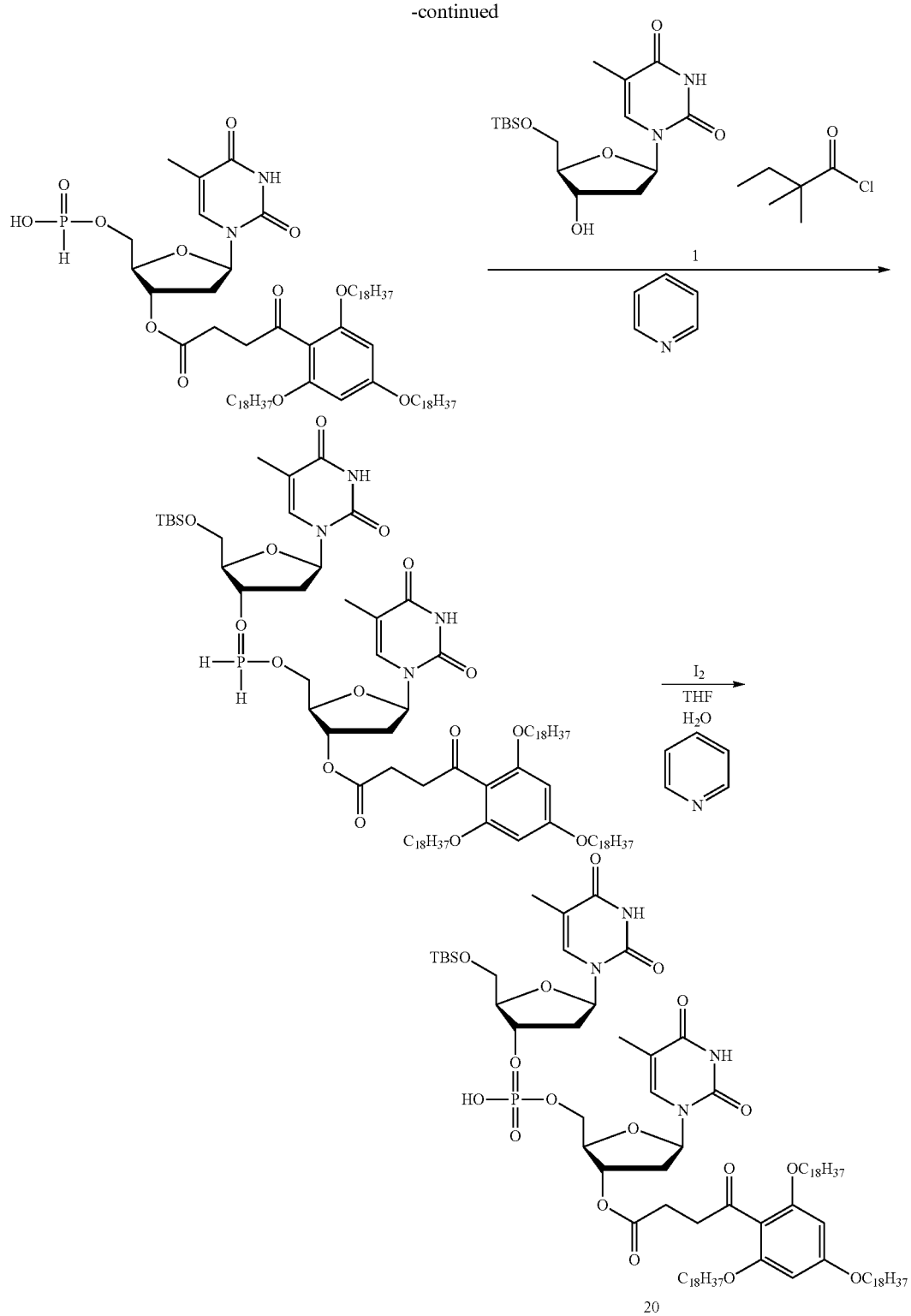

Step 1: Synthesis of Compound 18

In a nitrogen atmosphere, monoethyl succinate chloride (1.36 mL, 9.7 mmol) was added to a nitrobenzene (43 g) solution of Compound 17 (synthesized in accordance with the method described in Japanese Patent Application Kokai Publication No. 2011-126993) (4.26 g, 4.8 mmol) at 60° C. Aluminum chloride (1.30 g, 9.8 mmol) was added. The mixture was stirred at 60° C. for 2 hours and 2 minutes, cooled to room temperature, and washed by liquid separation with water two times. Methanol was added to the organic phase thus obtained to precipitate a solid, and the mixture was filtered to give a light yellow solid.

An aqueous potassium hydroxide (3.17 g, 48 mmol) solution was added to a THF (15 g) solution of the above solid, and the mixture was stirred for 1 hour and 25 minutes while performing heating under reflux. Water (2 g) was added, and the pH of the aqueous phase was controlled to 7 to 8 with concentrated hydrochloric acid.

Methylene chloride (38 g) and water (12 g) were added, and the liquids were separated. The organic phase thus obtained was vacuum concentrated. The residue was dissolved into THF. Methanol was added, and the resultant solid was recovered by filtration. Consequently, Compound 18 (3.70 g) was obtained as a brown solid.

$^1$H-NMR: (300 MHz; $C_5D_5N$) δ0.88 (t, 9H), 1.11-1.88 (m, 96H), 3.17 (t, 2H), 3.62 (t, 2H), 4.04 (t, 4H), 4.11 (t, 2H), 6.53 (s, 2H).

MS (ESI$^-$): [M−H]$^-$ 981.8884.

Step 2: Synthesis of Compound 19

In a nitrogen atmosphere, 2-(1H-benzotriazol-1-yl)-1,1,3,3-tetramethyluronium hexafluorophosphate [HBTU] (2.75 g, 7.3 mmol), diisopropylethylamine (1.23 mL, 7.2 mmol) and dimethylaminopyridine (0.91 g, 7.4 mmol) were added to a methylene chloride (22 g) solution of Compound 18 (3.56 g, 3.6 mmol) and Compound 1 (1.98 g, 5.6 mmol) at room temperature, and the mixture was stirred for 1 hour and 31 minutes. Water was added to the reaction mixture, and the liquids were separated. The aqueous phase was subjected to liquid separation with methylene chloride. The organic phases obtained were combined, washed with a saturated aqueous sodium chloride solution, and vacuum concentrated. Hexane was added to precipitate a solid, which was then removed by filtration. The crude product thus obtained was purified by silica gel chromatography (hexane-ethyl acetate) to give Compound 19 (2.85 g) as an orange oily matter.

$^1$H-NMR: (300 MHz; CDCl$_3$) δ0.13 (s, 6H), 0.88 (t, 9H), 0.93 (s, 9H), 1.14-1.87 (m, 96H), 1.92 (d, 3H), 2.05-2.14 (m, 1H), 2.39-2.45 (m, 1H), 2.67 (t, 2H), 3.09 (t, 2H), 3.88-3.94 (m, 8H), 4.11 (d, 1H), 5.27 (d, 1H), 6.05 (s, 2H), 6.35 (q, 1H), 7.55 (d, 1H), 8.01 (d, 1H).

MS (ESI$^+$): [M+H]$^+$ 1322.0619.

Step 3: Synthesis of Compound 20

In a nitrogen atmosphere, hydrogen fluoride-pyridine (3 μL) was added to a methylene chloride (0.3 mL) solution of Compound 19 (22.5 mg), and the mixture was stirred for 7 hours and 3 minutes. Trimethylsilyl chloride [TMSCl] (10 μL) was added. Pyridine (0.1 mL) was added, and phosphorous acid (2.9 mg) and 2,2-dimethylbutyryl chloride (20 μL) were added. Compound 1 (12.9 mg) was added. The mixture was stirred for 2 days. 2,2-Dimethylbutyryl chloride (10 μL) was added, and the mixture was stirred for 1 hour and 28 minutes. A 0.1 M solution of iodine in pyridine, THF and water (1 mL) was added, and the mixture was stirred for 1 day. A saturated solution of sodium thiosulfate in a mixed solvent of acetonitrile and water (acetonitrile/water=9/1 (by weight)) was added, and the mixture was filtered. Compound 20 was thus obtained.

MS(ESI$^-$): [M−H]$^-$ 1624.1104.

Example 11 (Synthesis of 2-mer): Synthesis of Compound 23

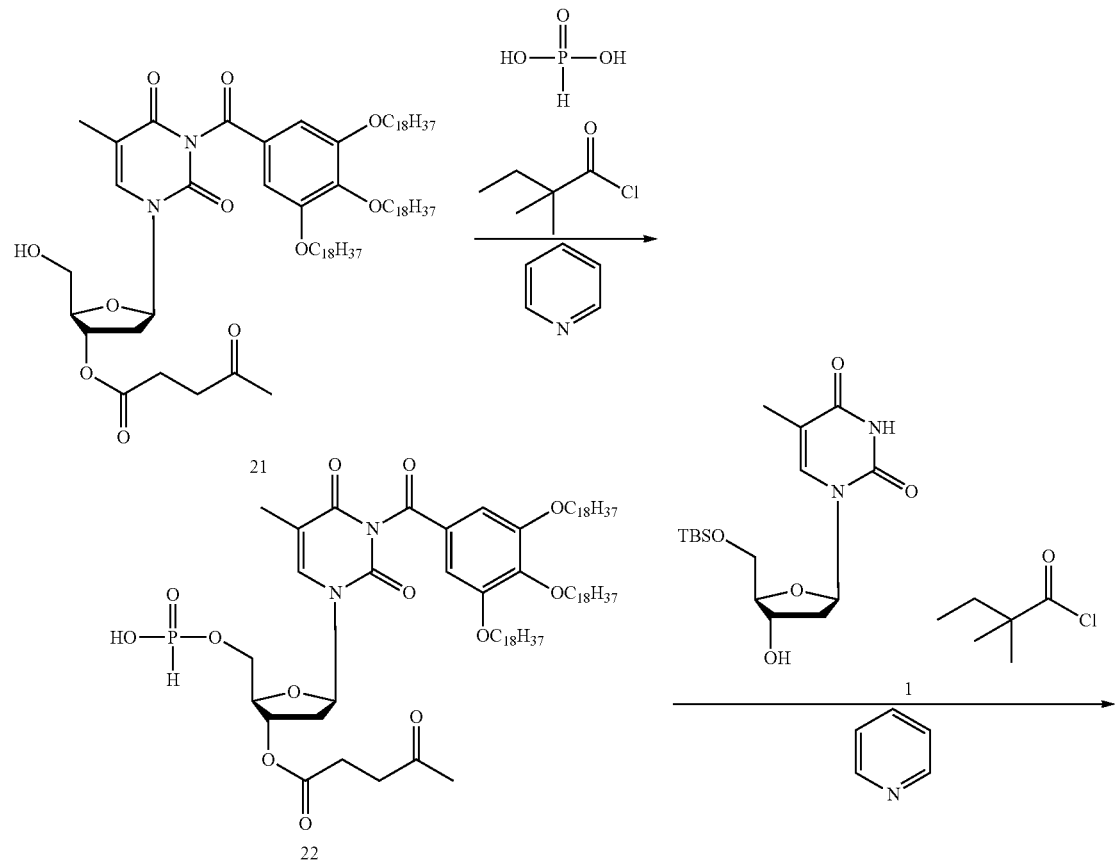

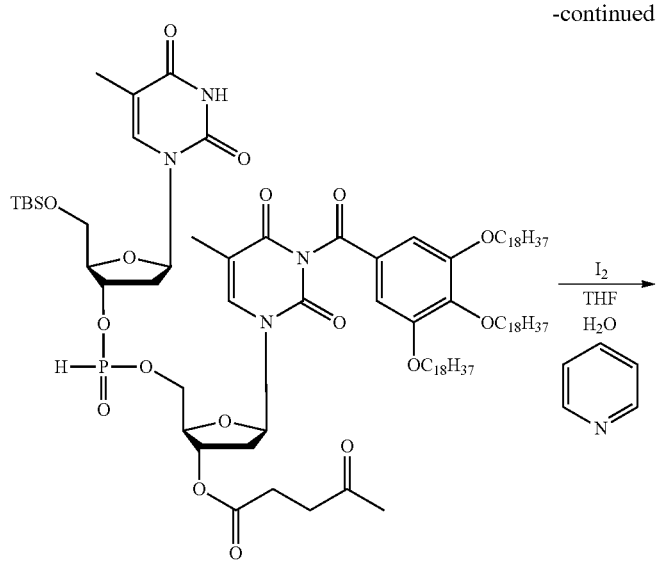
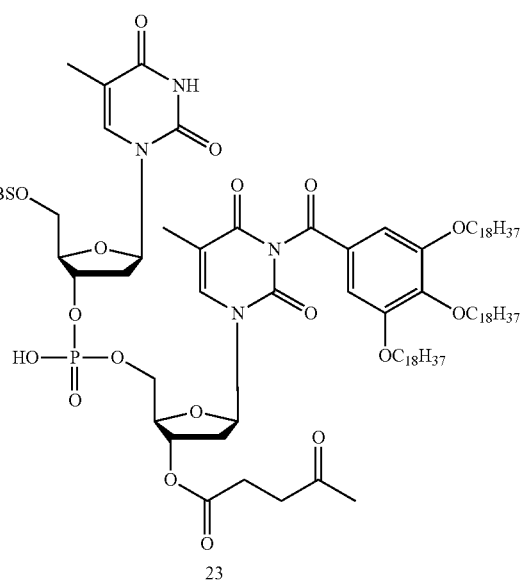

Step 1: Synthesis of Compound 22

In a nitrogen atmosphere, 2,2-dimethylbutyryl chloride (0.33 mL, 2.4 mmol) was added to a pyridine (11 mL) solution of phosphorous acid (329 mg, 4.0 mmol) at 40° C., and the mixture was stirred for 32 minutes. Compound 21 (synthesized in accordance with the method described in WO 2014/077292) (492 mg, 0.39 mmol) was added to the above solution, and a wash was made with pyridine (0.40 mL). Stirring was performed at 40° C. for 3 hours and 40 minutes, and acetonitrile was added to precipitate a solid. The mixture was cooled with ice and was filtered to give Compound 22 (495 mg) as a light yellow solid.

$^1$H-NMR: (300 MHz; CDCl$_3$) δ0.88 (t, 9H), 1.17-1.83 (m, 96H), 1.97 (d, 3H), 2.18 (s, 3H), 2.33-2.44 (m, 2H), 2.54-2.58 (m, 2H), 2.73-2.79 (m, 2H), 3.95-4.05 (m, 6H), 4.20 (t, 1H), 4.27 (d, 2H), 5.37 (d, 1H), 6.38 (t, 1H), 7.10 (s, 2H), 6.94 (d, 1H), 7.76 (d, 1H).
$^{31}$P-NMR: (300 MHz; CDCl$_3$) δ6.62.

Step 2: Synthesis of Compound 23

In a nitrogen atmosphere, 2,2-dimethylbutyryl chloride (0.14 mL, 1.0 mmol) was added to a pyridine (9 mL) solution of Compound 22 (453 mg) and Compound 1 (177 mg, 0.50 mmol) at 25° C., and the mixture was stirred for 28 minutes. 2,2-Dimethylbutyryl chloride (0.14 mL, 1.0 mmol) was added, and the mixture was stirred for 44 minutes. Thereafter, a 0.1 M solution of iodine in pyridine, THF and water (4.0 mL, 0.40 mmol) was added, and the mixture was stirred for 1 hour and 36 minutes. Trimethyl phosphite (7.8 μL, 0.066 mmol) was added. Acetonitrile was added to the reaction mixture to precipitate a solid. The mixture was vacuum concentrated, and acetonitrile was added. The mixture was cooled with ice and filtered to give Compound 23 (478 mg) as a light brown solid.

$^1$H-NMR: (300 MHz; CDCl$_3$) δ0.095-0.13 (m, 6H), 0.85-0.97 (m, 18H), 1.08-1.83 (m, 96H), 1.89-1.95 (m, 6H), 2.06-2.39 (m, 7H), 2.54-2.65 (m, 2H), 2.75-2.82 (m, 2H), 3.86-4.30 (m, 12H), 4.90-5.39 (m, 2H), 6.12-6.40 (m, 2H), 7.12 (d, 2H), 7.45-7.82 (m, 2H).
$^{31}$P-NMR: (300 MHz; CDCl$_3$) δ−1.27.

Example 12 (Synthesis of 2-mer): Synthesis of Compound 26

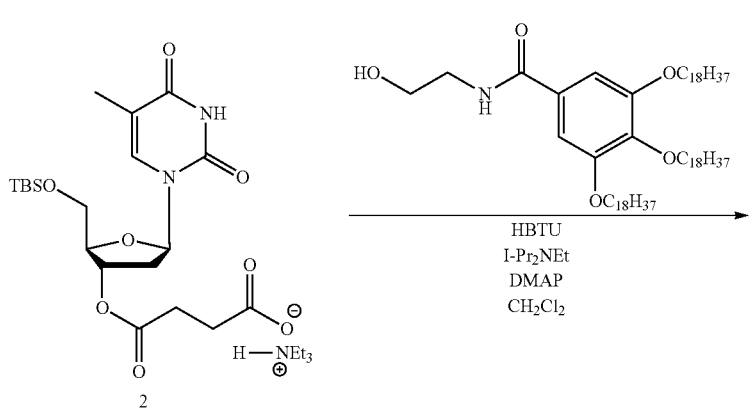

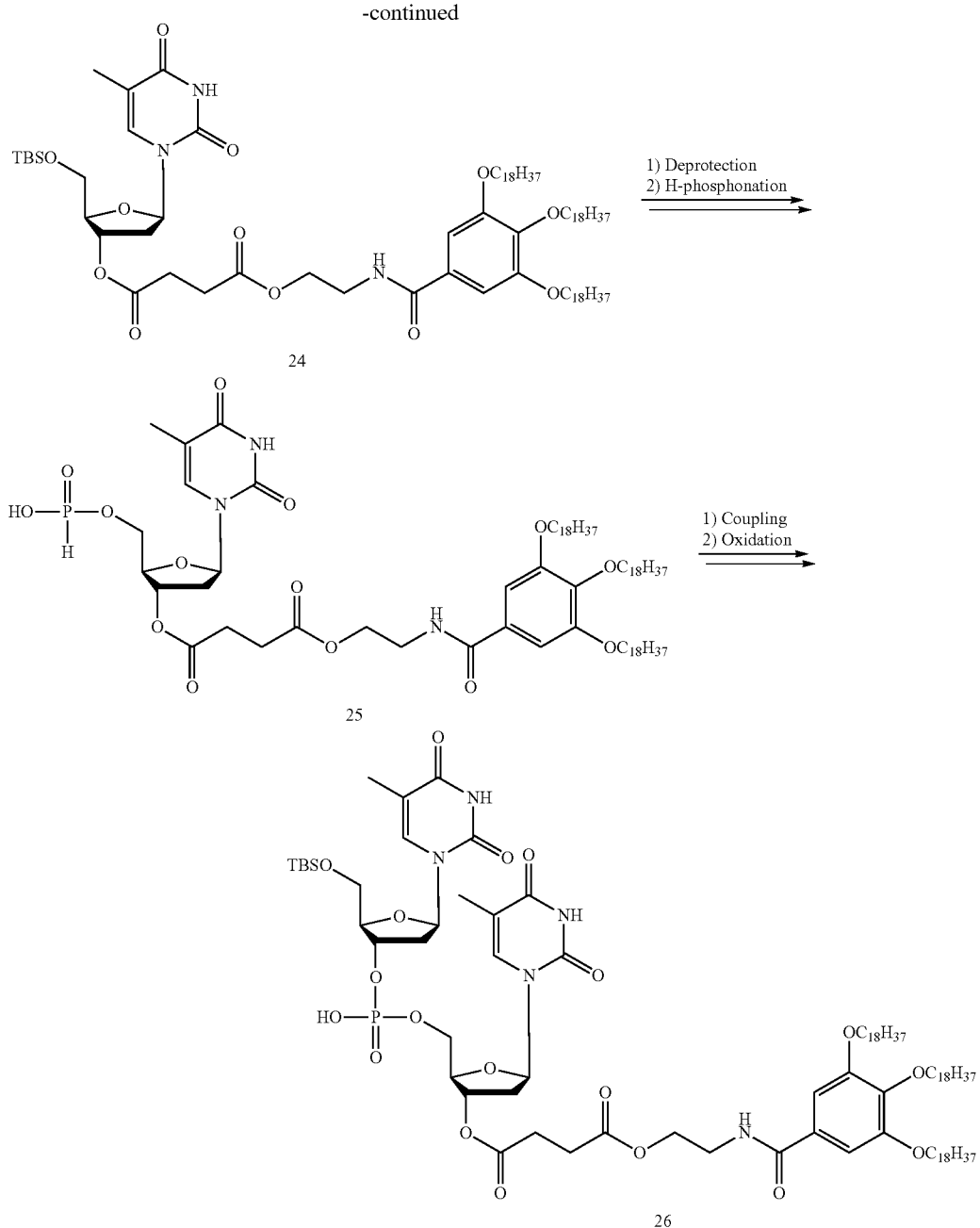

Step 1: Synthesis of Compound 24

In a nitrogen atmosphere, 2-(1H-benzotriazol-1-yl)-1,1,3,3-tetramethyluronium hexafluorophosphate [HBTU] (77 mg, 0.20 mmol), diisopropylethylamine (35 µL, 0.21 mmol) and dimethylaminopyridine (25 mg, 0.20 mmol) were added to a methylene chloride (1 mL) solution of Compound 2 (89 mg, 0.16 mmol) and N-(2-hydroxyethyl)-3,4,5-tris(octadecyloxy)benzamide (synthesized in accordance with the method described in Japanese Patent Application Kokai Publication No. 2001-122889) (100 mg, 0.10 mmol) at 40° C., and the mixture was stirred for 1 hour and 21 minutes. Methanol was added to the reaction mixture, and the resultant solid was recovered by filtration. Consequently, Compound 24 (135 mg, yield 93%) was obtained as a white solid.

$^1$H-NMR: (300 MHz; CDCl$_3$) δ0.096 (s, 3H), 0.11 (s, 3H), 0.88 (t, 9H), 0.91 (s, 9H), 1.12-1.84 (m, 96H), 1.92 (d, 3H), 2.04-2.14 (m, 1H), 2.34-2.41 (m, 1H), 2.68 (brs, 4H), 3.70 (q, 2H), 3.86 (s, 2H), 3.96-4.02 (m, 6H), 4.07 (s, 1H), 4.32 (t, 2H), 5.25 (d, 1H), 6.29-6.34 (m, 1H), 6.55 (t, 1H), 6.98 (s, 2H), 7.52 (d, 1H), 8.07 (brs, 1H).

MS (ESI$^+$): [M+H]$^+$ 1409.0956.

Step 2: Synthesis of Compound 25

In a nitrogen atmosphere, hydrogen fluoride-pyridine (8.3 µL, 0.32 mmol) was added to a methylene chloride (0.5 mL) solution of Compound 24 (99 mg, 0.070 mmol) at 40° C., and the mixture was stirred for 3 hours and 34 minutes. Hexamethyldisiloxane [TMS$_2$O] (53 mL, 0.25 mmol) was added. Pyridine (1 mL) was added. The mixture was vacuum concentrated. Again, pyridine (1 mL) was added, and the mixture was vacuum concentrated. Pyridine (0.8 mL) was added to give a pyridine solution of the deprotected compound.

In a nitrogen atmosphere, 2,2-dimethylbutyryl chloride (59 μL, 0.43 mmol) was added to a pyridine (2 mL) solution of phosphorous acid (57 mg, 0.693 mmol) at 40° C., and the mixture was stirred for 31 minutes. The pyridine solution of the deprotected compound was added to this mixture, and a wash was made with pyridine (0.5 mL). Stirring was performed at 40° C. for 1 hour and 12 minutes. 2,2-Dimethylbutyryl chloride (15 μL, 0.11 mmol) was added, and the mixture was stirred for 1 hour and 17 minutes. Acetonitrile was added to the reaction mixture to precipitate a solid. The mixture was cooled with ice and was thereafter filtered to give Compound 25 (78 mg) as a white solid.

$^1$H-NMR: (300 MHz; CDCl$_3$) δ0.88 (t, 9H), 1.18-1.83 (m, 96H), 1.91 (s, 3H), 2.19-2.36 (m, 2H), 2.65 (brs, 4H), 3.69 (brs, 2H), 3.95-4.01 (m, 6H), 4.13 (s, 1H), 4.17 (s, 1H), 4.20 (s, 1H), 4.32 (t, 2H), 5.28 (d, 1H), 6.29 (q, 1H), 6.80 (brs, 1H), 6.88 (d, 1H), 7.00 (s, 2H), 7.53 (s, 1H).
$^{31}$P-NMR: (300 MHz; CDCl$_3$) δ6.86.
MS (ESI$^-$): [M−H]$^-$ 1356.9650.

Step 3: Synthesis of Compound 26

In a nitrogen atmosphere, 2,2-dimethylbutyryl chloride (35 μL, 0.25 mmol) was added to a pyridine (1.4 mL) solution of Compound 25 (69 mg) and Compound 1 (28 mg, 78 mmol) at 25° C., and the mixture was stirred for 48 minutes. Thereafter, a 0.1 M solution of iodine in pyridine, THF and water (0.6 mL, 0.060 mmol) was added, and the mixture was stirred for 1 hour. Trimethyl phosphite (1.2 μL, 0.010 mmol) was added. The reaction mixture was vacuum concentrated. Acetonitrile was added, and the mixture was cooled with ice and was filtered to give Compound 26 (76 mg) as a light brown solid.

$^1$H-NMR: (300 MHz; CDCl$_3$) δ0.087-0.12 (m, 6H), 0.85-0.95 (m, 18H), 1.17-1.78 (m, 96H), 1.86-1.89 (m, 6H), 2.02-2.65 (m, 8H), 3.67-4.30 (m, 16H), 4.92-5.36 (m, 2H), 6.12-6.32 (m, 2H), 6.90 (brs, 1H), 6.99-7.03 (m, 2H), 7.45-7.60 (m, 2H).
$^{31}$P-NMR: (300 MHz; CDCl$_3$) δ−1.11.

Example 13 (Synthesis of 2-mer Using RNA): Synthesis of Compound 27

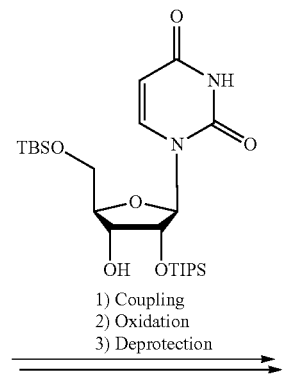

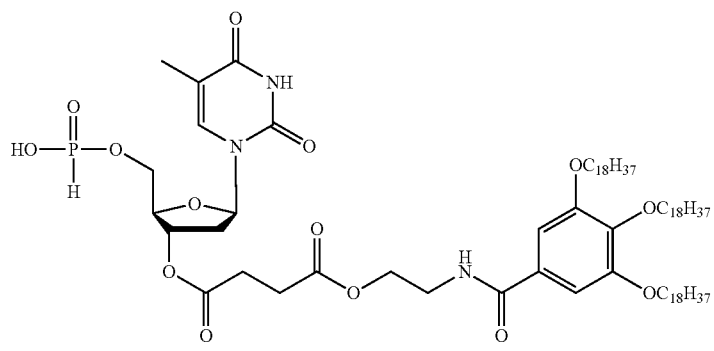

25

1) Coupling
2) Oxidation
3) Deprotection

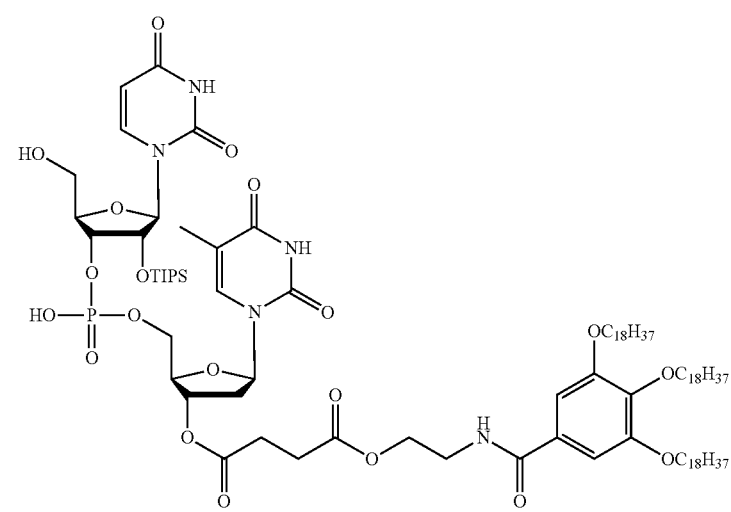

27

In a nitrogen atmosphere, 2,2-dimethylbutyryl chloride (9.4 μL, 69 μmol) was added to a pyridine (0.50 mL) solution of Compound 25 (9.4 mg) and 5'-O-(tert-butyldimethylsilyl)-2'-O-triisopropylsilyluridine (described in Reference Synthetic Example 2) (5.3 mg, 10 mmol) at 40° C., and the mixture was stirred for 37 minutes. Thereafter, a 0.05 M solution of iodine in pyridine and water (0.17 mL, 8.5 μmol) was added, and the mixture was stirred for 4 hours. Thereafter, the mixture was stirred at 80° C. for 15 hours and 23 minutes. The reaction mixture was vacuum concentrated to give Compound 27.

MS (ESI⁻): [M−H]⁻ 1755.1612.

Example 14 (Continuous Coupling and Deprotection): Synthesis of Compound 28

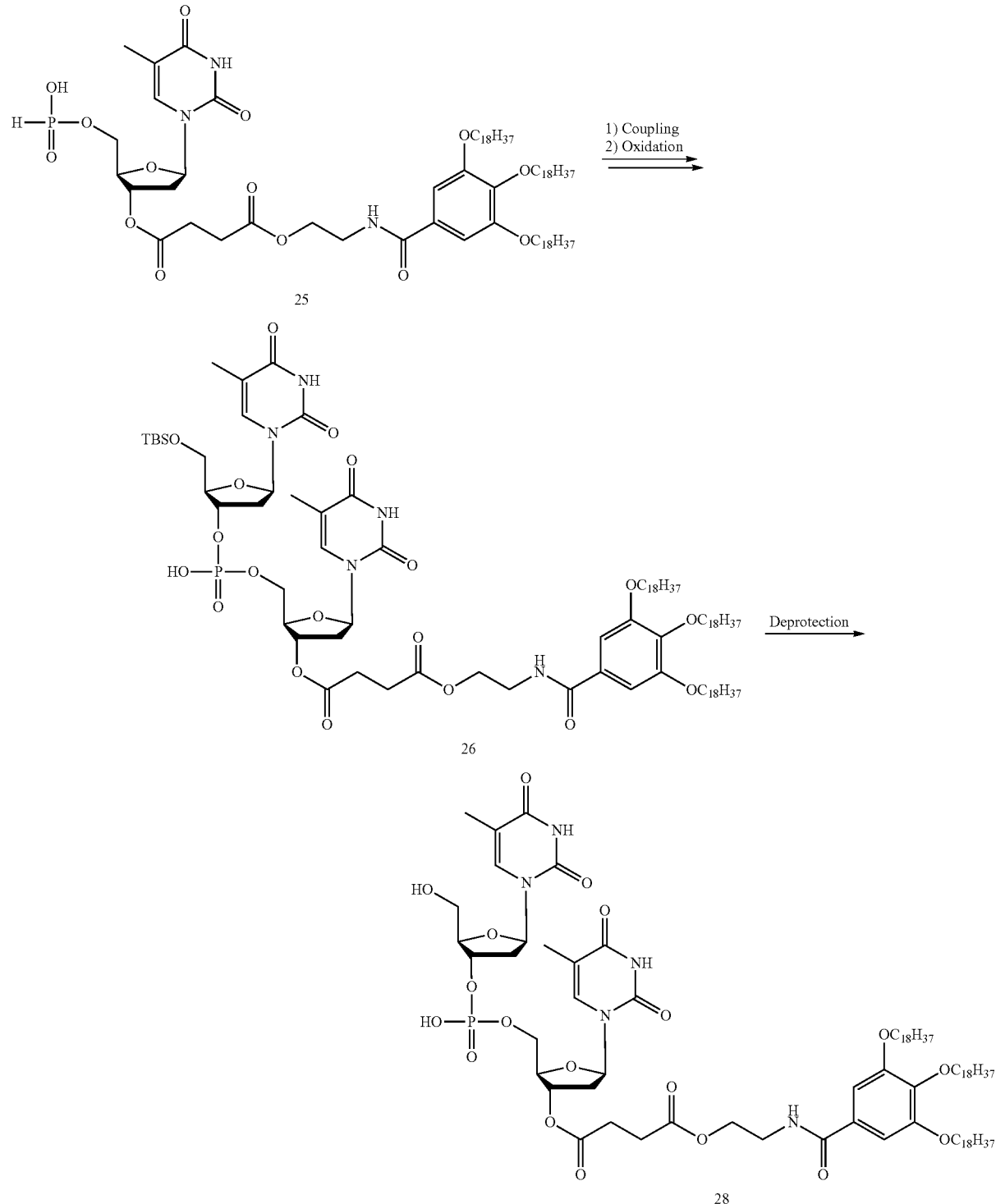

In a nitrogen atmosphere, 2,2-dimethylbutyryl chloride (47 μL, 0.34 mmol) was added to a pyridine (5.0 mL) solution of Compound 25 (100 mg) and Compound 1 (38 mg, 0.11 mmol) at 25° C., and the mixture was stirred for 14 minutes. Thereafter, a 0.05 M solution of iodine in pyridine and water (1.7 mL, 0.085 mmol) was added, and the mixture was stirred for 55 minutes. Further, a 0.05 M solution of iodine in pyridine and water (0.41 mL, 0.021 mmol) was added, and the mixture was stirred for 38 minutes. Thereafter, dimethyl phosphite (0.63 μL, 0.0069 mmol) was added, and the mixture was stirred at 100° C. for 5 hours and 57 minutes. The reaction mixture was cooled and added to acetonitrile (41 g) to precipitate a solid. The mixture was cooled with ice and filtered to give Compound 28 (0.11 g) as a skin color solid.

$^1$H-NMR: (300 MHz; CDCl$_3$) δ0.88 (t, 9H), 1.17-1.82 (m, 96H), 1.86 (s, 3H), 2.23-2.34 (m, 4H), 2.64 (brs, 4H), 3.67-4.31 (m, 16H), 5.04 (brs, 1H), 5.41 (s, 1H), 6.13 (t, 1H), 6.29 (t, 1H), 6.97-7.00 (m, 1H), 7.02 (s, 2H), 7.26-7.63 (m, 2H), 9.28 (brs, 2H).

$^{31}$P-NMR: (300 MHz; CDCl$_3$) δ−0.069.

Example 15 (Coupling using Bispentafluorophenyl Carbonate as Condensing Agent): Synthesis of Compound 29

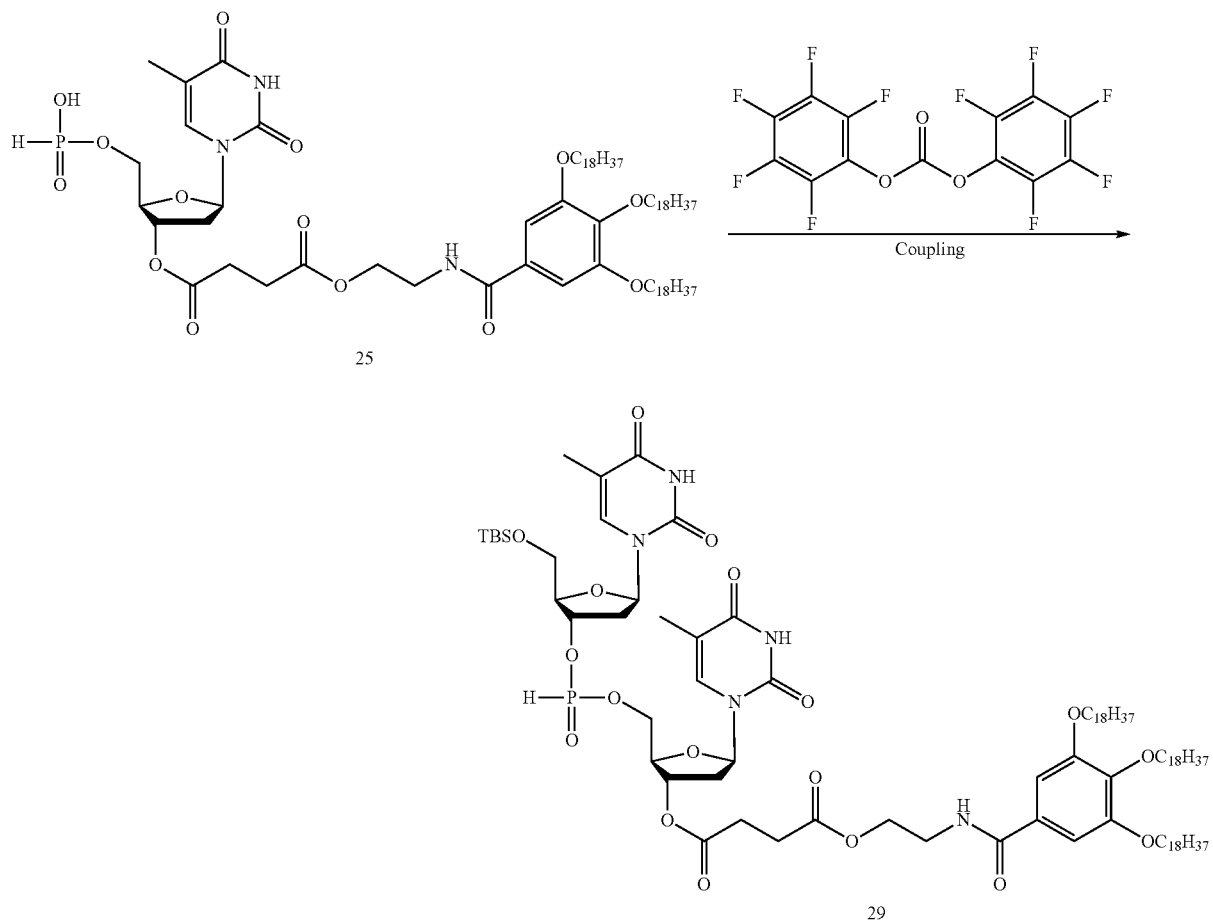

In a nitrogen atmosphere, bispentafluorophenyl carbonate (15.4 mg, 0.039 mmol) was added to a pyridine (0.50 mL) solution of Compound 25 (10 mg) and Compound 1 (4.2 mg, 0.012 mmol) at 25° C., and the mixture was stirred for 20 minutes. The reaction mixture was vacuum concentrated. Consequently, Compound 29 was obtained as the main product.

MS (ESI$^-$): [M−H]$^-$ 1711.1424.

Example 16 (1 Cycle Using Benzoyl Chloride as Condensing Agent): Synthesis of Compound 30
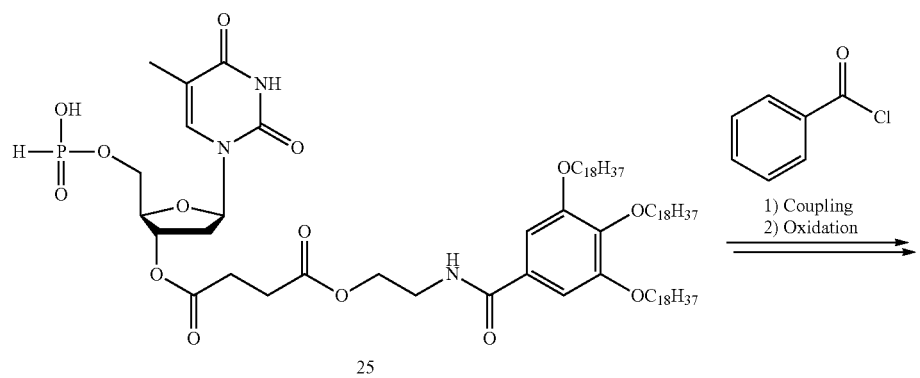
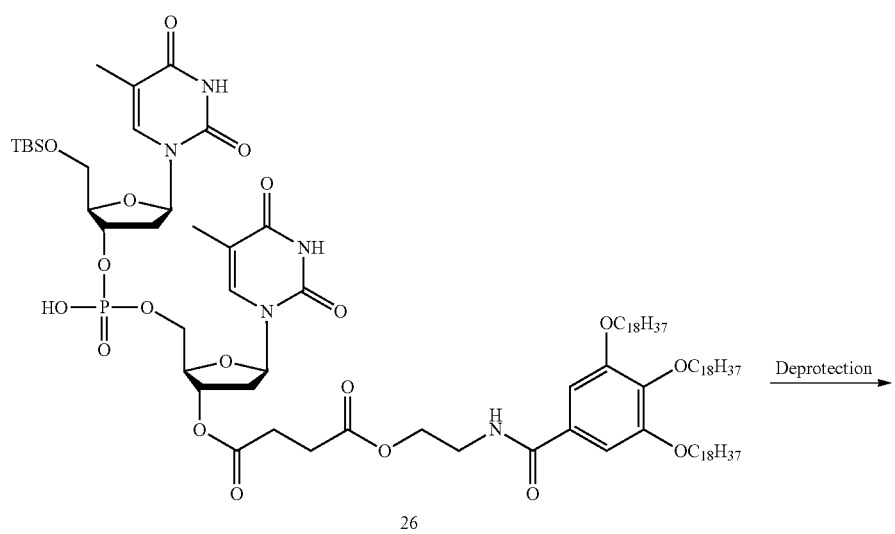
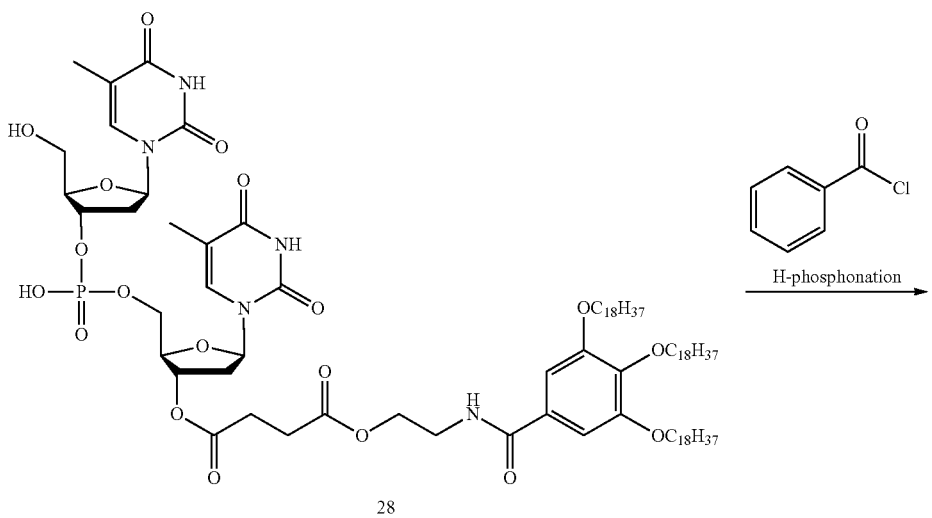

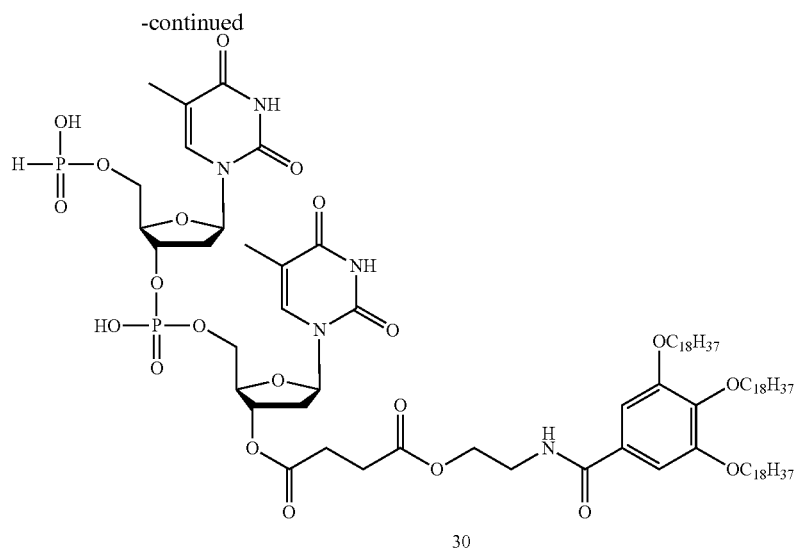

In a nitrogen atmosphere, benzoyl chloride (24 µL, 0.21 mmol) was added to a pyridine (5.0 mL) solution of Compound 25 (102 mg) and Compound 1 (39 mg, 0.11 mmol) at 25° C., and the mixture was stirred for 15 minutes. Thereafter, a 0.05 M solution of iodine in pyridine and water (2.1 mL, 0.11 mmol) was added, and the mixture was stirred for 36 minutes. Thereafter, dimethyl phosphite (3.2 µL, 0.035 mmol) was added. The mixture was stirred at 100° C. for 4 hours and 31 minutes. The reaction mixture was vacuum concentrated. Pyridine (5.0 mL) was added, and the mixture was vacuum concentrated. Thereafter, pyridine (5.0 mL) was added. Phosphorous acid (56 mg, 0.68 mmol) was added. At 40° C., benzoyl chloride (50 µL, 0.43 mmol) was added in three portions every 10 minutes. The mixture was stirred for 2 hours and 35 minutes. Benzoyl chloride (8.3 µL, 0.071 mmol) was added, and the mixture was stirred for 54 minutes. Thereafter, the reaction mixture was added to acetonitrile (44 g), and the resultant solid was recovered by filtration. Consequently, Compound 30 (0.11 g) was obtained as a light brown solid.

$^1$H-NMR: (300 MHz; CDCl$_3$) δ0.87 (t, 9H), 1.08-1.99 (m, 102H), 2.23-2.63 (m, 8H), 3.67 (brs, 2H), 3.96 (t, 6H), 4.15-4.27 (m, 6H), 5.08 (brs, 1H), 5.35 (s, 1H), 6.16 (s, 1H), 6.24 (s, 1H), 6.83 (d, 1H), 7.04 (s, 2H), 7.13 (brs, 1H), 7.47 (s, 1H), 7.53 (s, 1H), 9.86 (brs, 2H).

$^{31}$P-NMR: (300 MHz; CDCl$_3$) δ−1.59, 5.89.

Example 17 (1 Cycle with DNA and Continuous Deprotection): Synthesis of Compound 35

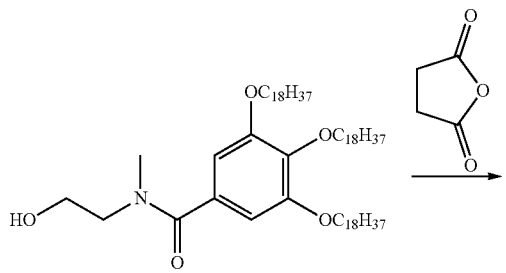

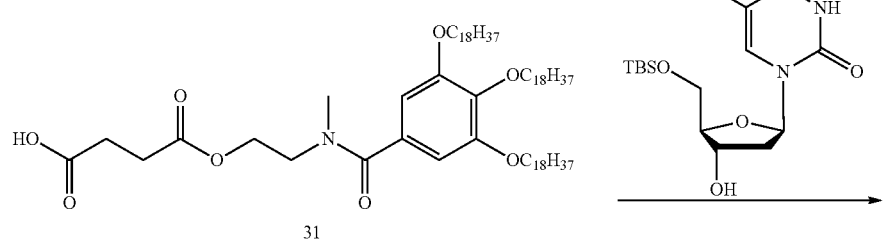

-continued
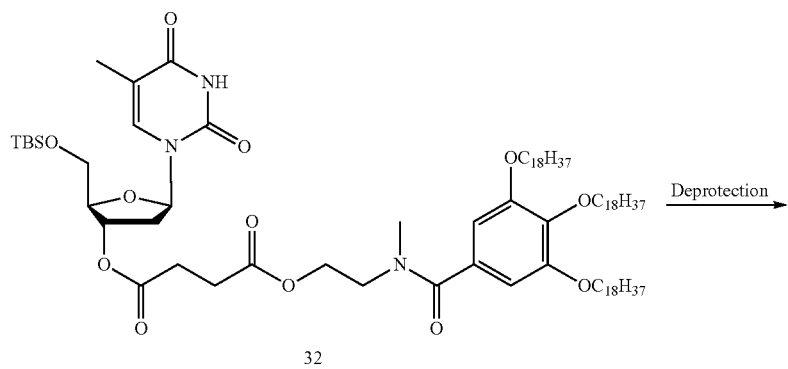
32
Deprotection →
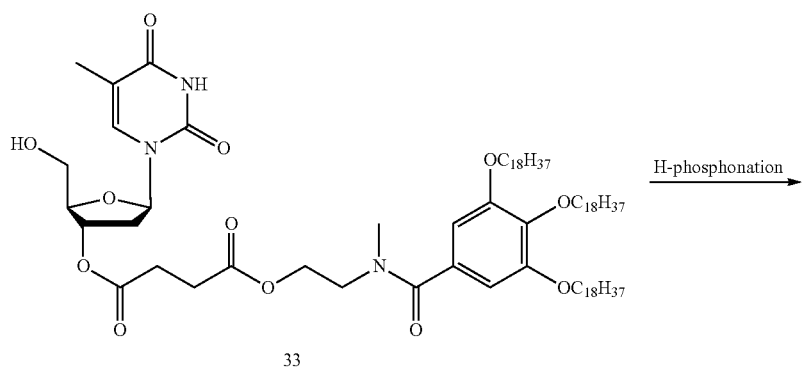
33
H-phosphonation →
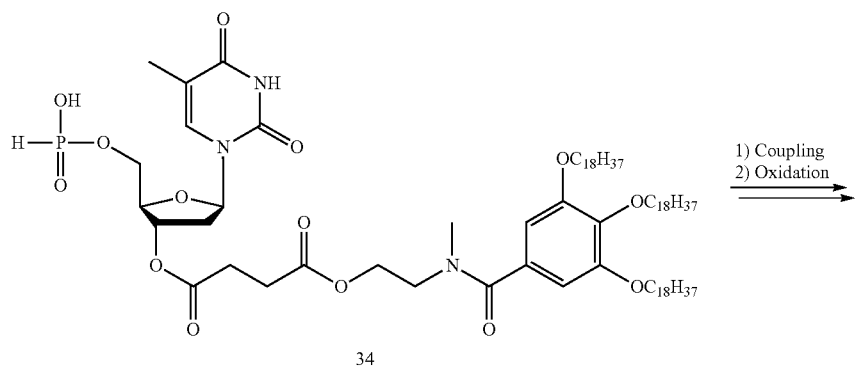
34
1) Coupling
2) Oxidation
⇒
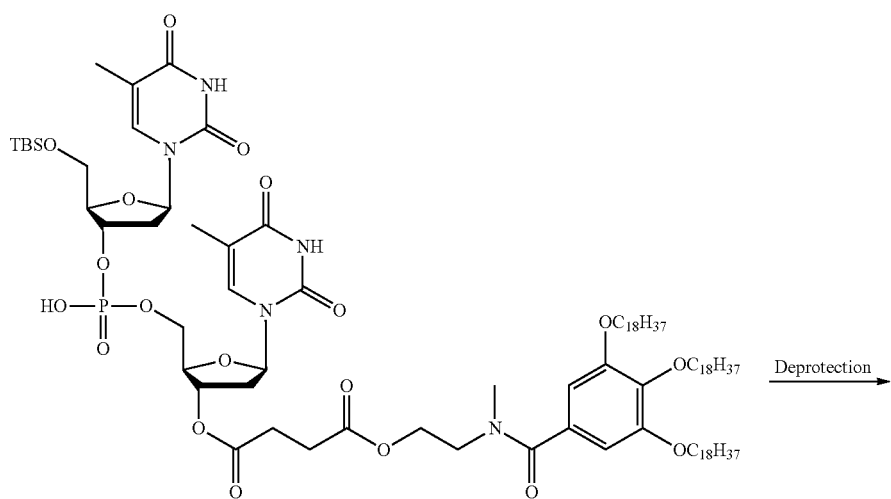
Deprotection →

-continued

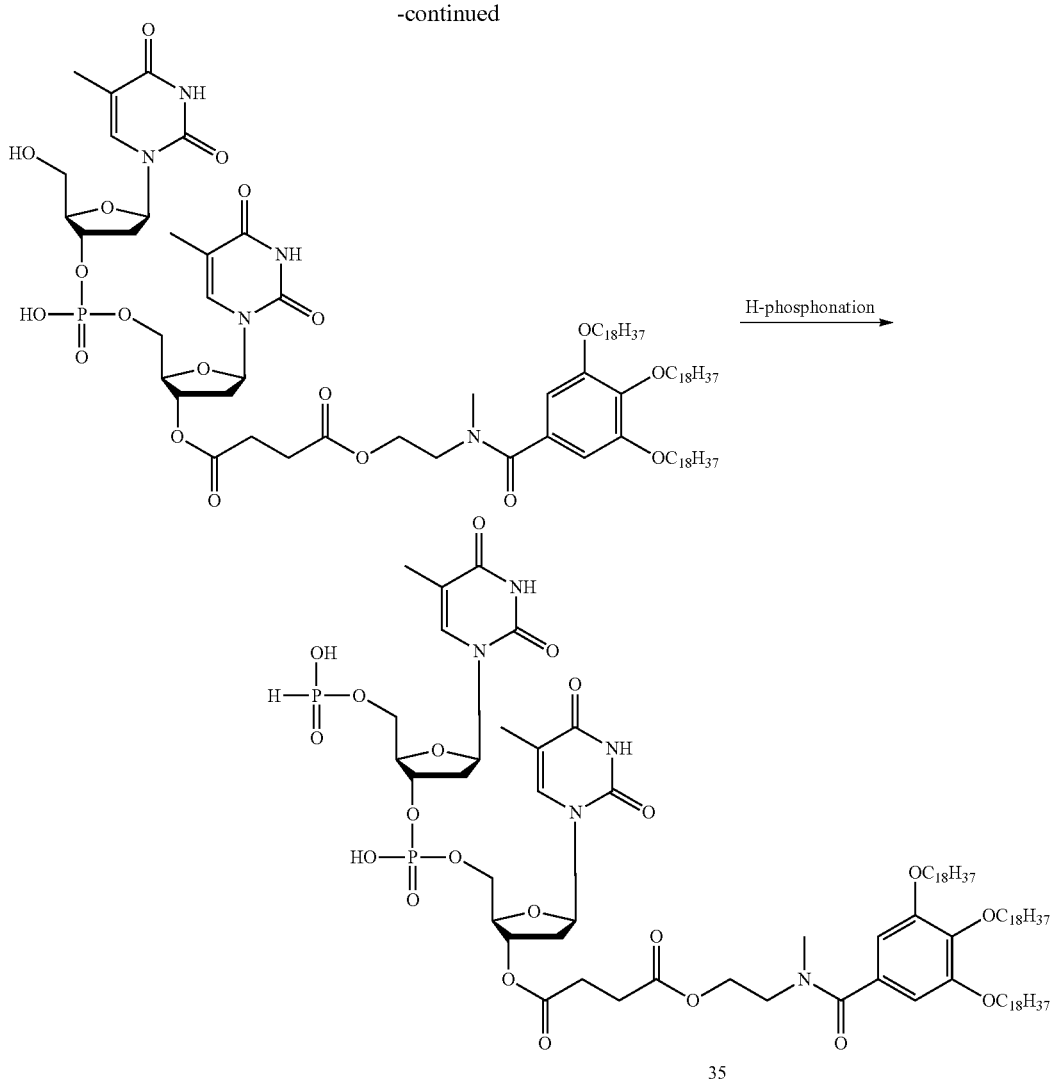

Step 1: Synthesis of Compound 31

In a nitrogen atmosphere, triethylamine (2.1 mL, 15 mmol) was added to a methylene chloride (50 g) solution of N-(2-hydroxyethyl)-N-methyl-3,4,5-tris(octadecyloxy)benzamide (synthesized in accordance with the method described in Japanese Patent Application Kokai Publication No. 2001-253896) (5.0 g, 5.1 mmol) and succinic anhydride (1.0 g, 10 mmol) at room temperature, and the mixture was stirred for 1 hour and 57 minutes. Thereafter, the reaction mixture was added to acetonitrile (513 g) to precipitate a solid, which was then recovered by filtration. Consequently, Compound 31 (5.3 g, yield 95%) was obtained as a white solid.

$^1$H-NMR: (300 MHz; CDCl$_3$) δ0.86-0.90 (m, 9H), 1.09-1.84 (m, 96H), 2.65 (s, 4H), 3.05 (s, 3H), 3.76 (brs, 2H), 3.96 (t, 6H), 4.38 (brs, 2H), 6.58 (s, 2H).

MS (ESI): [M–H]$^-$ 1082.9343.

Step 2: Synthesis of Compound 32

In a nitrogen atmosphere, HBTU (0.70 g, 1.8 mmol), diisopropylethylamine (0.31 mL, 1.8 mmol) and DMAP (0.23 g, 1.9 mmol) were added to a methylene chloride (25 mL) solution of Compound 31 (1.0 g, 0.92 mmol) and Compound 1 (0.51 g, 1.4 mmol) at room temperature, and the mixture was stirred for 1 hour and 9 minutes. Thereafter, the reaction mixture was added to methanol (102 g), and the resultant solid was recovered by filtration. Consequently, Compound 32 (1.3 g, yield 99%) was obtained as a white solid.

$^1$H-NMR: (300 MHz; CDCl$_3$) δ0.13 (s, 6H), 0.86-0.94 (m, 18H), 1.09-1.84 (m, 96H), 1.92 (s, 3H), 2.14-2.43 (m, 2H), 2.66 (brs, 4H), 3.06 (s, 3H), 3.68 (brs, 2H), 3.90-3.98 (m, 8H), 4.10 (s, 1H), 4.34 (brs, 2H), 5.27 (d, 1H), 6.34 (q, 1H), 6.57 (s, 2H), 7.54 (s, 1H), 8.07 (brs, 1H).

MS (ESI$^-$): [M–H]$^-$ 1421.1060.

Step 3: Synthesis of Compound 33

In a nitrogen atmosphere, a 1.0 M TBAF/THF solution (0.95 mL, 0.95 mmol) was added to a THF (10 mL) solution of Compound 32 (1.2 g, 0.86 mmol) at room temperature, and the mixture was stirred for 1 hour and 10 minutes. Thereafter, the reaction mixture was added to methanol (123 g), and the resultant solid was recovered by filtration. Consequently, Compound 33 (1.2 g, quantitative) was obtained as a light skin color solid.

$^1$H-NMR: (300 MHz; CDCl$_3$) δ0.88 (t, 9H), 1.03-1.84 (m, 96H), 1.92 (s, 3H), 2.36-2.41 (m, 2H), 2.65 (brs, 4H), 3.06 (s, 3H), 3.75 (brs, 2H), 3.86 (brs, 2H), 3.93-3.98 (m, 6H), 4.07 (d, 1H), 4.36 (brs, 2H), 5.30-5.34 (m, 1H), 6.21 (t, 1H), 6.59 (s, 2H), 7.51 (s, 1H), 8.21 (brs, 1H).

MS (ESI$^-$): [M–H]$^-$ 1307.0241.

Step 4: Synthesis of Compound 34

In a nitrogen atmosphere, 2,2-dimethylbutyryl chloride (0.68 mL, 5.0 mmol) was added to a pyridine (20 mL) solution of phosphorous acid (0.63 g, 7.6 mmol) at 40° C., and the mixture was stirred for 32 minutes. Compound 33 (1.0 g, 0.77 mmol) was added to the above solution, and the mixture was stirred at 40° C. for 3 hours and 3 minutes. 2,2-Dimethylbutyryl chloride (52 μL, 0.38 mmol) was added, and the mixture was stirred for 1 hour and 4 minutes. Thereafter, the reaction mixture was added to acetonitrile (210 g), and the resultant solid was recovered by filtration. Consequently, Compound 34 (1.0 g) was obtained as a white solid.

$^1$H-NMR: (300 MHz; CDCl$_3$) δ0.88 (t, 9H), 1.10-1.81 (m, 96H), 1.91 (s, 3H), 2.33-2.37 (m, 2H), 2.66 (brs, 4H), 3.06 (s, 3H), 3.68-3.80 (brs, 2H), 3.94-4.36 (m, 11H), 6.36 (q, 1H), 6.59 (s, 2H), 6.90 (d, 1H), 7.60 (s, 1H).

$^{31}$P-NMR: (300 MHz; CDCl$_3$) δ6.56.

MS (ESI$^-$): [M–H]$^-$ 1370.9904.

Step 5: Synthesis of Compound 35

In a nitrogen atmosphere, 2,2-dimethylbutyryl chloride (49 μL, 0.36 mmol) was added to a pyridine (2.0 mL) solution of Compound 34 (106 mg) and Compound 1 (43 mg, 0.12 mmol) at 25° C., and the mixture was stirred for 30 minutes. Thereafter, a 0.05 M solution of iodine in pyridine and water (2.0 mL, 0.10 mmol) was added, and the mixture was stirred for 38 minutes. Further, a 0.05 M solution of iodine in pyridine and water (0.13 mL, 0.0063 mmol) was added, and the mixture was stirred for 10 minutes. Thereafter, dimethyl phosphite (3.3 μL, 0.036 mmol) was added, and the mixture was stirred at 100° C. for 3 hours and 33 minutes. The reaction mixture was vacuum concentrated, and pyridine (5.0 mL) was added. Again, the mixture was vacuum concentrated and thereafter pyridine (1.5 mL) was added.

In a nitrogen atmosphere, 2,2-dimethylbutyryl chloride (64 μL, 0.46 mmol) was added to a pyridine (2.0 mL) solution of phosphorous acid (64 mg, 0.77 mmol) at 40° C., and the mixture was stirred for 28 minutes. The above reaction mixture including the deprotected compound was added to this solution, and the mixture was stirred at 40° C. for 1 hour and 5 minutes. 2,2-Dimethylbutyryl chloride (20 μL, 0.14 mmol) was added, and the mixture was stirred for 1 hour and 12 minutes. Thereafter, the reaction mixture was added to acetonitrile (51 g), and the resultant solid was recovered by precipitation filtration. Consequently, Compound 35 (0.12 g) was obtained as a brown solid.

$^1$H-NMR: (300 MHz; CDCl$_3$) δ0.88 (t, 9H), 1.15-1.89 (m, 102H), 2.23-2.38 (m, 4H), 2.66 (brs, 4H), 3.05 (s, 3H), 3.72 (brs, 2H), 3.93-4.35 (m, 14H), 5.11 (brs, 1H), 5.37 (s, 1H), 6.17 (brs, 1H), 6.28 (t, 1H), 6.58 (s, 2H), 6.83 (d, 1H), 7.46 (s, 1H), 7.54 (s, 1H), 9.61 (brs, 2H).

$^{31}$P-NMR: (300 MHz; CDCl$_3$) δ–1.52, 6.01.

MS (ESI$^-$): [M–H]$^-$ 1675.0476.

Examples 18 to 29 (Comparison of Condensing Agents): Synthesis of Compound 29

Compound 29 was obtained by performing the reaction under the same conditions as in Example 15, except that the condensing agent was changed to HBTU (16.1 mg, Example 18), 1,1'-carbonyldiimidazole [CDI] (5.6 mg, Example 19), methanesulfonyl chloride [MsCl] (2.8 μL, Example 20), (benzotriazol-1-yloxy)tripyrolidinophosphonium hexafluorophosphate [PyBOP] (20.8 mg, Example 21), N,N'-dicyclohexylcarbodiimide [DCC] (9.1 mg, Example 22), trifluoroacetic anhydride [TFAA] (4.7 μL, Example 23), pentafluorophenyl trifluoroacetate (6.1 μL, Example 24), p-toluenesulfonyl chloride (9.1 mg, Example 25), isobutyryl chloride (3.8 μL, Example 26), acetyl chloride (2.6 μL, Example 27), propionyl chloride (3.1 μL, Example 28) or butyryl chloride (3.7 μL, Example 29). In Examples 19, 20, 21, 22, 25 and 26, Compound 29 was obtained as the main product.

Example 30 (Synthesis of 2-mer Using Deoxycytidine): Synthesis of Compound 36

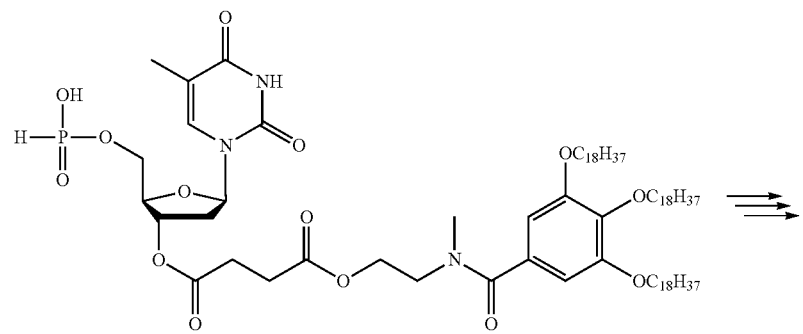

-continued

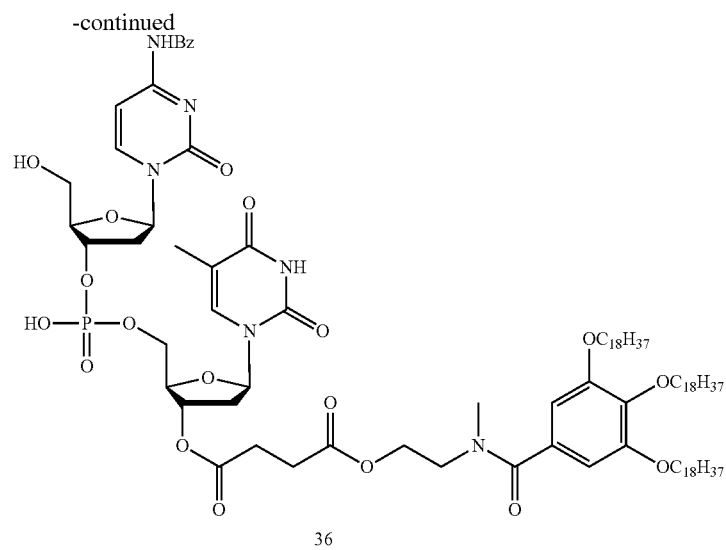

36

Compound 36 was obtained as the main product by performing the reaction under the same conditions as in Step 5 of Example 17, except that Compound 1 was replaced by $N^4$-benzoyl-5'-O-(tert-butyldimethylsilyl)-2'-deoxycytidine (manufactured by Tokyo Chemical Industry Co., Ltd.) (5.3 mg).

MS (ESI⁻): [M−H]⁻ 1700.0868.

Example 31 (Synthesis of 2-mer Using Deoxyadenosine): Synthesis of Compound 37

Compound 37 was obtained as the main product by performing the reaction under the same conditions as in Step 5 of Example 17, except that Compound 1 was replaced by $N^6$-benzoyl-5'-O-(tert-butyldimethylsilyl)-2'-deoxyadenosine (manufactured by Tokyo Chemical Industry Co., Ltd.) (5.4 mg).

MS (ESI⁺): [M+H]⁺ 1726.1283.

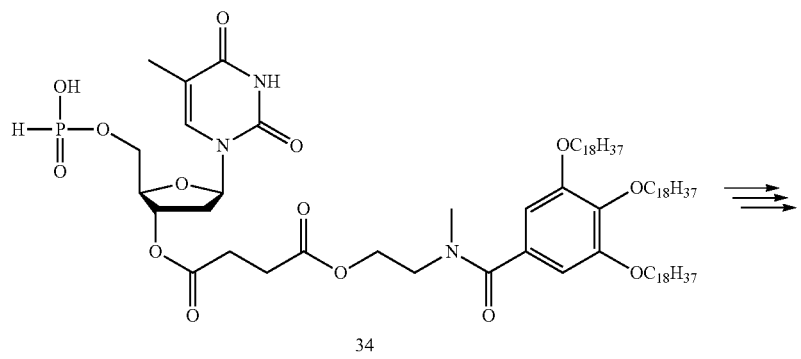

34

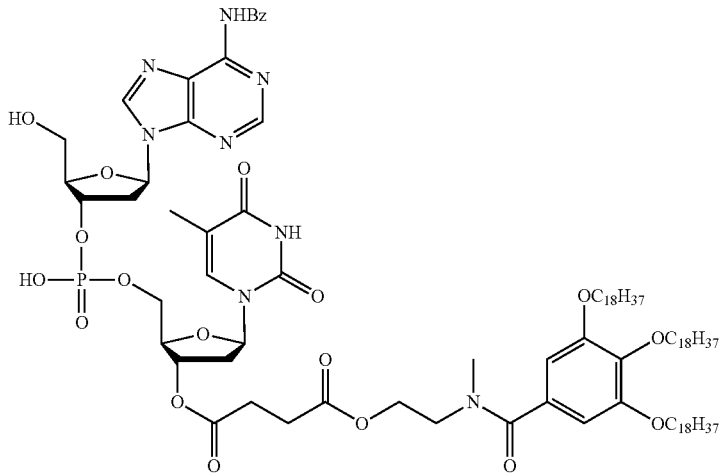

37

Example 32 (Synthesis of 2-mer Using Deoxyguanosine): Synthesis of Compound 38

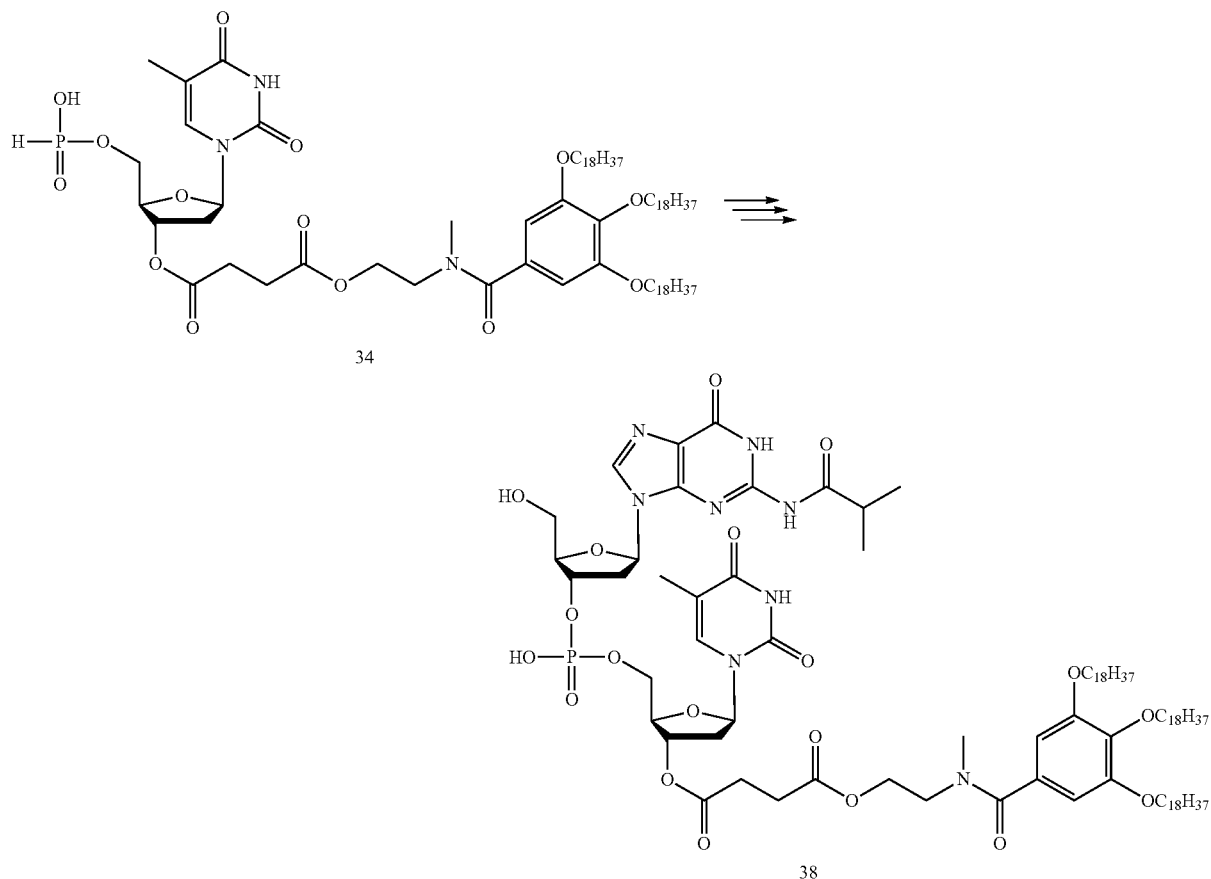

Compound 38 was obtained as the main product by performing the reaction under the same conditions as in Step 5 of Example 17, except that Compound 1 was replaced by $N^2$-isobutyryl-5'-O-(tert-butyldimethylsilyl)-2'-deoxyguanosine (manufactured by Tokyo Chemical Industry Co., Ltd.) (6.5 mg).

MS (ESI$^-$): [M−H]$^-$ 1706.1275.

Example 33 (Synthesis of Monomer and 2-Mer Having Pseudo Solid Phase-Protecting Group on Nucleobase): Synthesis of Compound 43

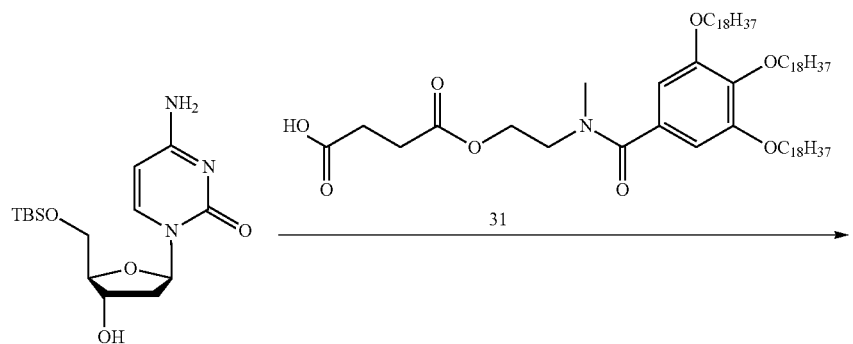

-continued
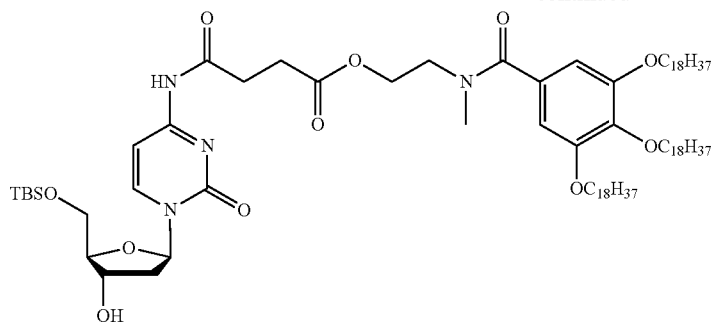
39
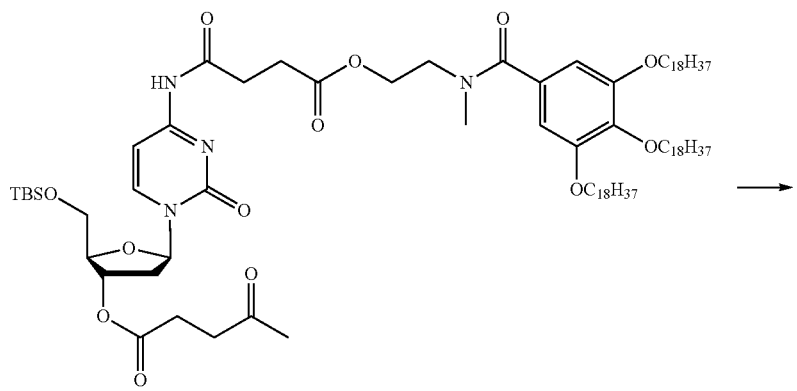
40
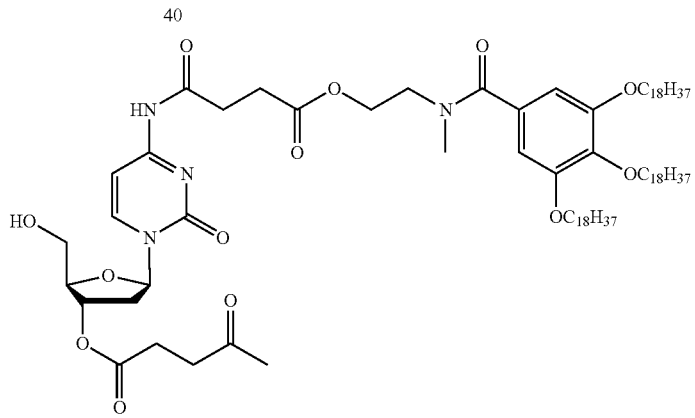
41
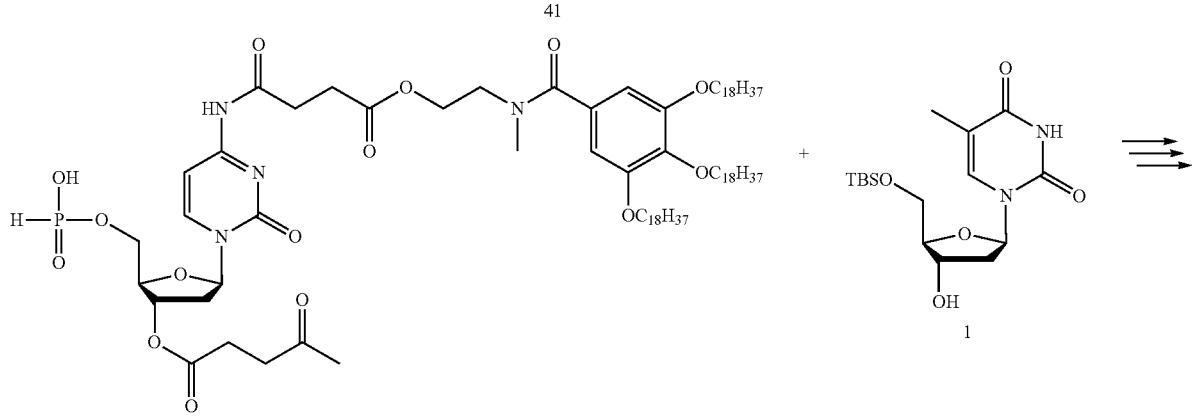
42

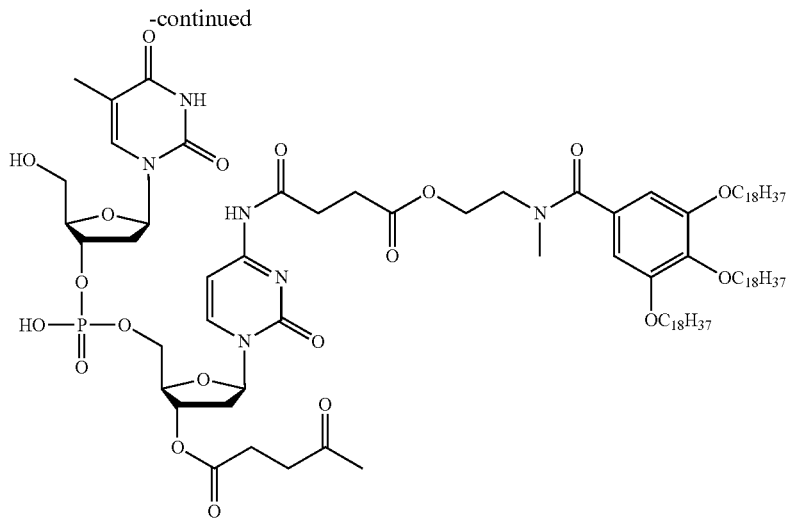

43

Step 1: Synthesis of Compound 39

In a nitrogen atmosphere, 1-hydroxybenzotriazole [HOBt] (anhydride) (0.74 g, 5.5 mmol) was added to a solution of 5'-O-(tert-butyldimethylsilyl)-2'-deoxycytidine (synthesized in accordance with the method described in The Journal of Organic Chemistry, 2011, vol. 76, pp. 105-126) (2.5 g, 7.3 mmol) and Compound 31 (5.3 g, 4.9 mmol) in a mixed solvent of methylene chloride (155 mL) and DMF (25 mL) at 40° C. Subsequently, 1-ethyl-3-(3-dimethylaminopropyl)carbodiimide hydrochloride salt [WSC.HCl] (1.9 g, 9.9 mmol) was added. The mixture was stirred for 1 hour and 40 minutes. The reaction mixture was vacuum concentrated, and the residue was added to methanol (503 g) to precipitate a solid. The mixture was then filtered. Consequently, Compound 39 (6.8 g, yield 98%) was obtained as a yellow solid.

$^1$H-NMR: (300 MHz; CDCl$_3$) δ0.09-0.10 (m, 6H), 0.84-0.90 (m, 18H), 1.20-1.81 (m, 96H), 2.12-2.21 (m, 1H), 2.28-2.36 (m, 1H), 2.61-2.77 (m, 5H), 3.05 (s, 3H), 3.76 (brs, 2H), 3.81-3.97 (m, 8H), 4.07 (q, 1H), 4.37 (brs, 2H), 4.40-4.45 (m, 1H), 6.29 (t, 1H), 6.57 (s, 2H), 7.31 (d, 1H), 8.31 (d, 1H), 8.88 (brs, 1H).

MS(ESI$^-$): [M−H]$^-$ 1406.1107.

Step 2: Synthesis of Compound 40

In a nitrogen atmosphere, WSC.HCl (1.4 g, 7.5 mmol) was added to a THF (69 g) solution of Compound 39 (6.7 g, 4.8 mmol), DMAP (0.062 g, 0.50 mmol) and levulinic acid (0.86 g, 7.4 mmol) at room temperature, and the mixture was stirred for 50 minutes. Thereafter, DMAP (0.26 g, 2.1 mmol) was added, and the mixture was stirred at room temperature for 3 days. The reaction mixture was filtered. The filtrate was vacuum concentrated, and the residue was dissolved by the addition of THF (38 g). The solution was added to acetonitrile (505 g), and the resultant solid was recovered by filtration. Consequently, Compound 40 (6.7 g, yield 93%) was obtained as a light yellow solid.

$^1$H-NMR: (300 MHz; CDCl$_3$) δ0.09 (s, 6H), 0.86-0.90 (m, 18H), 1.26-1.81 (m, 96H), 2.01-2.13 (m, 2H), 2.20 (s, 3H), 2.52-2.80 (m, 8H), 3.06 (s, 3H), 3.77 (brs, 2H), 3.86-3.98 (m, 8H), 4.20 (s, 1H), 4.38 (brs, 2H), 5.26 (d, 1H), 6.32-6.37 (m, 1H), 6.57 (s, 2H), 7.33 (d, 1H), 8.27 (d, 1H), 9.17 (brs, 1H).

MS (ESI): [M−H]$^-$ 1504.1412.

Step 3: Synthesis of Compound 41

In a nitrogen atmosphere, a 1.0 M TBAF/THF solution (28 mL, 28 mmol) was added to a THF (71 g) solution of Compound 37 (6.5 g, 4.3 mmol) and acetic acid (2.9 mL, 50 mmol) at 30° C., and the mixture was stirred for 4 hours and 53 minutes. Thereafter, the reaction mixture was added to methanol (531 g), and the resultant solid was recovered by filtration. Consequently, Compound 41 (6.0 g, quantitative) was obtained as a white solid.

$^1$H-NMR: (300 MHz; CDCl$_3$) δ0.88 (t, 9H), 1.20-1.80 (m, 96H), 2.20 (s, 3H), 2.38-2.80 (m, 10H), 3.05 (s, 3H), 3.78 (brs, 2H), 3.88-3.98 (m, 8H), 4.18 (d, 1H), 4.39 (brs, 2H), 5.36 (quint, 1H), 6.20 (dd, 1H), 6.59 (s, 2H), 7.21-7.31 (m, 1H), 8.19 (d, 1H).

MS (ESI): [M−H]$^-$ 1390.0541.

Step 4: Synthesis of Compound 42

In a nitrogen atmosphere, 2,2-dimethylbutyl chloride (1.28 mL, 9.3 mmol) was added to a pyridine (40 mL) solution of phosphorous acid (1.20 g, 14.6 mmol) at 40° C., and the mixture was stirred for 30 minutes. Compound 41 (2.0 g, 1.4 mmol) was added to this solution, and the mixture was stirred at 40° C. for 1 hour and 23 minutes. Thereafter, the reaction mixture was added to acetonitrile, and the resultant solid was recovered by filtration. Consequently, Compound 42 (2.2 g) was obtained as a white solid.

$^1$H-NMR: (300 MHz; CDCl$_3$) δ0.88 (t, 9H), 1.26-1.83 (m, 96H), 2.19 (s, 3H), 2.38-2.88 (m, 10H), 3.06 (s, 3H), 3.75 (brs, 2H), 3.92-4.35 (m, 11H), 5.37 (d, 1H), 6.17 (t, 1H), 6.58 (s, 2H), 6.88 (d, 1H), 7.26-7.28 (m, 1H), 8.51 (d, 1H).

$^{31}$P-NMR: (300 MHz; CDCl$_3$) δ5.73.

MS (ESI$^-$): [M−H]$^-$ 1454.0237.

Step 5: Synthesis of Compound 43

In a nitrogen atmosphere, 2,2-dimethylbutyryl chloride (45 μL, 0.33 mmol) was added to a pyridine (2.0 mL)

solution of Compound 42 (96 mg) and Compound 1 (36 mg, 0.10 mmol) at 40° C., and the mixture was stirred for 23 minutes. Thereafter, a 0.05 M solution of iodine in pyridine and water (2.6 mL, 0.13 mmol) was added, and the mixture was stirred for 1 hour and 29 minutes. Thereafter, dimethyl phosphite (3.0 μL, 0.033 mmol) was added. Water (0.26 mL, 14.4 mmol) was added, and thereafter the mixture was stirred at 70° C. for 15 hours and 55 minutes. The reaction mixture was vacuum concentrated. Consequently, Compound 43 was obtained as the main product.

MS (ESI⁻): [M–H]⁻ 1694.1110.

Example 34 (Synthesis of 2-mer): Synthesis of Compound 44 filtration, and the filtrate was washed with methylene chloride (6 g) two times. Hydrogen fluoride-pyridine (76.1 μL, 2.9 mmol) was added to this solution at room temperature, and the mixture was stirred for 18 hours and 57 minutes. TMSCl (0.29 mL, 2.3 mmol) was added, and the mixture was stirred for 17 minutes. Thereafter, the reaction mixture was vacuum concentrated. Pyridine was added, and the mixture was vacuum concentrated.

In a nitrogen atmosphere, 2,2-dimethylbutyryl chloride (0.80 mL, 5.8 mmol) was added to a pyridine (18 mL) solution of phosphorous acid (0.70 g, 8.5 mmol) at 40° C., and the mixture was stirred for 39 minutes. The above concentrate was added to this solution, and the mixture was stirred at 40° C. for 2 hours and 37 minutes. Thereafter, the

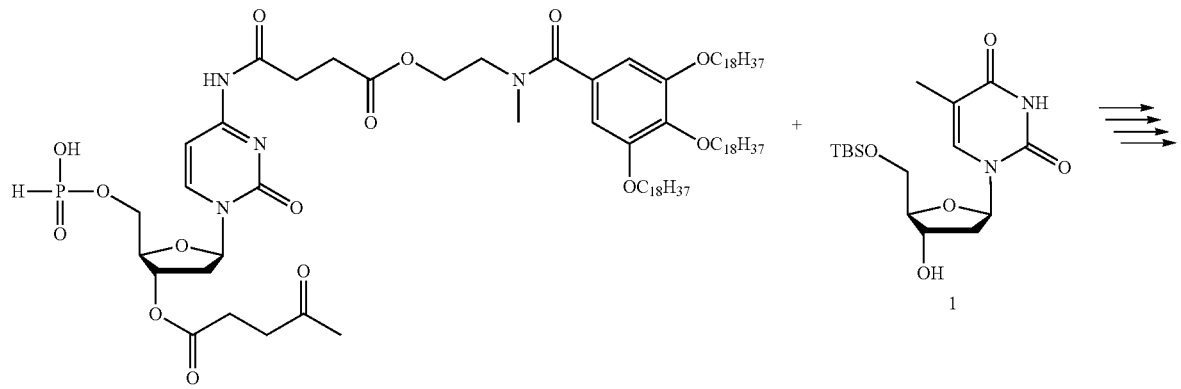

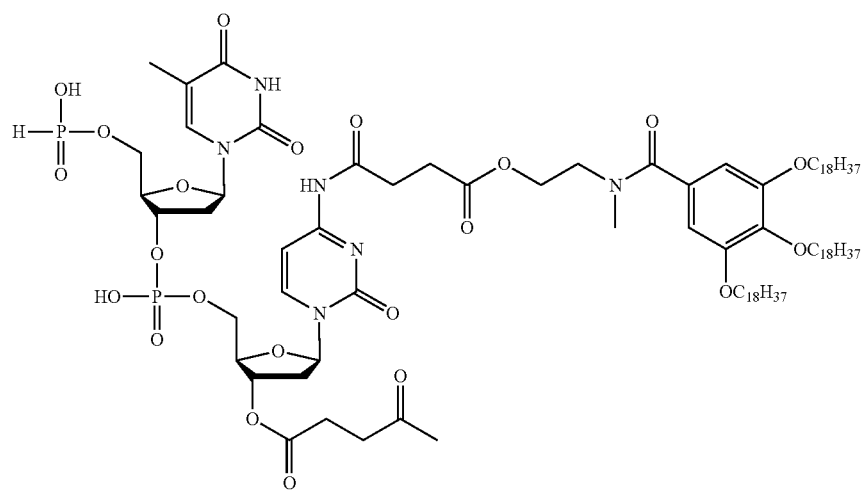

In a nitrogen atmosphere, 2,2-dimethylbutyryl chloride (0.45 mL, 3.3 mmol) was added to a pyridine (20 mL) solution of Compound 42 (1.0 g) and Compound 1 (0.35 g, 0.98 mmol) at 25° C., and the mixture was stirred for 17 minutes. Thereafter, a 0.1 M solution of iodine in pyridine, THF and water (9.8 mL, 0.98 mmol) was added, and the mixture was stirred for 38 minutes. Thereafter, the reaction mixture was vacuum concentrated. Toluene (27 g) was added and the mixture was vacuum concentrated, these operations being repeated three times. Thereafter, methylene chloride (12 g) was added. Insolubles were removed by reaction mixture was added to acetonitrile (518 g), and the resultant solid was recovered by filtration. Consequently, Compound 44 (1.0 g) was obtained as a light skin color solid.

¹H-NMR: (300 MHz; CDCl₃) δ0.88 (t, 9H), 1.15-1.83 (m, 96H), 1.90 (s, 3H), 2.18 (s, 3H), 2.46-2.95 (m, 12H), 3.06 (s, 3H), 3.68 (brs, 2H), 3.92-4.34 (m, 14H), 5.02 (s, 1H), 5.35 (s, 1H), 6.16 (t, 1H), 6.25 (t, 1H), 6.59 (s, 2H), 6.82 (d, 1H), 7.07 (d, 1H), 7.46 (s, 1H), 8.65 (d, 1H).

³¹P-NMR: (300 MHz; CDCl₃) δ−2.16, 4.97.

MS (ESI⁻): [M–H]⁻ 1758.0754.

Example 35 (Synthesis of 4-mer): Synthesis of Compound 46
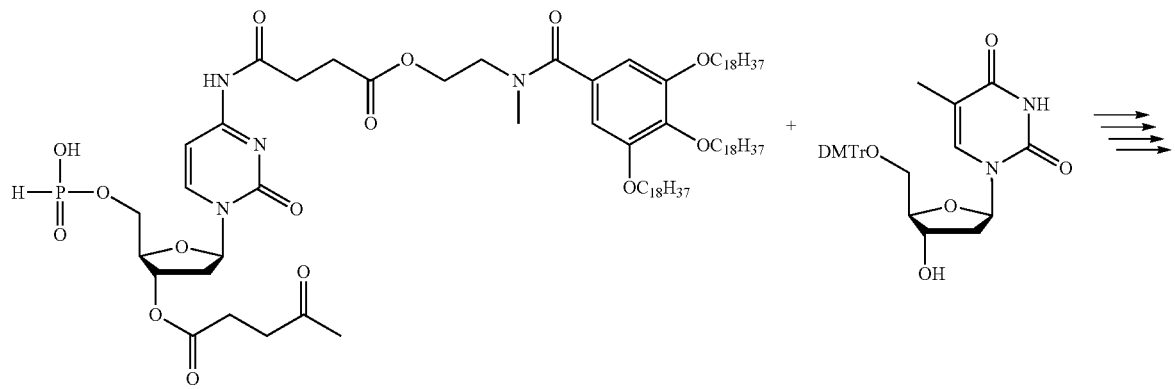
42
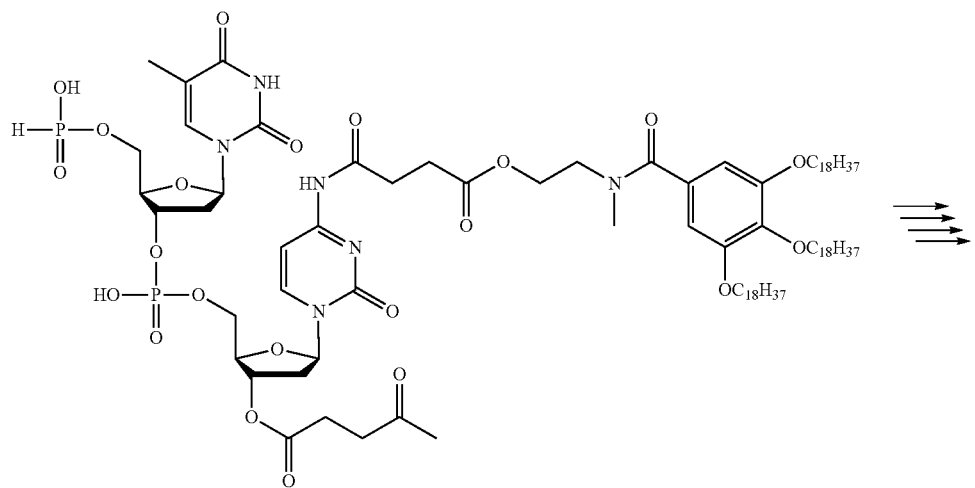
44
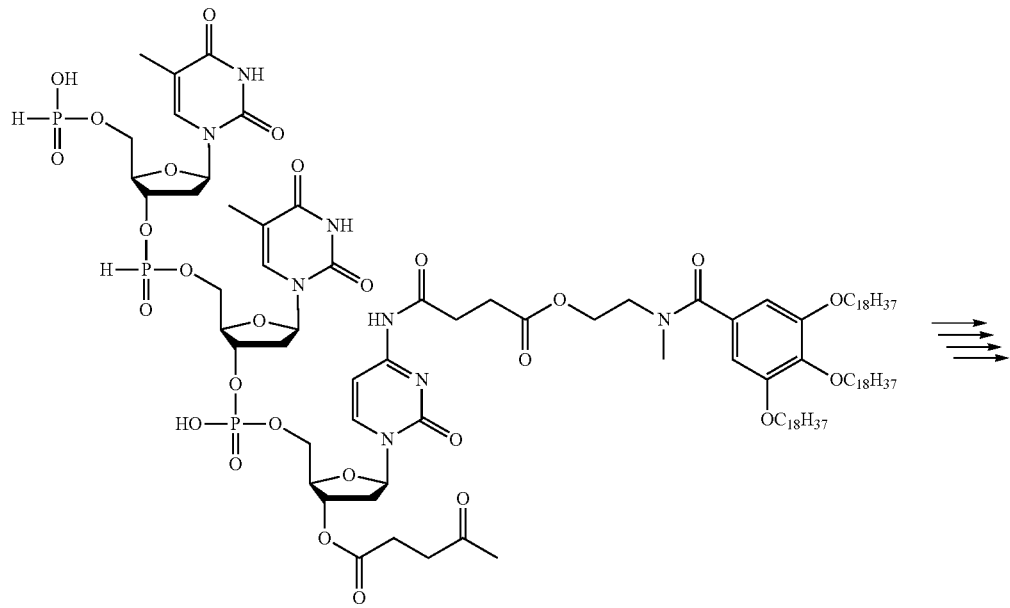
45

-continued

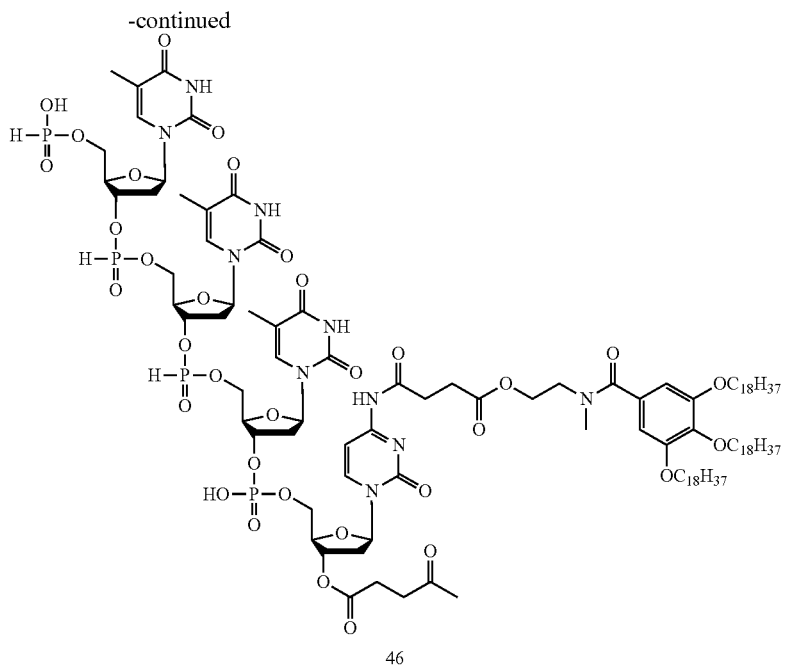

46

Step 1: Synthesis of Compound 44

In a nitrogen atmosphere, 2,2-dimethylbutyryl chloride (0.42 mL, 3.0 mmol) as a condensing agent was added to a pyridine (20 mL) solution of Compound 42 (0.94 g) and 5'-O-(4,4'-dimethoxytrityl)thymidine (manufactured by Tokyo Chemical Industry Co., Ltd.) (0.49 g, 0.91 mmol) at 25° C., and the mixture was stirred for 20 minutes (coupling reaction). Thereafter, a 0.1 M solution of iodine in pyridine, THF and water (9.1 mL, 0.91 mmol) was added, and the mixture was stirred for 20 minutes. Thereafter, trimethyl orthoformate (1.3 mL, 12 mmol) was added, and the mixture was stirred at 25° C. for 34 minutes. The reaction mixture was vacuum concentrated. Toluene (30 g) was added and the mixture was vacuum concentrated, these operations being repeated three times. Thereafter, methylene chloride (10 mL) was added. Insolubles were removed by suction filtration. The filtrate was extracted with methylene chloride (5 mL) two times. Pyrrole (0.13 mL, 1.8 mmol) and phosphonic acid (0.73 g, 9.1 mmol) were added to the solution at room temperature, and the mixture was stirred for 29 minutes. Pyridine (2.8 mL) was added at room temperature. Thereafter, 2,2-dimethylbutyryl chloride (0.83 mL, 6.0 mmol) was added in three portions every 10 minutes, and the mixture was stirred for 1 hour and 16 minutes. 2,2-Dimethylbutyryl chloride (0.14 mL, 1.0 mmol) was added, and the mixture was stirred for 45 minutes. Thereafter, the reaction mixture was added to acetonitrile (396 g), and the resultant solid was recovered by filtration. Consequently, Compound 44 (1.0 g) was obtained as a light gray solid.

MS (ESI$^-$): [M–H]$^-$ 1758.0512.

Step 2: Synthesis of Compound 45

In a nitrogen atmosphere, 2,2-dimethylbutyryl chloride (0.38 mL, 2.8 mmol) was added to a pyridine (20 mL) solution of Compound 44 (0.98 g) and 5'-O-(4,4'-dimethoxytrityl)thymidine (manufactured by Tokyo Chemical Industry Co., Ltd.) (0.45 g, 0.83 mmol) at 25° C., and the mixture was stirred for 27 minutes. Thereafter, a 0.1 M solution of iodine in pyridine, THF and water (8.3 mL, 0.83 mmol) was added, and the mixture was stirred for 44 minutes. Thereafter, trimethyl orthoformate (1.2 mL, 11 mmol) was added, and the mixture was stirred at 25° C. for 42 minutes. The reaction mixture was vacuum concentrated. Toluene (30 g) was added and the mixture was vacuum concentrated, these operations being repeated three times. Methylene chloride (10 mL) was added, and insolubles were removed by suction filtration. The filtrate was extracted with methylene chloride (5 mL) two times. Pyrrole (0.12 mL, 1.7 mmol) and phosphonic acid (0.69 g, 8.3 mmol) were added to this solution at 20° C., and the mixture was stirred for 30 minutes. Pyridine (2.8 mL) was added at 25° C. Thereafter, 2,2-dimethylbutyryl chloride (0.76 mL, 5.5 mmol) was added in three portions every 10 minutes, and the mixture was stirred for 39 minutes. 2,2-Dimethylbutyryl chloride (0.14 mL, 1.0 mmol) was added, and the mixture was stirred for 49 minutes. Thereafter, the reaction mixture was added to acetonitrile (396 g), and the resultant solid was recovered by filtration. Consequently, Compound 45 (1.2 g) was obtained as a light gray solid.

MS (ESI$^+$): [M+H]$^+$ 2064.1191.

Step 3: Synthesis of Compound 46

In a nitrogen atmosphere, 2,2-dimethylbutyl chloride (0.37 mL, 2.7 mmol) was added to a pyridine (20 mL) solution of Compound 45 (1.16 g) and 5'-O-(4,4'-dimethoxytrityl)thymidine (manufactured by Tokyo Chemical Industry Co., Ltd.) (0.43 g, 0.81 mmol) at 25° C., and the mixture was stirred for 29 minutes. Thereafter, a 0.1 M solution of iodine in pyridine, THF and water (8.1 mL, 0.81 mmol) was added, and the mixture was stirred for 25 minutes. Thereafter, trimethyl orthoformate (1.2 mL, 11 mmol) was added, and the mixture was stirred at 25° C. for 21 minutes. The reaction mixture was vacuum concentrated. Toluene (30 g) was added and the mixture was vacuum concentrated, these operations being repeated three times.

Methylene chloride (10 mL) was added, and insolubles were removed by suction filtration. The filtrate was washed with methylene chloride (5 mL) two times. Pyrrole (0.11 mL, 1.6 mmol) and phosphonic acid (0.65 g, 8.1 mmol) were added to this solution at 27 to 30° C., and the mixture was stirred for 24 minutes. Pyridine (3.0 mL) was added at 22 to 28° C. Thereafter, 2,2-dimethylbutyl chloride (0.74 mL, 5.4 mmol) was added in three portions every 10 minutes, and the mixture was stirred for 41 minutes. 2,2-Dimethylbutyryl chloride (0.49 mL, 3.6 mmol) was added, and the mixture was stirred for 1 hour and 20 minutes. Thereafter, the reaction mixture was added to acetonitrile (397 g), and the resultant solid was recovered by precipitation filtration. Consequently, Compound 46 (1.33 g) was obtained as a light gray solid.

MS (ESI$^+$): [M+H]$^+$ 2368.1574.

Example 36 (Synthesis of 2-mer Using RNA): Synthesis of Compound 47

In a nitrogen atmosphere, 2,2-dimethylbutyryl chloride (4.5 μL, 0.033 mmol) was added to a pyridine (0.20 mL) solution of Compound 42 (9.5 mg) and 2'-O-(tert-butyldimethylsilyl)-5'-O-(4,4'-dimethoxytrityl)uridine (purchased from KANTO CHEMICAL CO., INC.) (7.8 mg, 0.012 mmol) at 25° C., and the mixture was stirred for 35 minutes. Thereafter, a 0.1 M solution of iodine in pyridine, THF and water (98 μL, 0.098 mmol) was added, and the mixture was stirred for 20 minutes. The reaction mixture was vacuum concentrated. Toluene (1 mL) was added and the mixture was vacuum concentrated, these operations being repeated three times. Methylene chloride (0.30 mL) was added, and insolubles were removed by suction filtration. The filtrate was extracted with methylene chloride (0.20 mL×2 times). Pyrrole (2 μL, 0.029 mmol) and phosphonic acid (9.1 mg, 0.11 mmol) were added to this solution at room temperature, and the mixture was stirred for 30 minutes. The reaction mixture was vacuum concentrated. Consequently, Compound 47 was obtained as the main product.

MS (ESI$^-$): [M−H]$^-$ 1810.2131.

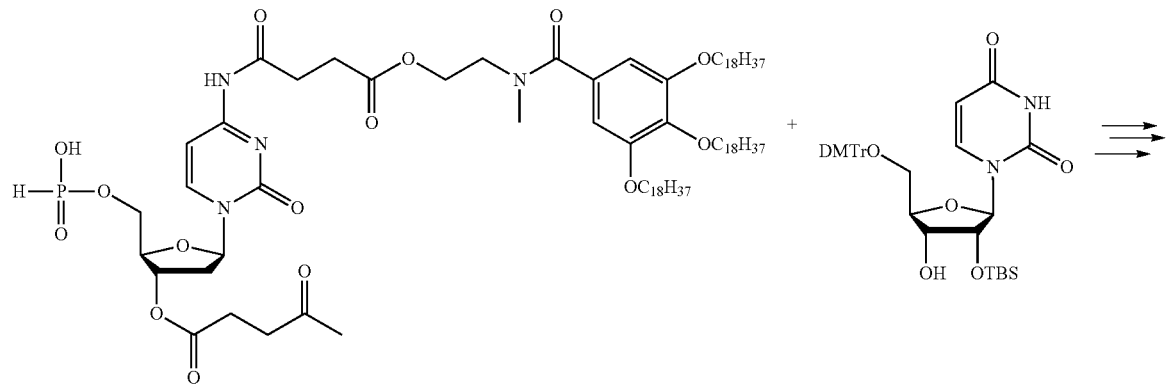

42

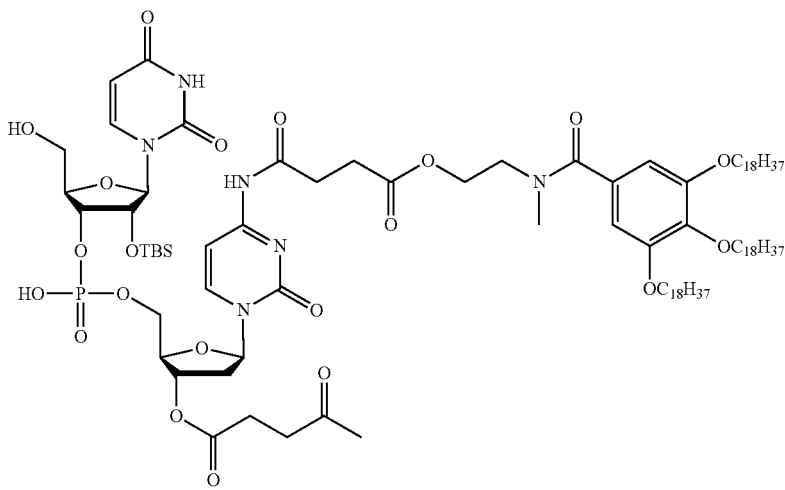

47

Example 37 (Synthesis of 2-mer): Synthesis of Compound 49

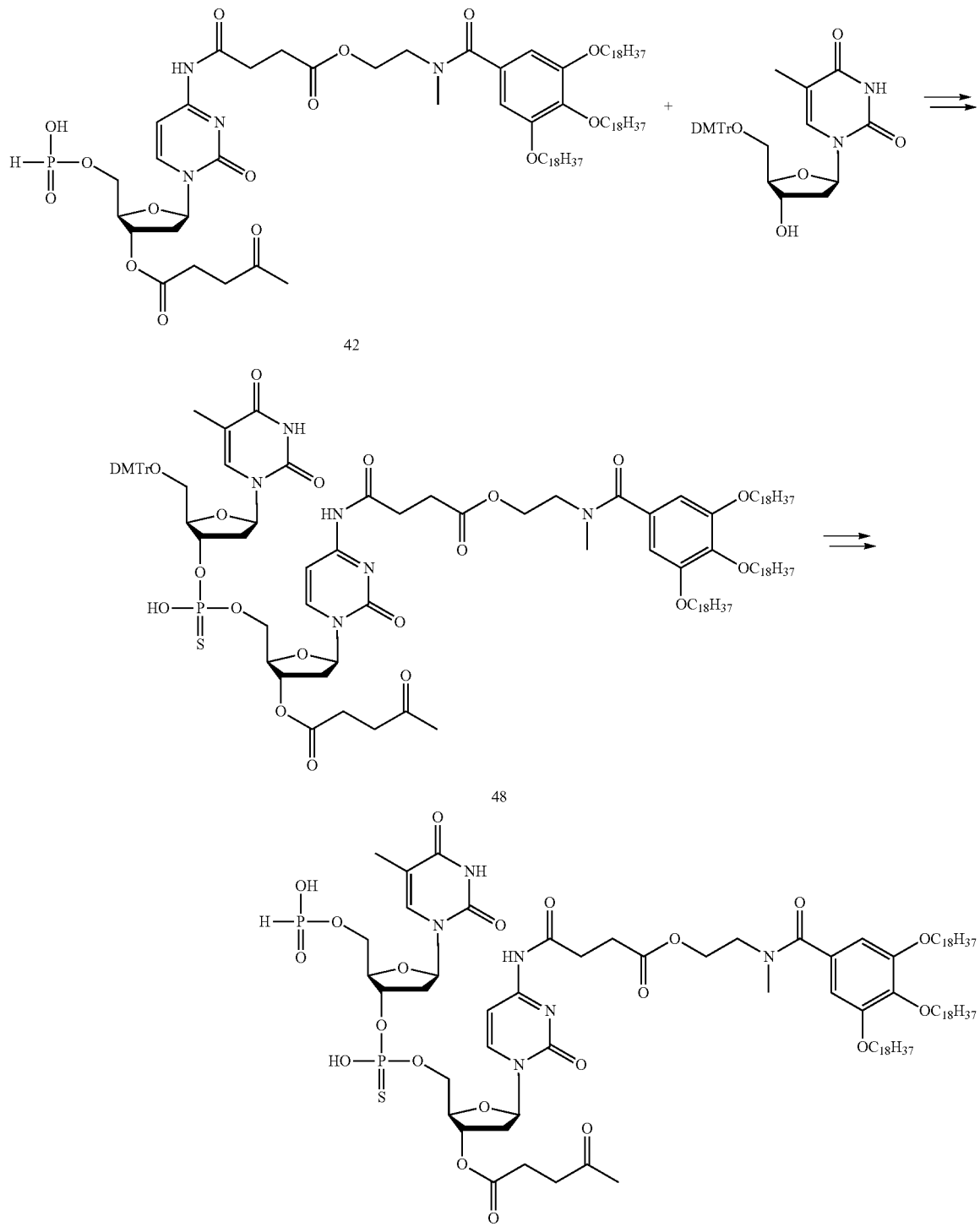

In a nitrogen atmosphere, 2,2-dimethylbutyryl chloride (46 μL, 0.34 mmol) was added to a pyridine (2.0 mL) solution of Compound 42 (104 mg) and 5'-O-(4,4'-dimethoxytrityl)thymidine (manufactured by Tokyo Chemical Industry Co., Ltd.) (58 mg, 107 mmol) at room temperature, and the mixture was stirred for 32 minutes, thereby performing the coupling reaction. Thereafter, elemental sulfur (3.2 mg, 0.10 mmol) as a sulfurizing agent was added, and the mixture was stirred for 1 hour and 32 minutes. The reaction mixture was vacuum concentrated. Toluene (4.0 mL) was added and the mixture was vacuum concentrated, these operations being repeated three times. Thereafter, methylene chloride (1.0 mL) was added, and insolubles were removed with a syringe filter. The filtrate was washed with methylene chloride (0.50 mL×2 times). Pyrrole (14 μL, 0.20 mmol) and phosphonic acid (80 mg, 1.0 mmol) were added to this solution at room temperature, and the mixture was stirred for 36 minutes, thereby performing the temporary protecting group removal reaction. Pyridine (0.30 mL) was added at room temperature. Thereafter 2,2-dimethylbutyryl chloride (92 μL, 0.67 mmol) was added in three portions every 10 minutes, and the mixture was stirred for 2 hours and 24 minutes. 2,2-Dimethylbutyryl chloride (16 μL, 0.12 mmol) was added, and the mixture was stirred for 40 minutes. Thereafter, the reaction mixture was added to acetonitrile (49 g), and the resultant solid was recovered by precipitation filtration. Consequently, Compound 49 (98 mg) was obtained as a white solid.

MS (ESI$^-$): [M−H]$^-$ 1774.0443.

Example 38 (Synthesis of 2-mer for Comparison of Sulfurizing Agent): Synthesis of Compound 49

The reaction was performed under the same conditions as in Example 37, except that the sulfurizing agent was changed to 3-amino-1,2,4-dithiazole-5-thione (11.8 mg). Consequently, Compound 49 (99 mg) was obtained as a light yellow solid.

Example 39 (Synthesis of 2-mer for Comparison of Sulfurizing Agent): Synthesis of Compound 48

The reaction was performed under the same conditions as in Example 37, except that the sulfurizing agent was changed to 3-((dimethylamino-methylidene)amino)-3H-1,2,4-dithiazole-3-thione [DDTT] (11.8 mg). The reaction mixture after the sulfurization was vacuum concentrated. Consequently, Compound 48 was obtained as the main product.

Example 40 (Synthesis of 2-mer for Comparison of Sulfurizing Agent): Synthesis of Compound 48

The reaction solution resulting from the coupling reaction under the same conditions as in Example 37 was divided into 4 portions. The reaction was performed using 3H-1,2-benzodithiol-3-one (3.7 mg) as the sulfurizing agent, and the reaction mixture after the sulfurization was vacuum concentrated. Consequently, Compound 48 was obtained as the main product.

Example 41 (Synthesis of 2-mer for Comparison of Sulfurizing Agent): Synthesis of Compound 48

The reaction was performed under the same conditions as in Example 37, except that a quarter of the reaction solution after the coupling reaction in Example 40 was used and that the sulfurizing agent was changed to 3H-1,2-benzodithiol-3-one-1,1-dioxide (3.3 mg). The reaction mixture after the sulfurization was vacuum concentrated. Consequently, Compound 48 was obtained as the main product.

Example 42 (Synthesis of 2-mer for Comparison of Sulfurizing Agent): Synthesis of Compound 48

The reaction was performed under the same conditions as in Example 37, except that a quarter of the reaction solution after the coupling reaction in Example 40 was used and that the sulfurizing agent was changed to tetraethylthiuram disulfide (4.4 mg). The reaction mixture after the sulfurization was vacuum concentrated. Consequently, Compound 48 was obtained as the main product.

Example 43 (Synthesis of 2-mer for Comparison of Sulfurizing Agent): Synthesis of Compound 48

The reaction was performed under the same conditions as in Example 37, except that the sulfurizing agent was changed to bis(phenylacetyl) disulfide (4.5 mg). The reaction mixture after the sulfurization was vacuum concentrated. Consequently, Compound 48 was obtained as the main product.

Example 44 (Synthesis of 2-mer for Comparison of Sulfurizing Agent): Synthesis of Compound 48

The reaction was performed under the same conditions as in Example 37, except that the sulfurizing agent was changed to N-(benzoylthio)-succinimide (synthesized in accordance with the method described in Synthesis, 1980, pp. 721-722) (3.7 mg). The reaction mixture after the sulfurization was vacuum concentrated. Consequently, Compound 48 was obtained as the main product.

Example 45 (Synthesis of 2-mer Using Deoxyadenosine): Synthesis of Compound 50

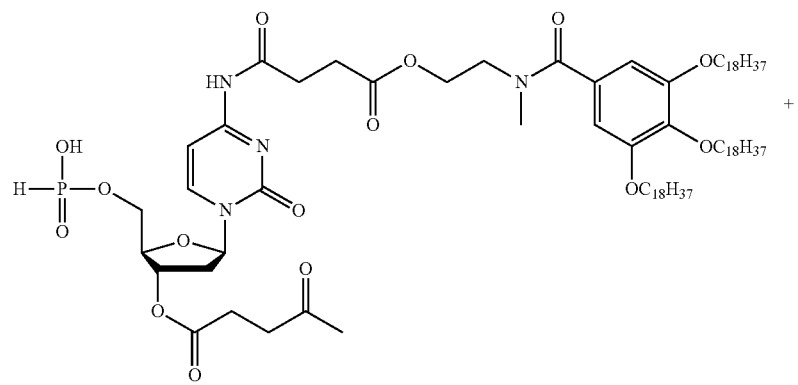

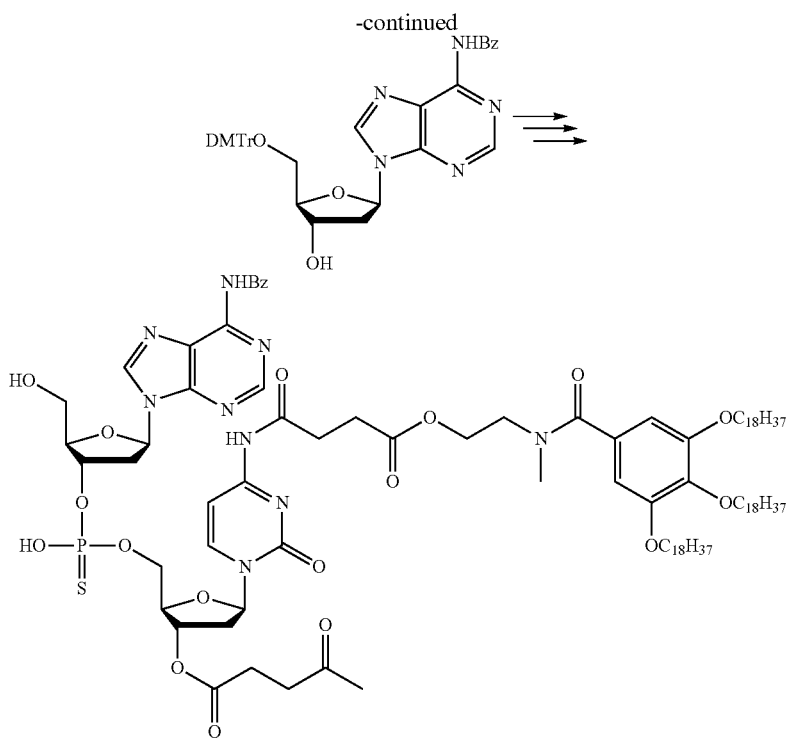

50

The reaction was performed under the same conditions as in Example 37, except that 5'-O-(4,4'-dimethoxytrityl)thymidine was changed to N⁶-benzoyl-5'-O-(4,4'-dimethoxytrityl)-2'-deoxyadenosine (manufactured by Tokyo Chemical Industry Co., Ltd.) (66.4 mg). The reaction mixture after the temporary protecting group removal reaction was vacuum concentrated. Consequently, Compound 50 was obtained.

MS (ESI⁻): [M−H]⁻ 1823.1213.

Example 46 (Synthesis of 2-mer Using Deoxyguanosine): Synthesis of Compound 51

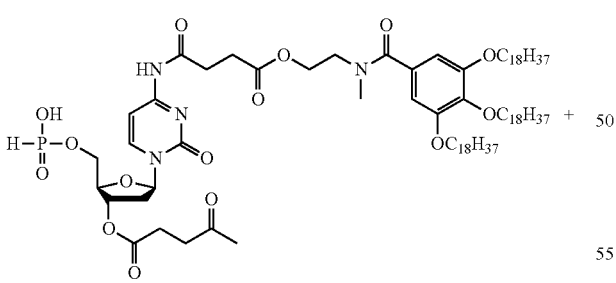

42

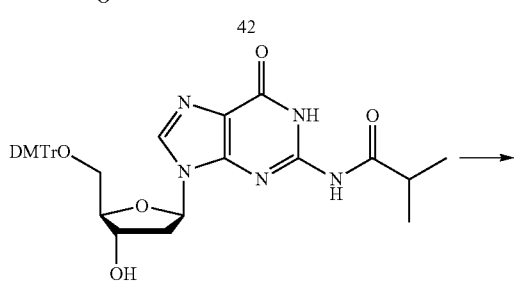

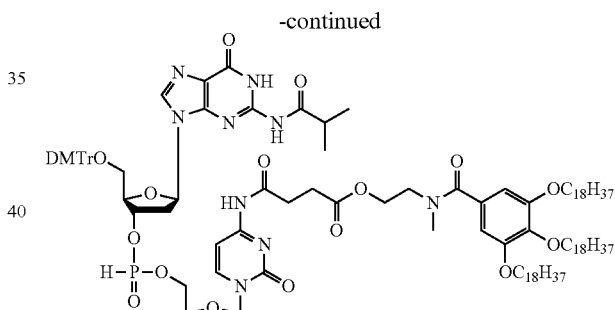

51

The reaction was performed under the same conditions as in Example 37, except that 5'-O-(4,4'-dimethoxytrityl)thymidine was changed to N²-isobutyryl-5'-O-(4,4'-dimethoxytrityl)-2'-deoxyguanosine (manufactured by Tokyo Chemical Industry Co., Ltd.) (6.6 mg). The reaction mixture after the coupling reaction was vacuum concentrated. Consequently, Compound 51 was obtained as the main product.

MS (ESI⁻): [M−H]⁻ 2075.2896.

Example 47 (Synthesis of 3-mer): Synthesis of Compound 52

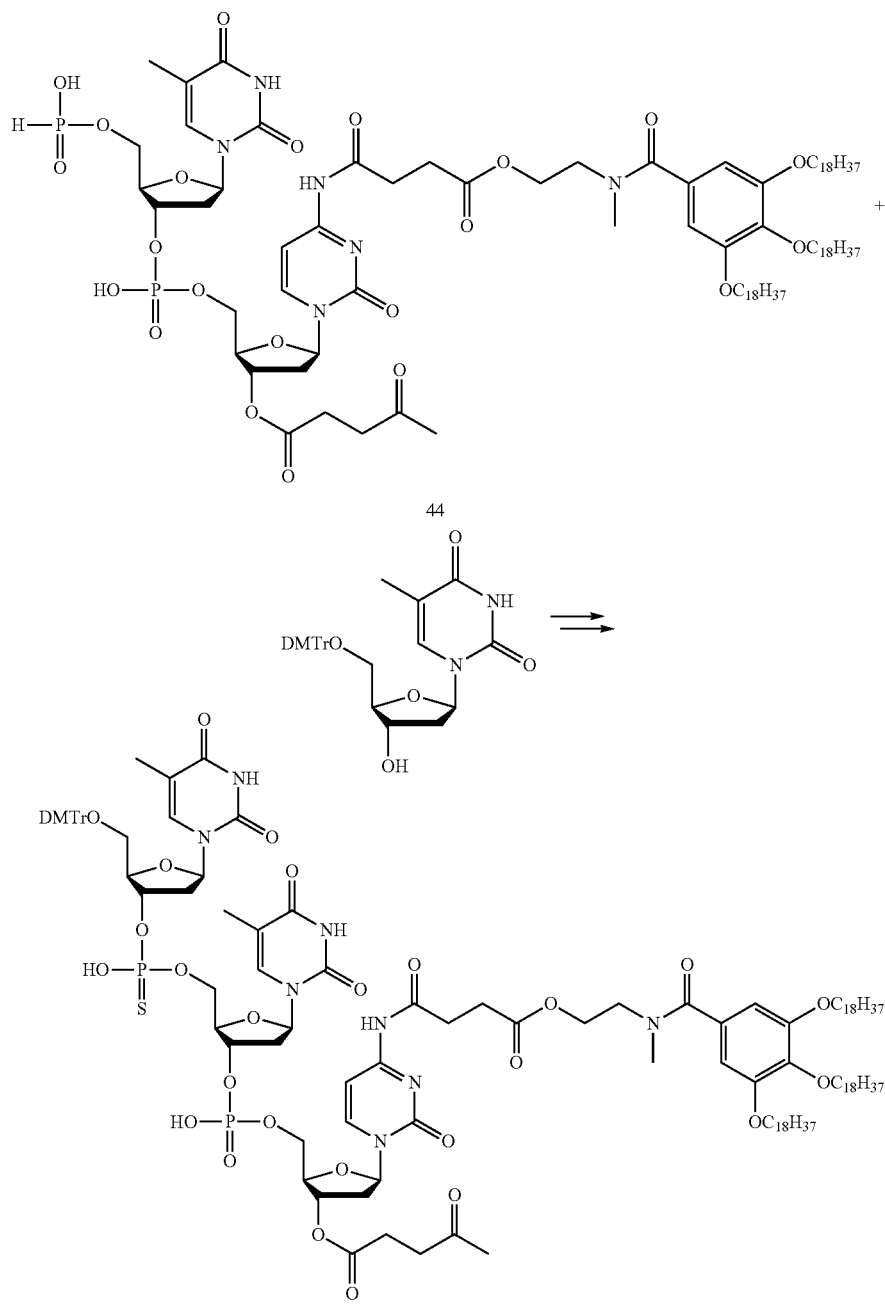

In a nitrogen atmosphere, 2,2-dimethylbutyryl chloride (3.8 μL, 0.028 mmol) was added to a pyridine (0.20 mL) solution of Compound 44 (9.5 mg) and 5'-O-(4,4'-dimethoxytrityl)thymidine (manufactured by Tokyo Chemical Industry Co., Ltd.) (6.0 mg, 0.011 mmol) at 25° C., and the mixture was stirred for 26 minutes. Thereafter, elemental sulfur (2.1 mg, 0.065 mmol) was added, and the mixture was stirred for 1 hour and 40 minutes. The reaction mixture was vacuum concentrated. Consequently, Compound 52 was obtained as the main product.

MS (ESI$^-$): [M–H]$^-$ 2316.2547.

Example 48 (Synthesis of H-phosphonate Diester 2-mer): Synthesis of Compound 53

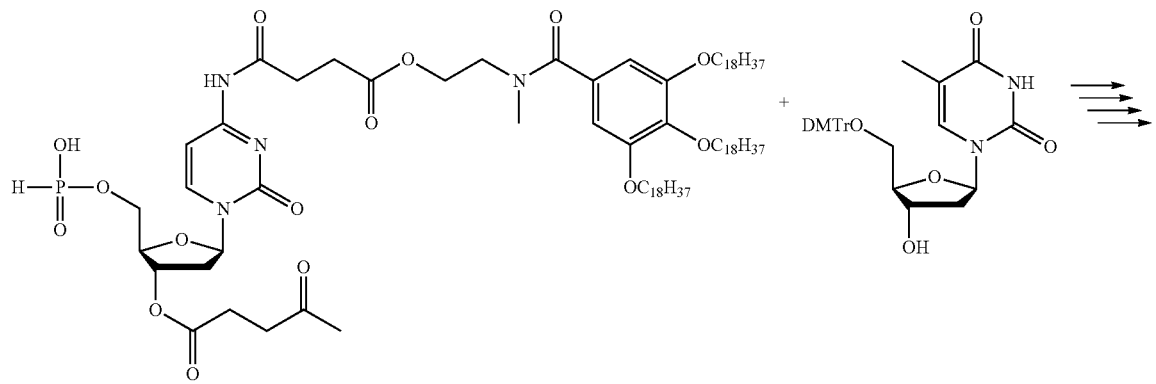

42

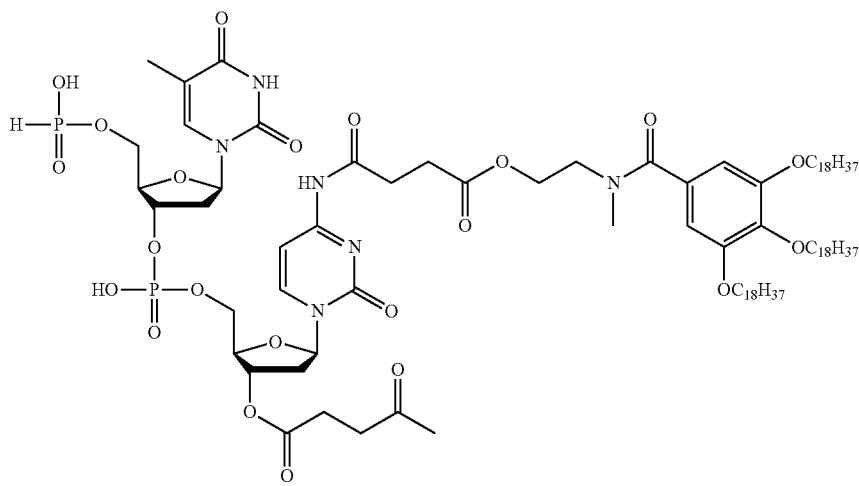

53

In a nitrogen atmosphere, pyridine (1.7 μL, 0.034 mmol) was added to a THF (0.20 mL) solution of Compound 42 (12 mg) and 5'-O-(4,4'-dimethoxytrityl)thymidine (manufactured by Tokyo Chemical Industry Co., Ltd.) (7.0 mg, 0.013 mmol) at 25° C., and thereafter 2,2-dimethylbutyryl chloride (4.6 μL, 0.034 mmol) was added. The mixture was stirred for 45 minutes. Thereafter, pyridine (1.7 μL, 0.034 mmol) was added, and the mixture was stirred for 18 minutes. Pyrrole (1.4 μL, 0.020 mmol) and phosphonic acid (8.5 mg, 0.10 mmol) were added to this solution at 25° C., and the mixture was stirred for 44 minutes. Methylene chloride (0.20 mL) was added, and the mixture was stirred for 1 hour and 20 minutes. Pyridine (30 μL) was added at 25° C. Thereafter, 2,2-dimethylbutyryl chloride (9.2 μL, 0.067 mmol) was added in three portions every 10 minutes, and the mixture was stirred for 35 minutes. Thereafter, the reaction mixture was added to acetonitrile (2 g), and the resultant solid was recovered by filtration. Consequently, Compound 53 was obtained.

MS (ESI−): [M−H]− 1742.1016.

Example 49 (H-phosphonation): Synthesis of Compound 5b (triethylamine Salt)

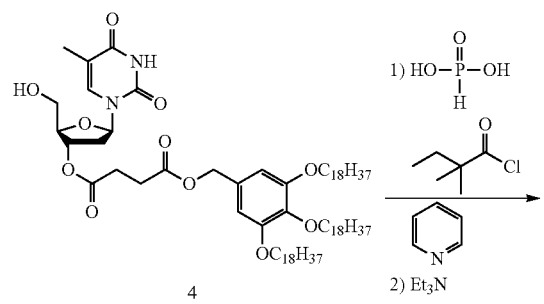

4

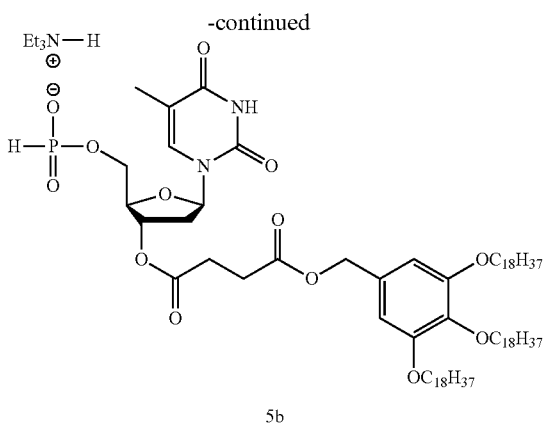

5b

In a nitrogen atmosphere, 2,2-dimethylbutyryl chloride (0.33 mL, 2.4 mmol) was added to a pyridine (10 mL) solution of phosphorous acid (345 mg, 4.2 mmol) at 40° C., and the mixture was stirred for 35 minutes. Compound 4 (497 mg, 0.40 mmol) was added to the reaction mixture, and the mixture was stirred at 40° C. for 1 hour and 2 minutes. 2,2-Dimethylbutyryl chloride (83 µL, 0.61 mmol) was added, and the mixture was stirred for 1 hour and 13 minutes. Triethylamine (2.8 mL, 20 mmol) was added. Thereafter, acetonitrile (211 g) was added to precipitate a solid, and the mixture was cooled with ice and was filtered. Consequently, Compound 5b (547 mg) was obtained as a white solid.

Example 50 (H-phosphonation): Synthesis of Compound 5c (N-methylimidazole Salt)

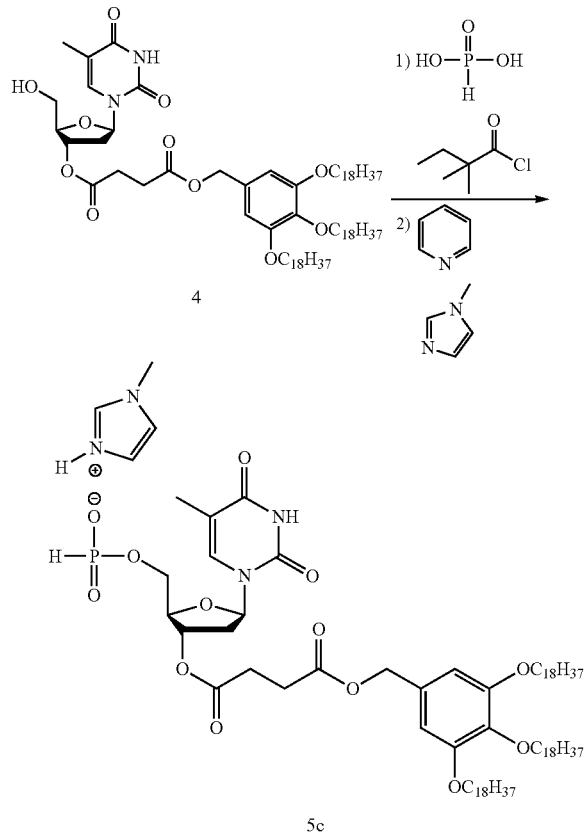

5c

In a nitrogen atmosphere, 2,2-dimethylbutyryl chloride (0.23 mL, 1.7 mmol) was added to a pyridine (7 mL) solution of phosphorous acid (241 mg, 2.9 mmol) at 40° C., and the mixture was stirred for 30 minutes. Compound 4 (350 mg, 0.28 mmol) was added to the reaction mixture, and the mixture was stirred at 40° C. for 1 hour and 49 minutes. 2,2-Dimethylbutyryl chloride (39 µL, 0.28 mmol) was added, and the mixture was stirred for 2 hours. The solution thus obtained was divided into 3 portions (corresponding to Compound 4: 0.093 mmol). N-methylimidazole (0.32 mL, 4.1 mmol) was added. Thereafter, acetonitrile (40 g) was added to precipitate a solid, and the mixture was cooled with ice and was filtered. Consequently Compound 5c (103 mg) was obtained as a solid.

$^1$H-NMR: (300 MHz, CDCl$_3$) δ0.88 (t, 9H), 1.26-1.83 (m, 96H), 1.92 (s, 3H), 2.32-2.36 (m, 2H), 2.67 (s, 4H), 3.89-3.98 {m, 6H+3H(N-methylimidazole)}, 4.18-4.21 (m, 3H), 5.02 (s, 2H), 5.41 (t, 1H), 6.38 (t, 1H), 6.53 (s, 2H), 6.93 (d, 1H), 7.04 (s, 1H,N-methylimidazole), 7.31 (s, 1H,N-methylimidazole), 7.73 (d, 1H), 8.84 (s, 1H,N-methylimidazole).

$^{31}$P-NMR: (300 MHz; CDCl$_3$) δ5.74.

Example 51 (H-phosphonation): Synthesis of Compound 5d (N-methylmorpholine Salt)

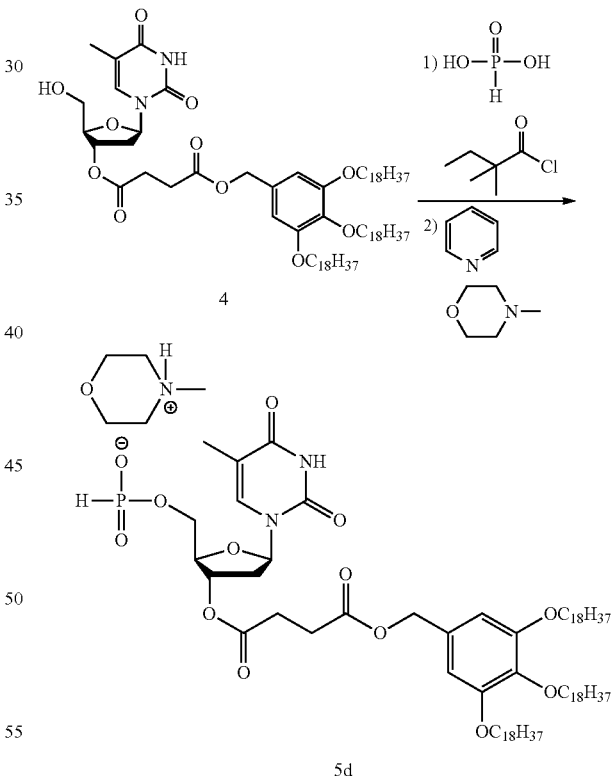

5d

N-methylmorpholine (0.45 mL, 4.1 mmol) was added to one of the three portions of the solution (corresponding to Compound 4: 0.093 mmol) prepared in Example 50. Thereafter, acetonitrile (43 g) was added to precipitate a solid, and the mixture was cooled with ice and was filtered. Consequently, Compound 5d (96 mg) was obtained as a solid.

$^1$H-NMR: (300 MHz; CDCl$_3$) δ0.88 (t, 9H), 1.09-1.84 (m, 96H), 1.96 (s, 3H), 2.01 (s, 3H,N-methylmorpholine), 2.31-2.36 (m, 2H), 2.68 (s, 4H), 2.76 (s, 4H,N-methylmorpholine), 3.90-3.98 {m, 6H+4H(N-methylmorpholine)}, 4.10-4.17 (m, 3H), 5.02 (s, 2H), 5.41 (t, 1H), 6.38 (t, 1H), 6.53 (s, 2H), 6.89 (d, 1H), 7.71 (d, 1H).

$^{31}$P-NMR: (300 MHz; CDCl$_3$) δ5.88.

Example 52 (Synthesis of 2-mer): Synthesis of Compound 54

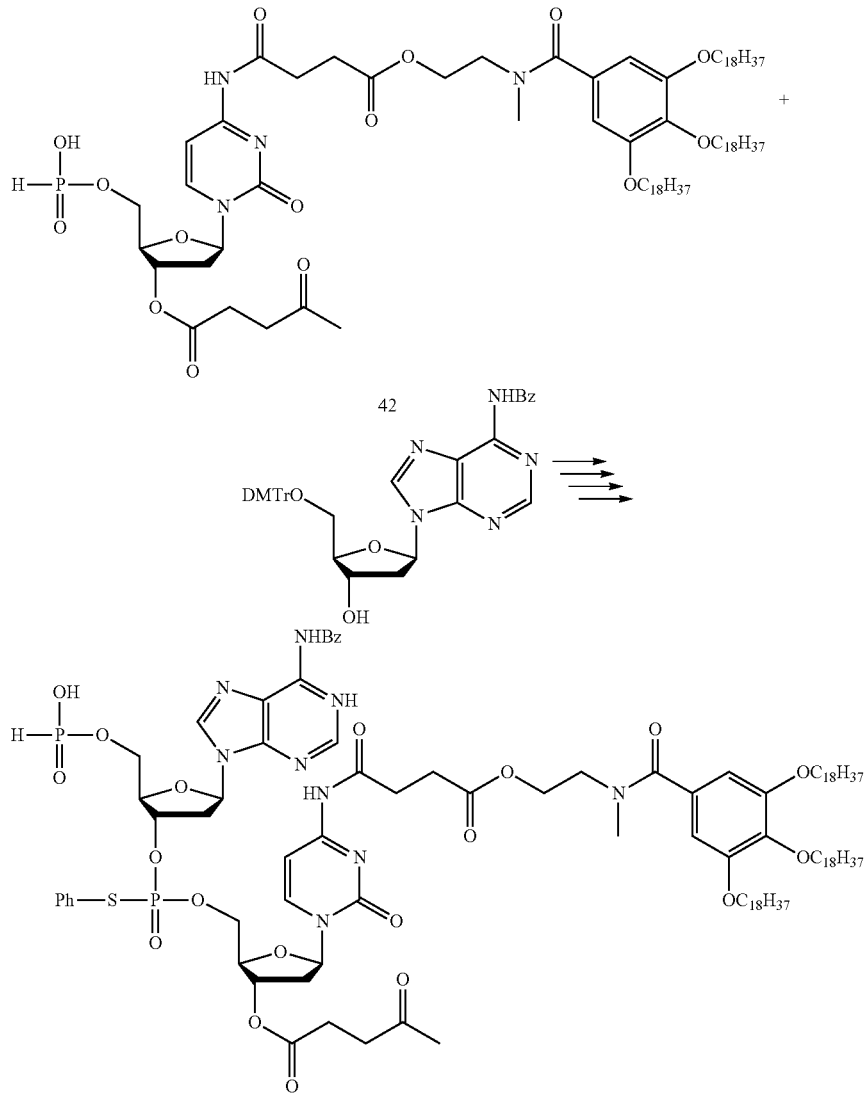

In a nitrogen atmosphere, 2,2-dimethylbutyryl chloride (28 μL, 0.20 mmol) as a condensing agent was added to a pyridine (2.0 mL) solution of Compound 42 (99 mg) and N$^6$-benzoyl-5'-O-(4,4'-dimethoxytrityl)-2'-deoxyadenosine (manufactured by Tokyo Chemical Industry Co., Ltd.) (66 mg, 0.10 mmol) at 25° C., and the mixture was stirred for 21 minutes. Thereafter, N-(phenylthio)phthalimide (27 mg, 0.11 mmol) as a sulfurizing agent was added, and the mixture was stirred for 43 minutes. Water (3.6 μL, 0.20 mmol) was added, and the mixture was stirred for 1 hour and 37 minutes. The reaction mixture was vacuum concentrated. Toluene (4.0 mL) was added and the mixture was vacuum concentrated, these operations being repeated three times. Methylene chloride (2.0 mL) was added, and pyrrole (14 μL, 0.20 mmol) and phosphonic acid (8.7 mg, 0.11 mmol) were added at room temperature. The mixture was stirred for 1 hour and 28 minutes, and thereby the temporary protecting group removal reaction was performed. Pyridine (0.30 mL) and phosphonic acid (74 mg, 0.90 mmol) were added at room temperature. Thereafter, 2,2-dimethylbutyryl chloride (92 μL, 0.67 mmol) was added in three portions every 10 minutes, and the mixture was stirred for 59 minutes. 2,2-Dimethylbutyryl chloride (31 μL, 0.22 mmol) was added, and the mixture was stirred for 42 minutes. Thereafter, the reaction mixture was added to acetonitrile (51 g), and the resultant solid was recovered by filtration. Consequently, Compound 54 (100 mg) was obtained as a white solid.

$^1$H-NMR: (300 MHz; CDCl$_3$) δ0.88 (t, 9H), 1.13-1.80 (m, 96H), 2.17-2.85 (m, 15H), 3.03 (s, 3H), 3.68-4.33 (m, 16H), 5.20-5.35 (m, 2H), 6.07-6.17 (m, 2H), 6.43-6.53 (m, 2H), 6.56 (s, 2H), 7.24-8.78 (m, 14H).

$^{31}$P-NMR: (300 MHz; CDCl$_3$) δ6.10, 25.20, 25.30.

MS (ESI$^+$): [M+H]$^+$ 1965.1202.

Example 53 (Synthesis of 2-mer for Comparison of Sulfurizing Agent): Synthesis of Compound 55

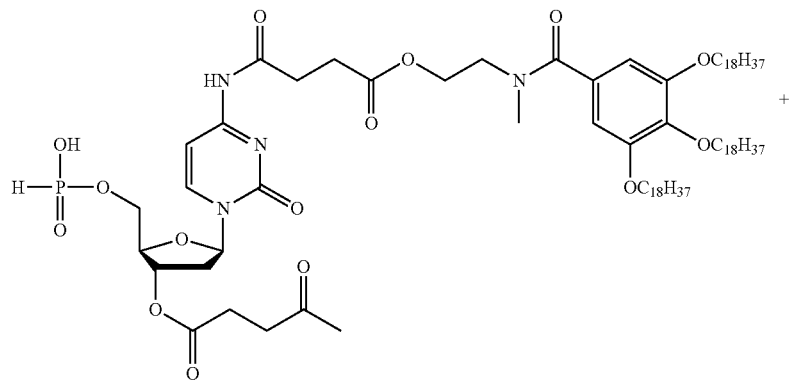

42

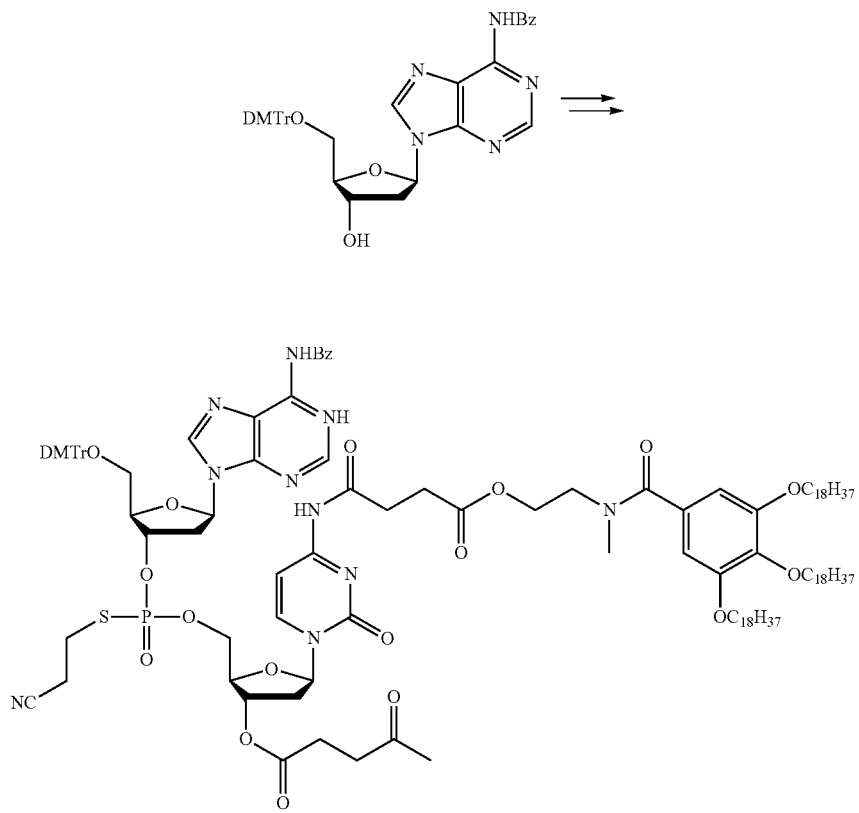

55

The reaction was performed under the same conditions as in Example 52, except that the sulfurizing agent was changed to N-[(2-cyanoethyl)thio]phthalimide (synthesized in accordance with the method described in Tetrahedron, 1997, vol. 53, pp. 14411-14416) (4.3 mg). The reaction mixture after the sulfurization was vacuum concentrated. Consequently, Compound 55 was obtained as the main product.

MS (ESI$^+$): [M+H]$^+$ 2180.2862.

Example 54 (Synthesis of 2-mer for Comparison of Sulfurizing Agent): Synthesis of Compound 56

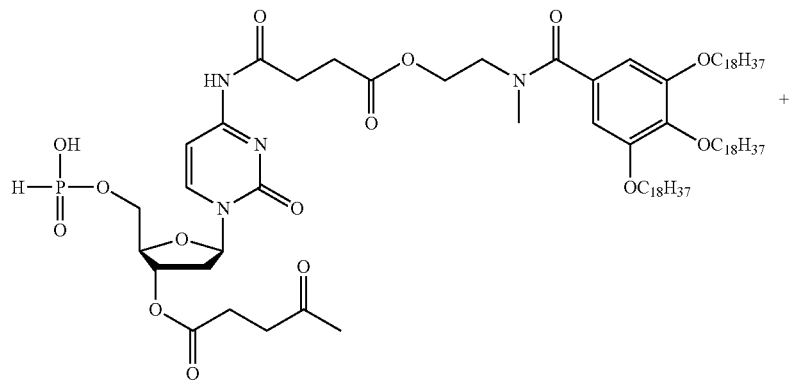

42

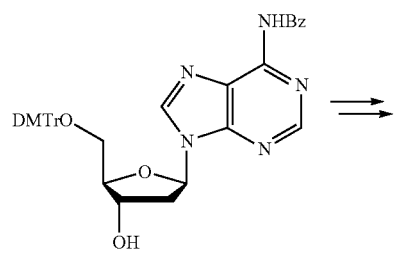

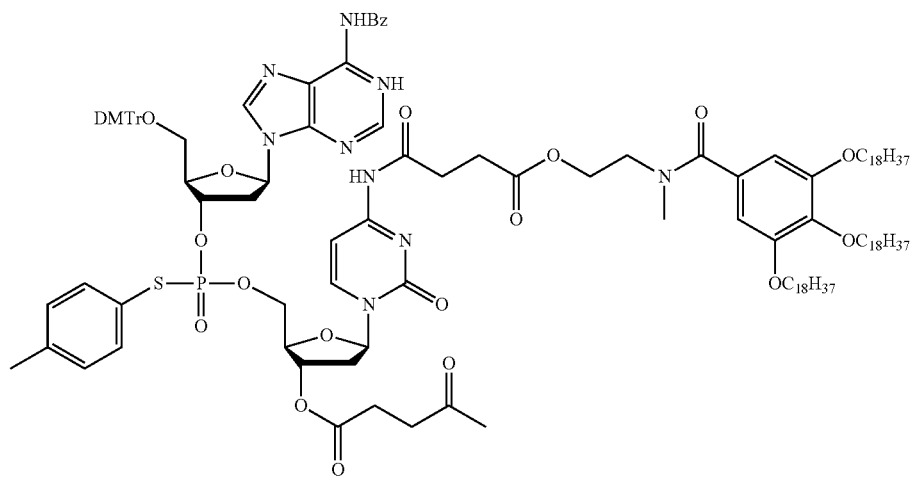

56

The reaction was performed under the same conditions as in Example 52, except that the sulfurizing agent was changed to N-[(p-methylphenyl)thio]phthalimide (synthesized in accordance with the method described in Nucleic Acids Research, 1999, vol. 27, pp. 963-971) (27 mg). The reaction mixture after the sulfurization was vacuum concentrated. Consequently, Compound 56 was obtained as the main product.

MS (ESI$^+$): [M+H]$^+$ 2217.2981.

Example 55 (Synthesis of 2-mer for Comparison of Sulfurizing Agent): Synthesis of Compound 57

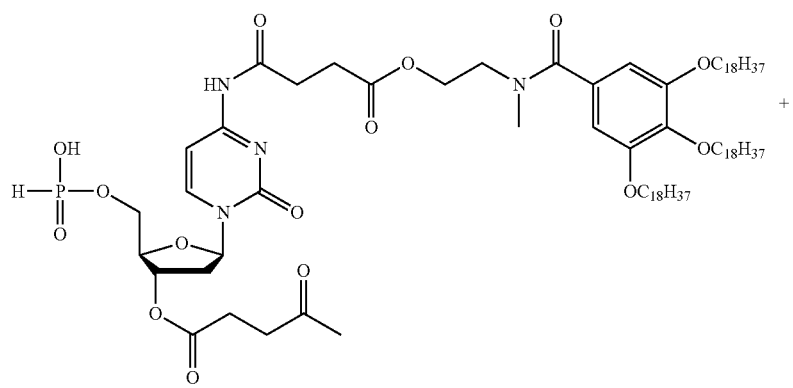

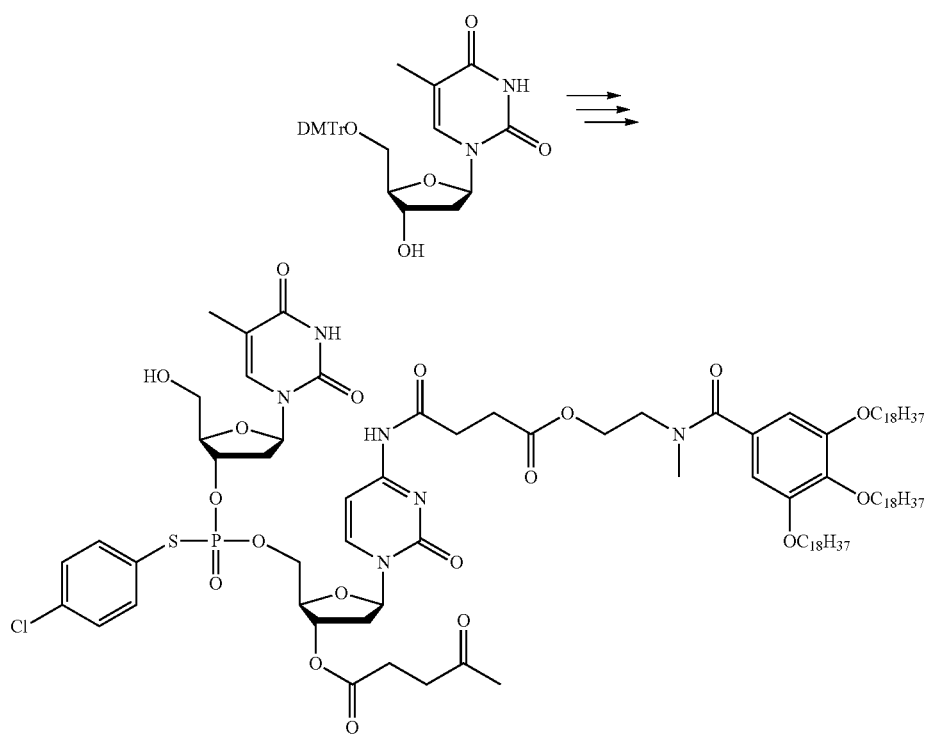

The reaction was performed under the same conditions as in Example 52, except that $N^6$-benzoyl-5'-O-(4,4'-dimethoxytrityl)-2'-deoxyadenosine was changed to 5'-O-(4,4'-dimethoxytrityl)thymidine (manufactured by Tokyo Chemical Industry Co., Ltd.) (5.2 mg), and that the sulfurizing agent was changed to N-[(p-chlorophenyl)thio]phthalimide (synthesized in accordance with the method described in Tetrahedron, 1997, vol. 53, pp. 14411-14416) (4.3 mg). The reaction mixture after the temporary protecting group removal reaction was vacuum concentrated. Consequently, Compound 57 was obtained as the main product.

MS (ESI$^+$): [M+H]$^+$ 1788.1262.

Example 56 (Synthesis of 2-mer for Comparison of Sulfurizing Agent): Synthesis of Compound 58

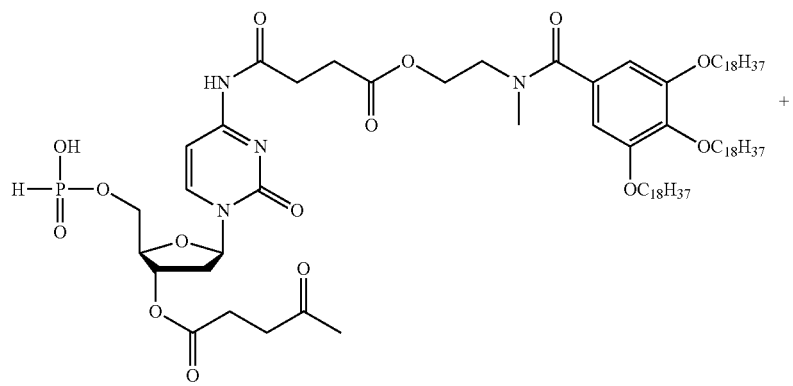

42

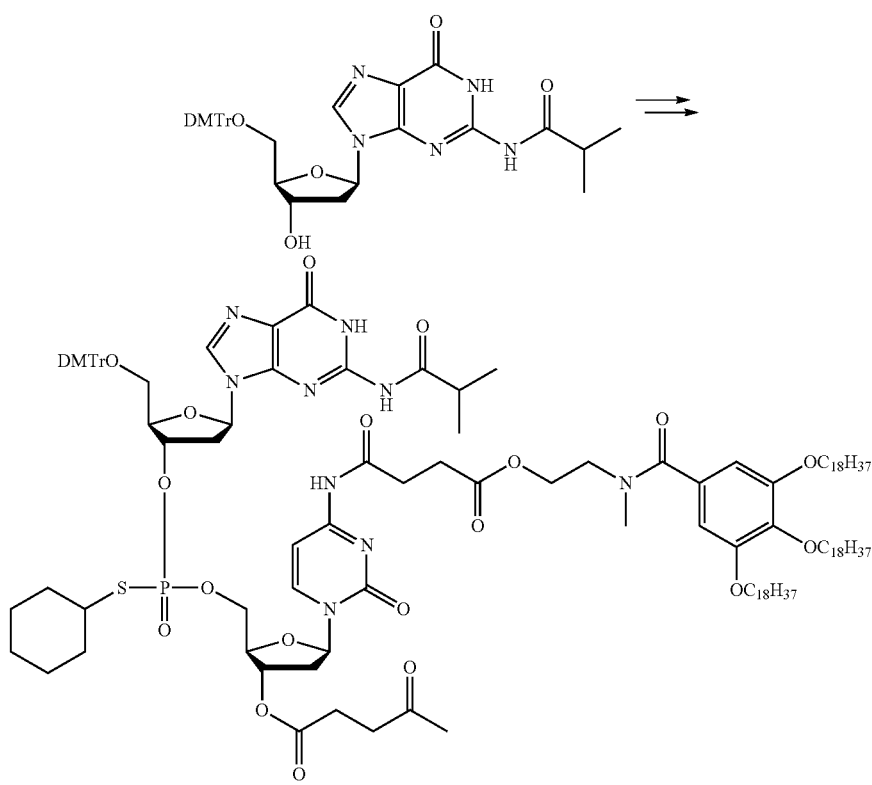

58

The reaction was performed under the same conditions as in Example 52, except that $N^6$-benzoyl-5'-O-(4,4'-dimethoxytrityl)-2'-deoxyadenosine was changed to $N^2$-isobutyryl-5'-O-(4,4'-dimethoxytrityl)-2'-deoxyguanosine (manufactured by Tokyo Chemical Industry Co., Ltd.) (7.0 mg) and that the sulfurizing agent was changed to N-(cyclohexylthio)phthalimide (3.3 mg). The reaction mixture after the sulfurization was vacuum concentrated. Consequently, Compound 58 was obtained.

MS (ESI$^+$): [M+H]$^+$ 2191.3401.

Example 57 (Synthesis of 2-mer): Synthesis of Compound 55

The reaction was performed under the same conditions as in Example 53, except that the condensing agent was changed to bispentafluorophenyl carbonate (9.1 mg). The reaction mixture after the sulfurization was vacuum concentrated. Consequently, Compound 55 was obtained as the main product.

Example 58 (Synthesis of 2-mer for Comparison of Sulfurizing Agent): Synthesis of Compound 59

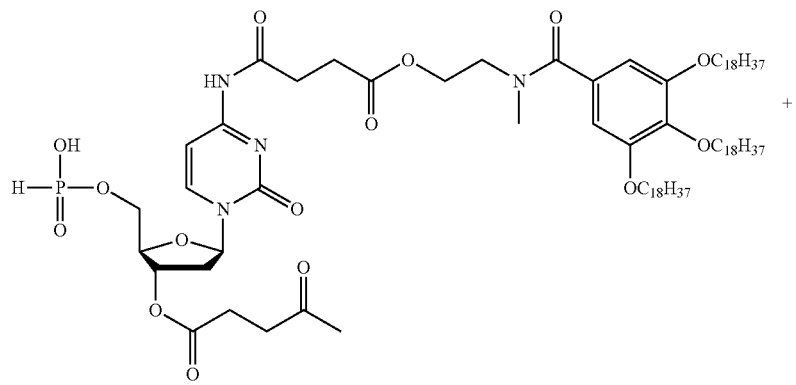

42

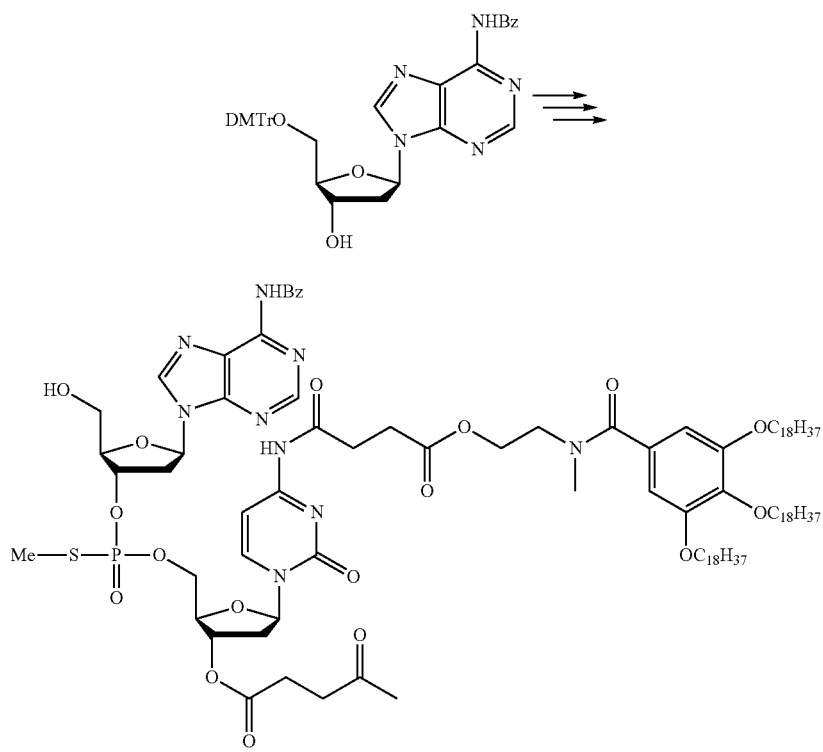

59

The reaction was performed under the same conditions as in Example 52, except that the sulfurizing agent was changed to N-(methylthio)phthalimide (synthesized in accordance with the method described in Tetrahedron, 1997, vol. 53, pp. 14411-14416) (9.9 mg). The reaction mixture after the temporary protecting group removal reaction was vacuum concentrated. Consequently, Compound 59 was obtained as the main product.

MS (ESI$^+$): [M+H]$^+$ 1839.1373.

Reference Synthetic Example 3 (Synthesis of Sulfurizing Agent): Synthesis of N-(dodecylthio)phthalimide

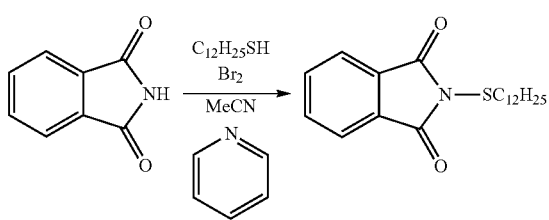

In a nitrogen atmosphere, dodecanethiol (6.8 mL, 29 mmol) was added to a solution of phthalimide (4.0 g, 27 mmol) in a mixed solvent of acetonitrile (15 mL) and pyridine (12 mL). A solution of bromine (1.7 mL, 33 mmol) in acetonitrile (20 mL) was added dropwise over a period of 40 minutes at room temperature, and the mixture was stirred at room temperature for 2 hours and 43 minutes. Methanol (32 g) and water (5 g) were added, and the mixture was cooled to 0° C. The resultant solid was recovered by filtration. Consequently, the target product (6.0 g) was obtained as a white solid.

$^1$H-NMR: (300 MHz; CDCl$_3$) δ0.88 (t, 3H), 1.08-1.64 (m, 20H), 2.88 (t, 2H), 7.75-7.80 (m, 2H), 7.89-7.95 (m, 2H).

MS (ESI$^+$): [M+H]$^+$ 348.2003.

Reference Synthetic Example 4 (Synthesis of Sulfurizing Agent): Synthesis of N-[(2-benzo[d]thiazolyl)thio]phthalimide

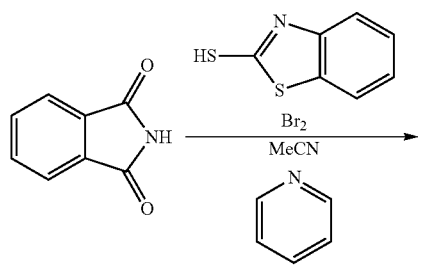

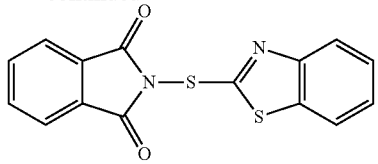

In a nitrogen atmosphere, 2-mercaptobenzothiazole (4.8 g, 29 mmol) was added to a solution of phthalimide (4.0 g, 27 mmol) in a mixed solvent of acetonitrile (15 mL) and pyridine (12 mL). A solution of bromine (1.7 mL, 33 mmol) in acetonitrile (20 mL) was added dropwise over a period of 38 minutes at room temperature. The mixture was stirred at room temperature for 4 hours and 30 minutes. Methanol (30 g) and water (5 g) were added, and the mixture was stirred for 17 minutes. The resultant solid was recovered by filtration. Consequently, the target product (6.8 g) was obtained as a light pink solid.

$^1$H-NMR: (300 MHz; CDCl$_3$) δ7.27-7.38 (m, 1H), 7.40-7.48 (m, 1H), 7.69-7.77 (m, 1H), 7.82-7.94 (m, 3H), 7.99-8.62 (m, 2H).

MS (ESI$^+$): [M+H]$^+$ 313.0090.

Example 59 (Synthesis of 2-mer for Comparison of Sulfurizing Agent): Synthesis of Compound 60

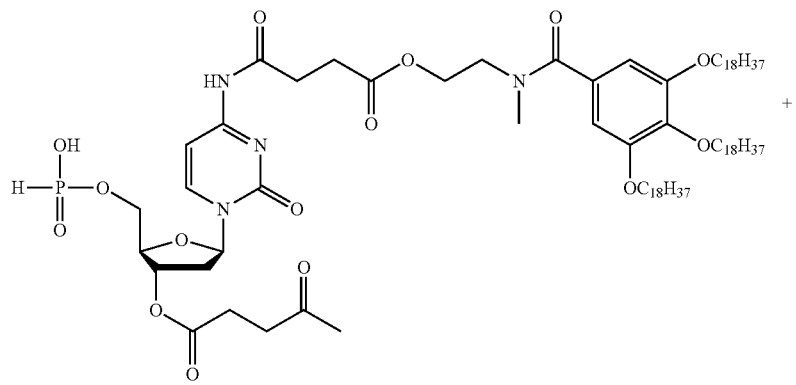

42

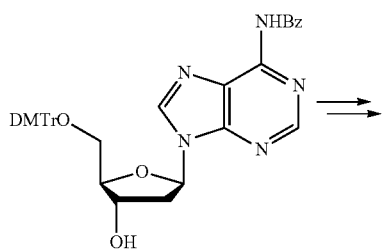

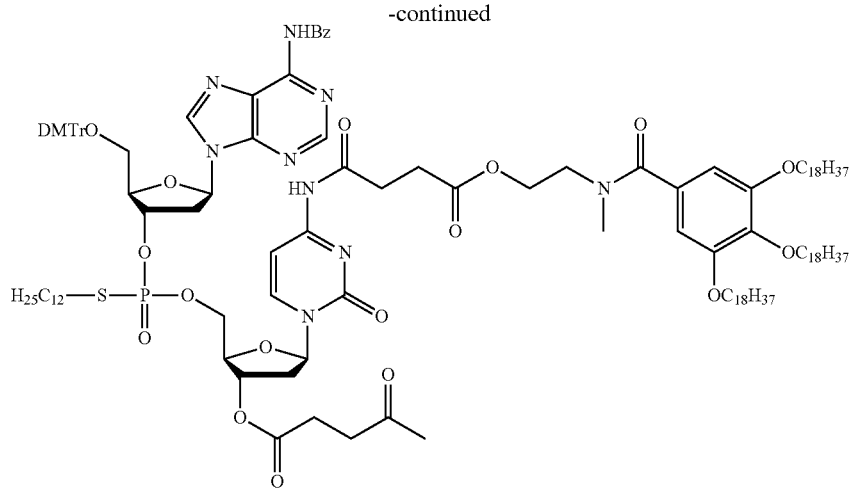

60

The reaction was performed under the same conditions as in Example 52, except that the sulfurizing agent was changed to N-(dodecylthio)phthalimide (4.0 mg).

The reaction mixture after the sulfurization was vacuum concentrated. Consequently, Compound 60 was obtained.

MS (ESI$^+$): [M+H]$^+$ 2295.4570.

Example 60 (Synthesis of 2-mer for Comparison of Sulfurizing Agent): Synthesis of Compound 61

The reaction was performed under the same conditions as in Example 52, except that the sulfurizing agent was changed to N-[(2-benzo[d]thiazolyl)thio]phthalimide (4.8 mg). The reaction mixture after the sulfurization was vacuum concentrated. Consequently, Compound 61 was obtained.

MS (ESI$^+$): [M+H]$^+$ 2277.2747.

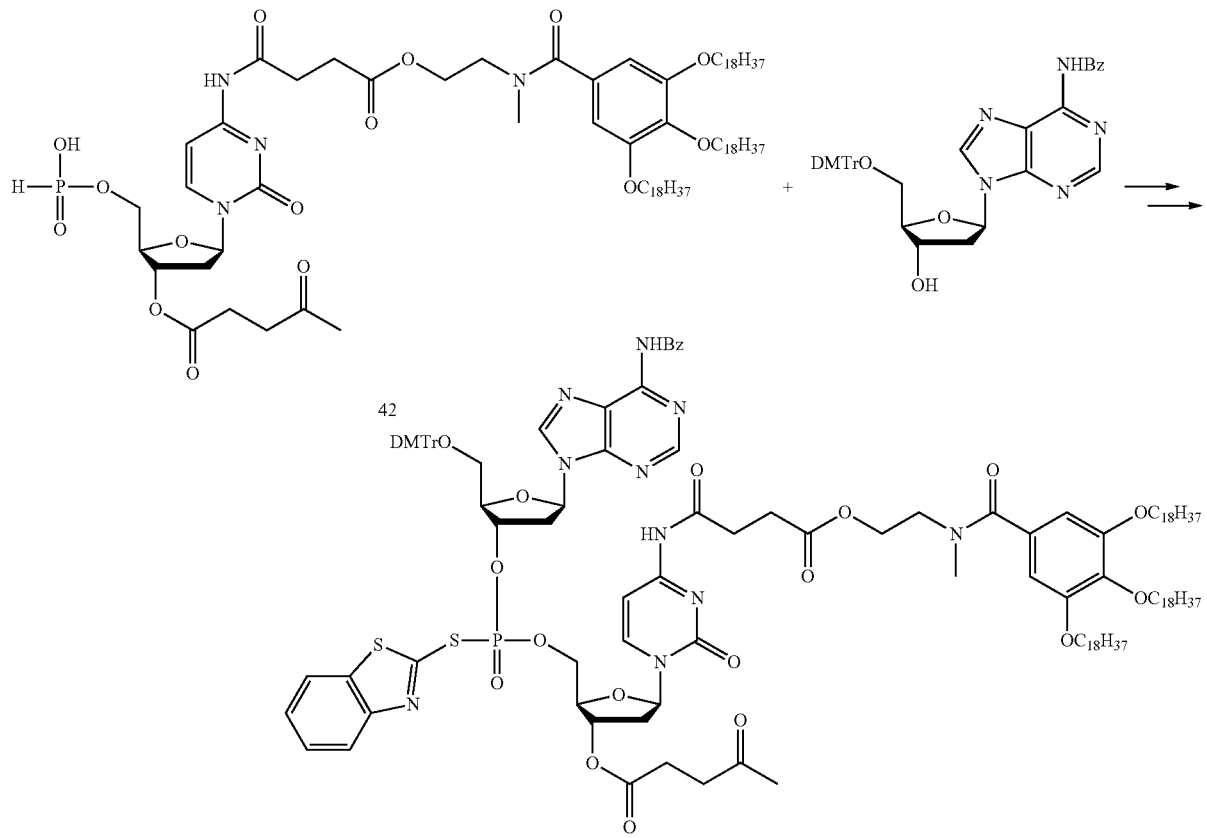

61

Example 61 (Synthesis of 2-mer for Comparison of Condensing Agent): Synthesis of Compound 55

The reaction was performed under the same conditions as in Example 53, except that the condensing agent was changed to pentafluorophenyl acetate (7.1 mg). The reaction mixture after the sulfurization was vacuum concentrated. Consequently, Compound 55 was obtained as the main product.

Example 62 (Synthesis of 2-mer for Comparison of Condensing Agent): Synthesis of Compound 55

The reaction was performed under the same conditions as in Example 53, except that the condensing agent was changed to diphenyl chlorophosphate (4.2 µL). The reaction mixture after the sulfurization was vacuum concentrated. Consequently, Compound 55 was obtained as the main product.

Example 63 (Synthesis of 2-mer for Comparison of Condensing Agent): Synthesis of Compound 55

The reaction was performed under the same conditions as in Example 52, except that the condensing agent was changed to bis(2-chlorophenyl) chlorophosphate (4.6 µL).

The reaction mixture after the sulfurization was vacuum concentrated. Consequently, Compound 55 was obtained as the main product.

Example 64 (Synthesis of 2-mer for Comparison of Condensing Agent): Synthesis of Compound 55

The reaction was performed under the same conditions as in Example 53, except that the condensing agent was changed to bis(2,4-dichlorophenyl) chlorophosphate (10.7 mg). The reaction mixture after the sulfurization was vacuum concentrated. Consequently, Compound 55 was obtained as the main product.

Example 65 (Synthesis of 2-mer for Comparison of Condensing Agent): Synthesis of Compound 55

The reaction was performed under the same conditions as in Example 53, except that the condensing agent was changed to bis(2,6-dimethylphenyl) chlorophosphate (7.1 mg). The reaction mixture after the sulfurization was vacuum concentrated. Consequently, Compound 55 was obtained as the main product.

Example 66 (Synthesis of 2-mer at 3'-TBDPS Group): Synthesis of Compound 65

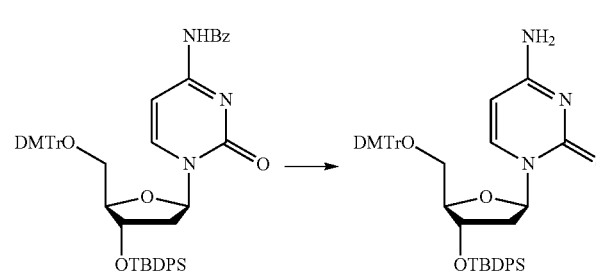
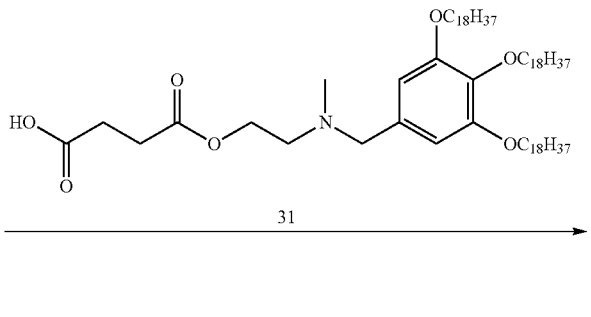

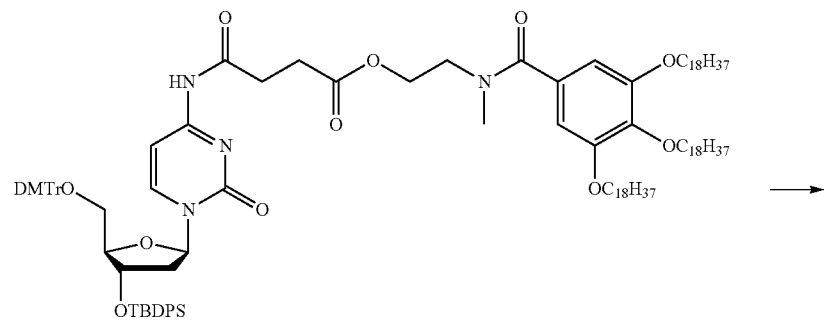

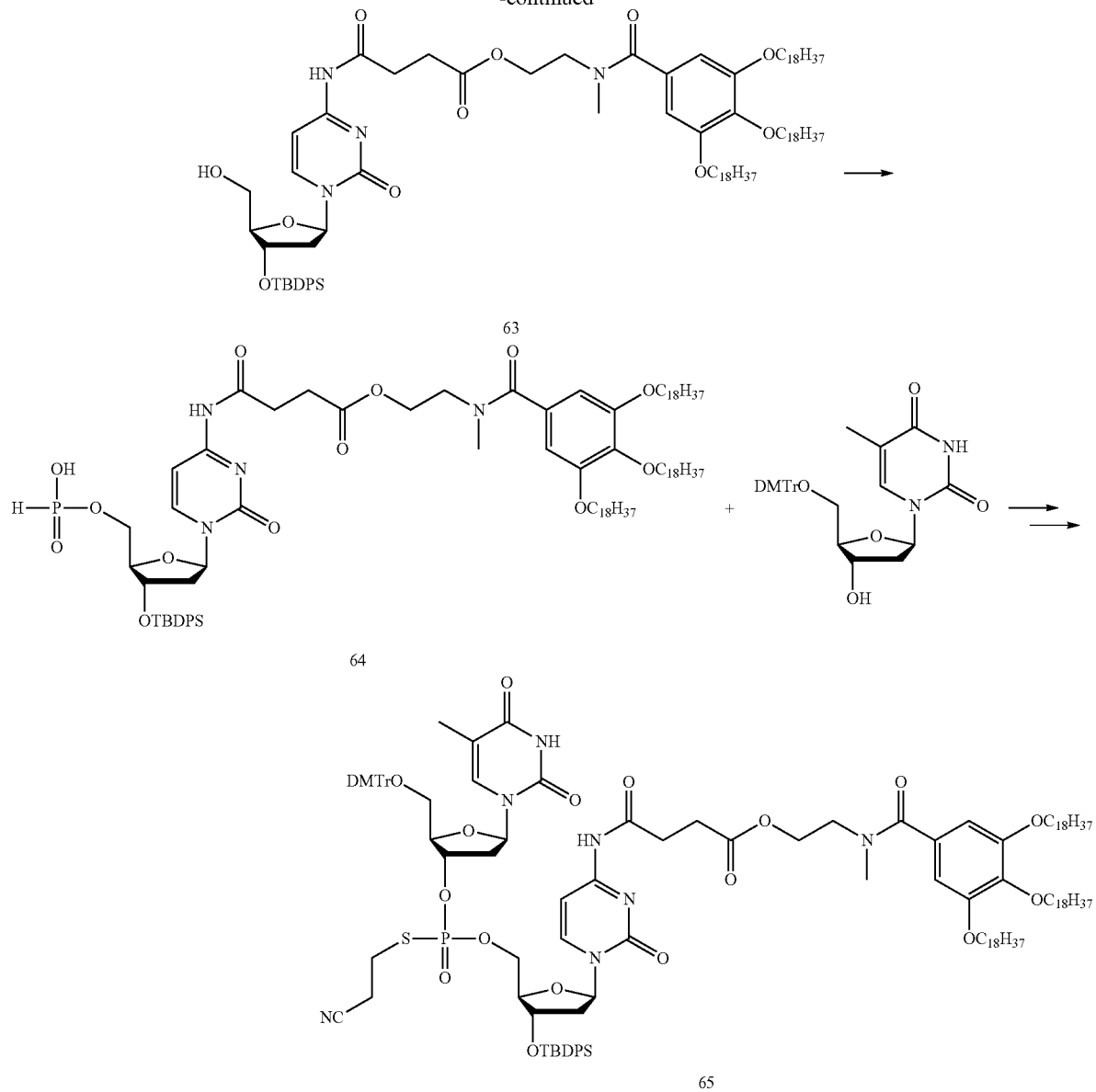

Step 1: Synthesis of 3'-O-(tert-butyldiphenylsilyl)-5'-O-(4,4'-dimethoxytrityl)-2'-deoxycytidine In a nitrogen atmosphere, a 40% aqueous methylamine solution (5.8 mL, 69 mmol) was added to a methanol (301 g) solution of $N^4$-benzoyl-3'-O-(tert-butyldiphenylsilyl)-5'-O-(4,4'-dimethoxytrityl)-2'-deoxycytidine (synthesized in accordance with the method described in Biochemistry, 2004, vol. 43, pp. 6167-6181) (6.5 g, 6.8 mmol) at room temperature, and the mixture was stirred for 23 hours and 26 minutes. The reaction mixture was vacuum concentrated, and the residue was purified by silica gel chromatography (chloroform-methanol). Consequently, the target product (5.1 g, yield 98%) was obtained as a foamy solid.

$^1$H-NMR: (300 MHz; CDCl$_3$) δ1.00 (s, 9H), 1.95-1.97 (m, 1H), 2.51-2.59 (m, 1H), 3.02-3.07 (m, 1H), 3.25-3.30 (m, 1H), 3.77 (s, 6H), 4.44-4.49 (m, 1H), 5.22 (d, 1H), 6.35 (t, 1H), 6.71-6.75 (m, 4H), 7.08-7.41 (m, 16H), 7.53-7.59 (m, 4H), 7.77 (d, 1H).

MS (ESI$^+$): [M+H]$^+$ 768.3391.

Step 2: Synthesis of Compound 62

In a nitrogen atmosphere, HOBt (anhydride) (0.35 g, 2.6 mmol) was added to a solution of 3'-O-(tert-butyldiphenylsilyl)-5'-O-(4,4'-dimethoxytrityl)-2'-deoxycytidine (2.5 g, 3.2 mmol) and Compound 31 (2.2 g, 2.0 mmol) in a mixed solvent of methylene chloride (70 mL) and pyridine (14 mL) at 40° C., and subsequently WSC.HCl (0.92 g, 4.8 mmol) was added. The mixture was stirred for 2 hours and 26 minutes. The reaction mixture was filtered to remove insolubles, and was vacuum concentrated. Thereafter, the residue was added to methanol (250 g) to precipitate a solid, which was then recovered by filtration. Consequently, Compound 62 (3.5 g) was obtained as a white solid.

$^1$H-NMR: (300 MHz; CDCl$_3$) δ0.88 (s, 9H), 1.01 (s, 9H), 1.26-1.81 (m, 96H), 1.91-1.99 (m, 1H), 2.68-2.71 (m, 5H), 3.04-3.08 (m, 4H), 3.25-3.29 (m, 1H), 3.77 (brs, 8H), 3.95 (t, 6H), 4.13-4.46 (m, 4H), 6.30 (t, 1H), 6.56 (s, 2H), 6.72-6.75 (m, 4H), 6.91 (d, 1H), 7.08-7.42 (m, 15H), 7.53-7.59 (m, 4H), 8.05 (d, 1H), 8.92 (brs, 1H).

MS (ESI$^+$): [M+H]$^+$ 1834.2754.

Step 3: Synthesis of Compound 63

In a nitrogen atmosphere, pyrrole (0.39 mL, 5.7 mmol) was added to a methylene chloride (35 g) solution of Compound 62 (3.5 g, 1.9 mmol) at room temperature. At 10° C., dichloroacetic acid (1.6 mL, 19 mmol) was added. The mixture was stirred for 1 hour and 53 minutes. Pyridine (0.77 mL, 9.5 mmol) was added. The reaction mixture was added to methanol (351 g), and the resultant solid was recovered by filtration. Consequently, Compound 63 (2.8 g) was obtained as a white solid.

$^1$H-NMR: (300 MHz; CDCl$_3$) δ0.88 (s, 9H), 1.08 (s, 9H), 1.26-1.82 (m, 96H), 2.16-2.25 (m, 1H), 2.51-2.59 (m, 1H), 2.69-2.75 (m, 4H), 3.04 (s, 3H), 3.19-3.24 (m, 1H), 3.61-3.65 (m, 3H), 3.92-4.43 (m, 10H), 6.21 (t, 1H), 6.57 (s, 2H), 7.21 (d, 1H), 7.35-7.45 (m, 6H), 7.60-7.66 (m, 4H), 8.03 (d, 1H), 9.02 (brs, 1H).

MS (ESI$^+$): [M+H]$^+$ 1532.1383.

Step 4: Synthesis of Compound 64

In a nitrogen atmosphere, 2,2-dimethylbutyryl chloride (0.41 mL, 3.0 mmol) was added to a pyridine (14 mL) solution of phosphorous acid (0.39 g, 4.7 mmol) at 40° C., and the mixture was stirred for 30 minutes. Compound 63 (0.70 g, 0.46 mmol) was added to this solution at 30° C., and the mixture was stirred at 30° C. for 46 minutes. Thereafter, 2,2-dimethylbutyryl chloride (0.38 mL, 2.7 mmol) was added, and the mixture was stirred for 58 minutes. The reaction mixture was added to acetonitrile (200 g), and the resultant solid was recovered by filtration. Consequently, Compound 64 (0.70 g) was obtained as a white solid.

MS (ESI$^+$): [M+H]$^+$ 1596.1098.

Step 5: Synthesis of Compound 65

In a nitrogen atmosphere, bispentafluorophenyl carbonate (0.57 g, 1.4 mmol) was added to a pyridine (20 mL) solution of Compound 64 (0.70 g) and 5'-O-(4,4'-dimethoxytrityl) thymidine (0.37 g, 0.68 mmol) at room temperature, and the mixture was stirred for 24 minutes. Thereafter, N-[(2-cyanoethyl)thio]phthalimide (0.17 g, 0.71 mmol) was added, and the mixture was stirred for 16 hours and 54 minutes. The reaction mixture was added to methanol (200 g), and the resultant solid was recovered by filtration. Consequently, Compound 65 (0.88 g) was obtained.

$^1$H-NMR: (300 MHz; CDCl$_3$) δ0.88 (s, 9H), 1.07 (s, 9H), 1.25-2.01 (m, 97H), 2.33-2.93 (m, 10H), 3.04 (s, 3H), 3.32-4.34 (m, 24H), 5.08-5.18 (m, 1H), 6.25-6.36 (m, 2H), 6.58 (s, 2H), 6.82-6.85 (m, 4H), 7.22-7.65 (m, 21H), 7.79-7.85 (m, 1H), 8.96 (brs, 1H), 9.28 (brs, 1H).

$^{31}$P-NMR: (300 MHz; CDCl$_3$) δ27.08, 27.20.

MS (ESI$^+$): [M+H]$^+$ 2207.3152.

Example 67 (Deprotection of 3'-TBDPS Group): Synthesis of Compound 66

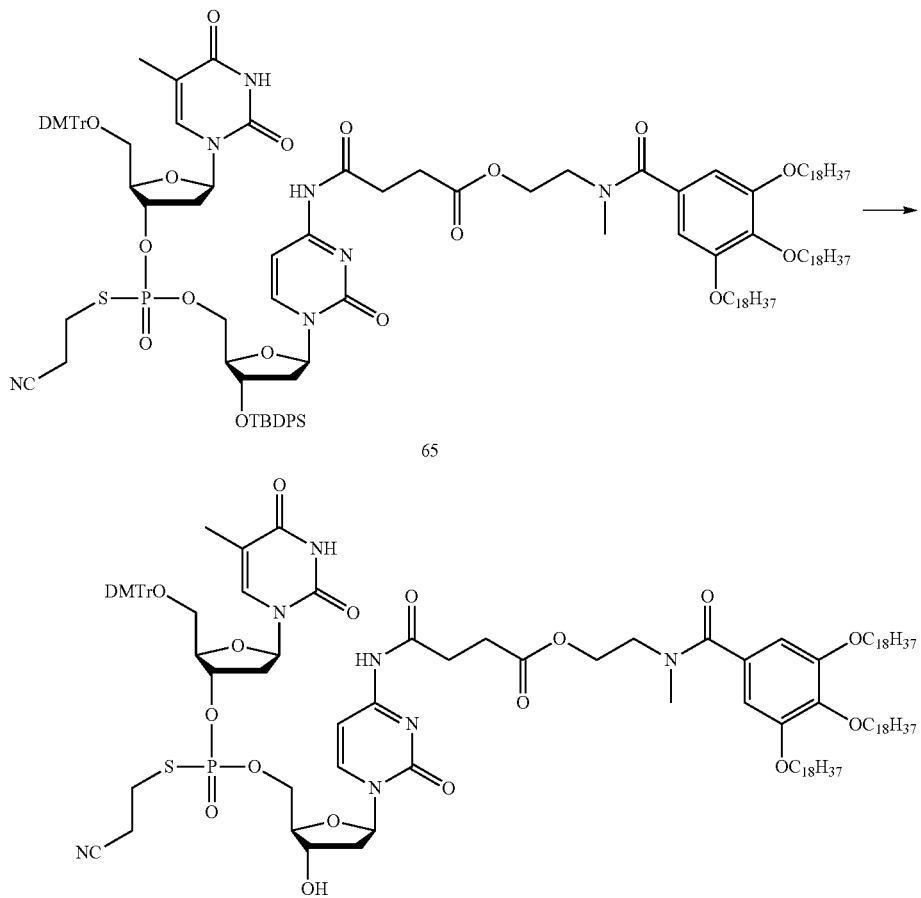

In a nitrogen atmosphere, hydrogen fluoride-pyridine (1.3 μL, 0.045 mmol) was added to a methylene chloride (0.20 mL) solution of Compound 65 (10 mg) at room temperature, and the mixture was stirred for 3 hours and 45 minutes. The reaction mixture was vacuum concentrated. Consequently, Compound 66 was obtained.
MS (ESI$^+$): [M+H]$^+$ 1969.2010.
Example 68 (Synthesis of 4-mer): Synthesis of Compound 69
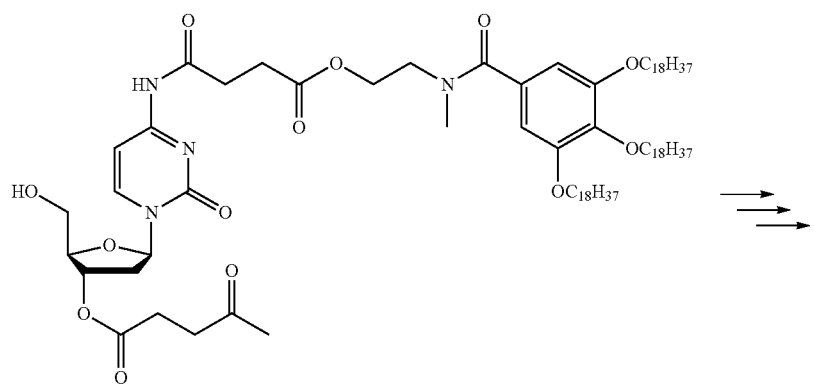
41
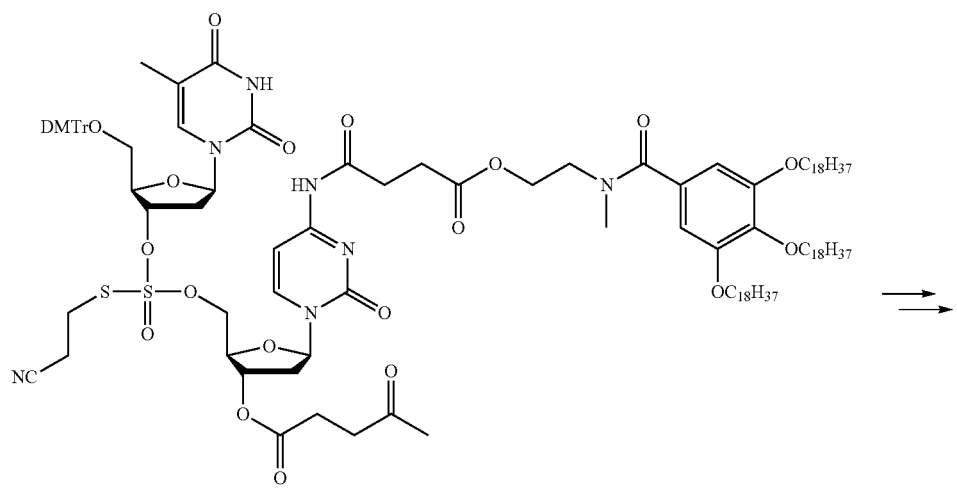
62
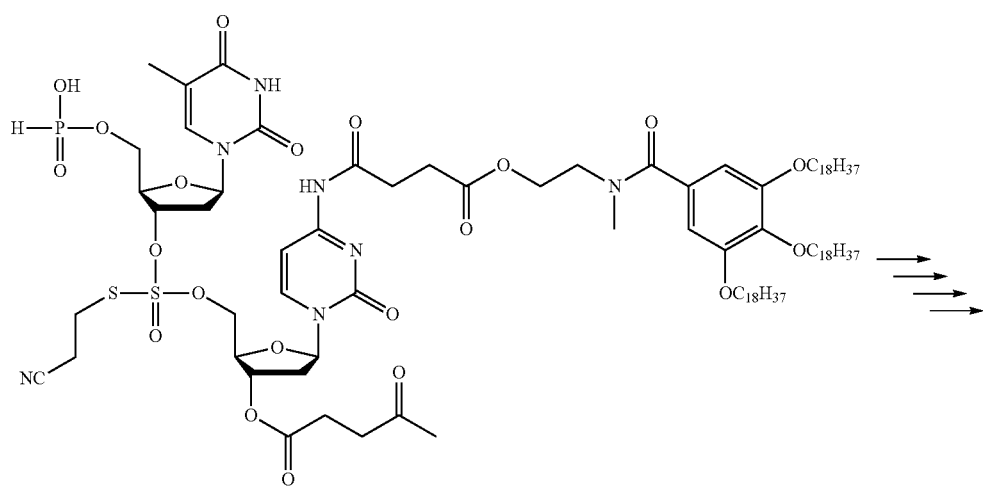
67

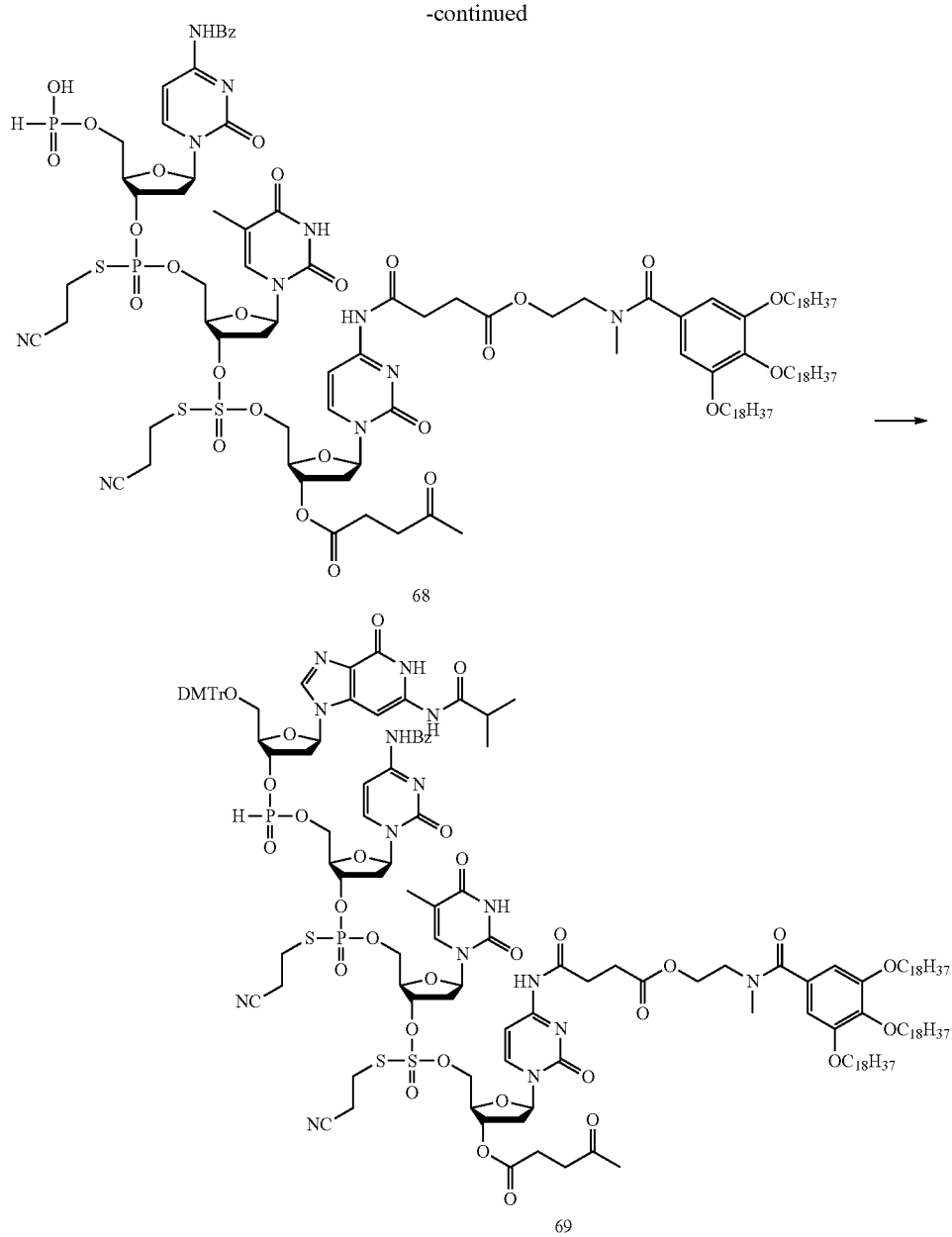

Step 1: Synthesis of Compound 67

In a nitrogen atmosphere, 5'-O-(4,4'-dimethoxytrityl)thymidine (manufactured by Tokyo Chemical Industry Co., Ltd.) (0.34 g, 0.62 mmol) and bispentafluorophenyl carbonate (0.74 g, 1.9 mmol) were added to a pyridine (20 mL) solution of Compound 42 (1.5 g), and the mixture was stirred for 22 minutes. Thereafter, N-[(2-cyanoethyl)thio]phthalimide (0.19 g, 0.81 mmol) was added. The mixture was stirred for 15 hours and 29 minutes to give a reaction solution including Compound 82. Thereafter, triethyl phosphite (90 μL, 0.52 mmol) and water (0.28 mL, 16 mmol) were added, and the mixture was stirred at 25° C. for 1 hour. The reaction mixture was vacuum concentrated. Toluene (25 g) was added and the mixture was vacuum concentrated, these operations being repeated three times. Thereafter, methylene chloride (20 mL) was added. Pyrrole (0.11 mL, 1.6 mmol) and phosphonic acid (1.0 g, 13 mmol) were added at 10° C., and the mixture was stirred for 1 hour and 15 minutes. Pyridine (3.0 mL) was added. Thereafter, 2,2-dimethylbutyryl chloride (0.96 mL, 7.0 mmol) was added in 4 portions every 10 minutes at room temperature, and the mixture was stirred for 33 minutes. 2,2-Dimethylbutyryl chloride (0.48 mL, 3.5 mmol) was added, and the mixture was stirred for 35 minutes. Thereafter, the reaction mixture was added to acetonitrile (200 g), and the resultant solid was recovered by filtration. Consequently, Compound 67 (1.9 g) was obtained as a white solid.

MS (ESI$^+$): [M+H]$^+$ 1829.0819.

Step 2: Synthesis of Compound 68

The reaction was performed under the same conditions as in Step 1, except that Compound 42 was replaced by Compound 67, and that 5'-O-(4,4'-dimethoxytrityl)thymidine was replaced by N⁴-benzoyl-5'-O-(4,4'-dimethoxytrityl)-2'-deoxycytidine (manufactured by Tokyo Chemical Industry Co., Ltd.) (0.60 g). Consequently, Compound 68 (0.97 g) was obtained as a white solid.

MS (ESI⁺): [M+H]⁺ 2291.1664.

Step 3: Synthesis of Compound 69

In a nitrogen atmosphere, bispentafluorophenyl carbonate (0.65 g, 1.7 mmol) was added to a pyridine (20 mL) solution of Compound 68 (0.96 g) and N²-isobutyryl-5'-O-(4,4'-dimethoxytrityl)-2'-deoxyguanosine (manufactured by Tokyo Chemical Industry Co., Ltd.) (0.51 g, 0.80 mmol) at 25° C., and the mixture was stirred for 10 minutes. The reaction mixture was vacuum concentrated. Consequently, Compound 69 was obtained.

MS (ESI⁺): [M+H]⁺ 2912.4312.

Example 69 (Synthesis of 4-mer): Synthesis of Compound 70

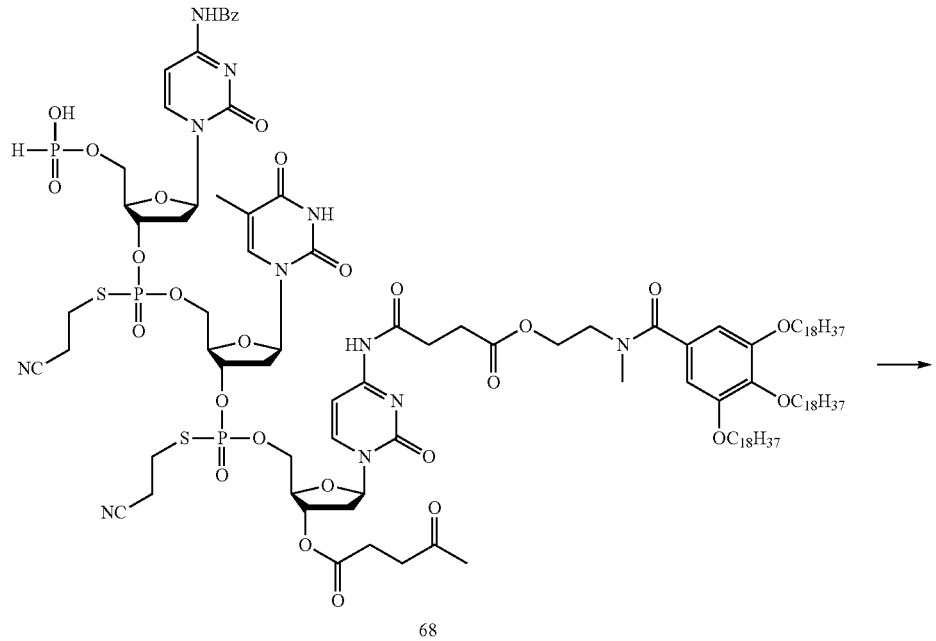

68

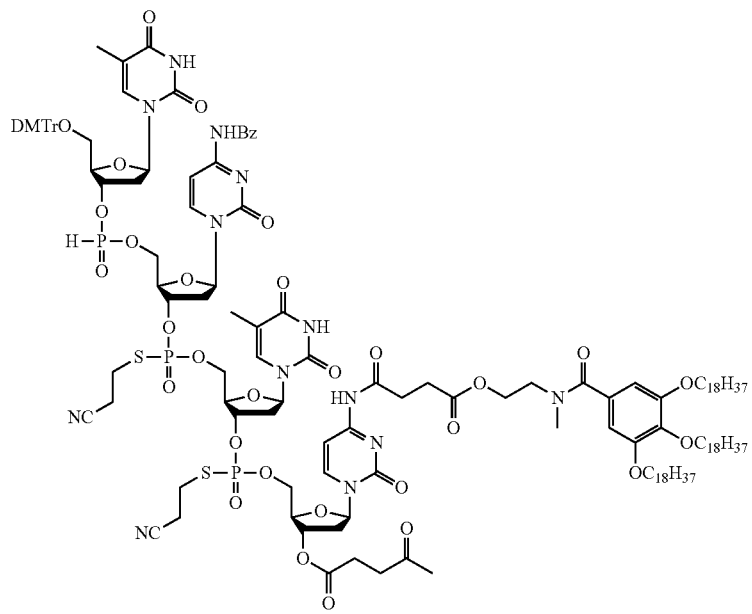

70

Compound 70 was obtained by performing the reaction under the same conditions as in Step 1 of Example 68, except that Compound 42 was replaced by Compound 68.
MS (ESI⁻): [M+H]⁺ 2817.3753.

Example 70 (Synthesis of 4-mer): Synthesis of Compound 71

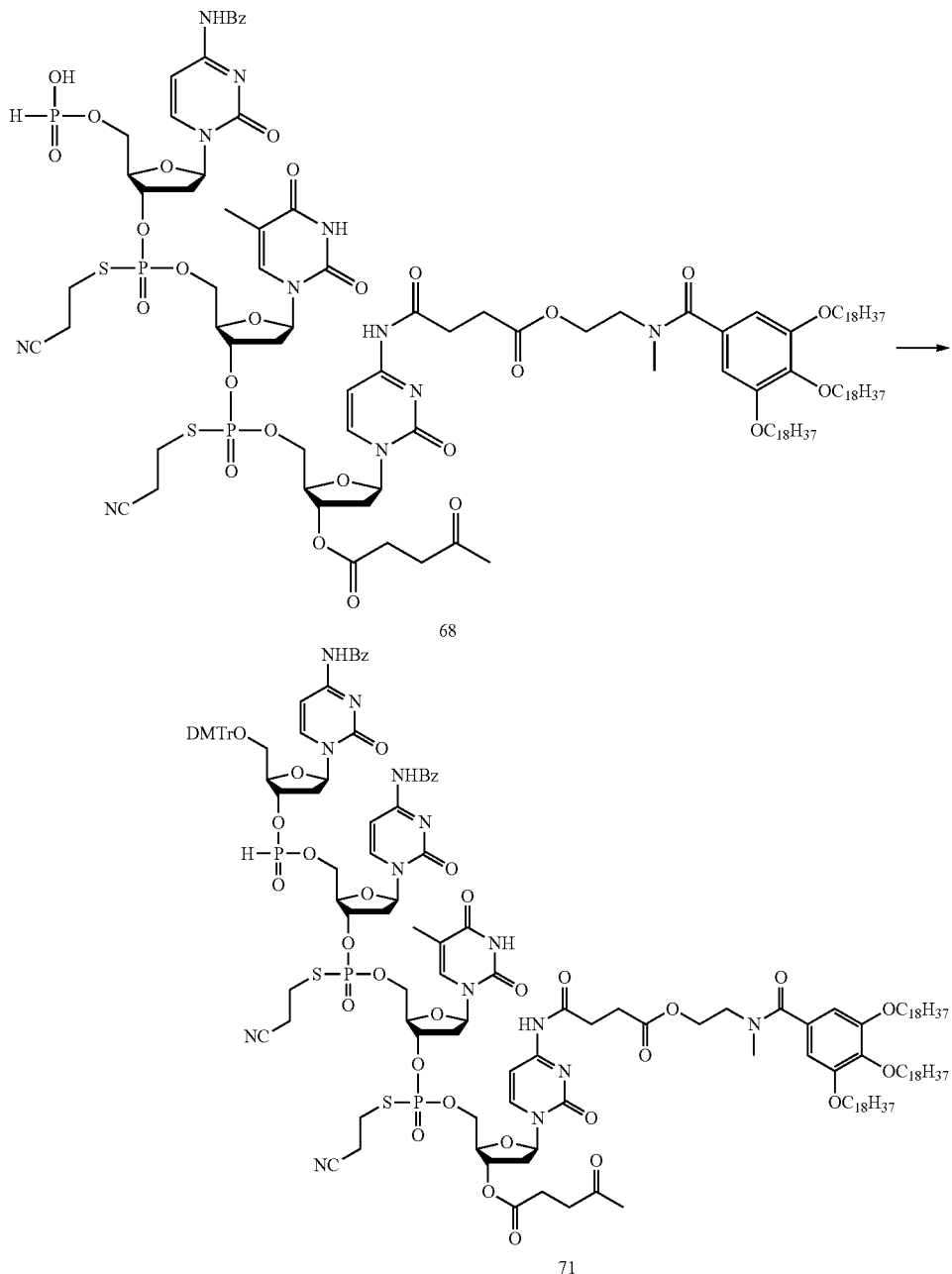

Compound 71 was obtained by performing the reaction under the same conditions as in Step 1 of Example 68, except that Compound 42 was replaced by Compound 68, and that 5'-O-(4,4'-dimethoxytrityl)thymidine was replaced by N⁴-benzoyl-5'-O-(4,4'-dimethoxytrityl)-2'-deoxycytidine (manufactured by Tokyo Chemical Industry Co., Ltd.) (5.4 mg).
MS (ESI⁺): [M+H]⁺ 2906.4242.

Example 71 (Synthesis of 4-mer): Synthesis of Compound 72

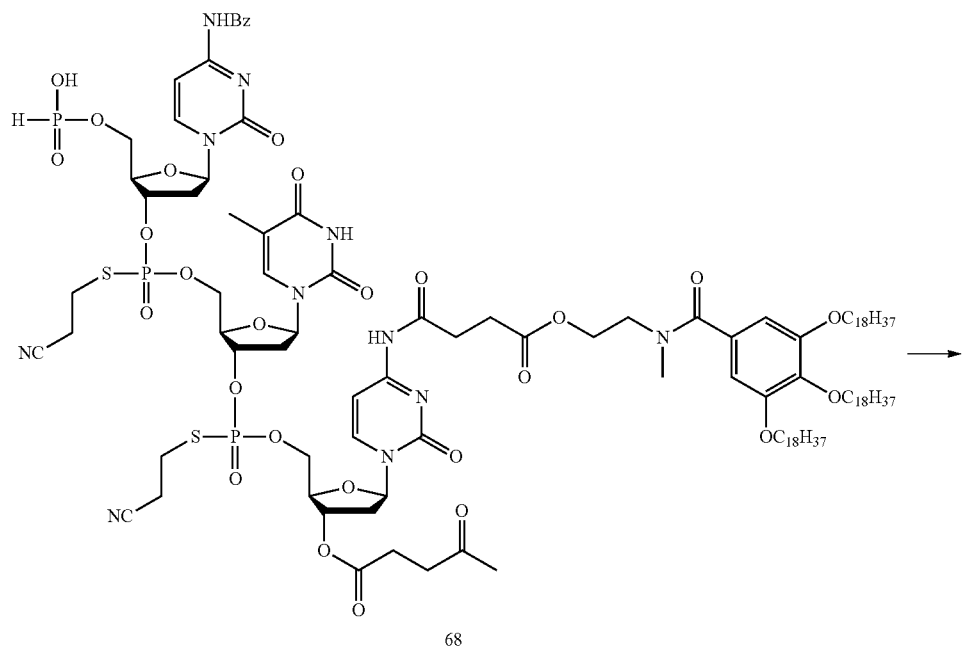

68

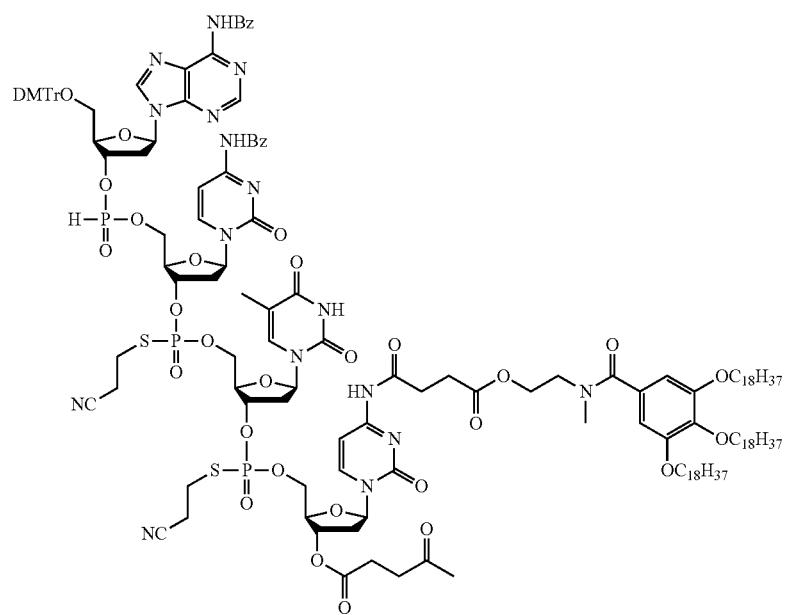

72

Compound 72 was obtained by performing the reaction under the same conditions as in Step 1 of Example 68, except that Compound 42 was replaced by Compound 68, and that 5'-O-(4,4'-dimethoxytrityl)-2'-thymidine was replaced by $N^6$-benzoyl-5'-O-(4,4'-dimethoxytrityl)-2'-deoxyadenosine (manufactured by Tokyo Chemical Industry Co., Ltd.) (4.9 mg).

MS (ESI$^+$): [M+H]$^+$ 2930.4184.

Example 72 (Synthesis of 5-mer): Synthesis of Compound 74
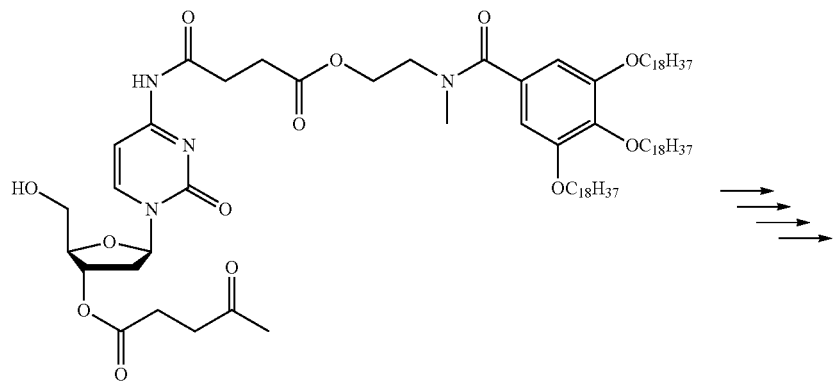
41
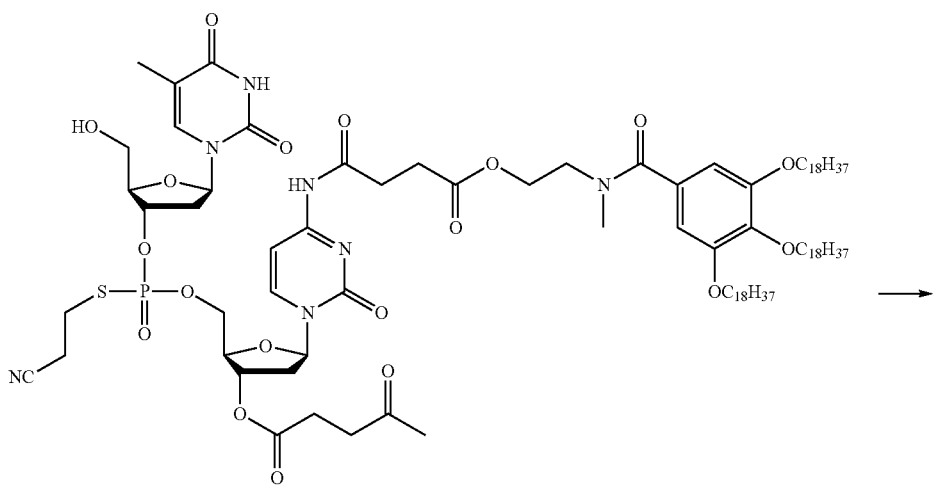
95
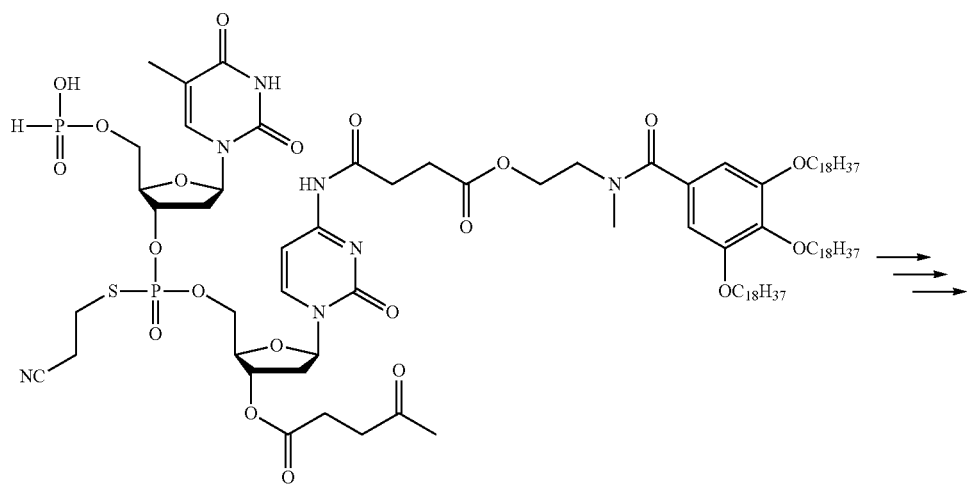
67

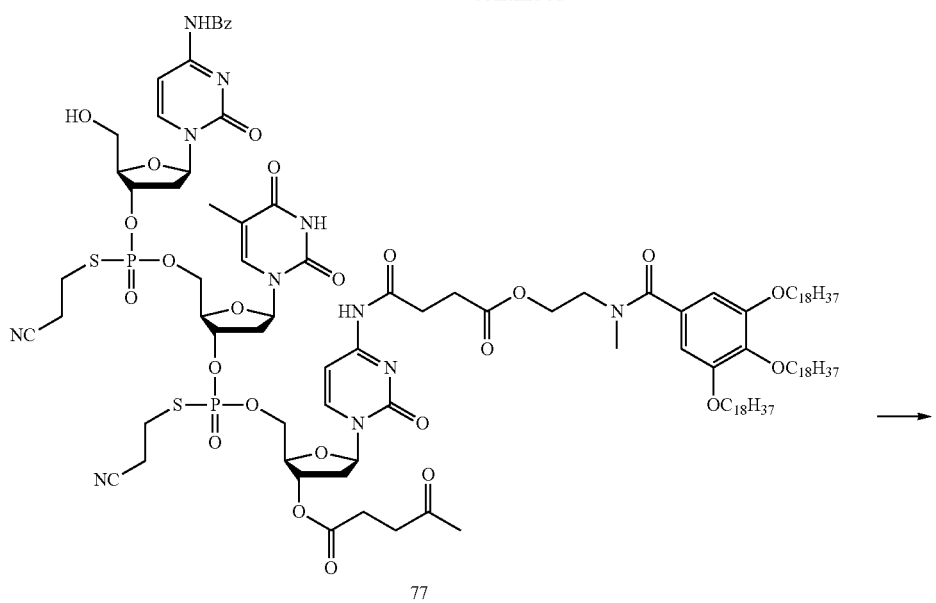
77
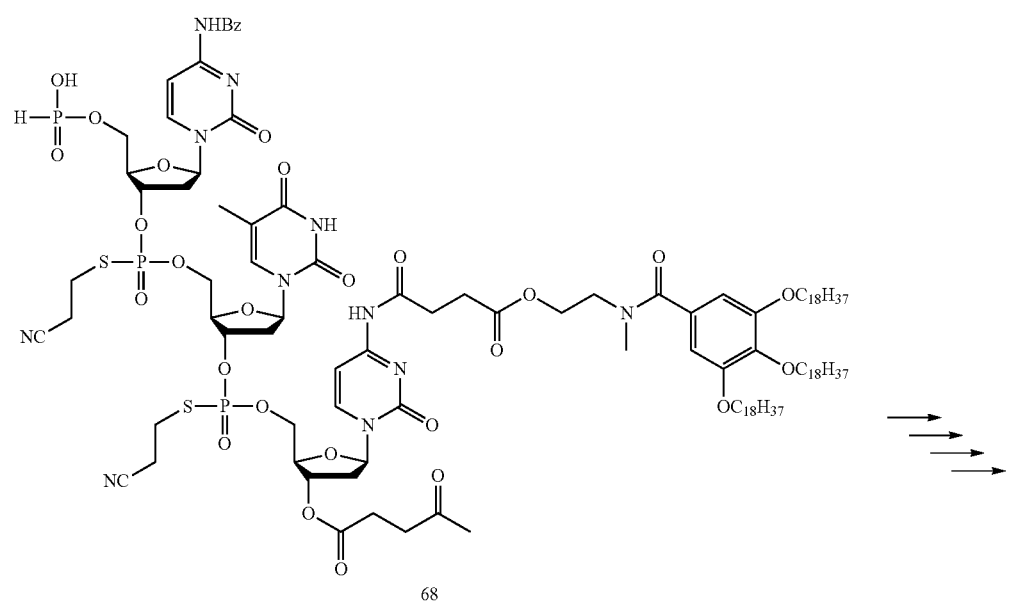
68

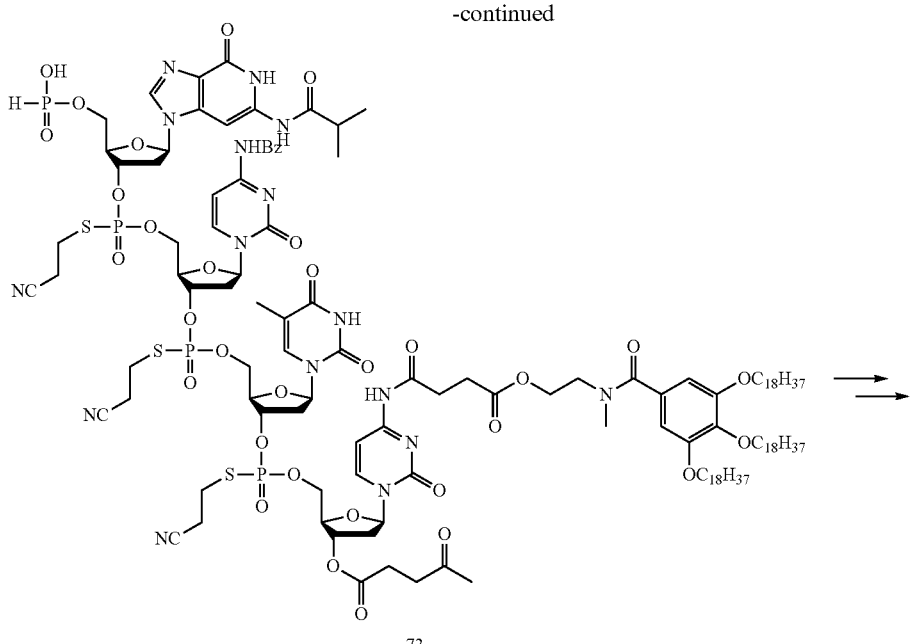

73

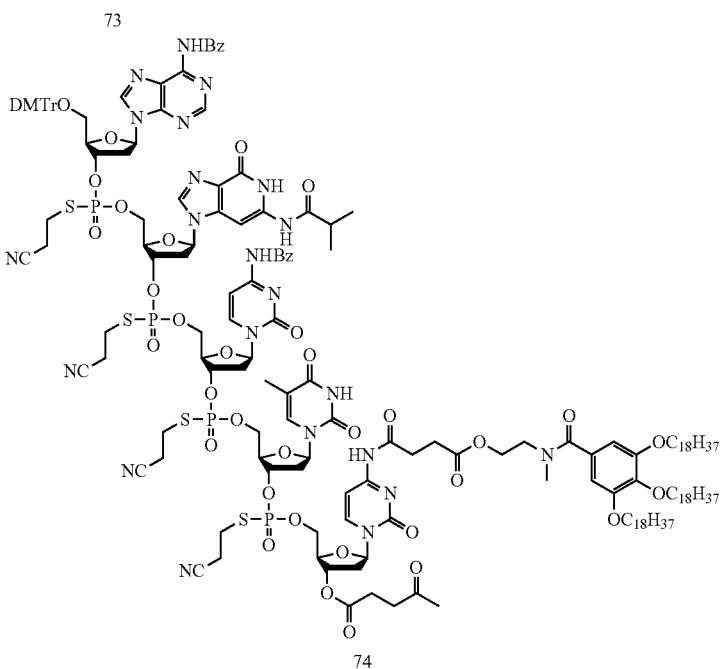

74

Step 1: Synthesis of Compound 67

In a nitrogen atmosphere, 5'-O-(4,4'-dimethoxytrityl)thymidine (manufactured by Tokyo Chemical Industry Co., Ltd.) (0.44 g, 0.80 mmol) and bispentafluorophenyl carbonate (0.67 g, 1.7 mmol) were added to a pyridine (20 mL) solution of Compound 42 (1.2 g), and the mixture was stirred for 23 minutes. Thereafter, N-[(2-cyanoethyl)thio]phthalimide (0.19 g, 0.83 mmol) was added, and the mixture was stirred for 1 hour and 32 minutes. Thereafter, triethyl phosphite (90 μL, 0.52 mmol) and water (0.28 mL, 16 mmol) were added, and the mixture was stirred at 25° C. for 50 minutes. The reaction mixture was vacuum concentrated. Toluene (25 g) was added and the mixture was vacuum concentrated, these operations being repeated three times. Methylene chloride (20 mL) was added. Pyrrole (0.11 mL, 1.6 mmol) and dichloroacetic acid (0.43 mL, 5.3 mmol) were added at 10° C., and the mixture was stirred for 2 hours and 27 minutes. Pyridine (3.0 mL) was added, and the mixture was brought to room temperature. The reaction mixture was added to acetonitrile (200 g), and the resultant solid was recovered by filtration. Consequently, Compound 95 (0.72 g) was obtained as a light skin color solid.

$^1$H-NMR: (300 MHz; CDCl$_3$) δ0.88 (t, 9H), 1.25-1.89 (m, 99H), 2.20 (s, 3H), 2.21-2.89 (m, 13H), 3.06-3.20 (m, 5H), 3.21-3.98 (m, 11H), 4.19-4.4.44 (m, 6H), 5.32-5.34 (m, 2H), 6.10-6.23 (m, 2H), 6.58 (s, 2H), 7.41 (t, 1H), 7.51 (d, 1H), 7.95-8.08 (m, 1H), 8.70-9.60 (m, 2H).

$^{31}$P-NMR: (300 MHz; CDCl$_3$) δ27.55, 27.94.

MS (ESI$^+$): [M+H]$^+$ 1765.1162.

In a nitrogen atmosphere, phosphonic acid (0.56 g, 6.8 mmol) was added to a solution of Compound 95 (0.72 g) in a mixed solvent of methylene chloride (15 mL) and pyridine (2.3 mL) at room temperature. 2,2-Dimethylbutyryl chloride (0.56 mL, 4.1 mmol) was added in 4 portions every 10 minutes, and the mixture was stirred for 31 minutes. 2,2-Dimethylbutyryl chloride (0.42 mL, 3.1 mmol) was added, and the mixture was stirred for 23 minutes. Thereafter, the reaction mixture was added to acetonitrile (203 g), and the resultant solid was recovered by filtration. Consequently, Compound 67 (0.72 g) was obtained as a white solid.

Step 2: Synthesis of Compound 68

In a nitrogen atmosphere, $N^4$-benzoyl-5'-O-(4,4'-dimethoxytrityl)-2'-deoxycytidine (manufactured by Tokyo Chemical Industry Co., Ltd.) (0.49 g, 0.77 mmol) and bispentafluorophenyl carbonate (0.60 g, 1.5 mmol) were added to a pyridine (19 mL) solution of Compound 67 (0.72 g), and the mixture was stirred for 22 minutes. Thereafter, N-[(2-cyanoethyl)thio]phthalimide (0.18 g, 0.76 mmol) as a sulfurizing agent was added, and the mixture was stirred for 1 hour and 10 minutes. Thereafter, the reaction mixture was divided into two portions. One of the portions was vacuum concentrated. Toluene (10 g) was added and the mixture was vacuum concentrated, these operations being repeated three times. Thereafter, methylene chloride (10 mL) was added. Pyrrole (51 µL, 0.74 mmol) and dichloroacetic acid (0.20 mL, 2.4 mmol) were added at 10° C., and the mixture was stirred for 2 hours and 10 minutes. Pyridine (1.2 mL) was added, and the mixture was brought to room temperature. The reaction mixture was further divided into two portions. One of the portions was added to acetonitrile (50 g), and the resultant solid was recovered by precipitation filtration. Consequently, Compound 77 (0.18 g) was obtained as a light skin color solid.

In a nitrogen atmosphere, phosphonic acid (0.12 g, 1.5 mmol) was added to a solution of Compound 77 (0.18 g) in a mixed solvent of methylene chloride (3.0 mL) and pyridine (0.50 mL) at room temperature. 2,2-Dimethylbutyryl chloride (0.13 mL, 0.96 mmol) was added in 4 portions every 10 minutes, and the mixture was stirred for 57 minutes. 2,2-Dimethylbutyryl chloride (33 µL, 0.24 mmol) was added, and the mixture was stirred for 40 minutes. Thereafter, the reaction mixture was added to acetonitrile (51 g), and the resultant solid was recovered by filtration. Consequently, Compound 68 (0.15 g) was obtained as a white solid.

Step 3: Synthesis of Compound 73

The reaction was performed under the same conditions as in Step 2, except that Compound 67 was replaced by Compound 68, and that $N^4$-benzoyl-5'-O-(4,4'-dimethoxytrityl)-2'-deoxycytidine was replaced by $N^2$-isobutyryl-5'-O-(4,4'-dimethoxytrityl)-2'-deoxyguanosine (manufactured by Tokyo Chemical Industry Co., Ltd.) (86 mg). Consequently, Compound 73 (0.12 g) was obtained as a white solid.

MS (ESI$^+$): [M+H]$^+$ 2759.2472.

Step 4: Synthesis of Compound 74

The reaction was performed under the same conditions as in Step 2, except that Compound 67 was replaced by Compound 73, and that $N^4$-benzoyl-5'-O-(4,4'-dimethoxytrityl)-2'-deoxycytidine was replaced by $N^6$-benzoyl-5'-O-(4,4'-dimethoxytrityl)-2'-deoxyadenosine (manufactured by Tokyo Chemical Industry Co., Ltd.) (66 mg). The reaction mixture after the sulfurization was vacuum concentrated. Consequently, Compound 74 was obtained as the main product.

MS (ESI$^+$): [M+2H]$^{2+}$ 1742.2655.

Example 73 (Deprotection of 3'-levulinyl Group: Synthesis of Compound 75)

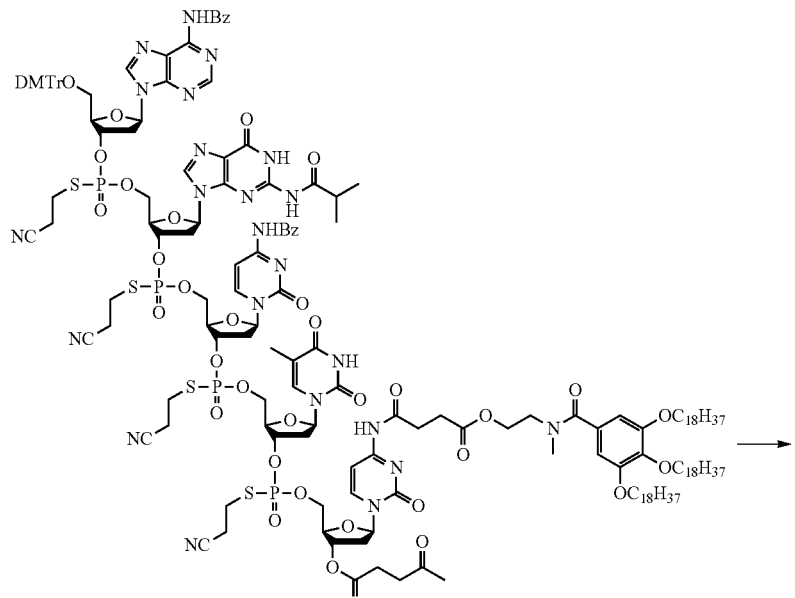

74

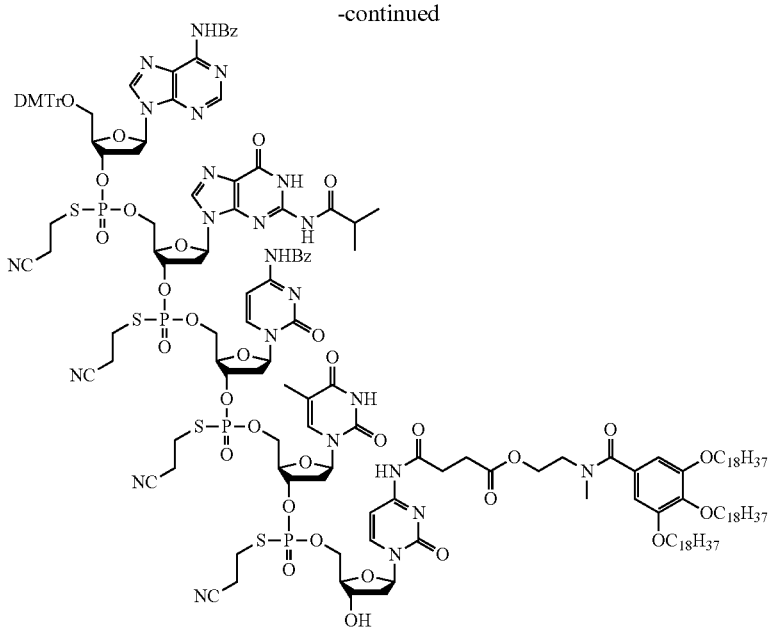

75

Half of the reaction mixture after the sulfurization obtained in Step 4 of Example 72 was cooled to 0° C., and hydrazine monohydrate (4.4 µL, 0.091 mmol) was added thereto. The mixture was stirred for 3 hours and 40 minutes. Further, hydrazine monohydrate (2.2 µL, 0.045 mmol) was added, and the mixture was stirred for 1 hour and 7 minutes. Acetylacetone (50 µL) was added. Thereafter, the reaction mixture was added to acetonitrile (25 g), and the resultant solid was recovered by filtration. Consequently, Compound 75 was obtained.

MS (ESI$^+$): [M+2H]$^{2+}$ 1693.2314.

Example 74 (Deprotection of 3'-levulinyl Group): Synthesis of Compound 76

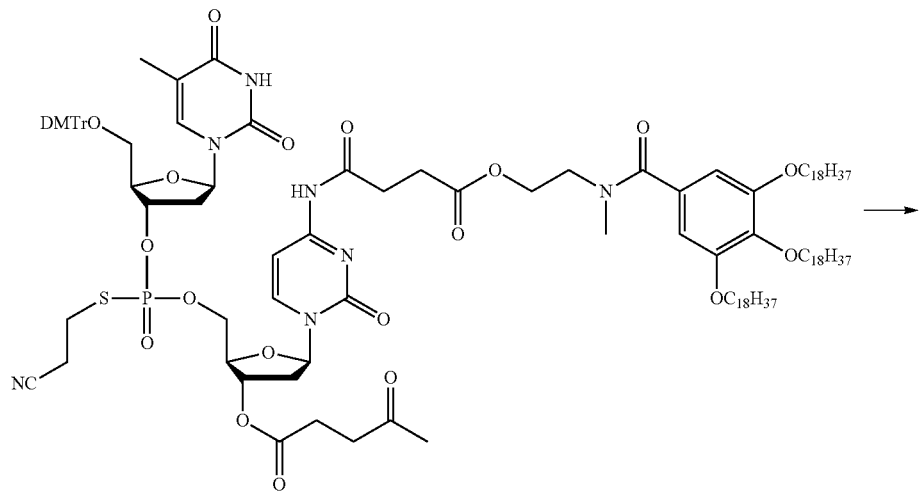

82

-continued

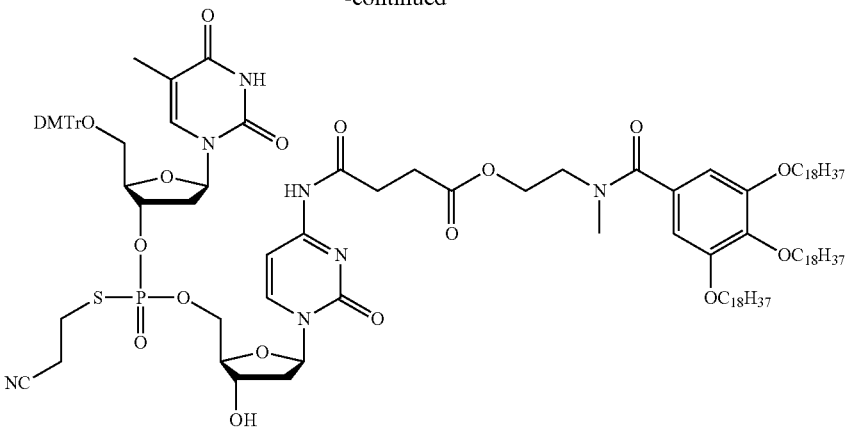

76

At room temperature, hydrazine monohydrate (1.3 μL) was added to 0.5 wt % of the reaction mixture after the sulfurization from Step 1 of Example 68 which included Compound 82. The mixture was stirred for 4 hours. The reaction mixture was vacuum concentrated. Consequently, Compound 76 was obtained.

MS (ESI$^+$): [M+H]$^+$ 1969.2134.

Example 75 (Deprotection of 3'-levulinyl Group): Synthesis of Compound 78

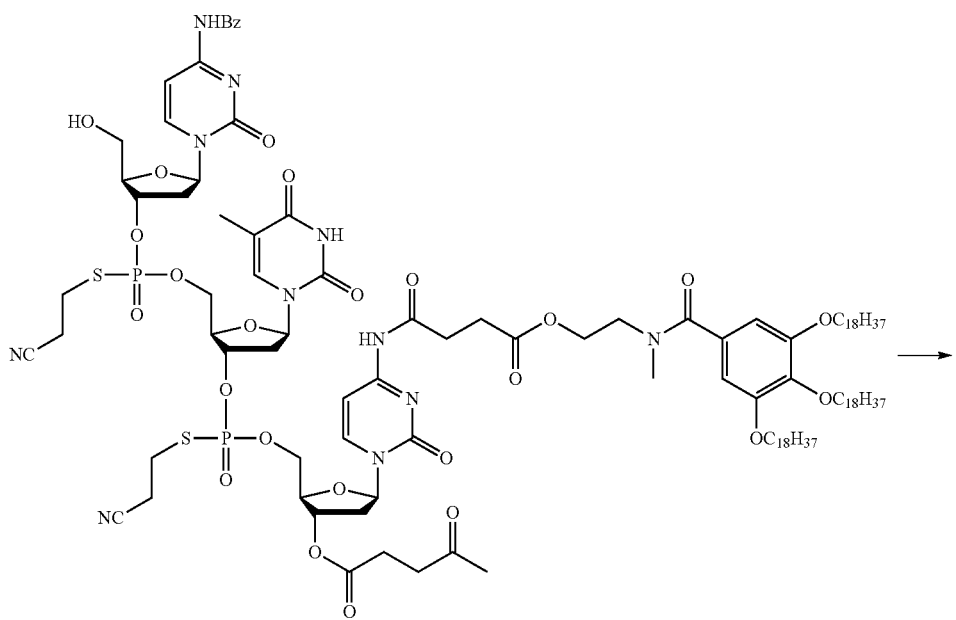

77

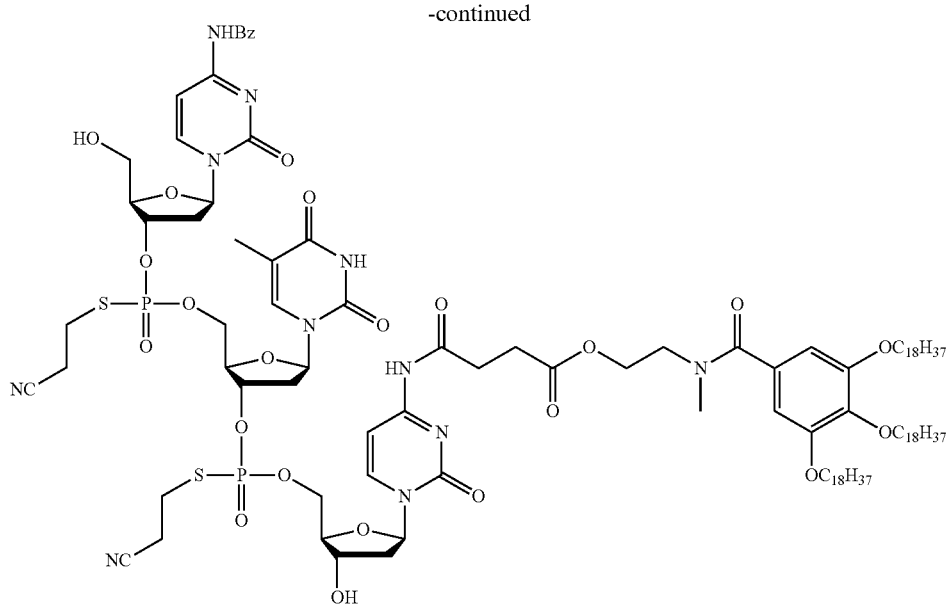

78

In a nitrogen atmosphere, a solution of Compound 77 (99 mg, 45 μmol) in a mixed solvent of methylene chloride (2.0 mL) and acetic acid (0.40 mL) was cooled to 0° C. Hydrazine monohydrate (5.2 μL, 0.11 mmol) was added, and the mixture was stirred for 10 hours and 28 minutes. The reaction mixture was vacuum concentrated. The residue was added to methanol (30 g), and the resultant solid was recovered by filtration. Consequently, Compound 78 (70 mg) was obtained.

MS (ESI$^+$): [M+H]$^+$ 2129.1466.

Example 76 (Synthesis of 2-mer for Comparison of Sulfurizing Agent): Synthesis of Compound 82

The reaction was performed under the same conditions as in Step 2 of Example 68, except that the sulfurizing agent was changed to N-[(2-cyanoethyl)thio]succinimide (synthesized in accordance with the method described in Journal of the Chemical Society, Perkin Transactions 1, 2002, pp. 2619-2633) (13.7 mg). The reaction mixture after the sulfurization was vacuum concentrated. Consequently, Compound 82 was obtained.

Example 77 (Introduction of Pseudo Solid Phase-Protecting Group into Adenine): Synthesis of Compound 79

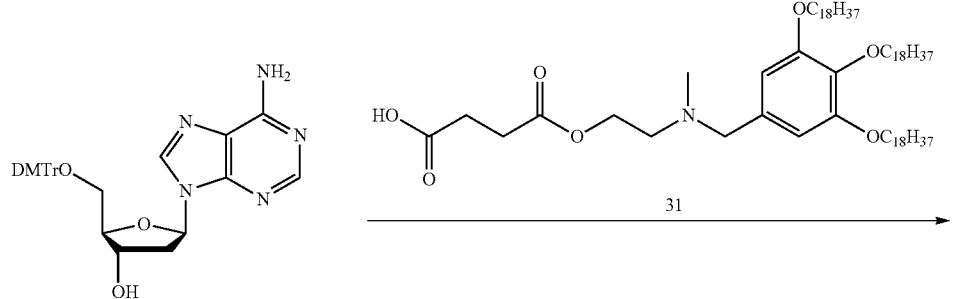

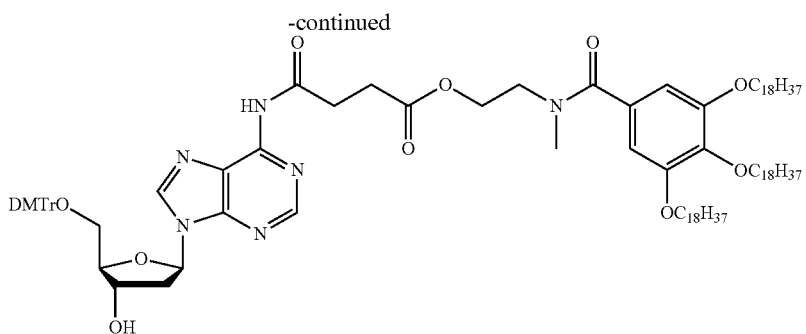

79

In a nitrogen atmosphere, HOBt (anhydride) (7.0 mg, 0.052 mmol) was added to a solution of 5'-O-(4,4'-dimethoxytrityl)-2'-deoxyadenosine (manufactured by Tokyo Chemical Industry Co., Ltd.) (41 mg, 0.075 mmol) and Compound 31 (53 mg, 0.049 mmol) in a mixed solvent of methylene chloride (1.5 mL) and pyridine (0.30 mL) at 40° C., and subsequently WSC.HCl (17.7 mg, 0.092 mmol) was added. The mixture was stirred for 5 hours. The reaction mixture was vacuum concentrated. Consequently, Compound 79 was obtained.

MS (ESI$^+$): [M+H]$^+$ 1620.1583.

Example 78 (Introduction of Pseudo Solid Phase-Protecting Group into Guanine): Synthesis of Compound 80

In a nitrogen atmosphere, HOBt (anhydride) (7.2 mg, 0.053 mmol) was added to a solution of 5'-O-(4,4'-dimethoxytrityl)-2'-deoxyguanosine (manufactured by Tokyo Chemical Industry Co., Ltd.) (43 mg, 0.075 mmol) and Compound 31 (50 mg, 0.046 mmol) in a mixed solvent of methylene chloride (1.5 mL) and pyridine (0.30 mL) at 40° C., and subsequently WSC.HCl (18.4 mg, 0.096 mmol) was added. The mixture was stirred for about 1 week. The reaction mixture was vacuum concentrated. Consequently, Compound 80 was obtained.

MS (ESI$^+$): [M+H]$^+$ 1636.1879.

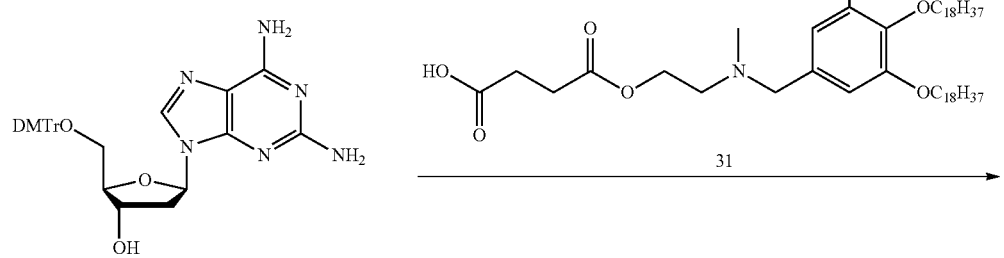

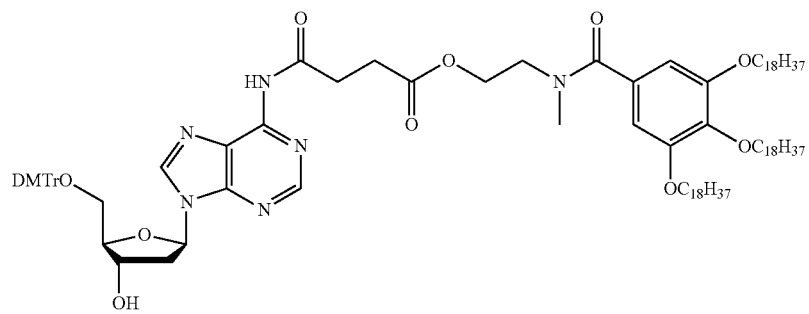

80

Reference Synthetic Example 5 (Levulinylation at 3'-Position of Adenosine): Synthesis of 5'-O-(4,4'-dimethoxytrityl)-3'-O-levulinyl-2'-deoxyadenosine Reference Synthetic Example 6 (Levulinylation at 3'-position of Guanosine): Synthesis of 5'-O-(4,4'-dimethoxytrityl)-3'-O-levulinyl-2'-deoxyguanosine

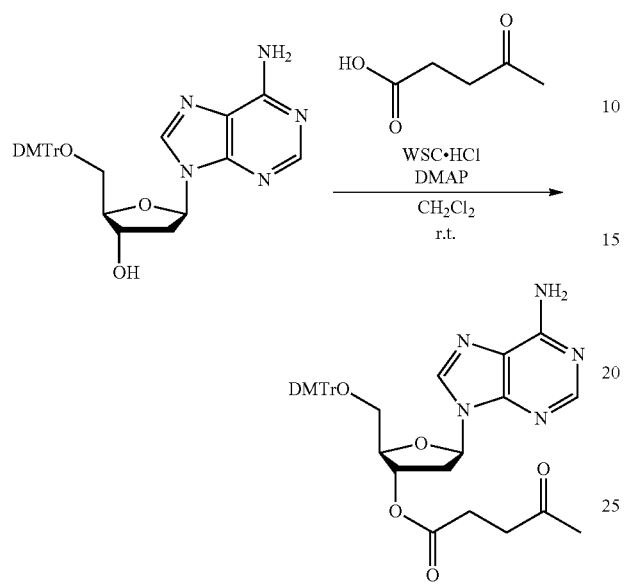

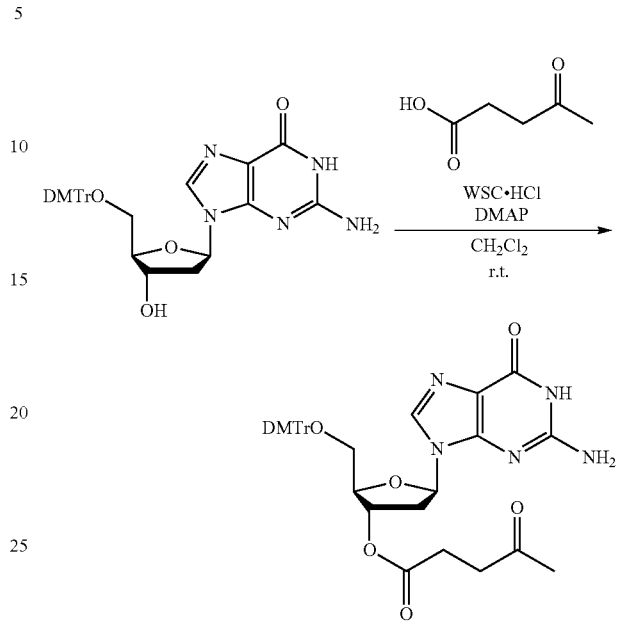

In a nitrogen atmosphere, WSC.HCl (1.3 g, 6.8 mmol) was added to a methylene chloride (50 mL) solution of 5'-O-(4,4'-dimethoxytrityl)-2'-deoxyadenosine (manufactured by Chem-Impex International, Inc.) (2.6 g, 4.6 mmol), DMAP (58 mg, 0.48 mmol) and levulinic acid (0.80 g, 6.9 mmol) at room temperature, and the mixture was stirred for 3 hours and 55 minutes. A solution of acetic acid (0.45 mL) and triethylamine (0.78 mL) in water (20 g) was added. The mixture was stirred for 5 minutes, and the liquids were separated. Water (20 g) was added to the organic phase, the mixture was stirred for 3 minutes, and the liquids were separated. The solvent of the organic phase thus obtained was distilled away under vacuum, and the residue was purified by silica gel chromatography (chloroform-methanol). Consequently, 5'-O-(4,4'-dimethoxytrityl)-3'-O-levulinyl-2'-deoxyadenosine (2.8 g, yield 93%) was obtained as a light yellow foamy solid.

$^1$H-NMR: (300 MHz; CDCl$_3$) δ2.21 (s, 3H), 2.58-2.66 (m, 3H), 2.76-2.81 (m, 2H), 2.90-3.00 (m, 1H), 3.42 (d, 2H), 3.78 (s, 6H), 4.29 (s, 1H), 5.51 (d, 1H), 5.96 (s, 2H), 6.43-6.48 (m, 1H), 6.80 (d, 4H), 7.18-7.44 (m, 9H), 7.97 (s, 1H), 8.28 (s, 1H).

MS (ESI$^+$): [M+H]$^+$ 652.2741.

In a nitrogen atmosphere, WSC.HCl (1.0 g, 5.4 mmol) was added to a methylene chloride (60 mL) solution of 5'-O-(4,4'-dimethoxytrityl)-2'-deoxyadenosine (manufactured by Chem-Impex International, Inc.) (1.5 g, 2.6 mmol), DMAP (39 mg, 0.32 mmol) and levulinic acid (0.63 g, 5.4 mmol) at room temperature, and the mixture was stirred for 27 hours and 44 minutes. A solution of acetic acid (0.26 mL) and triethylamine (0.46 mL) in water (20 g) was added. The mixture was stirred for 23 minutes, and the liquids were separated. Water (21 g) was added to the organic phase, the mixture was stirred for 8 minutes, and the liquids were separated. The solvent of the organic phase thus obtained was distilled away under vacuum. Consequently, 5'-O-(4,4'-dimethoxytrityl)-3'-O-levulinyl-2'-deoxyguanosine (1.8 g) was obtained as a light yellow solid.

$^1$H-NMR: (300 MHz; CDCl$_3$) δ2.20 (s, 3H), 2.49-2.94 (m, 6H), 3.39 (s, 2H), 3.77 (d, 6H), 4.24 (s, 1H), 5.52 (d, 1H), 6.07 (s, 2H), 6.19-6.24 (m, 1H), 6.80 (d, 4H), 7.19-7.40 (m, 9H), 7.63 (s, 1H), 11.97 (brs, 1H).

MS (ESI$^+$): [M+H]$^+$ 668.2715.

Example 79 (Introduction of Pseudo Solid Phase-Protecting Group into Guanine): Synthesis of Compound 81

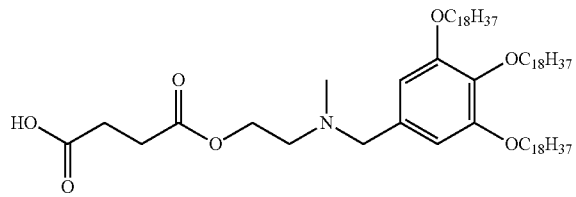

31

-continued

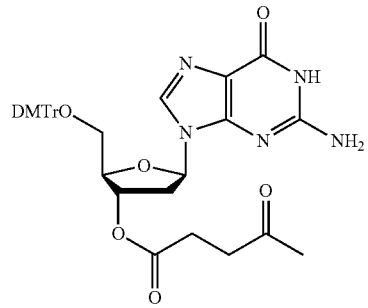 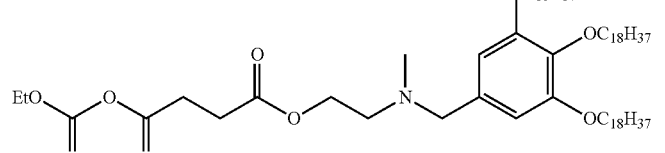

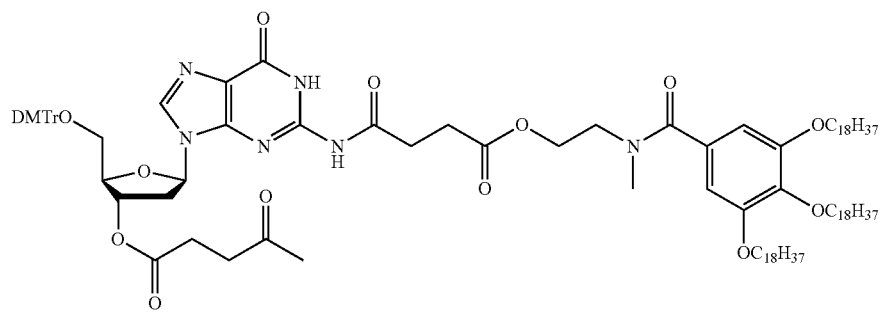

81

In a nitrogen atmosphere, ethyl chloroformate (1.3 μL, 0.014 mmol) was added to a methylene chloride (1.0 mL) solution of Compound 31 (8.9 mg, 8.2 μmol) at room temperature, and subsequently triethylamine (1.9 μL, 0.014 mmol) was added. The mixture was stirred for 1 hour and 57 minutes. Further, ethyl chloroformate (1.3 μL, 0.014 mmol) and triethylamine (1.9 μL, 0.014 mmol) were added, and the mixture was stirred for 36 minutes. Thereafter, 5'-O-(4,4'-dimethoxytrityl)-3'-O-levulinyl-2'-deoxyguanosine (10.5 mg, 0.016 mmol) was added at room temperature, and the mixture was stirred for 59 minutes. Thereafter, triethylamine (0.10 mL, 0.72 mmol) was added at room temperature. The mixture was heated to 40° C. and was stirred for 3 hours and 3 minutes. The reaction mixture was vacuum concentrated. Consequently, Compound 81 was obtained.

MS (ESI$^+$): [M+H]$^+$ 1734.1983.

Example 80 (Introduction of Pseudo Solid Phase-Protecting Group into Guanine): Synthesis of Compound 81

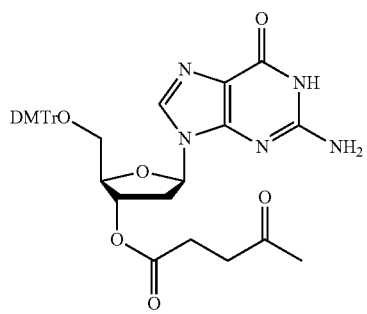 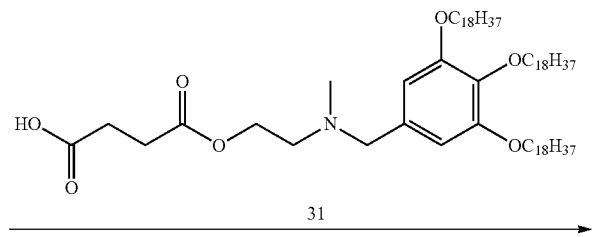

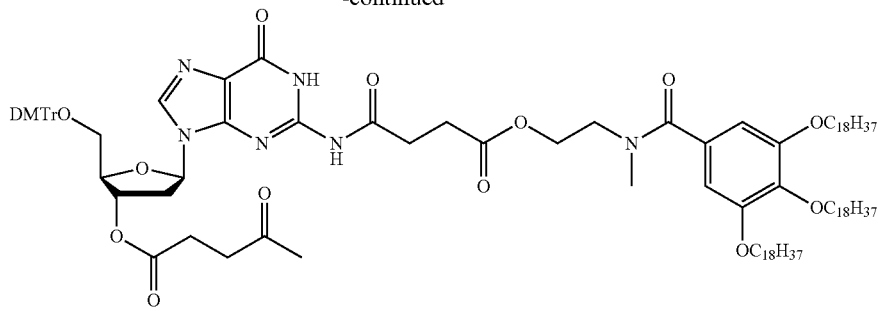

81

In a nitrogen atmosphere, diisopropylethylamine (0.78 mL, 4.6 mmol), DMAP (0.57 g, 4.7 mmol) and WSC.HCl (0.89 g, 4.6 mmol) were added in this order to a methylene chloride (100 mL) solution of 5'-O-(4,4'-dimethoxytrityl)-3'-O-levulinyl-2'-deoxyguanosine (0.94 g, 1.4 mmol) and Compound 31 (1.0 g, 0.93 mmol) at 40° C., and the mixture was stirred for 3 hours and 21 minutes. The reaction mixture was vacuum concentrated. Methanol (100 g) was added, and the resultant solid was recovered by filtration. Consequently, a crude product (1.5 g) of Compound 81 was obtained. The crude product was purified by silica gel chromatography (chloroform-methanol) to give Compound 81 (47 mg).

$^1$H-NMR: (300 MHz; CDCl$_3$) δ0.88 (t, 9H), 126-1.81 (m, 96H), 2.19 (s, 3H), 2.20-2.60 (m, 7H), 2.75-2.80 (m, 2H), 2.94-3.06 (m, 4H), 3.37 (d, 2H), 3.38-3.79 (m, 8H), 3.95 (t, 6H), 3.90-4.50 (m, 3H), 5.50 (d, 1H), 6.12-6.20 (m, 1H), 6.57 (s, 2H), 6.76-6.80 (m, 4H), 7.19-7.43 (m, 9H), 7.79 (s, 1H), 9.34 (brs, 1H), 11.89 (brs, 1H).

MS (ESI$^+$): [M+H]$^+$ 1734.1951.

Reference Synthetic Example 7: Synthesis of 5'-O-(tert-butyldimethylsilyl)-3'-O-levulinylthymidine

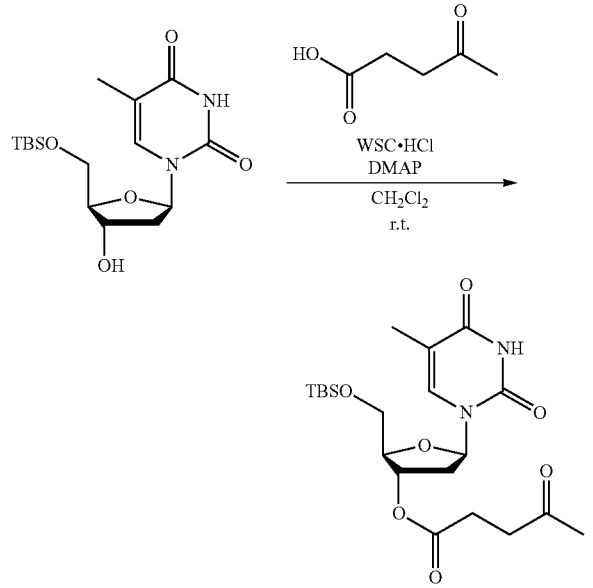

In a nitrogen atmosphere, WSC.HCl (4.6 g, 24 mmol) was added to a THF (38 g) solution of Compound 1 (5.3 g, 15 mmol), DMAP (0.17 g, 1.4 mmol) and levulinic acid (2.8 g, 24 mmol) at room temperature, and the mixture was stirred for 15 hours and 13 minutes. A solution of acetic acid (1.5 g, 26 mmol) and triethylamine (2.6 g, 19 mmol) in water (38 g) was added, and the mixture was stirred for 5 minutes. Ethyl acetate (37 g) was added. The mixture was stirred for 14 minutes, and the liquids were separated. The solvent of the organic phase thus obtained was distilled away under vacuum. Consequently, 5'-O-(tert-butyldimethylsilyl)-3'-O-levulinylthymidine (6.9 g) was obtained as a light orange solid.

$^1$H-NMR: (300 MHz; CDCl$_3$) δ0.13 (s, 6H), 0.93 (s, 9H), 1.92 (d, 3H), 2.05-2.15 (m, 1H), 2.21 (s, 3H), 2.39-2.45 (m, 1H), 2.58-2.62 (m, 2H), 2.76-2.81 (m, 2H), 3.90-3.91 (m, 2H), 4.099-4.103 (m, 1H), 5.26 (d, 1H), 6.37 (q, 1H), 7.55 (d, 1H), 9.34 (brs, 1H).

Example 81 (Synthesis of Nucleoside Having Pseudo Solid Phase-Protecting Group at 3-Position of Thymine): Synthesis of Compound 85

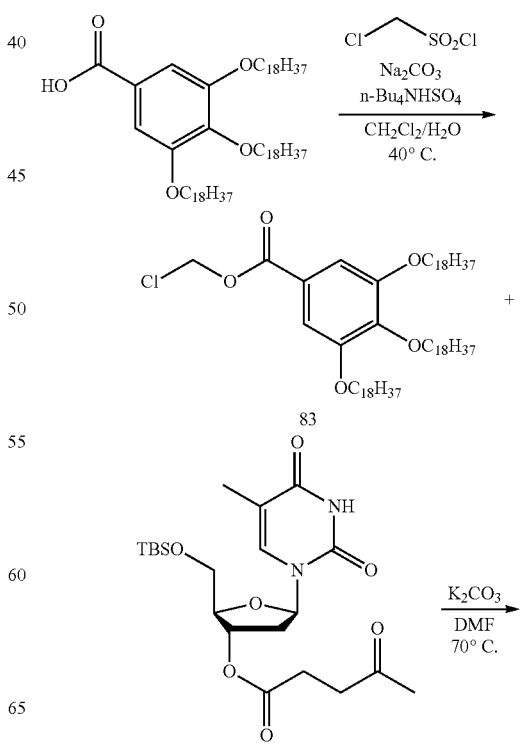

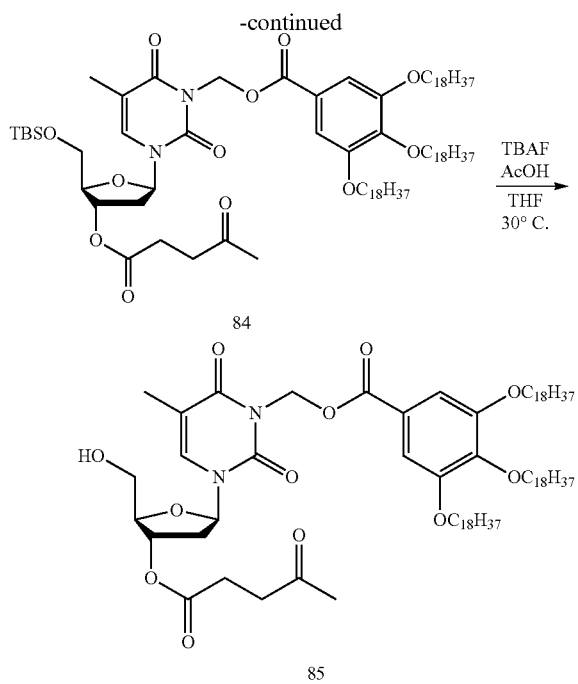

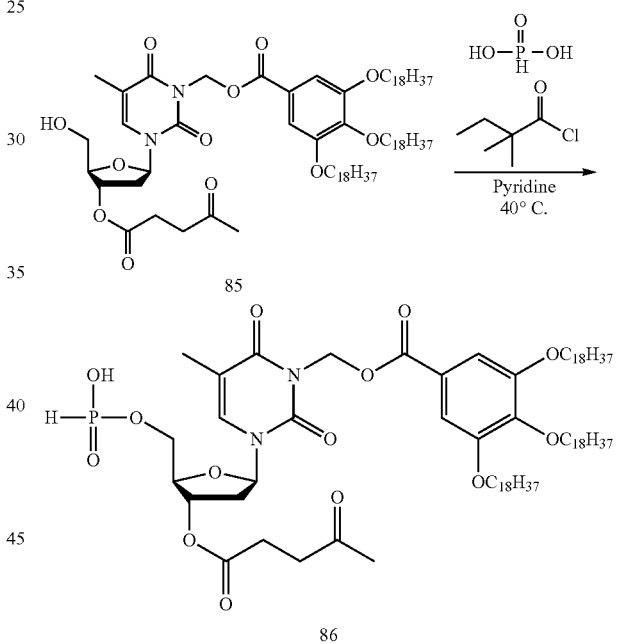

Step 1: Synthesis of Compound 83

In a nitrogen atmosphere, chloromethanesulfonyl chloride (0.39 mL, 3.9 mmol) was added to a solution of 3,4,5-tris(octadecyloxy)benzoic acid (synthesized in accordance with the method described in WO 2014/077292) (3.0 g, 3.2 mmol), sodium carbonate (1.1 g, 10 mmol) and tetra-n-butylammonium hydrogen sulfate (0.13 g, 0.38 mmol) in a mixed solvent of methylene chloride (71 g) and water (30 g) at room temperature, and the mixture was stirred for 2 hours and 42 minutes. Further, chloromethanesulfonyl chloride (60 µL, 0.60 mmol) was added. The mixture was stirred for 18 minutes, heated to 40° C., and stirred for 10 minutes. The stirring was terminated, and the liquids were separated. Methylene chloride was added to the aqueous phase to perform extraction. The organic phases obtained were combined. The solvent was distilled away under vacuum. Acetonitrile (70 g) was added, and the resultant solid was recovered by filtration. Consequently, Compound 83 was obtained as a white solid (3.16 g).

$^1$H-NMR: (300 MHz; CDCl$_3$) δ0.86-0.90 (m, 9H), 1.26-1.84 (m, 96H), 3.99-4.05 (m, 6H), 5.93-6.01 (m, 2H), 7.27-7.36 (m, 2H).

Step 2: Synthesis of Compound 84

In a nitrogen atmosphere, potassium carbonate (0.21 g, 1.5 mmol) was added to a DMF (50 mL) solution of Compound 83 (1.0 g, 1.1 mmol) and 5'-O-(tert-butyldimethylsilyl)-3'-O-levulinylthymidine (0.71 g, 1.6 mmol) at 70° C., and the mixture was stirred for 2 hours and 5 minutes. Further, potassium carbonate (0.91 g, 6 mmol) was added, and the mixture was stirred for 2 hours and 44 minutes. Thereafter, the reaction mixture was added to acetonitrile (201 g), and the resultant solid was recovered by filtration. Consequently, Compound 84 (1.01 g) was obtained as a yellow solid.

$^1$H-NMR: (300 MHz; CDCl$_3$) δ0.14 (s, 6H), 0.86-0.93 (m, 18H), 1.26-1.81 (m, 96H), 2.13-2.43 (m, 5H), 2.56-2.60 (m, 2H), 2.74-2.79 (m, 2H), 3.92-4.12 (m, 9H), 5.26 (d, 1H), 6.22 (q, 2H), 6.42 (q, 1H), 7.22 (s, 2H), 7.59 (s, 1H).

MS (ESI$^+$): [M+H]$^+$ 1394.0827.

Step 3: Synthesis of Compound 85

In a nitrogen atmosphere, a 1.0 M TBAF/THF solution (3.5 mL, 3.5 mmol) was added to a THF (10 mL) solution of Compound 84 (0.94 g, 0.67 mmol) and acetic acid (0.41 mL, 7.2 mmol) at 30° C., and the mixture was stirred for 4 hours and 2 minutes. Thereafter, the reaction mixture was added to methanol (100 g), and the resultant solid was recovered by filtration. Consequently, Compound 85 (0.85 g, yield 99% (Step 3)) was obtained as a yellow solid.

$^1$H-NMR: (300 MHz; CDCl$_3$) δ0.88 (t, 9H), 1.26-1.81 (m, 96H), 2.20 (s, 3H), 2.39-2.44 (m, 2H), 2.58-2.60 (m, 2H), 2.76-2.78 (m, 2H), 3.93 (t, 3H), 3.96-4.01 (m, 6H), 4.11 (d, 1H), 5.34-5.38 (m, 1H), 6.21 (q, 2H), 6.32 (t, 1H), 7.21 (s, 2H), 7.61 (d, 1H).

MS (ESI$^+$): [M+H]$^+$ 1279.9950.

Example 82 (H-phosphonation): Synthesis of Compound 86

In a nitrogen atmosphere, 2,2-dimethylbutyryl chloride (0.45 mL, 3.3 mmol) was added to a pyridine (15 mL) solution of phosphorous acid (0.40 g, 4.9 mmol) at 40° C., and the mixture was stirred for 39 minutes. Compound 85 (0.65 g, 0.51 mmol) was added to this solution, and the mixture was stirred at 40° C. for 1 hour and 27 minutes. Thereafter, the reaction mixture was added to acetonitrile (151 g), and the resultant solid was recovered by filtration. Consequently, Compound 86 (0.66 g) was obtained as a white solid.

$^1$H-NMR: (300 MHz; CDCl$_3$) δ0.88 (t, 9H), 1.26-1.81 (m, 96H), 1.97 (d, 3H), 2.19 (s, 3H), 2.34-2.41 (m, 2H), 2.55-2.59 (m, 2H), 2.74-2.78 (m, 2H), 3.96-4.01 (m, 6H), 4.20-4.29 (m, 3H), 5.39 (d, 1H), 6.20 (q, 2H), 6.45-6.50 (m, 1H), 6.96 (d, 1H), 7.21 (s, 2H), 7.76-7.81 (m, 1H).

$^{31}$P-NMR: (300 MHz; CDCl$_3$) δ6.28.

MS (ESI$^-$): [M−H]$^-$ 1341.9722.

Example 83 (Synthesis of 2-mer): Synthesis of Compound 87

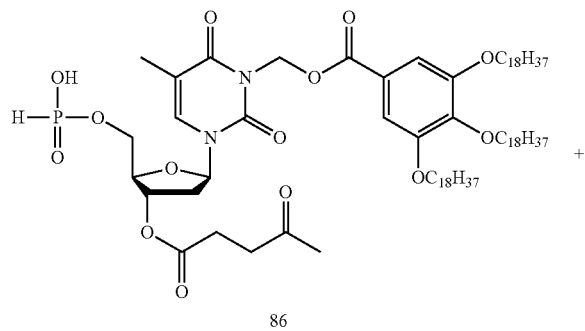

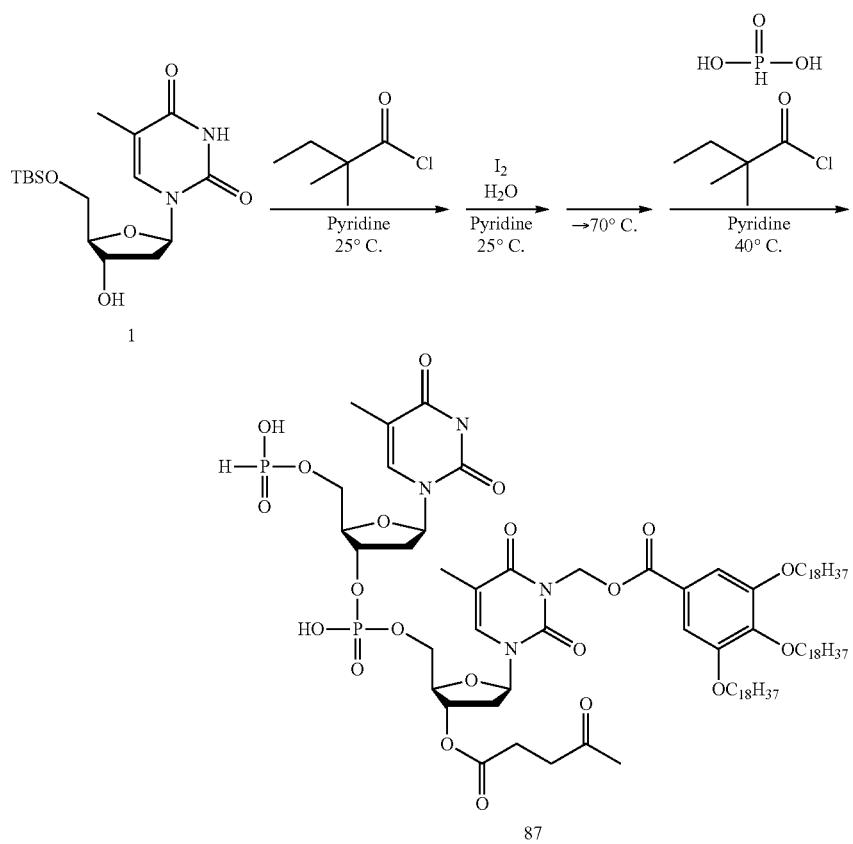

In a nitrogen atmosphere, 2,2-dimethylbutyryl chloride (24 µL, 0.18 mmol) was added to a pyridine (1.0 mL) solution of Compound 86 (51 mg) and Compound 1 (19 mg, 0.053 mmol) at 25° C., and the mixture was stirred for 19 minutes. Thereafter, a 0.05 M solution of iodine in pyridine and water (1.1 mL, 0.055 mmol) was added, and the mixture was stirred for 36 minutes. Thereafter, water (0.14 mL) was added. The mixture was heated to 70° C. and was stirred for 15 hours and 43 minutes. Thereafter, the reaction mixture was vacuum concentrated. Pyridine was added and the mixture was vacuum concentrated, these operations being performed two times. Consequently, a reaction mixture was obtained which included a compound deprotected from the TBS group.

In a nitrogen atmosphere, 2,2-dimethylbutyryl chloride (49 µL, 0.36 mmol) was added to a pyridine (1.5 mL) solution of phosphorous acid (43 mg, 0.52 mmol) at 40° C., and the mixture was stirred for 38 minutes. The above reaction mixture including the deprotected compound was added to this solution, and the mixture was stirred at 40° C. for 2 hours and 14 minutes. Thereafter, the reaction mixture was added to acetonitrile (26 g), and the resultant solid was recovered by filtration. Consequently, Compound 87 (52 mg) was obtained as a brown solid.

$^1$H-NMR: (300 MHz, CDCl$_3$) δ0.88 (t, 9H), 1.08-1.83 (m, 96H), 1.89 (s, 3H), 1.94 (s, 3H), 2.19 (s, 3H), 2.23-2.79 (m, 8H), 3.96-4.00 (m, 6H), 4.18-4.41 (m, 6H), 5.18 (brs, 1H), 5.38 (d, 1H), 6.14-6.25 (m, 3H), 6.43-6.48 (m, 1H), 6.86 (d, 1H), 7.21 (s, 2H), 7.46 (s, 1H), 7.65 (s, 1H).

$^{31}$P-NMR: (300 MHz; CDCl$_3$) δ−1.10, 6.08.

MS (ESI$^-$): [M−H]$^-$ 1646.0226.

Example 84 (Synthesis of 2-mer): Synthesis of Compound 88

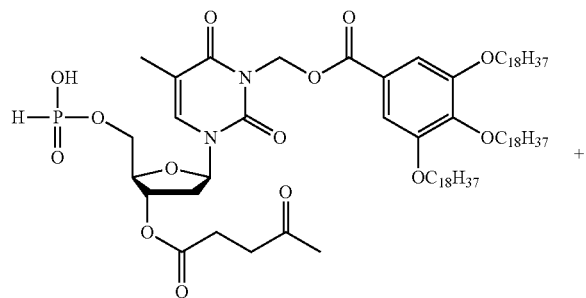

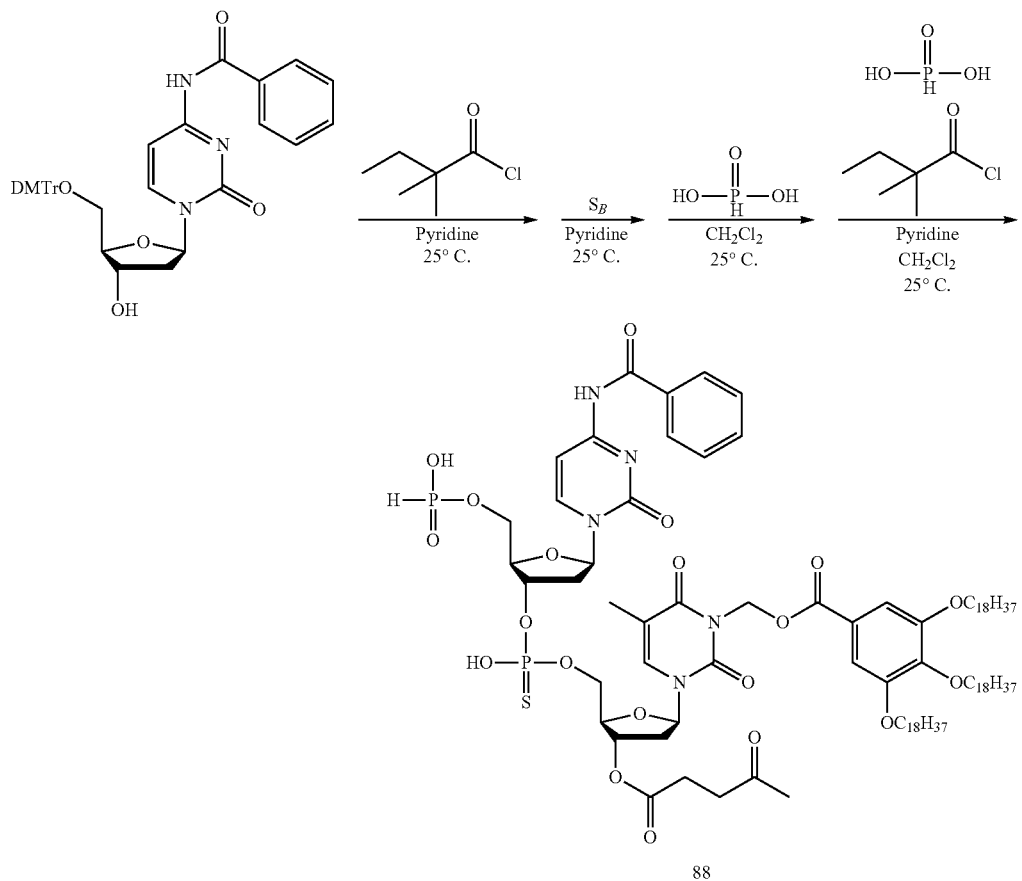

In a nitrogen atmosphere, 2,2-dimethylbutyryl chloride (15 µL, 0.11 mmol) was added to a pyridine (1.0 mL) solution of Compound 86 (52 mg) and N⁴-benzoyl-5'-O-(4,4'-dimethoxytrityl)-2'-deoxycytidine (manufactured by Tokyo Chemical Industry Co., Ltd.) (36 mg, 0.057 mmol) at 25° C., and the mixture was stirred for 53 minutes. Thereafter, elemental sulfur (13 mg, 0.41 mmol) was added, and the mixture was stirred for 2 hours and 10 minutes. Thereafter, the reaction mixture was vacuum concentrated. Toluene (2 mL) was added and the mixture was vacuum concentrated, these operations being repeated three times. Methylene chloride (0.50 mL) was added, and insolubles were removed by suction filtration. The filtrate was washed with methylene chloride (0.25 mL×2 times). Pyrrole (7.4 µL, 0.11 mmol) and phosphonic acid (46 mg, 0.56 mmol) were added to this solution at room temperature, and the mixture was stirred for 51 minutes. Pyridine (0.15 mL) was added at room temperature. Thereafter, 2,2-dimethylbutyryl chloride (49 µL, 0.36 mmol) was added in three portions every 10 minutes, and the mixture was stirred for 35 minutes. 2,2-Dimethylbutyryl chloride (16 µL, 0.12 mmol) was added, and the mixture was stirred for 45 minutes. Thereafter, the reaction mixture was added to acetonitrile (26 g), and the resultant solid was recovered by filtration. Consequently, Compound 88 (47 mg) was obtained as a light yellow solid.

$^1$H-NMR: (300 MHz; CDCl$_3$) δ0.88 (t, 9H), 0.98-1.99 (m, 99H), 2.13-2.34 (m, 7H), 2.56 (brs, 2H), 2.75 (brs, 2H), 3.97-4.21 (m, 12H), 5.17-5.35 (m, 2H), 6.14-6.21 (m, 3H), 6.44 (t, 1H), 6.93 (d, 1H), 7.20 (s, 2H), 7.54-8.34 (m, 8H).

$^{31}$P-NMR: (300 MHz; CDCl$_3$) δ5.11, 59.77, 61.38.

MS (ESI⁻): [M−H]⁻ 1751.0079.

Example 85 (Synthesis of Nucleoside Having Pseudo Solid Phase-Protecting Group at 3-Position of Thymine): Synthesis of Compound 90

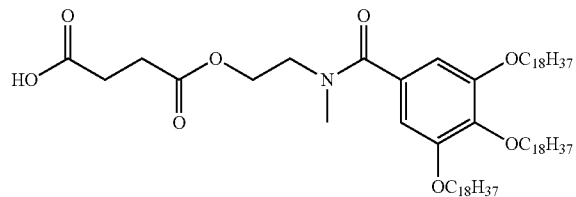

31

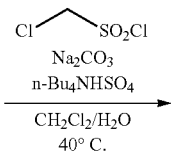

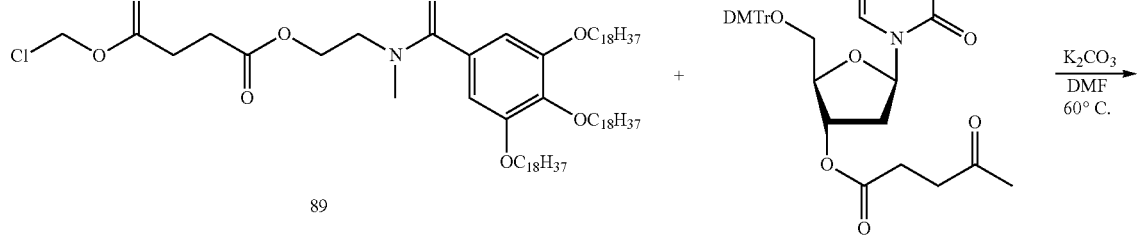

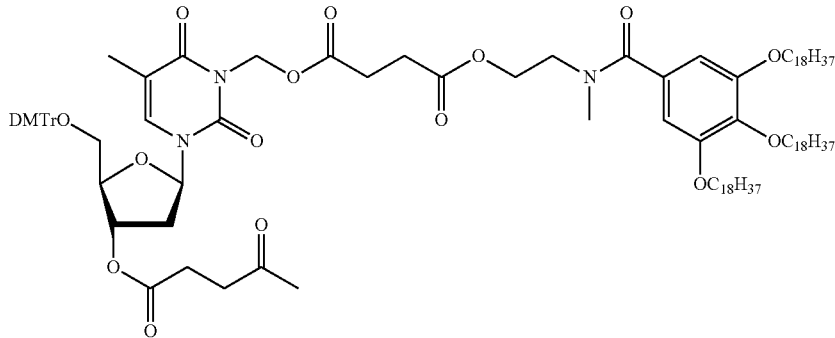

90

Step 1: Synthesis of Compound 89

In a nitrogen atmosphere, chloromethanesulfonyl chloride (0.20 mL, 2.0 mmol) was added to a solution of Compound 31 (1.0 g, 0.92 mmol), sodium carbonate (0.36 g, 3.4 mmol) and tetra-n-butylammonium hydrogen sulfate (34 mg, 0.11 mmol) in a mixed solvent of methylene chloride (30 g) and water (10 g) at room temperature, and the mixture was stirred for 41 minutes. Thereafter, the mixture was heated to 40° C. and was stirred for 2 hours and 19 minutes. The stirring was terminated, and the liquids were separated. Methylene chloride was added to the aqueous phase thus obtained to perform extraction. The organic phases obtained were combined. The solvent was distilled away under vacuum. Acetonitrile (50 g) was added, and the resultant solid was recovered by filtration. Consequently, Compound 89 was obtained as a light yellow solid (0.96 g).

$^1$H-NMR: (300 MHz; CDCl$_3$) δ0.88 (t, 9H), 1.26-1.84 (m, 96H), 2.70-2.73 (m, 4H), 3.05 (s, 3H), 3.74 (brs, 2H), 3.93-3.98 (m, 6H), 4.36 (brs, 2H), 5.69 (s, 2H), 6.58 (s, 2H).
MS (ESI$^-$): [M+H]$^+$ 1132.9248.

Step 2: Synthesis of Compound 90

In a nitrogen atmosphere, potassium carbonate (20 mg, 0.15 mmol) was added to a DMF (0.20 mL) solution of Compound 89 (11 mg, 9.7 μmol) and 5'-O-(4,4'-dimethoxytrityl)-3'-O-levulinylthymidine (synthesized in accordance with the method described in WO 2014/077292) (10 mg, 0.016 mmol) at 60° C., and the mixture was stirred for 19 hours and 30 minutes. The reaction mixture was vacuum concentrated. Consequently, Compound 90 was obtained.
MS (ESI$^-$): [M+H]$^+$ 1739.1983.

Example 86 (Synthesis of Nucleoside Having Pseudo Solid Phase-Protecting Group at 3-Position of Thymine): Synthesis of Compound 91

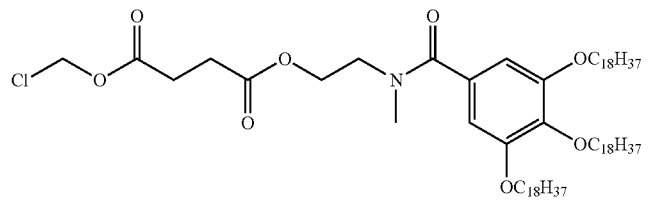

89

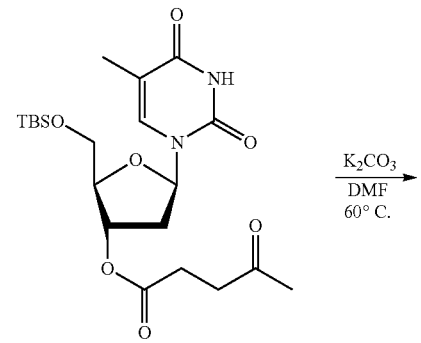

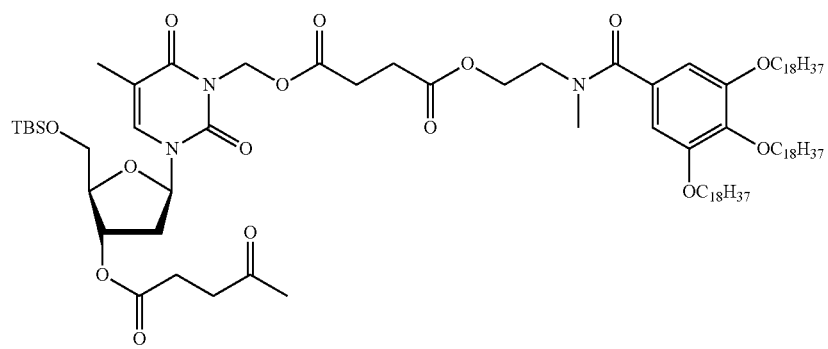

91

The reaction was performed under the same conditions as in Step 2 of Example 85, except that 5'-O-(4,4'-dimethoxytrityl)-3'-O-levulinylthymidine was changed to 5'-O-(tert-butyldimethylsilyl)-3'-O-levulinylthymidine (11 mg). The reaction mixture was vacuum concentrated. Consequently, Compound 91 was obtained.

MS (ESI$^-$): [M+H]$^+$ 1551.1540.

Example 87 (Synthesis of 2-mer in Methylene Chloride Solvent): Synthesis of Compound 43

In a nitrogen atmosphere, 2,2-dimethylbutyryl chloride (45 μL, 0.33 mmol) was added to a methylene chloride (2.0 mL) solution of Compound 42 (98 mg), Compound 1 (36 mg, 0.10 mmol) and pyridine (53 μL, 0.66 mmol) at 25° C., and the mixture was stirred for 50 minutes. Thereafter, a 0.1 M solution of iodine in pyridine, THF and water (0.98 mL, 0.098 mmol) was added, and the mixture was stirred for 38 minutes. Thereafter, dimethyl phosphite (3.0 μL, 0.033 mmol) was added. Methylene chloride (1.0 mL) was added. The mixture was vacuum concentrated. Methylene chloride (5.0 mL) was added. Again, the mixture was vacuum concentrated. Insolubles were removed by suction filtration. The filtrate was washed with methylene chloride (1.0 mL×2 times). Hydrogen fluoride-pyridine (84.5 μL, 3.3 mmol) was added to this solution at 40° C., and the mixture was stirred for 5 hours and 33 minutes. TMSCl (0.41 mL, 3.3 mmol) was added, and the reaction mixture was vacuum concentrated. Consequently, Compound 43 was obtained.

Example 88 (Synthesis of 2-mer in THF Solvent): Synthesis of Compound 43

In a nitrogen atmosphere, 2,2-dimethylbutyryl chloride (38 μL, 0.28 mmol) was added to a THF (1.5 mL) solution of Compound 42 (85 mg), Compound 1 (30 mg, 0.084 mmol) and pyridine (45 μL, 0.55 mmol) at 25° C., and the mixture was stirred for 14 minutes. Thereafter, a 0.1 M solution of iodine in pyridine, THF and water (1.2 mL, 0.12 mmol) was added. The mixture was stirred for 3 hours and 49 minutes. Thereafter, dimethyl phosphite (3.0 μL, 0.033 mmol) was added. The reaction mixture was vacuum concentrated. Toluene (3.0 mL) was added and the mixture was vacuum concentrated, these operations being repeated three times. Thereafter, methylene chloride (1.0 mL) was added, and insolubles were removed by suction filtration. The filtrate was washed with methylene chloride (1.0 mL×2 times). Hydrogen fluoride-pyridine (6.5 μL, 0.25 mmol) was added to this solution at 25° C., and the mixture was stirred at 40° C. overnight. Thereafter, the reaction mixture was vacuum concentrated. Consequently, Compound 43 was obtained.

Example 89 (Comparison of Condensing Agent):
Synthesis of Compound 92

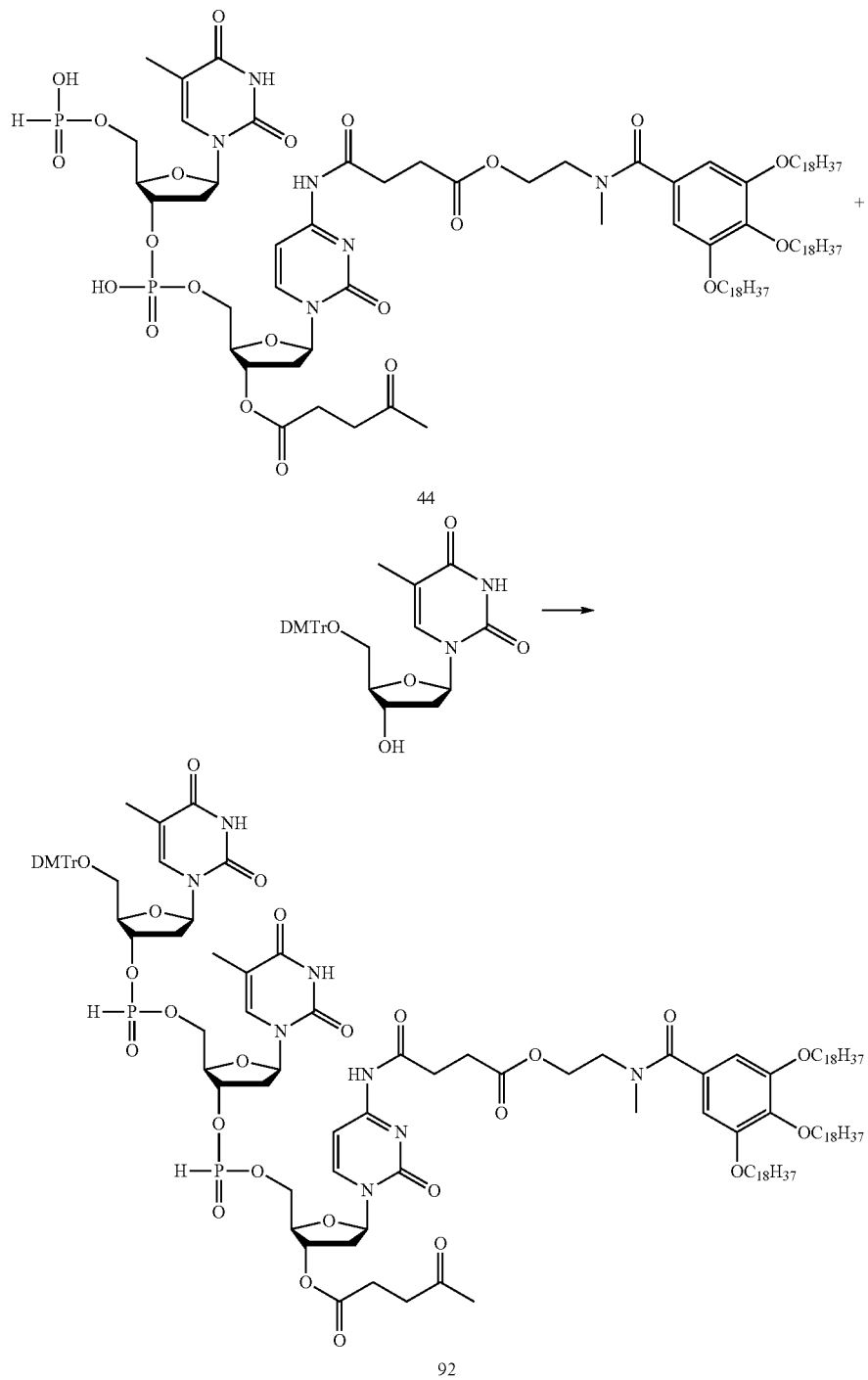

The reaction was performed under the same conditions as in Step 2 of Example 35, except that the condensing agent was changed to 2,4,6-triisopropylbenzenesulfonyl chloride (8.4 mg). The reaction mixture after the coupling reaction was vacuum concentrated. Consequently, Compound 92 was obtained as the main product.

MS (ESI⁻): [M+H]⁻ 2284.3243.

Example 90 (Comparison of Condensing Agent):
Synthesis of Compound 92

The reaction was performed under the same conditions as in Step 2 of Example 35, except that the condensing agent was changed to 2,4-mesitylenedisulfonyl dichloride (8.8 mg). The reaction mixture after the coupling reaction was vacuum concentrated. Consequently, Compound 92 was obtained as the main product.

Example 91 (Comparison of Condensing Agent): Synthesis of Compound 92

The reaction was performed under the same conditions as in Step 2 of Example 35, except that the condensing agent was changed to 1-adamantanecarbonyl chloride (5.5 mg). The reaction mixture after the coupling reaction was vacuum concentrated. Consequently, Compound 92 was obtained as the main product.

Example 92 (Synthesis of Monomer and 2-mer Having Pseudo Solid Phase-Protecting Group on Nucleobase): Synthesis of Compound 41

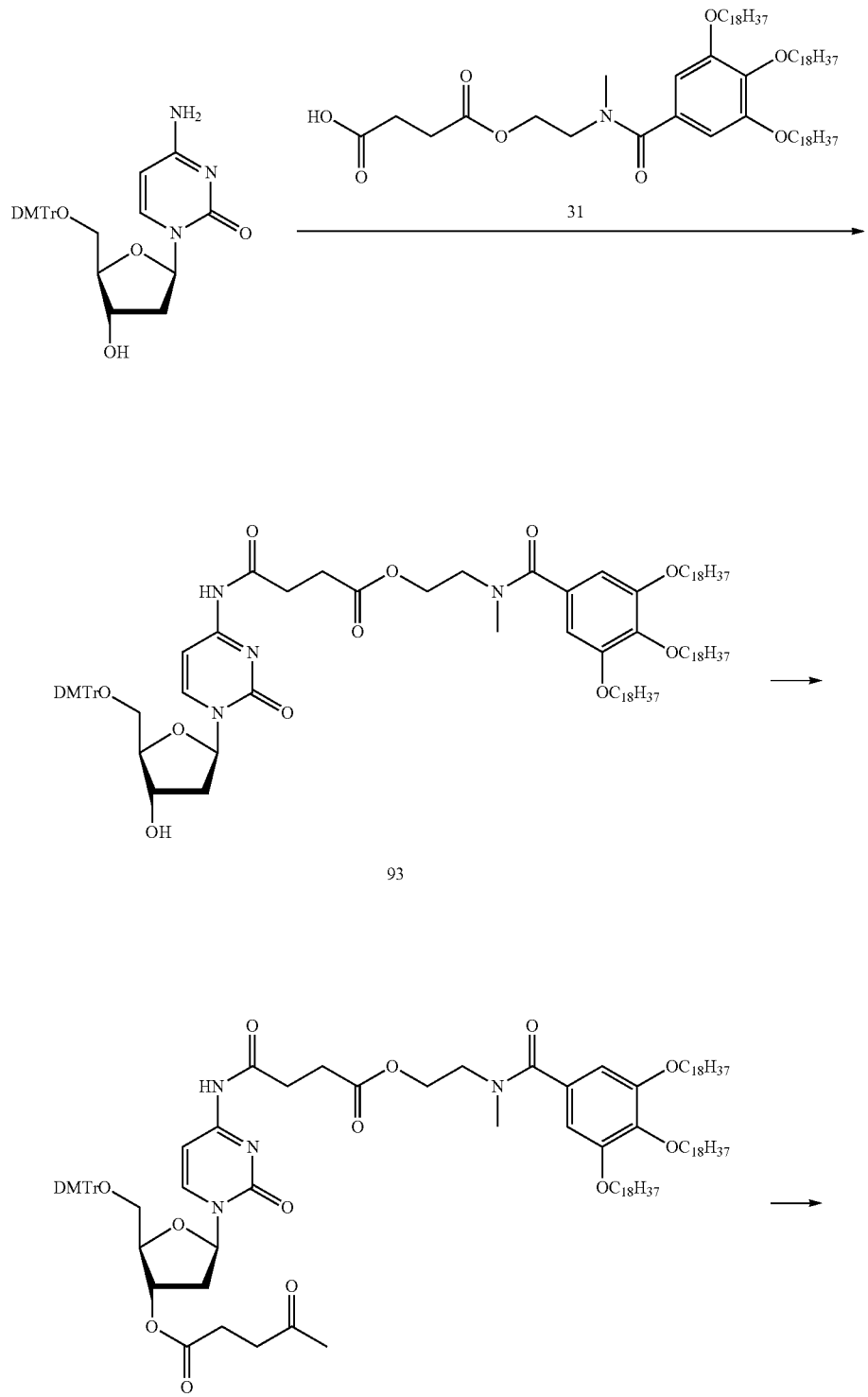

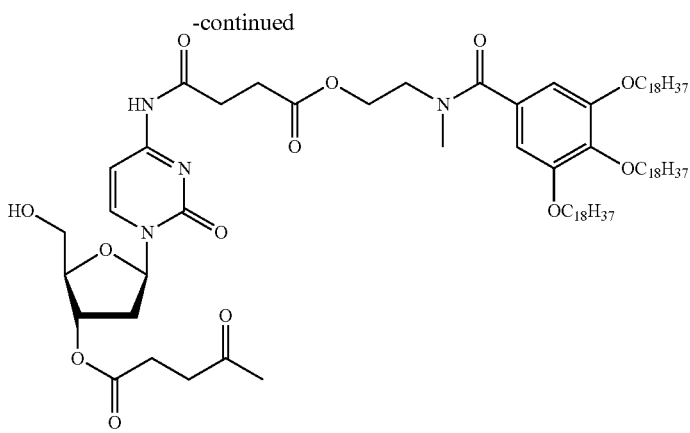

41

Step 1: Synthesis of Compound 93

The reaction was performed under the same conditions as in Step 2 of Example 66, except that 3'-O-(tert-butyldiphenylsilyl)-5'-O-(4,4'-dimethoxytrityl)-2'-deoxycytidine was replaced by 5'-O-(4,4'-dimethoxytrityl)-2'-deoxycytidine (manufactured by Chem-Impex International, Inc.) (4.0 g). Consequently, Compound 93 (7.4 g) was obtained as a white solid.

$^1$H-NMR: (300 MHz; CDCl$_3$) δ0.88 (t, 9H), 1.19-1.80 (m, 96H), 2.17-2.28 (m, 1H), 2.69-2.80 (m, 5H), 3.05 (s, 3H), 3.41-3.79 (m, 10H), 3.92-3.97 (m, 6H), 4.09-4.46 (m, 4H), 6.24 (t, 1H), 6.57 (s, 2H), 6.84 (d, 4H), 7.15-7.40 (m, 10H), 8.20 (d, 1H), 9.27 (brs, 1H).

MS (ESI$^+$): [M+H]$^+$ 1596.1595.

Step 2: Synthesis of Compound 94

In a nitrogen atmosphere, WSC.HCl (1.4 g, 7.5 mmol) was added to a methylene chloride (70 mL) solution of Compound 93 (7.4 g, 4.7 mmol), DMAP (0.065 g, 0.53 mmol) and levulinic acid (0.87 g, 7.5 mmol) at room temperature, and the mixture was stirred for 5 hours and 4 minutes. Thereafter, the reaction mixture was added to acetonitrile (504 g), and the resultant solid was recovered by filtration. Consequently, Compound 94 (7.9 g) was obtained as a light yellow solid.

$^1$H-NMR: (300 MHz; CDCl$_3$) δ0.88 (t, 9H), 1.20-1.81 (m, 96H), 2.19 (s, 3H), 2.23-2.33 (m, 1H), 2.51-2.60 (m, 2H), 2.70-2.80 (m, 7H), 3.06 (s, 3H), 3.44 (d, 2H), 3.79 (brs, 8H), 3.93-3.98 (m, 6H), 4.03-4.36 (m, 3H), 5.39 (d, 2H), 6.27 (t, 1H), 6.57 (s, 2H), 6.81-6.85 (m, 4H), 7.11 (d, 1H), 7.21-7.36 (m, 9H), 8.07 (d, 1H), 9.32 (brs, 1H).

Step 3: Synthesis of Compound 41

In a nitrogen atmosphere, pyrrole (0.71 mL, 10 mmol) and dichloroacetic acid (1.4 mL, 17 mmol) were added to a methylene chloride (50 g) solution of Compound 94 (5.8 g, 3.4 mmol) at room temperature, and the mixture was stirred for 23 minutes. Pyridine (1.4 mL, 17 mmol) was added. The reaction mixture was added to methanol (502 g), and the resultant solid was recovered by filtration. Consequently, Compound 41 (4.6 g) was obtained as a white solid.

Example 93 (Deprotection of 3'-levulinyl Group): Synthesis of Compound 78

The reaction was performed at room temperature under the same conditions as in Example 75, except that hydrazine monohydrate was replaced by acetohydrazide (7.6 mg). The reaction mixture was vacuum concentrated. Consequently, Compound 78 was obtained.

Example 94 (Deprotection of 3'-levulinyl Group): Synthesis of Compound 78

In a nitrogen atmosphere, a solution of Compound 77 (10 mg, 4.5 μmol) in a mixed solvent of methylene chloride (0.20 mL) and pyridine (0.20 mL) was cooled to 0° C., and hydrazinium sulfate (10.7 mg, 0.082 mmol) was added. The mixture was stirred at 40° C. overnight. The reaction mixture was vacuum concentrated. Consequently, Compound 78 was obtained.

Example 95 (Deprotection of 3'-levulinyl Group): Synthesis of Compound 78

The reaction was performed at 40° C. under the same conditions as in Example 75, except that hydrazine monohydrate was replaced by ethylenediamine (1.5 μL). The reaction mixture was vacuum concentrated. Consequently, Compound 78 was obtained.

Example 96 (Deprotection of 3'-levulinyl Group): Synthesis of Compound 78

The reaction was performed under the same conditions as in Example 75, except that hydrazine monohydrate was replaced by hydrazine acetate salt (0.7 mg). The reaction mixture was vacuum concentrated. Consequently, Compound 78 was obtained as the main product.

Example 97 (Deprotection of 3'-levulinyl Group): Synthesis of Compound 78

The reaction was performed under the same conditions as in Example 75, except that hydrazine monohydrate was replaced by phenylhydrazine (2.5 mg). The reaction mixture was vacuum concentrated. Consequently, Compound 78 was obtained.

Example 98 (Deprotection of 3'-levulinyl Group): Synthesis of Compound 78

The reaction was performed under the same conditions as in Example 75, except that hydrazine monohydrate was replaced by p-toluenesulfonylhydrazine (2.0 mg). The reaction mixture was vacuum concentrated. Consequently, Compound 78 was obtained.

Example 99 (Deprotection of 3'-levulinyl Group): Synthesis of Compound 78

The reaction was performed under the same conditions as in Example 75, except that hydrazine monohydrate was replaced by methyl carbazate (3.1 mg). The reaction mixture was vacuum concentrated. Consequently, Compound 78 was obtained.

Example 100 (Deprotection of 3'-levulinyl Group): Synthesis of Compound 96

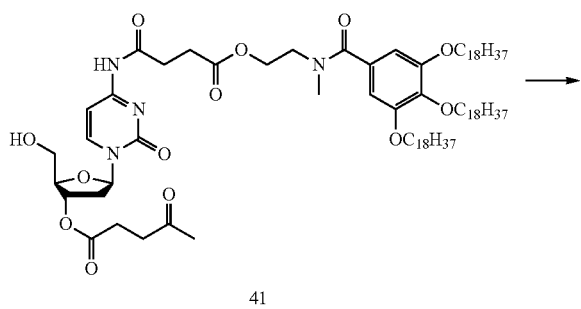

41

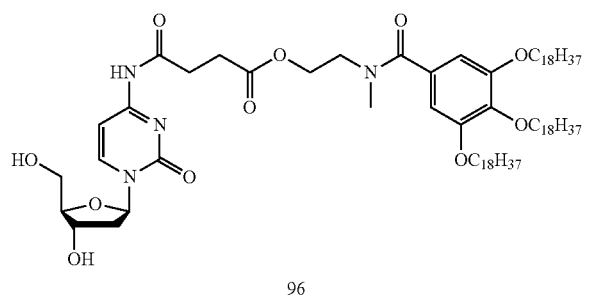

96

In a nitrogen atmosphere, a solution of hydrazine monohydrate (0.50 mg, 10.3 mmol) in a mixed solvent of methylene chloride (0.20 mL) and acetic acid (40 μL) was cooled to 0° C., and a methylene chloride (0.10 mL) solution of Compound 41 (10 mg, 7.3 μL) was added. The mixture was stirred for 5 hours. The reaction mixture was analyzed by LC-MS, and Compound 96 was identified.

Example 101 (Deprotection of 3'-levulinyl Group): Synthesis of Compound 96

In a nitrogen atmosphere, Chirazyme L-2 (3.7 mg) was added to a 0.15 M phosphate buffer solution (pH 6.8) (0.23 g). Thereafter, a 1,4-dioxane (1.0 g) solution of Compound 41 (9.0 mg, 6.5 μmol) was added. The mixture was heated to 40° C. and was stirred for 13 hours and 20 minutes. The reaction mixture was analyzed by LC-MS, and Compound 96 was identified.

Example 102 (Deprotection of 3'-levulinyl Group): Synthesis of Compound 96

In a nitrogen atmosphere, Chirazyme L-5 (10 mg) was added to a 0.15 M phosphate buffer solution (pH 6.8) (0.21 g). Thereafter, a 1,4-dioxane (1.0 g) solution of Compound 41 (10 mg, 7.2 μmol) was added. The mixture was heated to 40° C. and was stirred for 13 hours and 20 minutes. The reaction mixture was analyzed by LC-MS, and Compound 96 was identified.

Example 103 (Synthesis of 5-mer having Hydroxyl Group at 3'-terminal): Synthesis of Compound 97

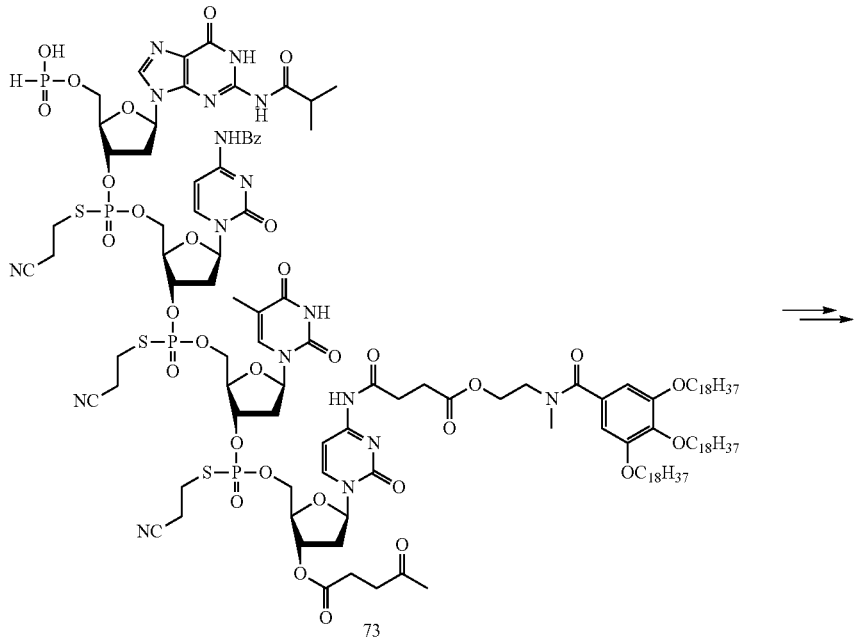

73

-continued

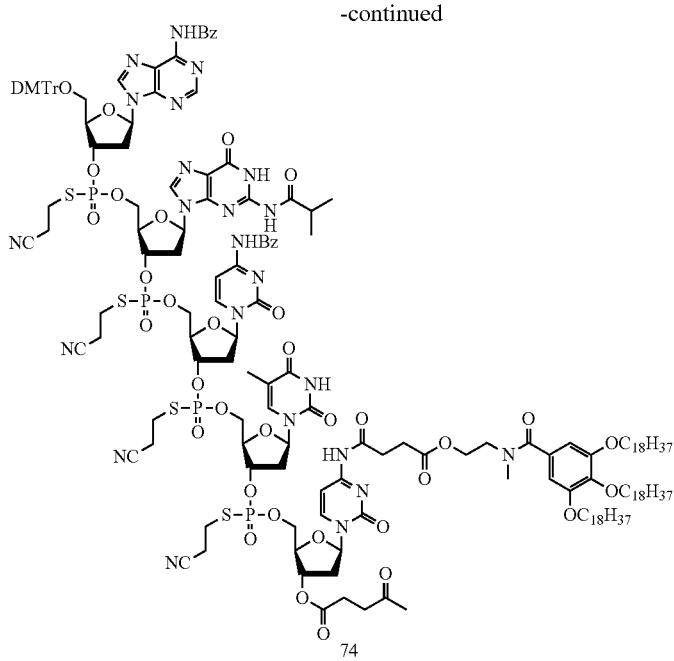

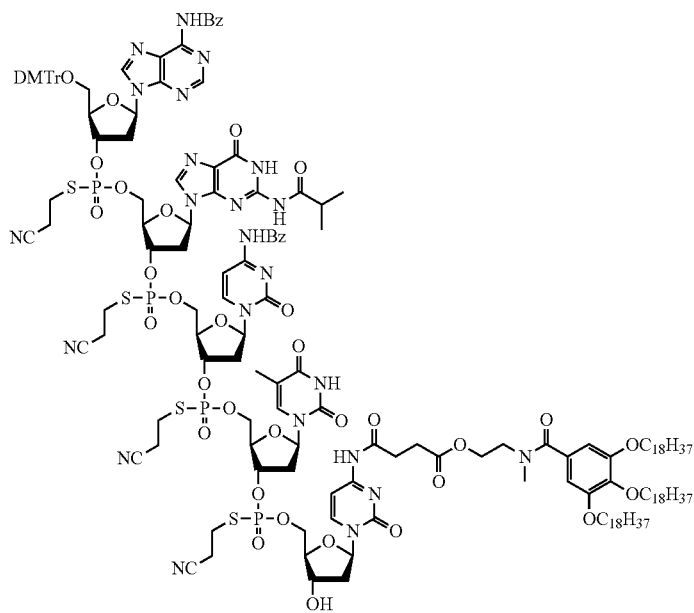

Step 1: Synthesis of Compound 74

The reaction was performed under the same conditions as in Step 4 of Example 72. The reaction mixture after the sulfurization was added to methanol, and the resultant solid was recovered by filtration. Consequently, Compound 74 (2.3 g, 90%) was obtained as a light skin color solid.

Step 2: Synthesis of Compound 97

In a nitrogen atmosphere, a THF (20 mL) solution of Compound 74 (0.50 g, 0.14 mmol) was cooled to 0° C., and acetic acid (3.0 mL) was added. Thereafter, hydrazine monohydrate (14 μL, 0.29 mmol) was added, and the mixture was stirred for 6 hours. Acetylacetone (100 μL) was added to the reaction mixture. The resultant mixture was brought to room temperature and was vacuum concentrated. The residue was added to methanol (102 g), and the resultant solid was recovered by filtration. Consequently, Compound 97 (0.45 g) was obtained.

MS (ESI$^+$): [M+2H]$^{2+}$ 1693.2456.

Example 104 (Synthesis of 5-mer Having H-Phosphonate Group at 5'-Terminal): Synthesis of Compound 99
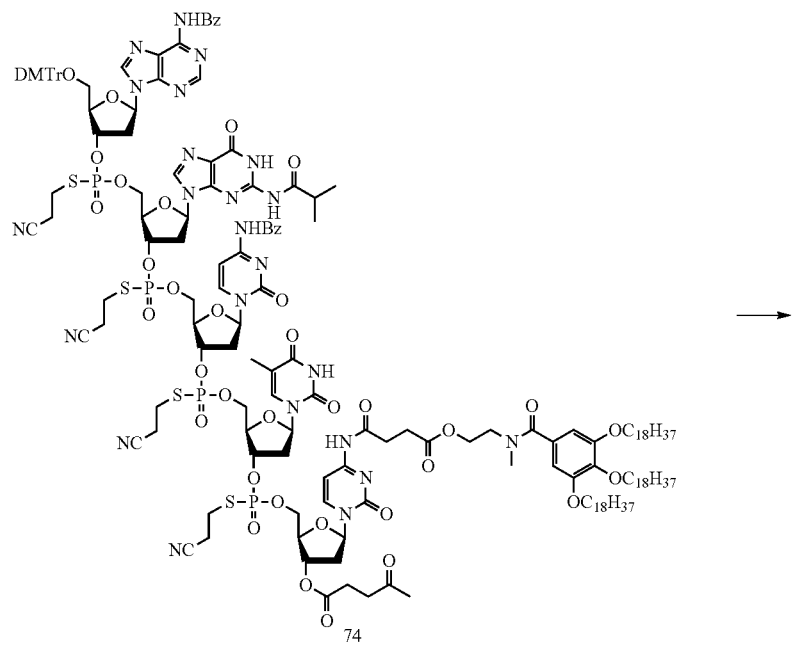
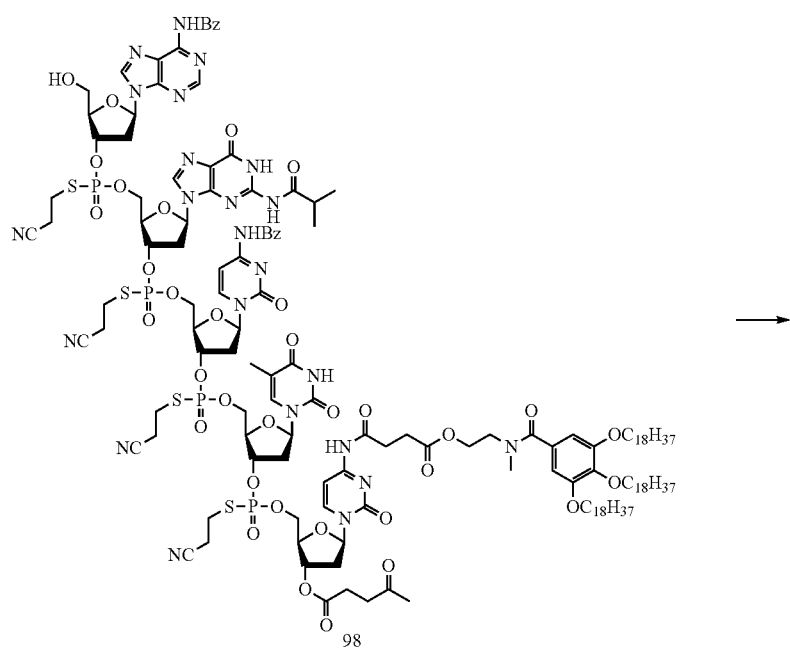

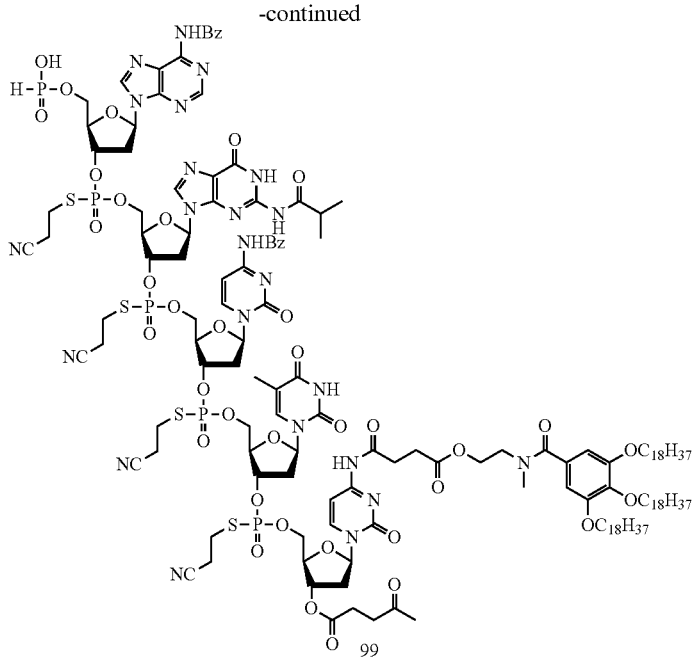

Step 1: Synthesis of Compound 98

In a nitrogen atmosphere, a methylene chloride solution (10 mL) of Compound 74 (0.51 g, 0.15 mmol) was cooled to 10° C., and pyrrole (30 µL, 0.43 mmol) was added. The mixture was stirred for 14 minutes. Thereafter, dichloroacetic acid (82 µL, 1.0 mmol) was added. The mixture was stirred for 4 hours and 3 minutes. Pyridine (1.5 mL) was added, and the mixture was brought to room temperature. The reaction mixture was added to acetonitrile (86 g), and the resultant solid was recovered by filtration. Consequently, Compound 98 (0.46 g) was obtained.

MS (ESI$^+$): [M+2H]$^{2+}$ 1591.1922.

Step 2: Synthesis of Compound 99

In a nitrogen atmosphere, phosphonic acid (0.20 g, 2.4 mmol) was added to a solution of Compound 98 (0.45 g, 0.14 mmol) in a mixed solvent of methylene chloride (5.0 mL) and pyridine (1.0 mL) at 40° C. 2,2-Dimethylbutyryl chloride (0.19 mL, 1.4 mmol) was added in 4 portions every 10 minutes, and the mixture was stirred for 1 hour and 53 minutes. 2,2-Dimethylbutyl chloride (0.42 mL, 0.71 mmol) was added, and the mixture was stirred for 1 hour and 8 minutes. Thereafter, the reaction mixture was added to acetonitrile (84 g), and the resultant solid was recovered by filtration. Consequently, Compound 99 (0.42 g) was obtained as a white solid.

MS (ESI$^+$): [M+2H]$^{2+}$ 1623.1824.

Example 105 (Synthesis of 5-mer): Synthesis of Compound 99

In a nitrogen atmosphere, a methylene chloride solution (0.20 mL) of Compound 74 (10 mg, 2.9 µmol) and pyrrole (60 µL, 8.6 µmmol) was cooled to 10° C., and phosphonic acid (0.71 mg, 8.6 µmol) was added. The mixture was stirred for 1 hour and 35 minutes. The reaction mixture was analyzed by LC-MS, and Compound 98 was identified as the main product. Thereafter, pyridine (30 µL) was added, and the mixture was brought to room temperature. 2,2-Dimethylbutyryl chloride (8.0 µL, 58 µmmol) was added, and the mixture was stirred for 30 minutes. The reaction mixture was analyzed by LC-MS, and Compound 99 was identified as the main product.

Example 106 (Synthesis of 10-mer): Synthesis of Compound 100
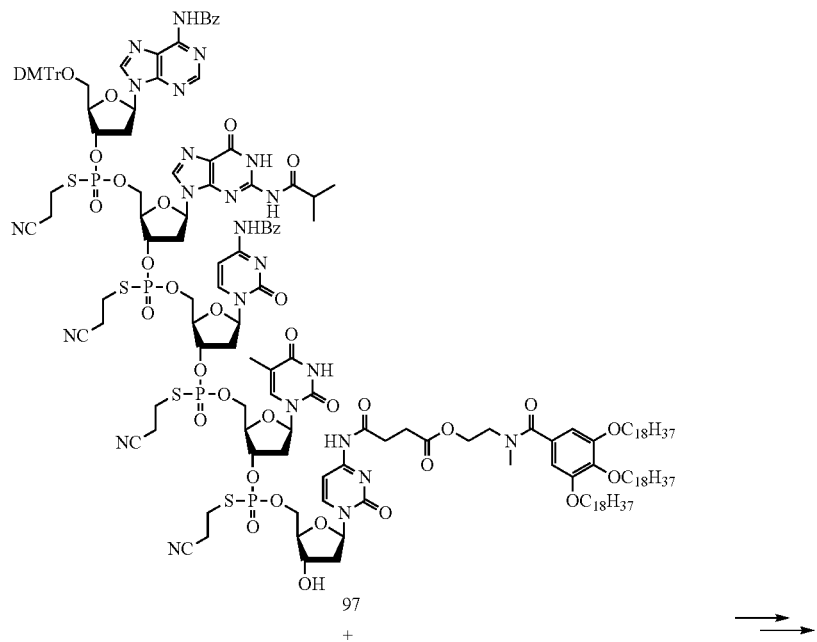
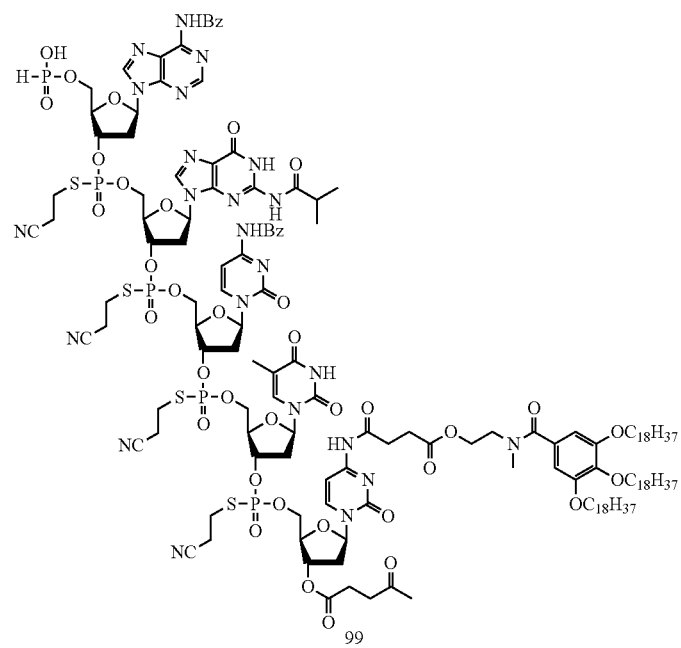

-continued
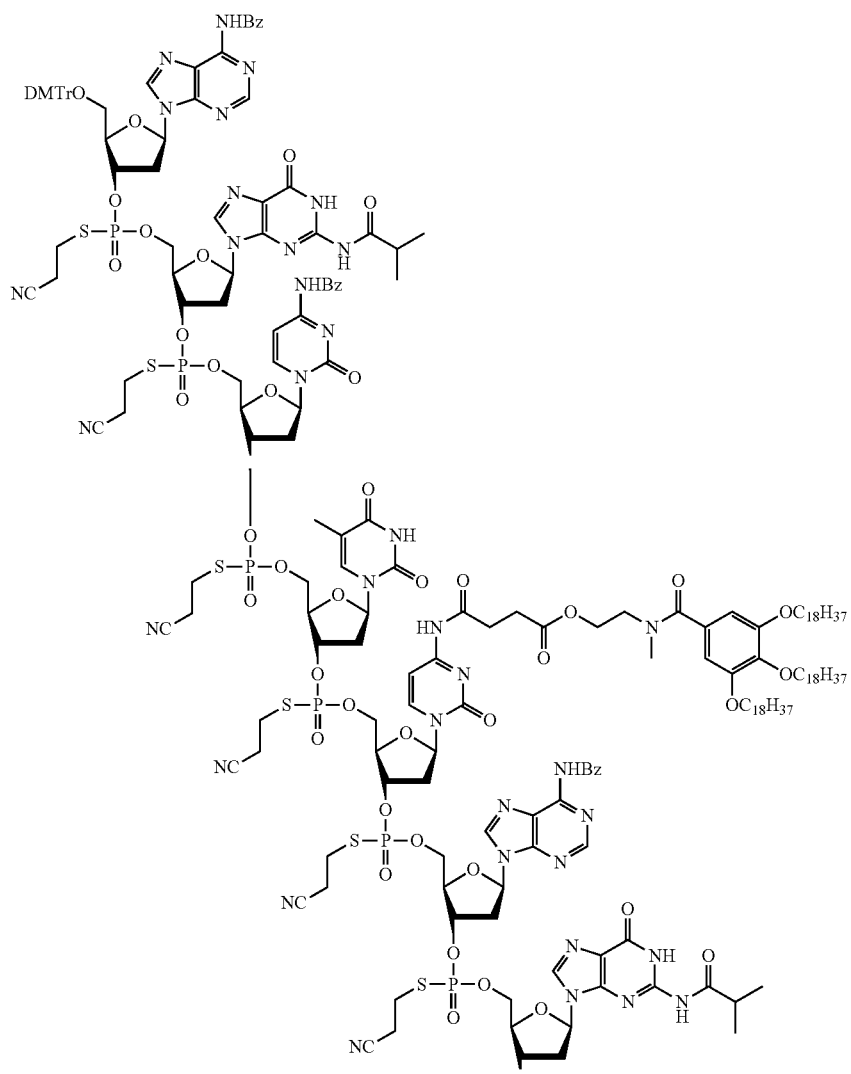
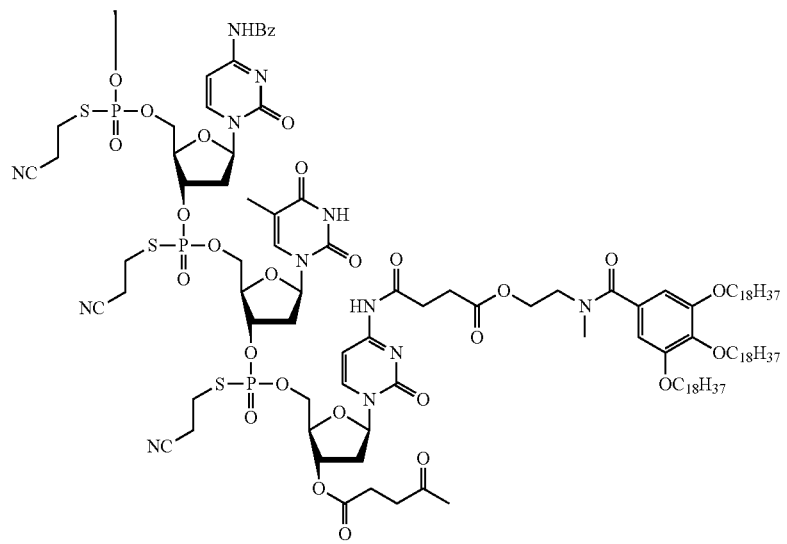

In a nitrogen atmosphere, bispentafluorophenyl carbonate (0.80 g, 2.0 mmol) was added to a pyridine (10 mL) solution of Compound 97 (0.44 g, 0.13 mmol) and Compound 99 (0.41 g) at room temperature, and the mixture was stirred for 11 minutes. Thereafter, N-[(2-cyanoethyl)thio]phthalimide (62 mg, 0.27 mmol) as a sulfurizing agent was added, and the mixture was stirred for 1 hour and 52 minutes. The reaction mixture was added to methanol (102 g), and the resultant solid was recovered by filtration. Consequently, Compound 100 (0.81 g) was obtained.

MS (ESI⁺): [M+3H]³⁺ 2232.9346.

Example 107 (Synthesis of 10-mer Having Hydroxyl Group at 3'-terminal): Synthesis of Compound 101

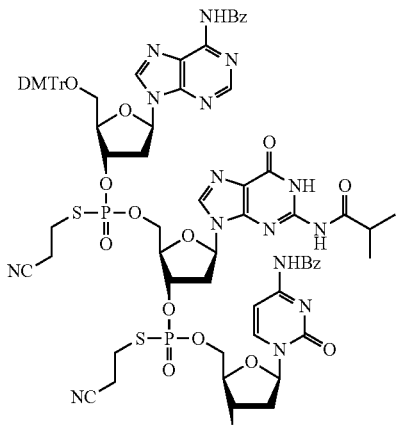

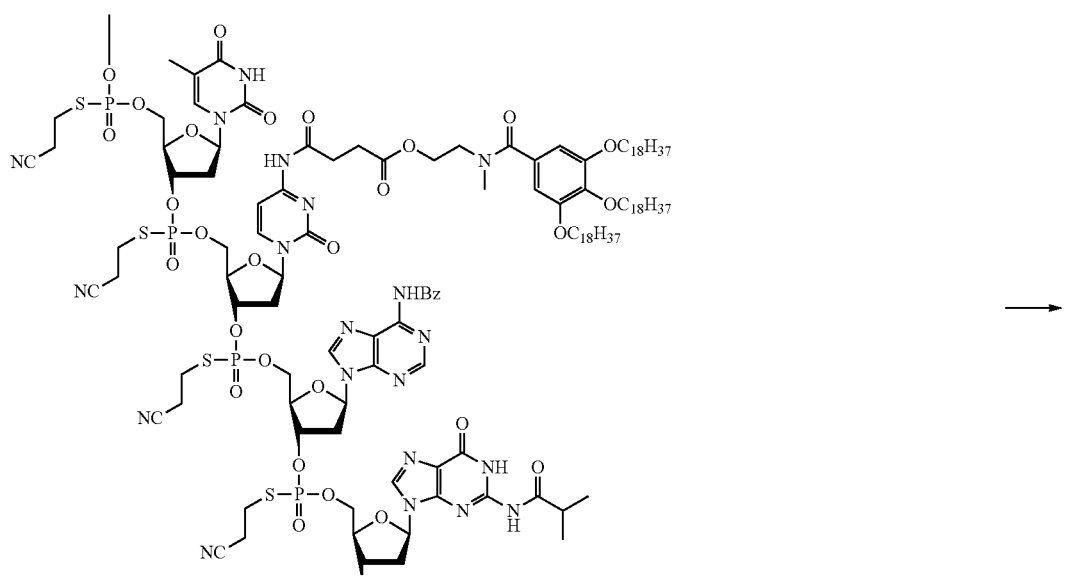

-continued
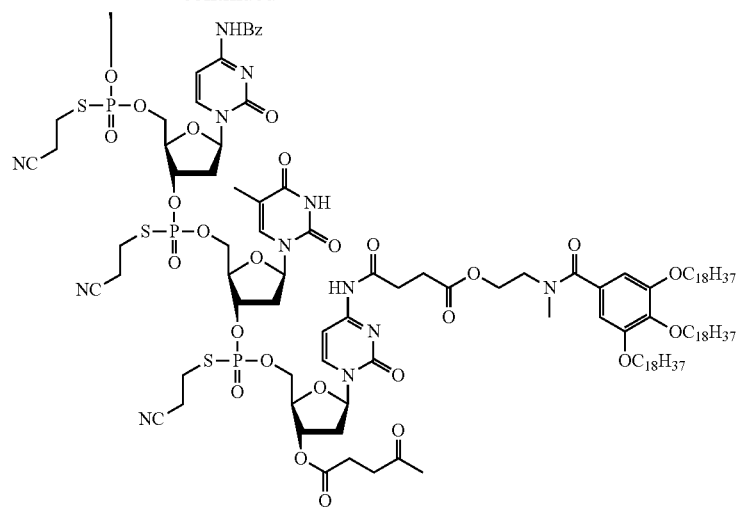
100
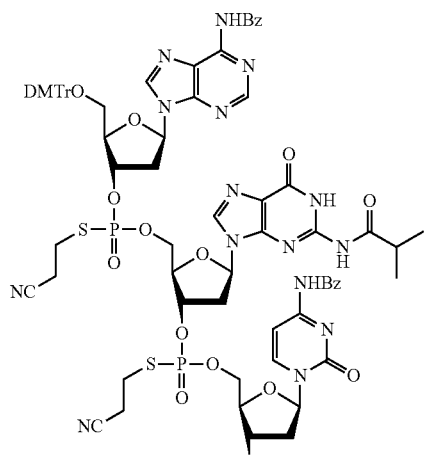

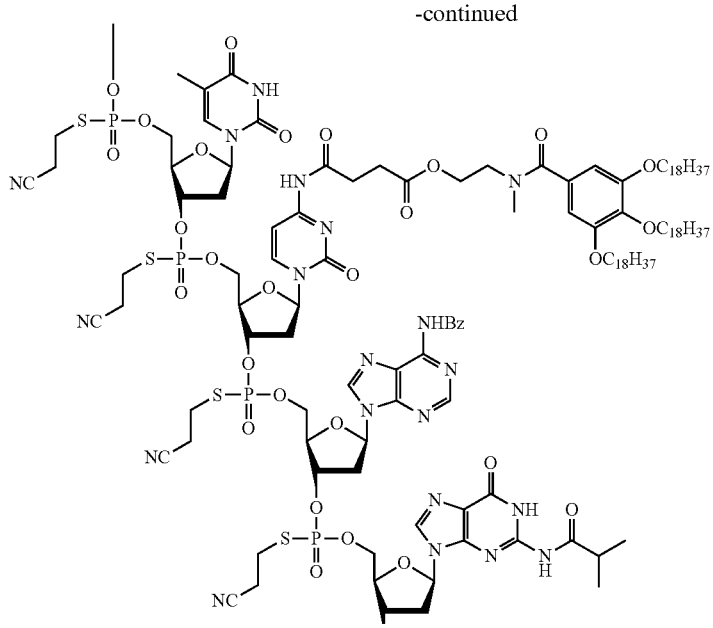

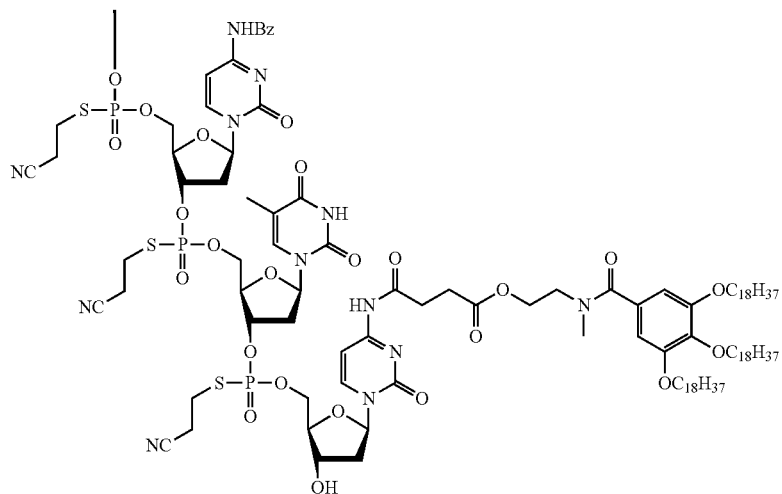

101

In a nitrogen atmosphere, a THF (15 mL) solution of Compound 100 (0.39 g, 58 µmol) was cooled to 0° C., and acetic acid (2.3 mL) was added. Thereafter, hydrazine monohydrate (5.5 µL, 0.11 mmol) was added, and the mixture was stirred for 7 hours. Further, hydrazine monohydrate (5.5 µL, 0.11 mmol) was added, and the mixture was stirred for 1 hour and 12 minutes. Acetylacetone (0.50 mL) was added to the reaction mixture. The mixture was brought to room temperature and was vacuum concentrated. Thereafter, the concentrate was added to methanol (100 g), and the resultant solid was recovered by filtration. Consequently, Compound 101 (0.35 g) was obtained.

In a nitrogen atmosphere, a THF (3.0 mL) solution of Compound 101 (0.15 g, 23 µmol) was cooled to 10° C., and acetic acid (0.90 mL) was added. Thereafter, hydrazine monohydrate (7.5 µL, 0.15 mmol) was added, and the mixture was stirred for 30 minutes. The reaction mixture was added to methanol (57 g), and the resultant solid was recovered by filtration. Consequently, Compound 101 (0.14 g) was obtained.

MS (ESI$^+$): [M+3H]$^{3+}$ 2200.2656.

Example 108 (Synthesis of 10-mer Having H-phosphonate Group at 5'-terminal): Synthesis of Compound 103
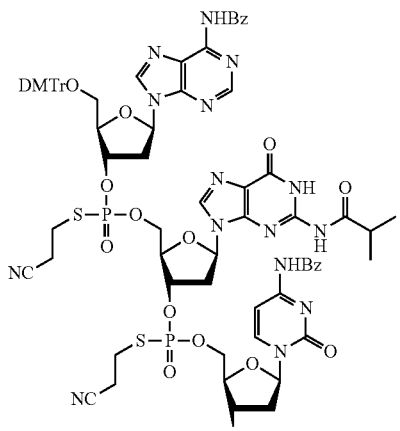
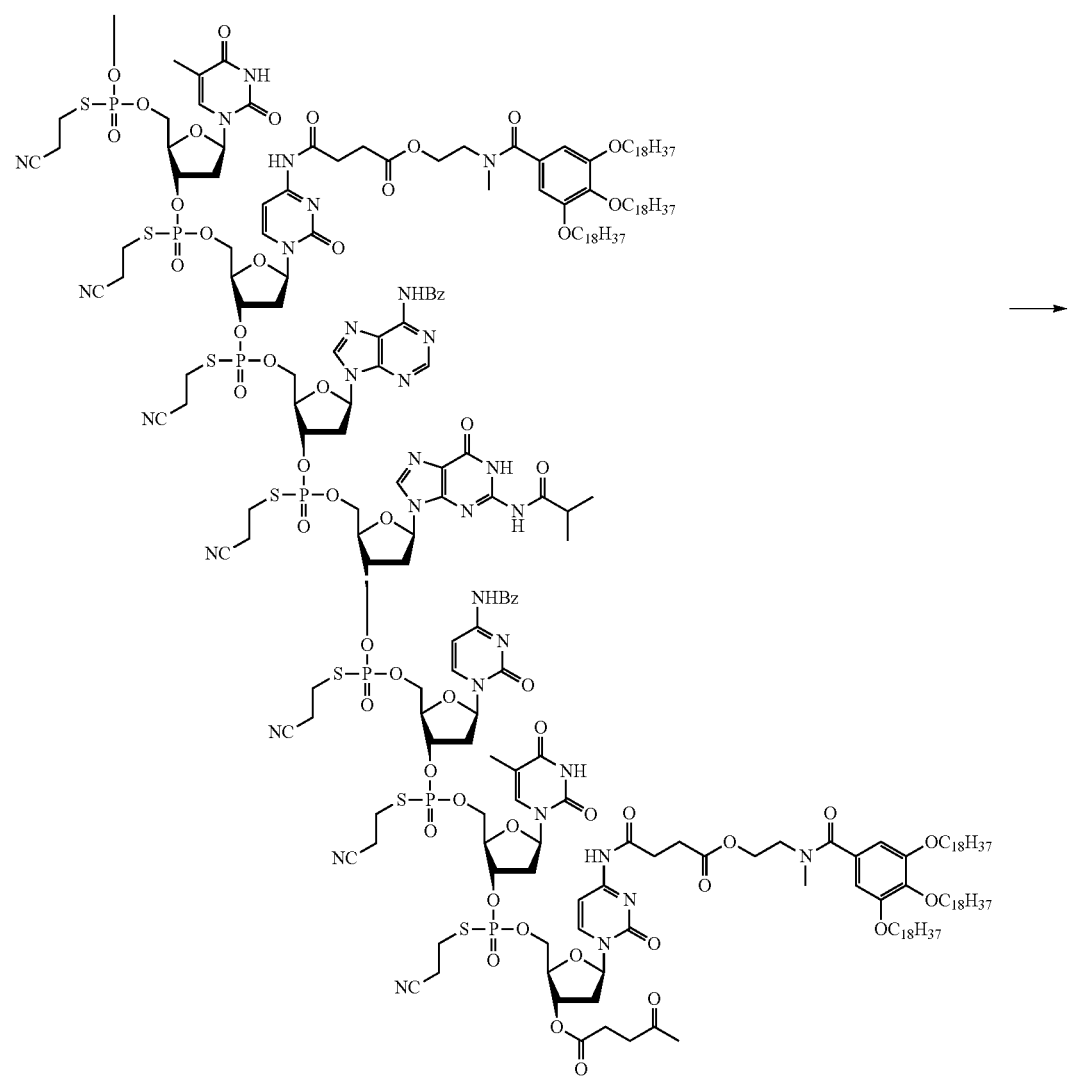

-continued
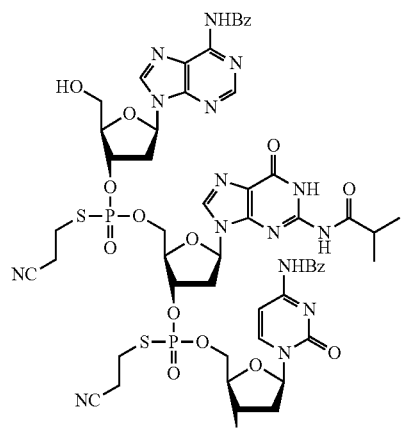
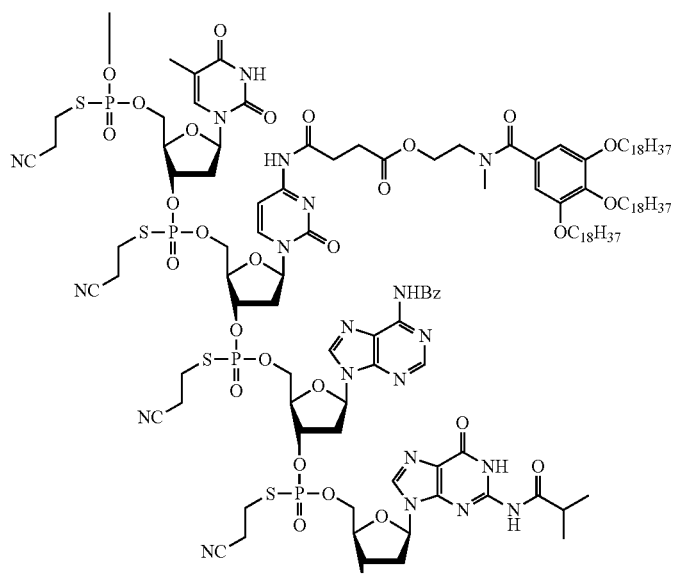
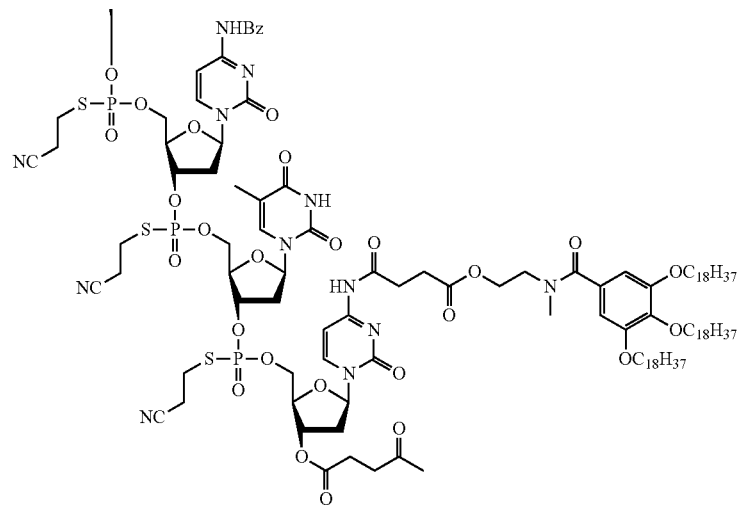

-continued
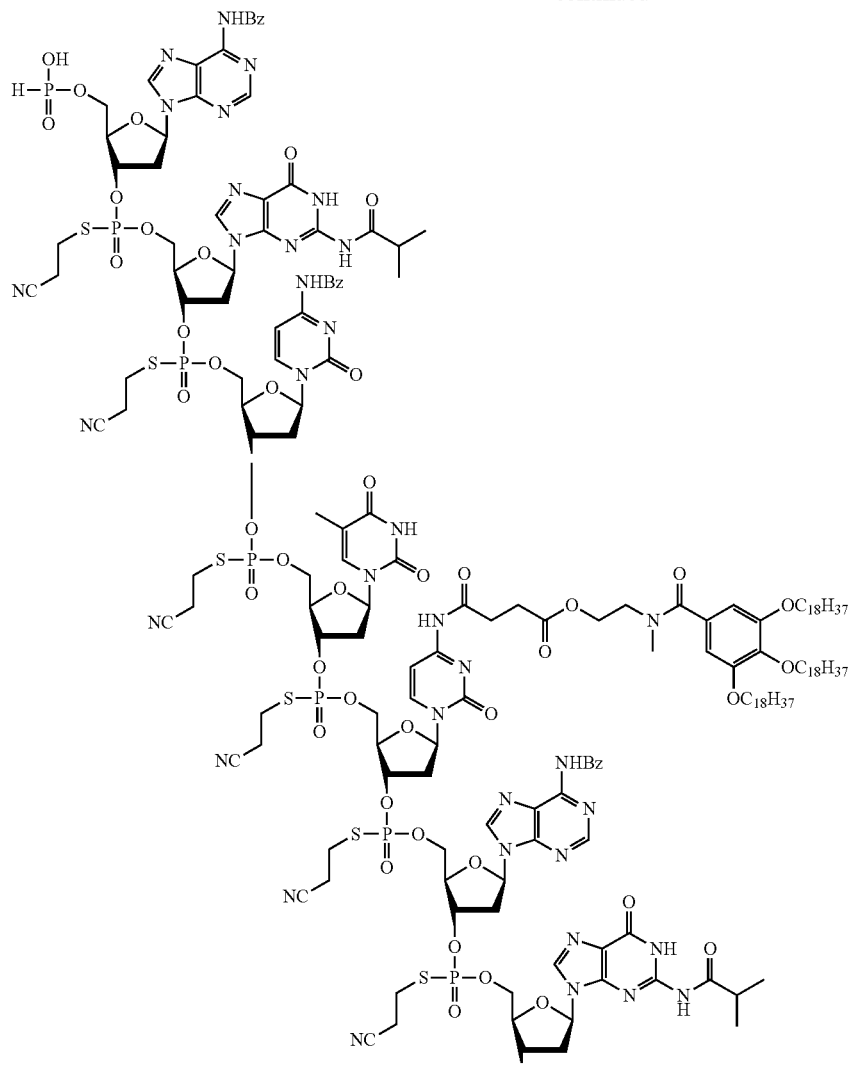
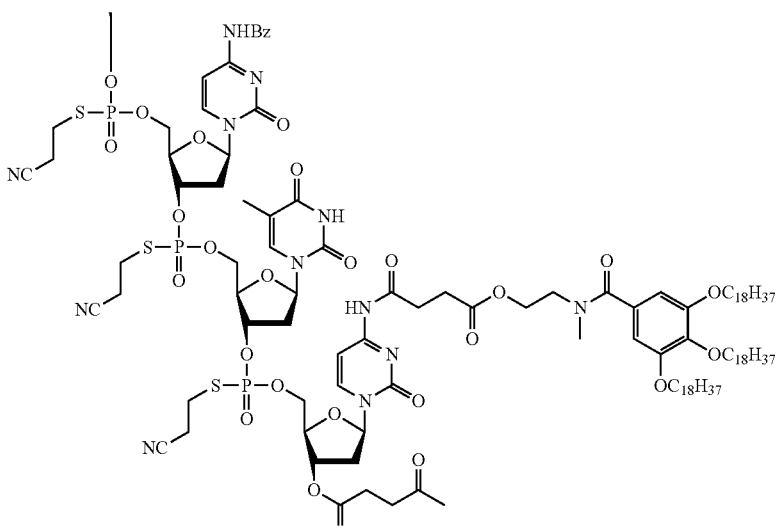

Step 1: Synthesis of Compound 102

In a nitrogen atmosphere, a methylene chloride solution (8.0 mL) of Compound 100 (0.39 g, 58 μmol) and indole (21 mg, 0.18 mmol) was cooled to 10° C., and dichloroacetic acid (33 μL, 0.40 mmol) was added. The mixture was stirred for 2 hours. Further, dichloroacetic acid (14 μL, 0.17 mmol) was added, and the mixture was stirred for 2 hours and 32 minutes. Pyridine (0.60 mL) was added, and the mixture was brought to room temperature. The reaction mixture was added to methanol (100 g), and the resultant solid was recovered by filtration. Consequently, Compound 102 (0.35 g) was obtained.

MS (ESI$^+$): [M+3H]$^{3+}$ 2132.2235.

Step 2: Synthesis of Compound 103

In a nitrogen atmosphere, phosphonic acid (38 mg, 0.46 mmol) was added to a solution of Compound 102 (0.17 g, 27 μmol) in a mixed solvent of methylene chloride (1.0 mL) and pyridine (0.20 mL) at 40° C. 2,2-Dimethylbutyryl chloride (36 μL, 0.27 mmol) was added in 4 portions every 10 minutes, and the mixture was stirred for 1 hour and 5 minutes. 2,2-Dimethylbutyryl chloride (73 μL, 0.53 mmol) was added, and the mixture was stirred for 49 minutes. Thereafter, the reaction mixture was added to acetonitrile (51 g), and the resultant solid was recovered by filtration. Consequently, Compound 103 (0.17 g) was obtained as a white solid.

MS (ESI$^+$): [M+3H]$^{3+}$ 2153.5570.

Example 109 (Synthesis of 11-mer): Synthesis of Compound 104

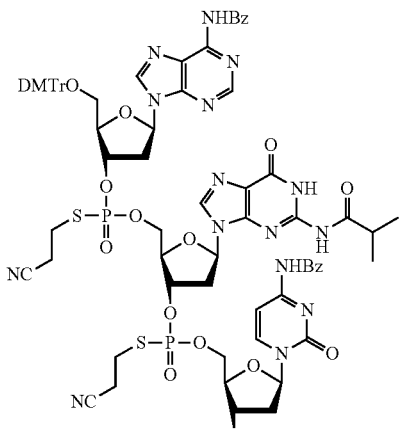

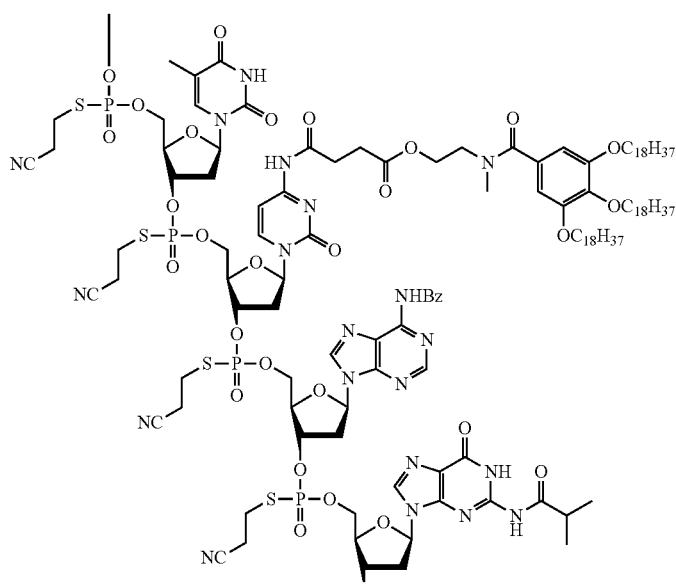

-continued
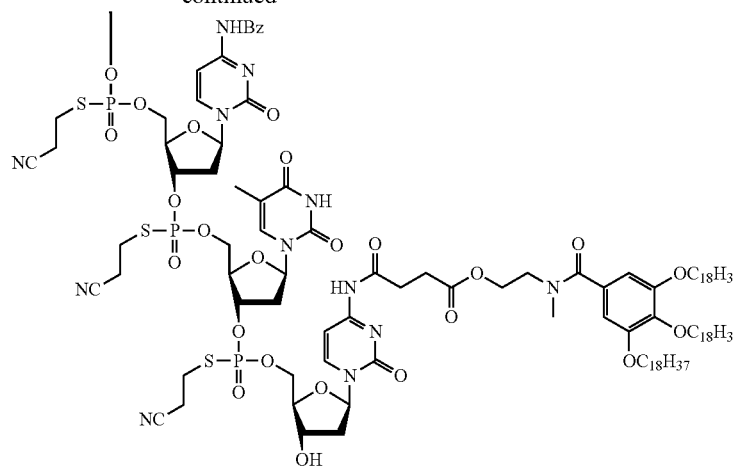
101
+
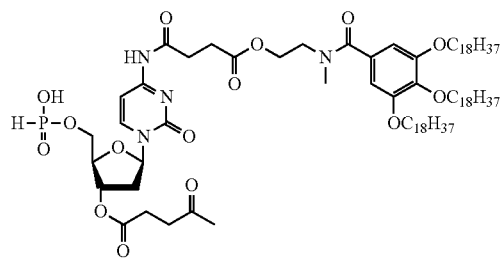
42
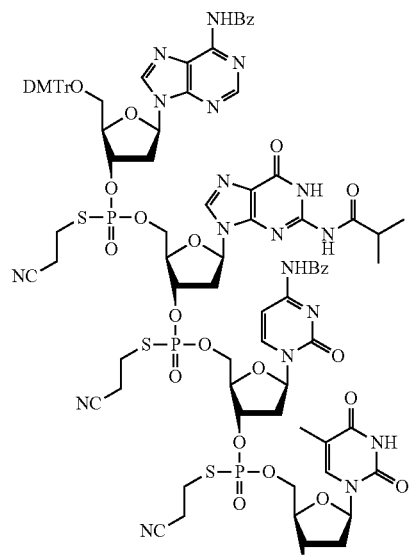

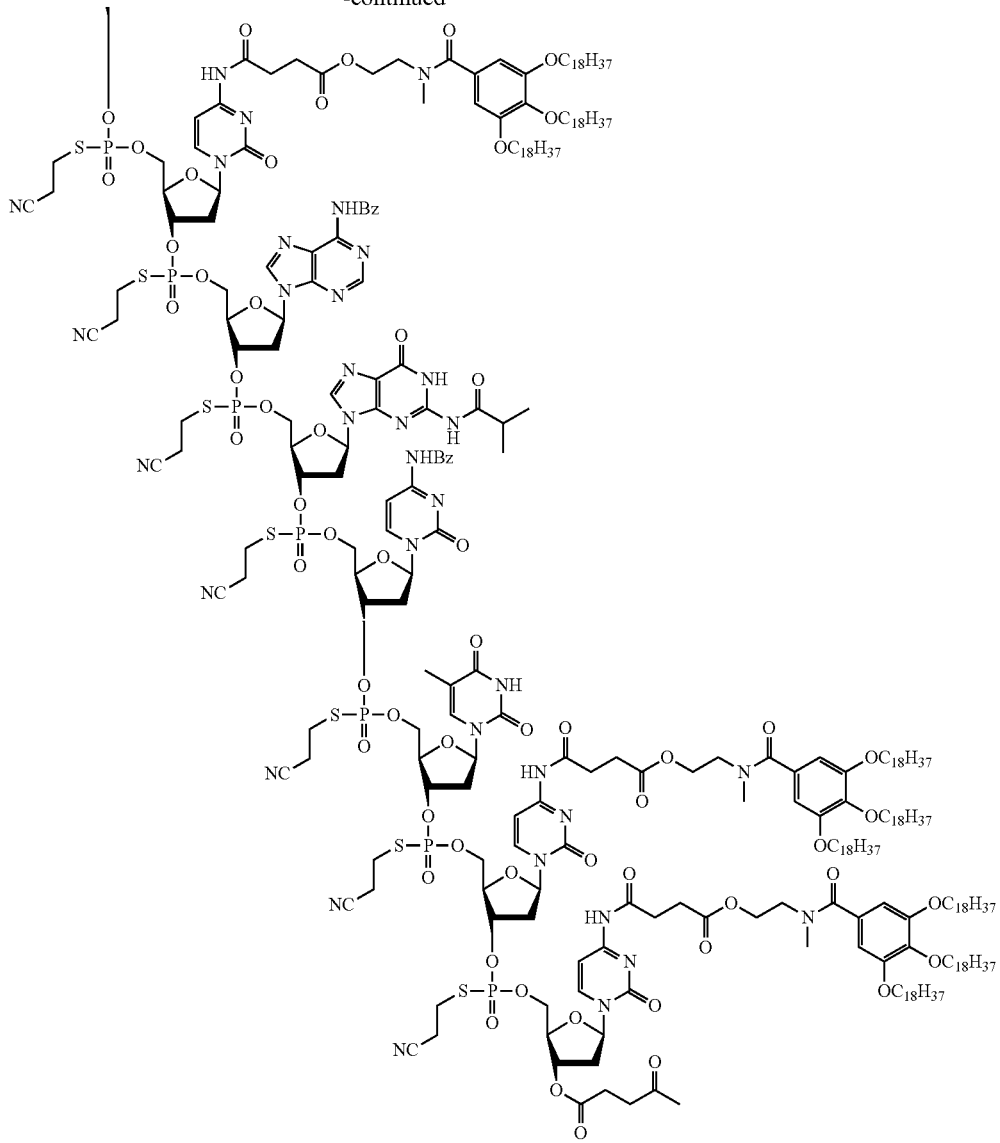

104

In a nitrogen atmosphere, bispentafluorophenyl carbonate (50 mg, 0.13 mmol) was added to a pyridine (0.20 mL) solution of Compound 101 (5.5 mg, 0.83 μmol) and Compound 42 (2.7 mg) at room temperature, and the mixture was stirred for 3 hours and 8 minutes. Thereafter, N-[(2-cyanoethyl)thio]phthalimide (3.4 mg, 15 μmol) as a sulfurizing agent was added, and the mixture was stirred for 1 hour. The reaction mixture was analyzed by LC-MS, and Compound 104 was identified.

MS (ESI$^+$): [M+3H]$^{3+}$ 2707.5985.

Example 110 (Synthesis of 11-mer): Synthesis of Compound 105

+

-continued
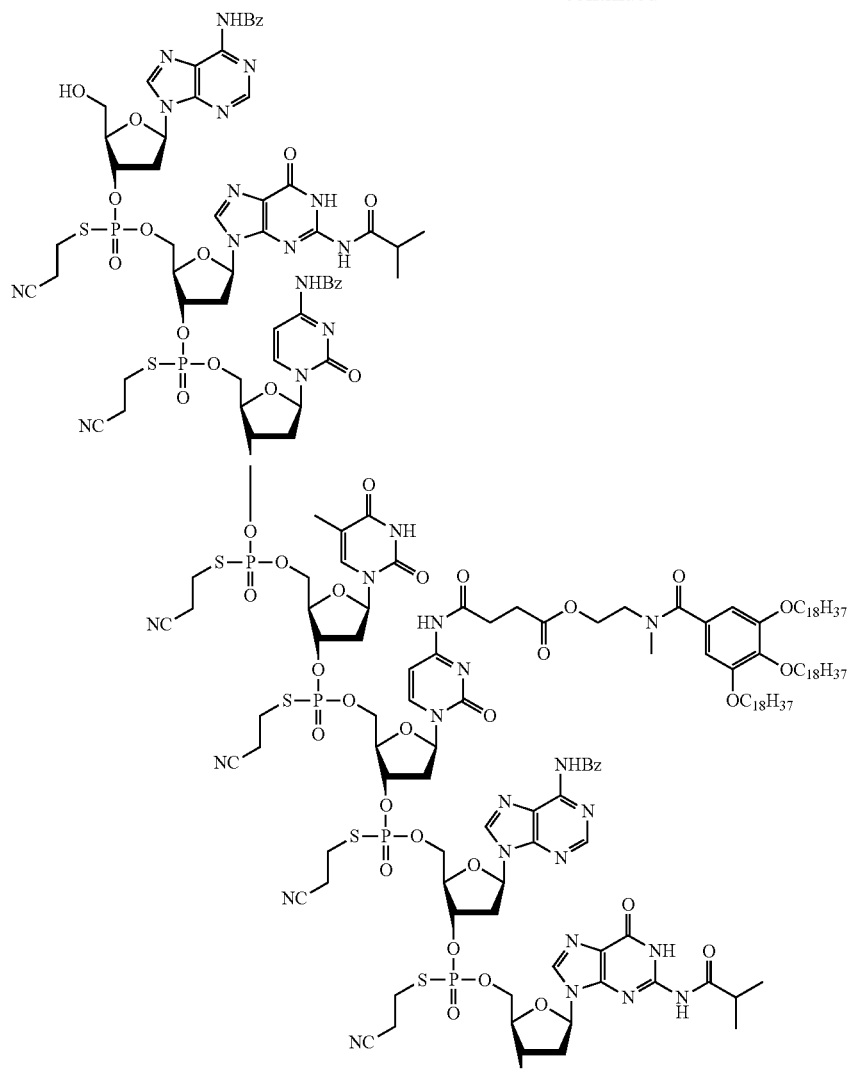
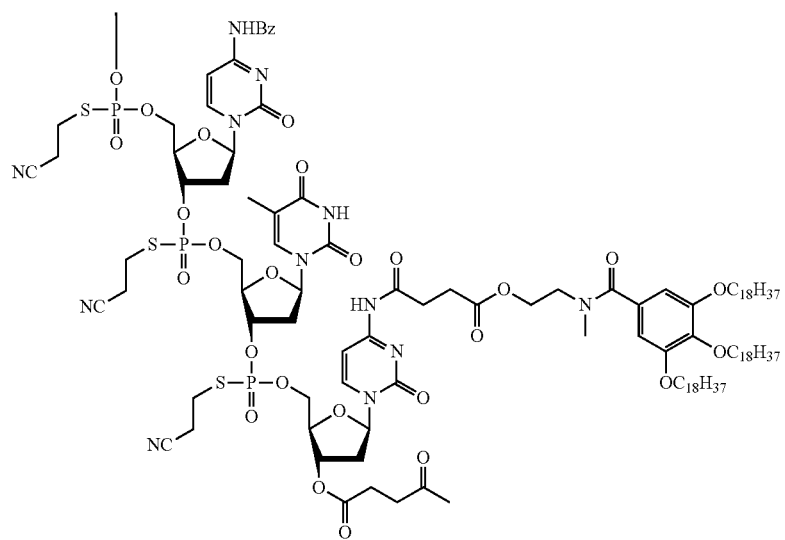

-continued
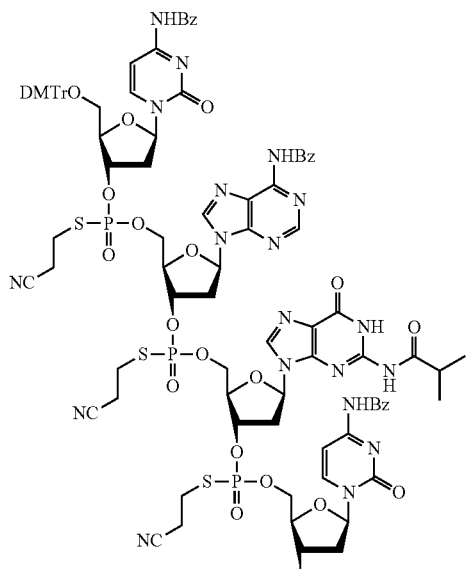
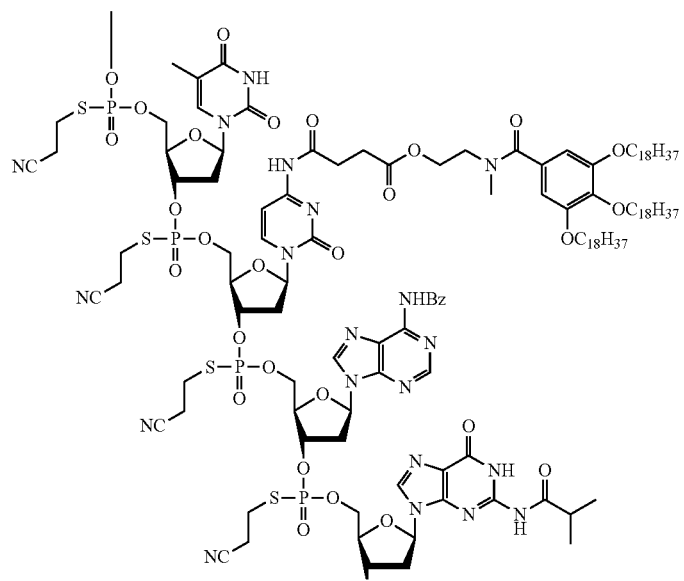

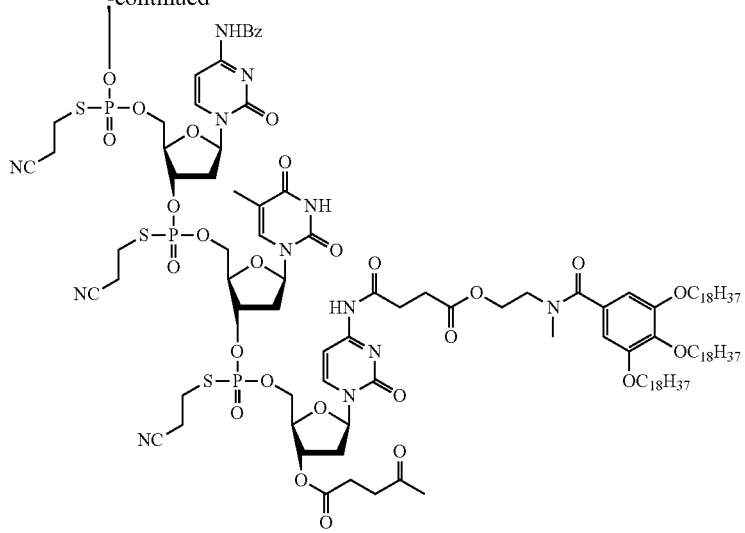

105

In a nitrogen atmosphere, bispentafluorophenyl carbonate (28 mg, 72 μmol) was added to a pyridine (0.20 mL) solution of Compound 102 (5.8 mg, 0.91 μmol) and 5'-O-(4,4'-dimethoxytrityl)-3'-O-hydroxyphosphynyl-2'-deoxycytidine triethylamine salt (manufactured by ChemGenes Corporation) (2.3 mg, 2.9 μmol) at room temperature, and the mixture was stirred for 1 hour and 40 minutes. Thereafter, N-[(2-cyanoethyl)thio]phthalimide (3.6 mg, 16 μmol) as a sulfurizing agent was added, and the mixture was stirred for 1 hour. The reaction mixture was analyzed by LC-MS, and Compound 105 was identified as the main product.

MS (ESI$^+$): [M+3H]$^{3+}$ 2386.9640.

Example 111 (Synthesis of 11-mer): Synthesis of Compound 105

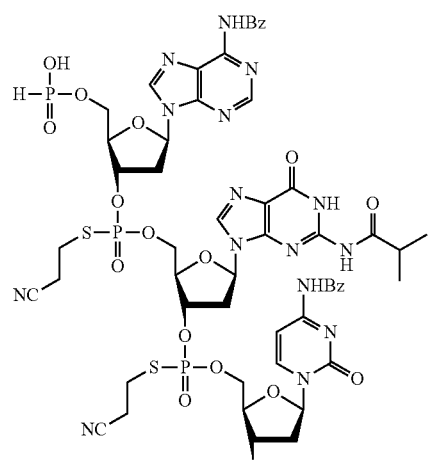

-continued
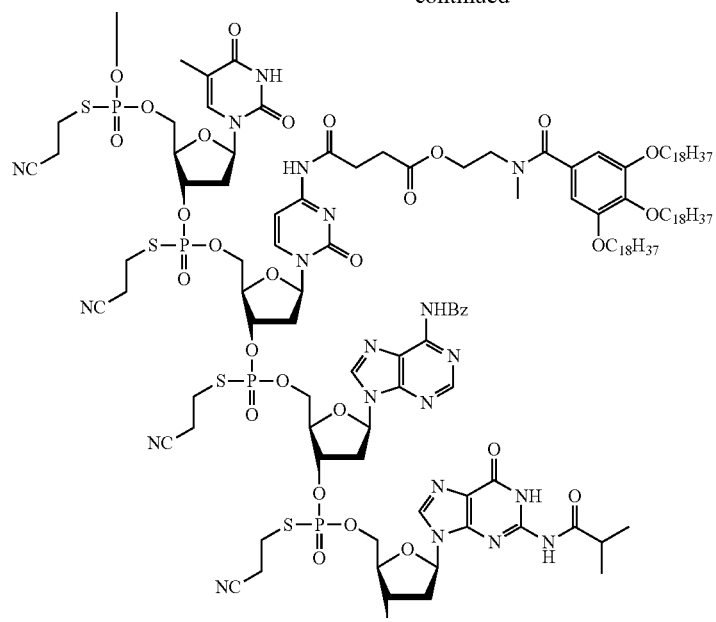
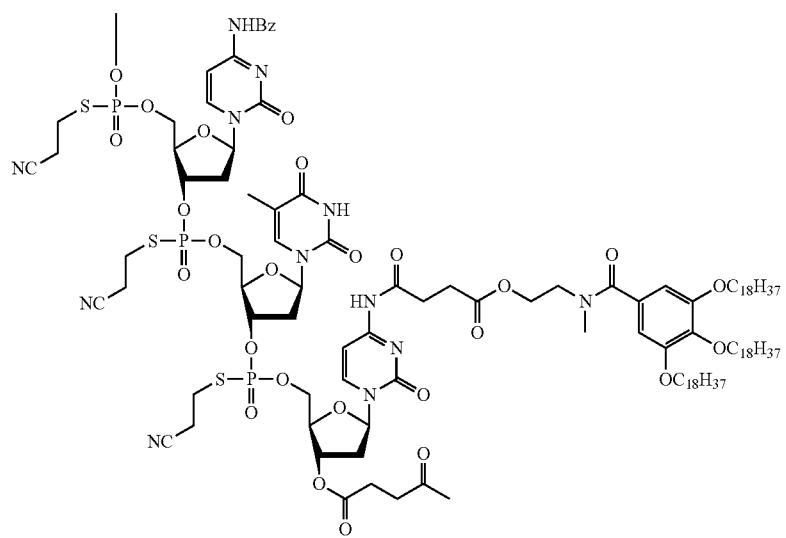

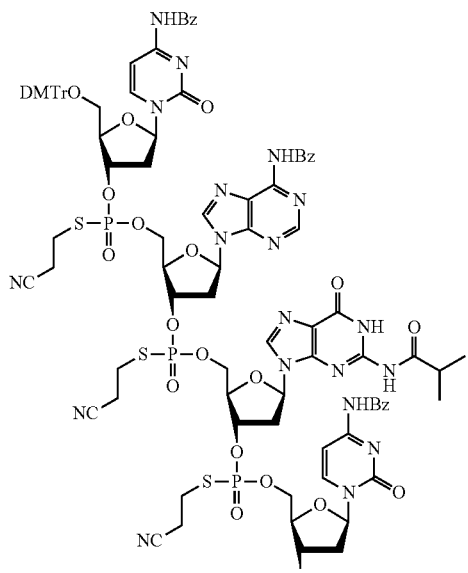
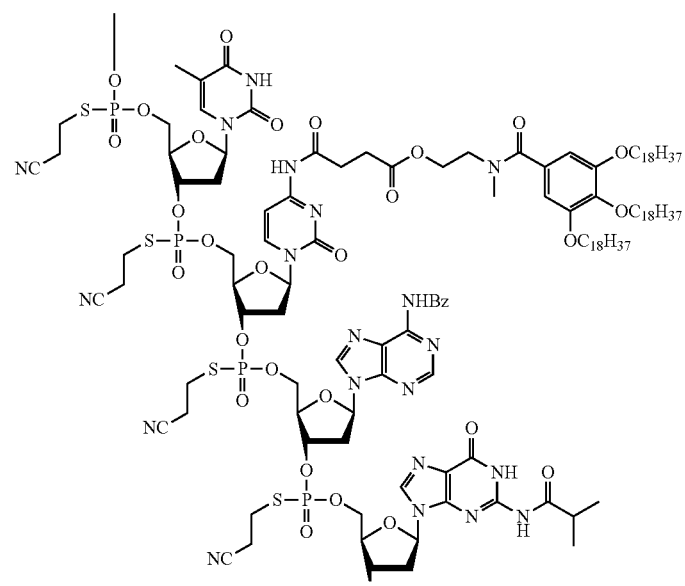

-continued

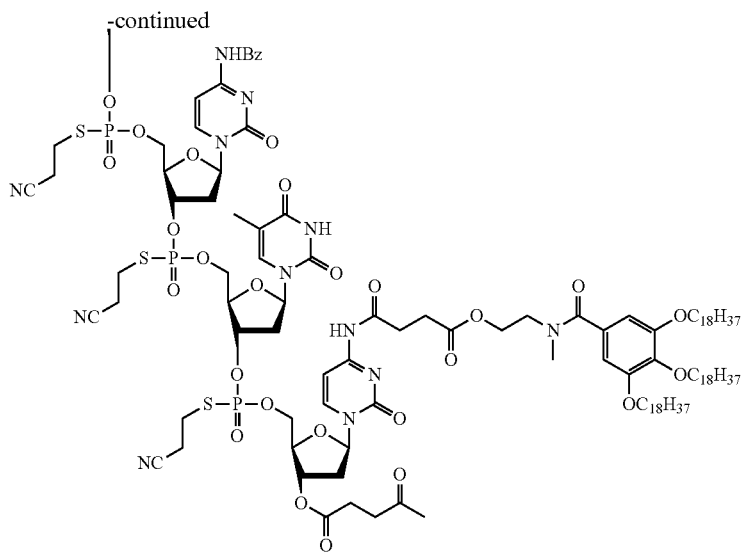

105

In a nitrogen atmosphere, bispentafluorophenyl carbonate (23 mg, 57 μmol) was added to a pyridine (0.20 mL) solution of Compound 103 (4.5 mg, 0.70 μmol) and $N^4$-benzoyl-5'-O-(4,4'-dimethoxytrityl)-2'-deoxycytidine (manufactured by Tokyo Chemical Industry Co., Ltd.) (2.9 mg, 4.6 μmol) at room temperature, and the mixture was stirred for 28 minutes. Thereafter, N-[(2-cyanoethyl)thio]phthalimide (2.8 mg, 12 μmol) as a sulfurizing agent was added, and the mixture was stirred for 1 hour. The reaction mixture was analyzed by LC-MS, and Compound 105 was identified.

Example 112 (Synthesis of 10-mer Having H-Phosphonate Group at 3'-Terminal): Synthesis of Compound 106

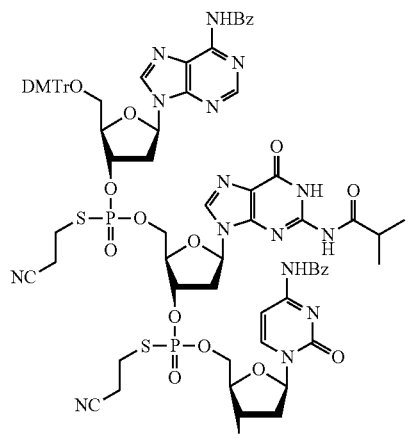

-continued
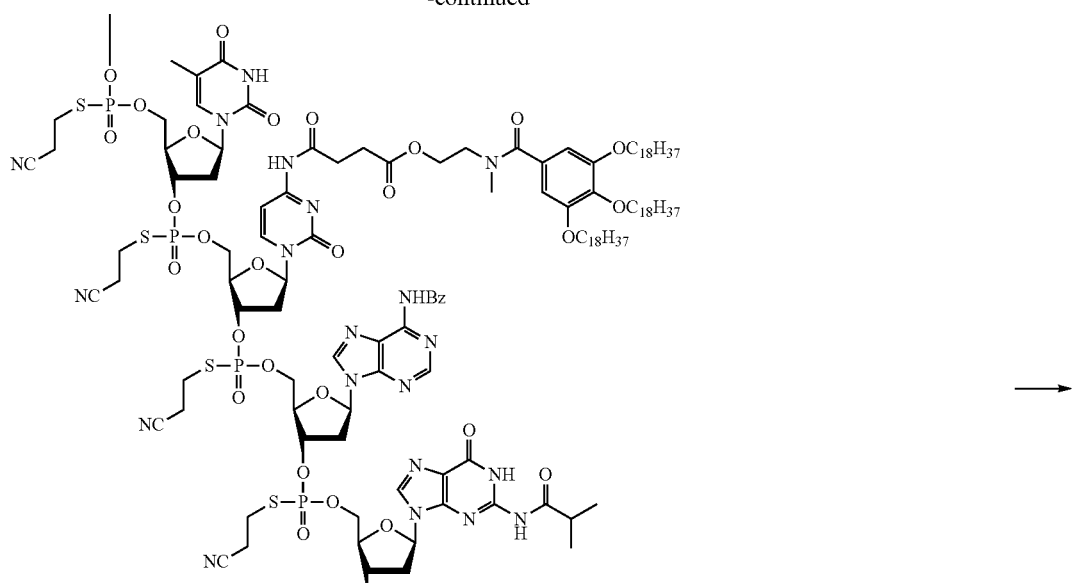
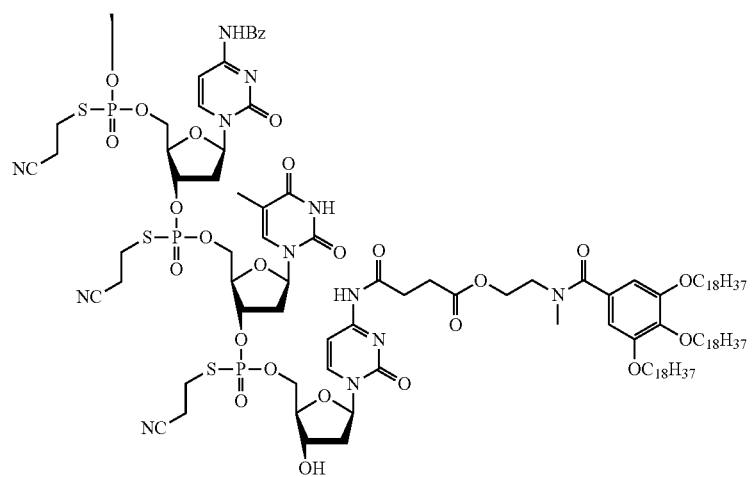

-continued

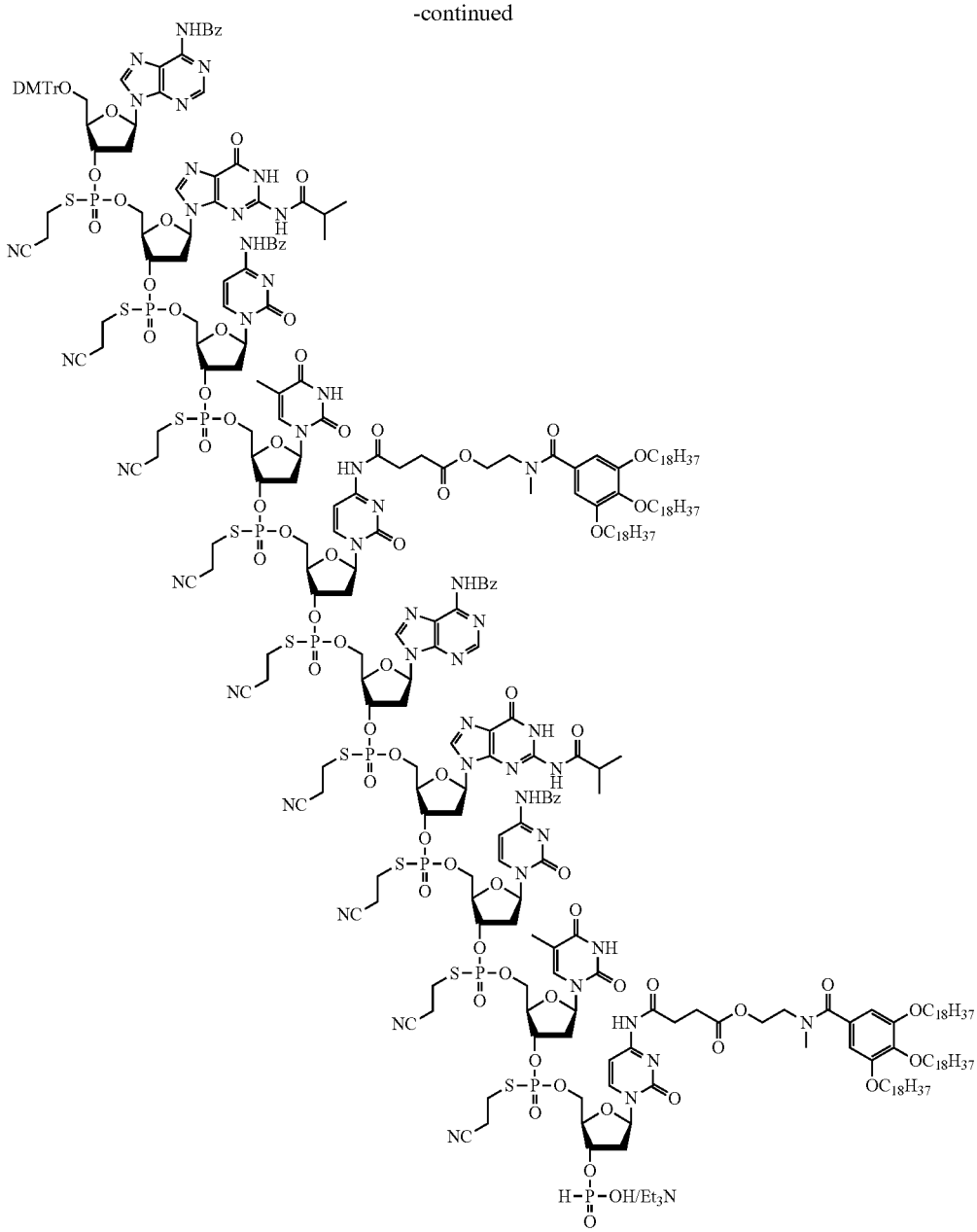

106

In a nitrogen atmosphere, Compound 101 (9.3 mg, 1.4 µmol) was added to a pyridine (0.20 mL) solution of diphenyl phosphite (2.0 µL, 10 µmol) at room temperature, and the mixture was stirred at room temperature for 3 hours and 7 minutes. Thereafter, diphenyl phosphite (2.0 µL, 10 µmol) was added, and the mixture was stirred at room temperature for 11 hours and 50 minutes. Water and triethylamine were sequentially added. The reaction mixture was analyzed by LC-MS, and Compound 106 was identified.

MS (ESI$^+$): [M+3H]$^{3+}$ 2221.5833.

Example 113 (Deprotection of 10-mer): Synthesis of Compound 107
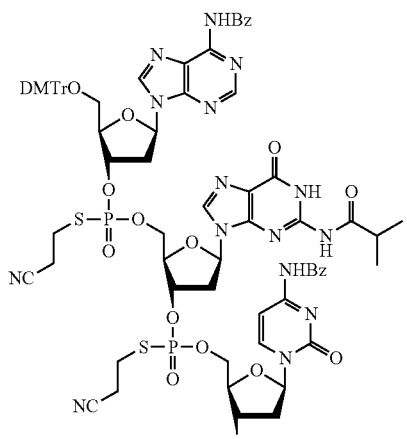
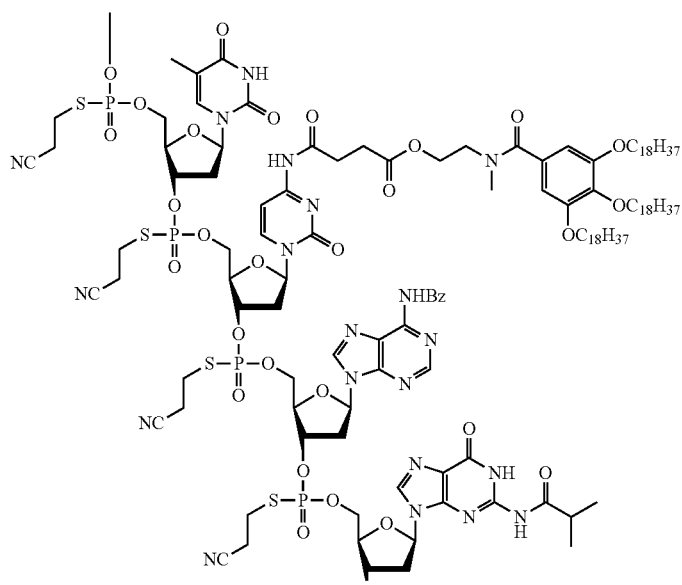
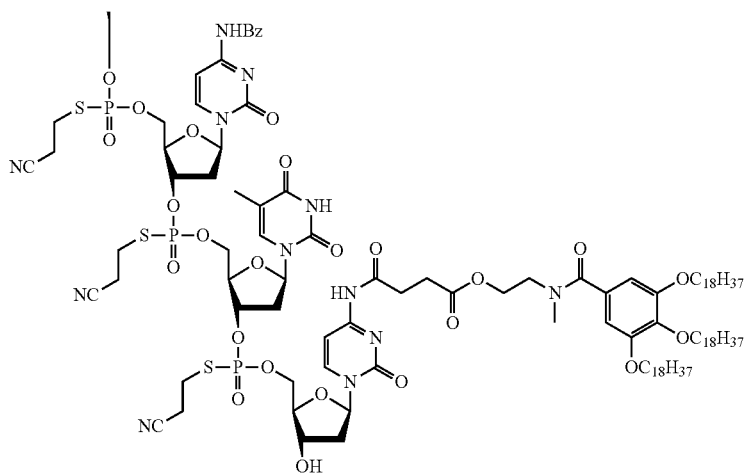

-continued
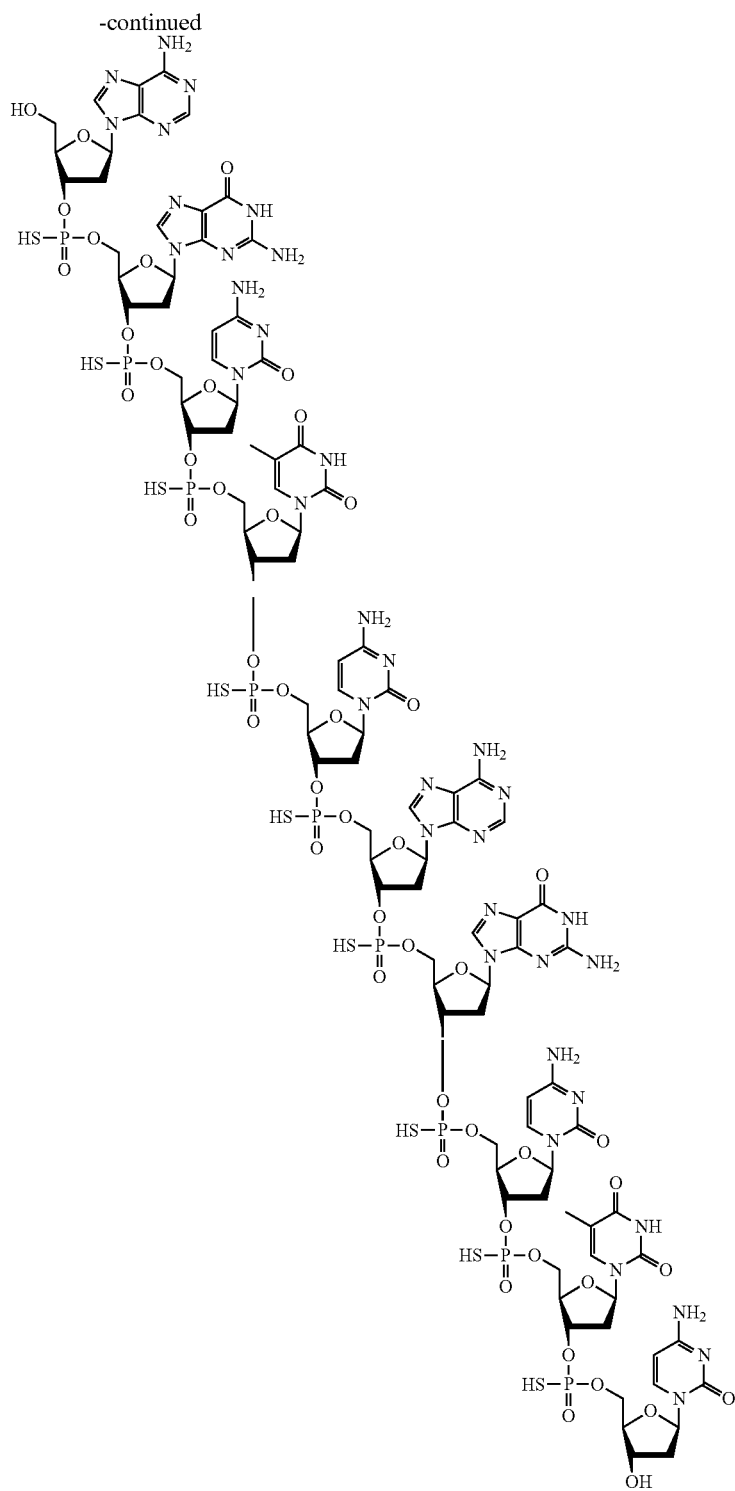
107
In a nitrogen atmosphere, an ethanol (0.15 g) suspension of Compound 101 (8.7 mg, 1.3 µmol) was heated to 45° C., and a 40% aqueous methylamine solution (0.50 mL) was added. The mixture was stirred for 20 minutes. The reaction mixture was analyzed by LC-MS, and Compound 107 was identified.
MS (ESI$^+$): [M+2H]$^{2+}$ 1566.1633

Example 114 (Synthesis of 5-mer Having H-Phosphonate Group at 3'-Terminal): Synthesis of Compound 108
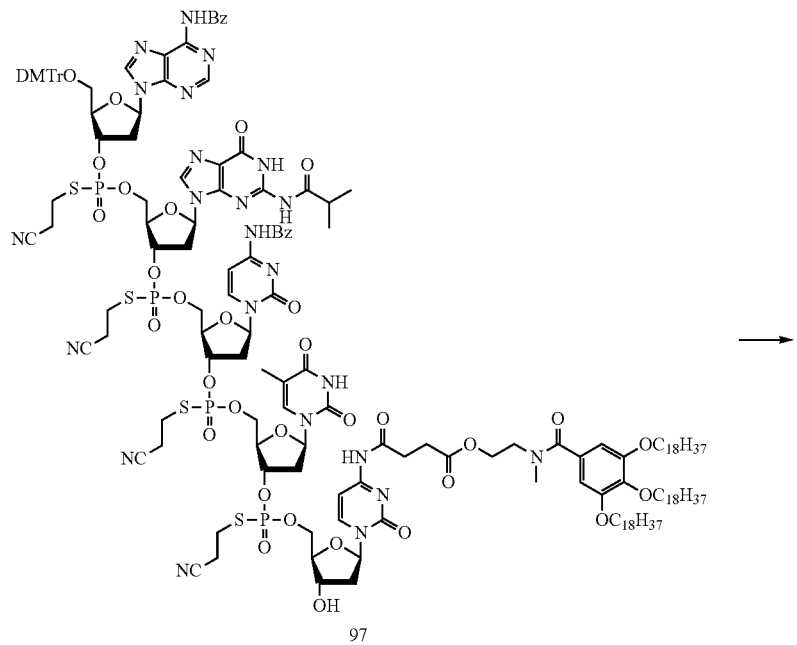
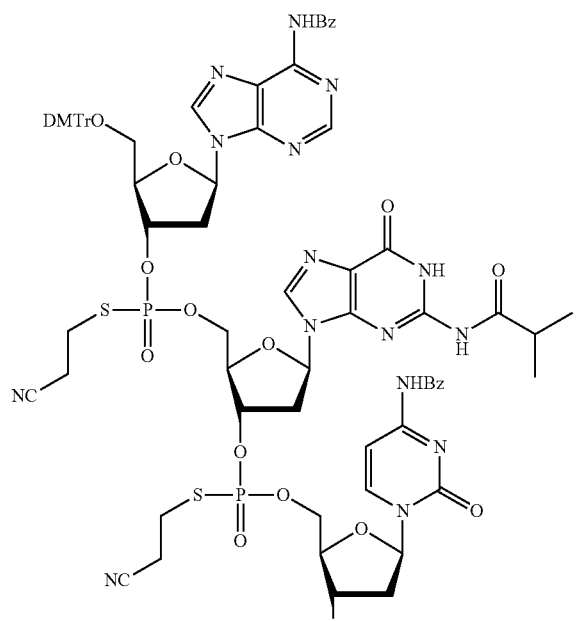

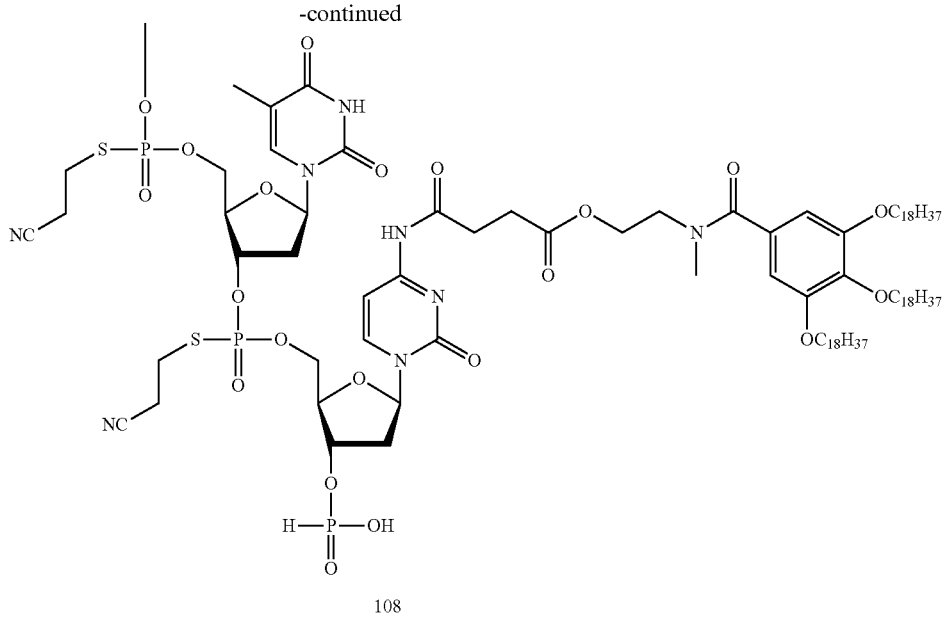

108

In a nitrogen atmosphere, Compound 97 (9.0 mg, 2.7 µmol) was added to a pyridine (0.20 mL) solution of diphenyl phosphite (3.9 µL, 20 µmol) at room temperature, and the mixture was stirred at room temperature for 1 hour. Thereafter, water (50 µL) was added. The reaction mixture was added to acetonitrile, and the resultant solid was recovered by filtration. Consequently, Compound 108 (0.80 mg) was obtained as a white solid.

MS (ESI$^+$): [M+2H]$^{2+}$ 1725.2231.

Example 115 (Synthesis of 15-mer): Synthesis of Compound 109

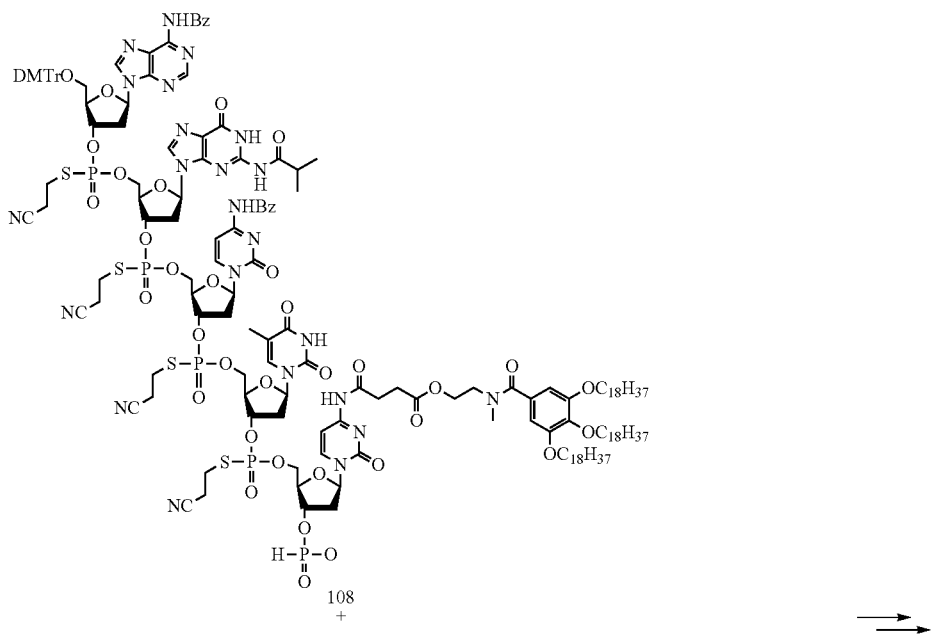

108
+

-continued
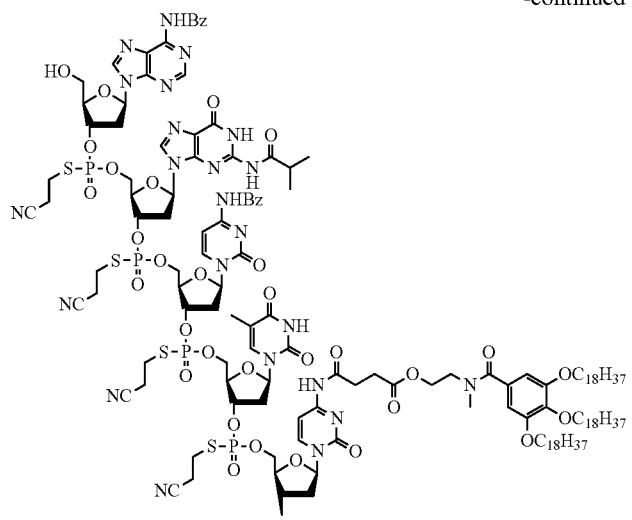
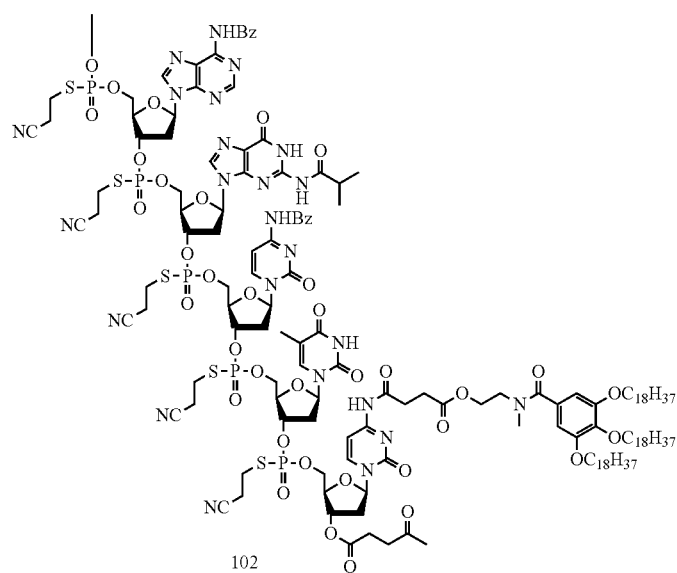
102
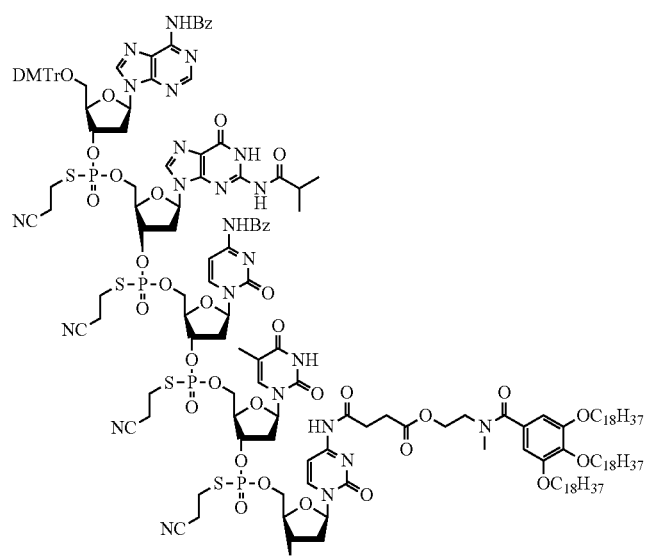

-continued
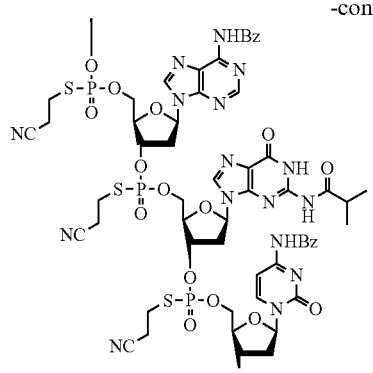
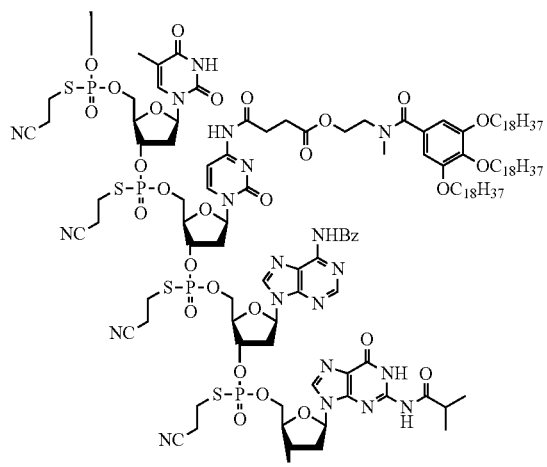
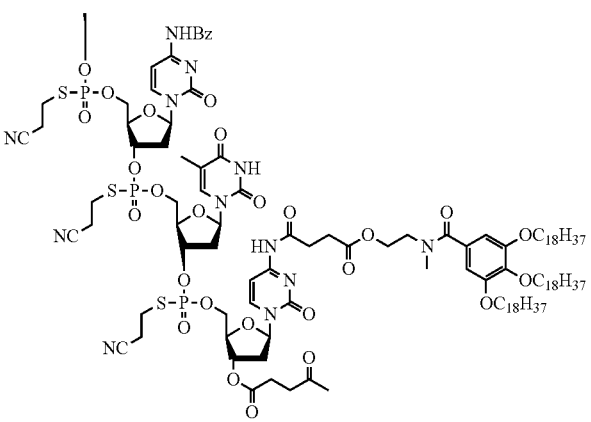
109
In a nitrogen atmosphere, bispentafluorophenyl carbonate (29 mg, 73 μmol) was added to a pyridine (0.20 mL) solution of Compound 102 (1.7 mg, 0.27 μmol) and Compound 108 (0.80 mg) at room temperature, and the mixture was stirred for 30 minutes. The reaction mixture was analyzed by LC-MS, and Compound 109 was identified.
MS (ESI$^+$): [M+4H]$^{4+}$ 2457.0209.

Example 116 (Synthesis of 15-Mer): Synthesis of Compound 110
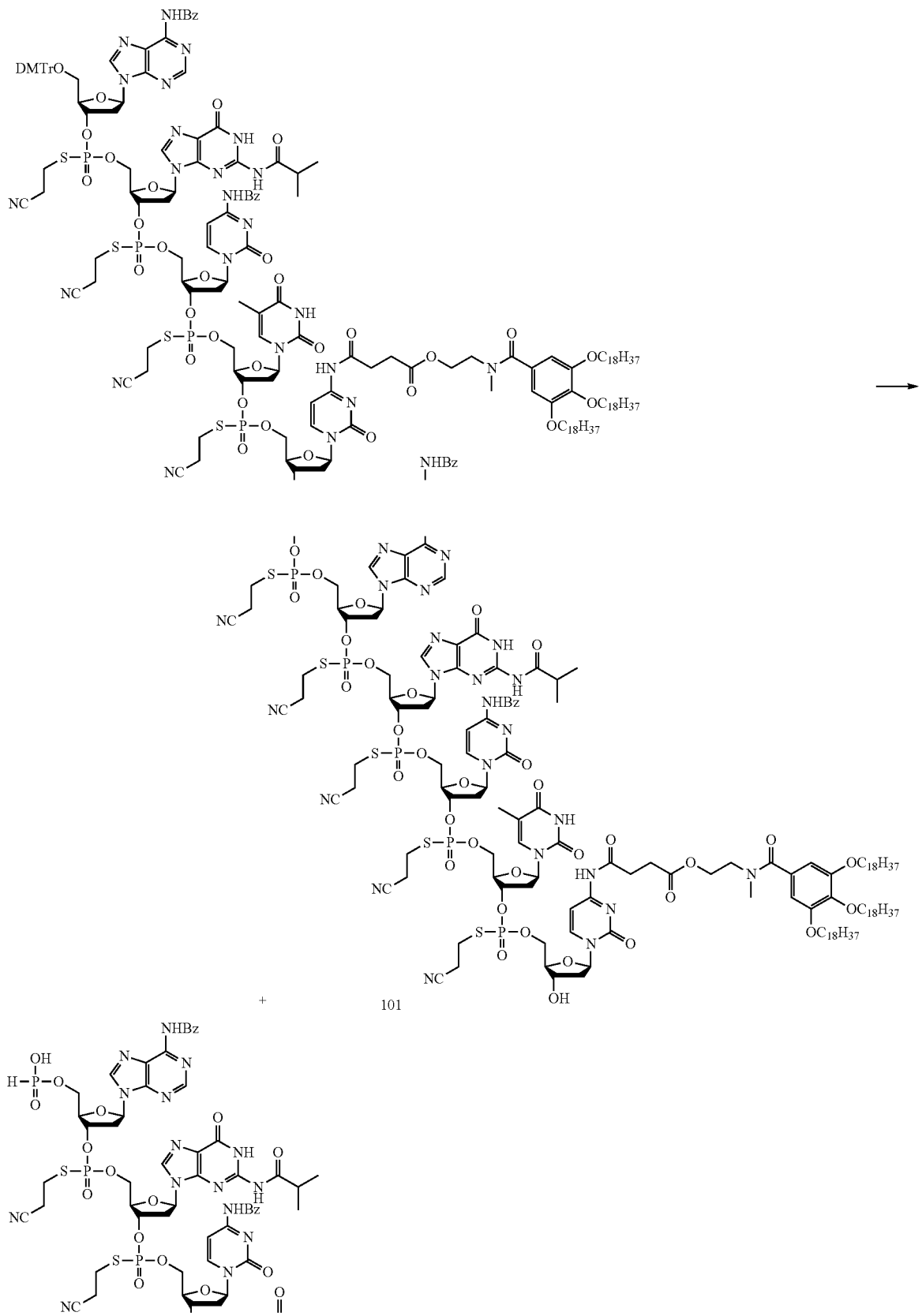

-continued
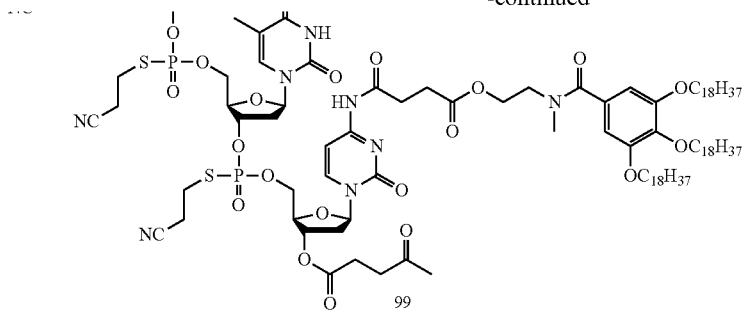
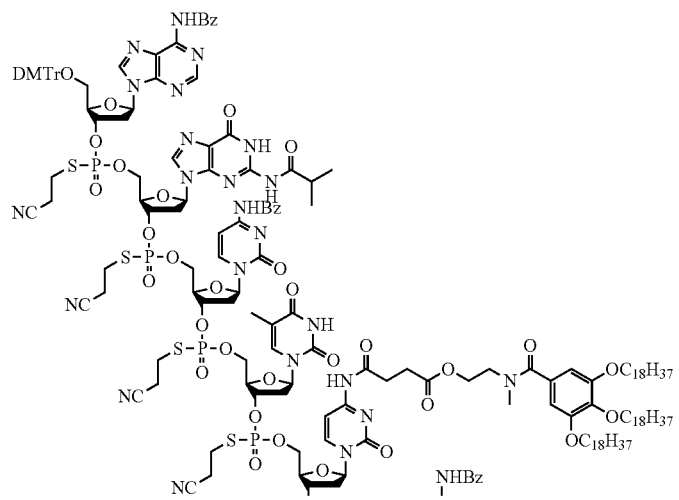
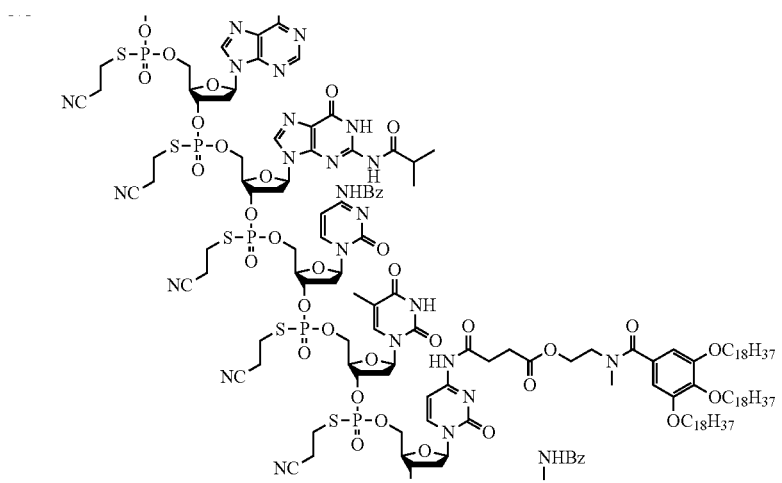

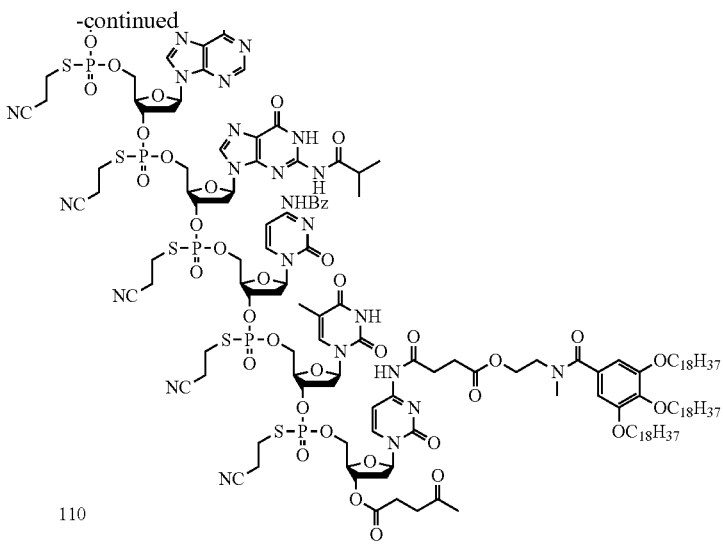

110

In a nitrogen atmosphere, bispentafluorophenyl carbonate (64 mg, 0.16 mmol) was added to a pyridine (0.20 mL) solution of Compound 101 (11 mg, 1.7 μmol) and Compound 99 (4.8 mg) at room temperature, and the mixture was stirred for 1 hour and 5 minutes. Thereafter, N-[(2-cyanoethyl)thio]phthalimide (5.0 mg, 22 μmol) as a sulfurizing agent was added, and the mixture was stirred for 1 hour. The reaction mixture was analyzed by LC-MS, and Compound 110 was identified.

MS (ESI$^+$): [M+4H]$^{4+}$ 2478.2707.

Example 117 (Introduction of Pseudo Solid Phase-Protecting Group into Adenine): Synthesis of Compound 111

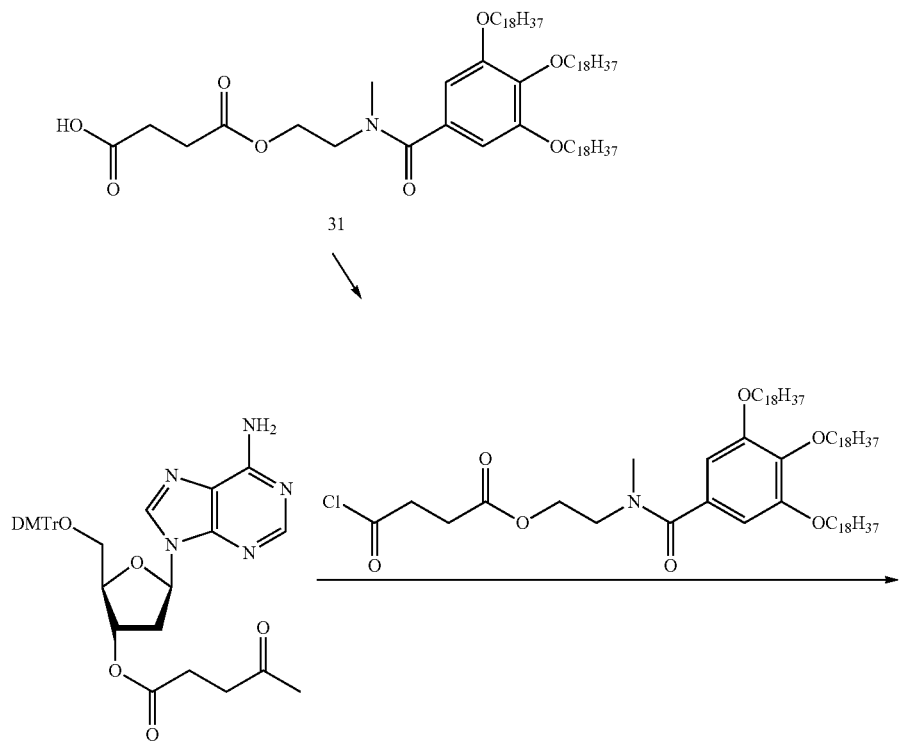

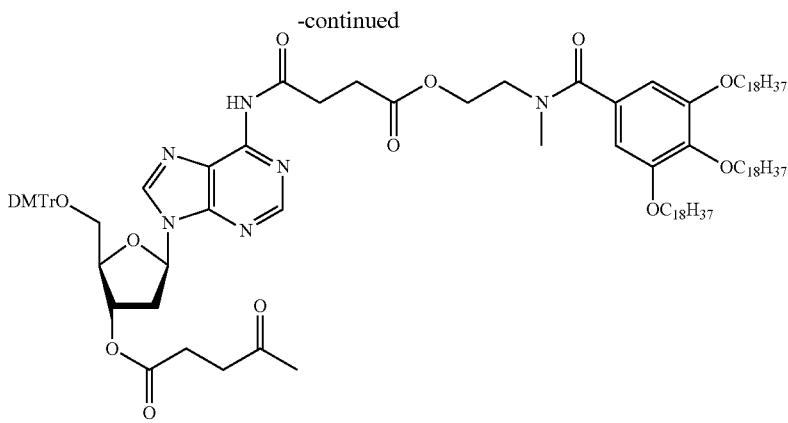

111

In a nitrogen atmosphere, a solution of Compound 31 (11 mg, 10 μmol) in a mixed solvent of methylene chloride (0.20 mL) and DMF (5.0 μL) was cooled to 10° C., and thionyl chloride (4.0 μL, 55 μmol) was added. Thereafter, the mixture was brought to room temperature and was stirred for 58 minutes. The reaction mixture was added to a methylene chloride (0.20 mL) solution of 5'-O-(4,4'-dimethoxytrityl)-3'-O-levulinyl-2'-deoxyadenosine (12 mg, 18 μmol) and diisopropylethylamine (14 μL, 83 μmol) at 10° C., and the mixture was stirred for 1 hour and 20 minutes. The reaction mixture was analyzed by LC-MS, and Compound 111 was identified.

MS (ESI$^+$): [M+H]$^+$ 1718.2007.

Example 118 (Introduction of Pseudo Solid Phase-Protecting Group into Guanine): Synthesis of Compound 81

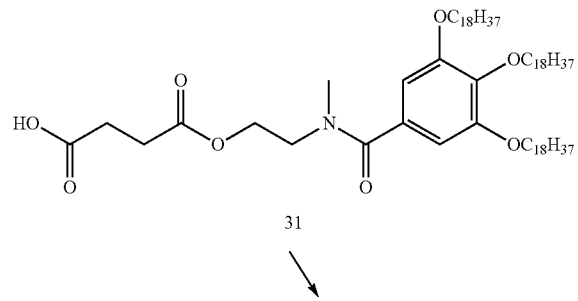

31

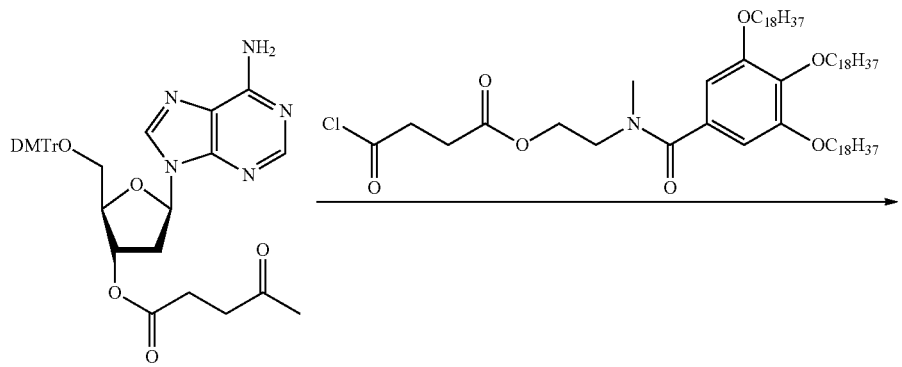

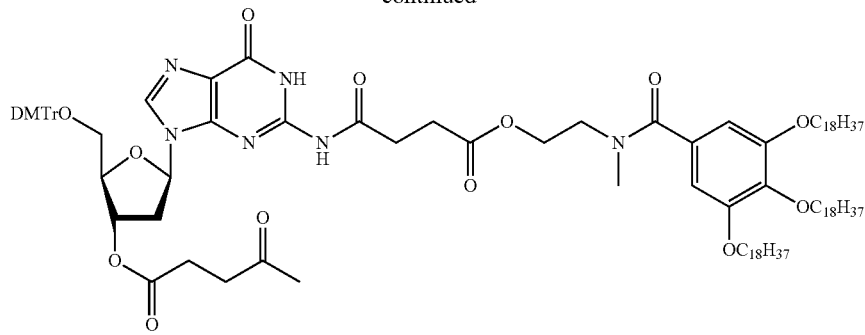

81

In a nitrogen atmosphere, thionyl chloride (4.0 μL, 55 μmol) was added to a solution of Compound 31 (12 mg, 11 μmol) in a mixed solvent of methylene chloride (0.30 mL) and DMF (5.0 μL) at room temperature, and the mixture was stirred for 20 minutes. The reaction mixture was added to a methylene chloride (0.20 mL) solution of 5'-O-(4,4'-dimethoxytrityl)-3'-O-levulinyl-2'-deoxyguanosine (10 mg, 15 μmol) and diisopropylethylamine (28 μL, 0.17 mmol) at room temperature, and the mixture was stirred for 30 minutes. The reaction mixture was analyzed by LC-MS, and Compound 81 was identified.

Example 119 (Introduction of Pseudo Solid Phase-Protecting Group into Adenine): Synthesis of Compound 112

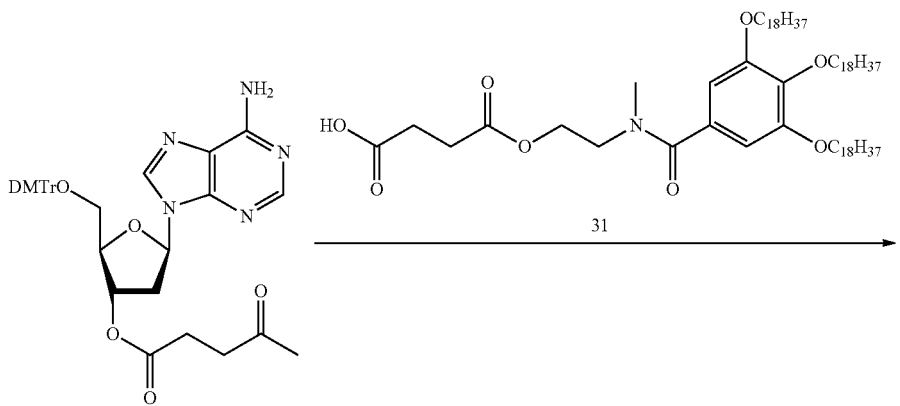

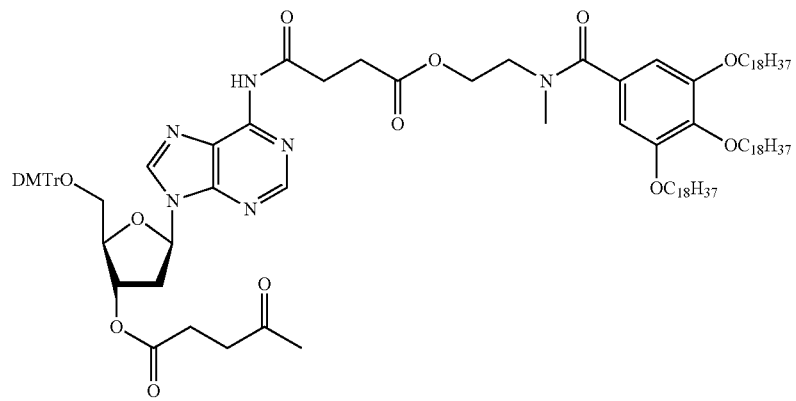

112

In a nitrogen atmosphere, DMAP (0.56 g, 4.6 mmol) and WSC.HCl (0.90 g, 4.7 mmol) were added in this order to a methylene chloride (100 mL) solution of 5'-O-(4,4'-dimethoxytrityl)-3'-O-levulinyl-2'-deoxyadenosine (0.93 g, 1.4 mmol) and Compound 31 (1.1 g, 0.97 mmol) at 40° C., and the mixture was stirred for 16 hours and 35 minutes. The reaction mixture was vacuum concentrated. Methanol (102 g) was added, and the resultant solid was recovered by filtration. Consequently, a crude product (1.3 g) of Compound 112 was obtained. The crude product was purified by silica gel chromatography (chloroform-methanol) to give Compound 112 (0.68 g).

$^1$H-NMR: (300 MHz; CDCl$_3$) δ0.85 (t, 9H), 125-1.81 (m, 96H), 2.21 (s, 3H), 2.59-3.07 (m, 11H), 3.26-3.78 (m, 12H), 3.93-4.31 (m, 9H), 5.53 (d, 1H), 6.48-6.49 (m, 1H), 6.59 (s, 2H), 6.77-6.80 (m, 4H), 7.20-7.38 (m, 9H), 8.10 (s, 1H), 8.61 (s, 1H), 8.83 (brs, 1H).

MS (ESI$^+$): [M+H]$^+$ 1718.2015.

Example 120 (Transformation of 5'-Functional Group of Adenosine Having Pseudo Solid Phase-Protecting Group): Synthesis of Compound 114

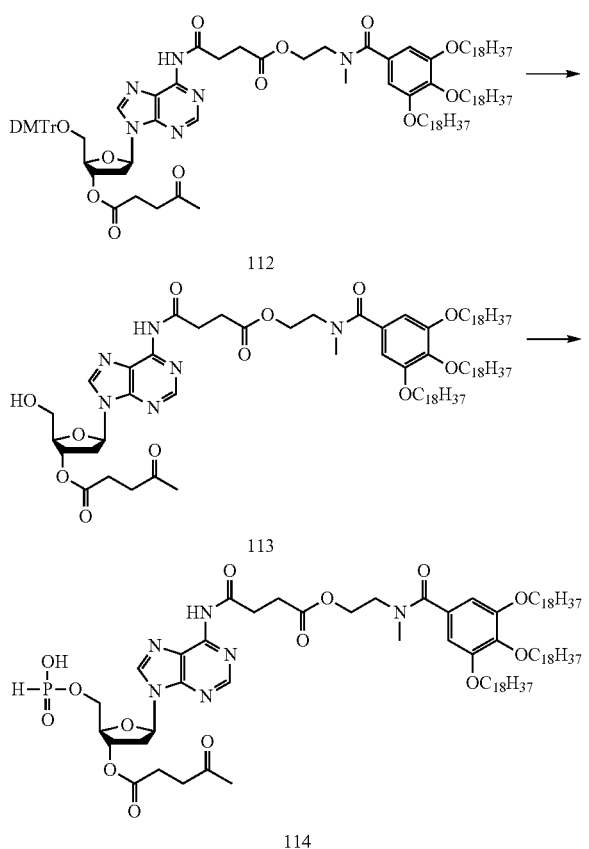

Step 1: Synthesis of Compound 113

In a nitrogen atmosphere, a methylene chloride (1.0 mL) solution of Compound 112 (0.29 g, 0.17 mmol) was cooled to 10° C., and pyrrole (35 µL, 0.51 mmol) was added. The mixture was stirred for 5 minutes. Thereafter, dichloroacetic acid (42 µL, 0.51 mmol) was added, and the mixture was stirred for 1 hour and 13 minutes. Pyridine (0.14 mL) was added, and the mixture was brought to room temperature. The reaction mixture was added to acetonitrile (50 g), and the resultant solid was recovered by filtration. Consequently, Compound 113 (0.20 g) was obtained.

$^1$H-NMR: (300 MHz; CDCl$_3$) δ0.88 (t, 9H), 1.16-1.83 (m, 96H), 2.22 (s, 3H), 2.45-2.51 (m, 1H), 2.59-2.63 (m, 2H), 2.79-2.83 (m, 4H), 3.07-3.20 (m, 4H), 3.27-4.29 (m, 15H), 5.56 (d, 1H), 6.31-6.36 (m, 1H), 6.58 (s, 2H), 8.06 (d, 1H), 8.64 (s, 1H), 8.93 (brs, 1H).

MS (ESI$^+$): [M+H]$^+$ 1416.0785.

Step 2: Synthesis of Compound 114

In a nitrogen atmosphere, a pyridine (0.30 mL) solution of phosphonic acid (17 mg, 0.21 mmol) was heated to 40° C., and 2,2-dimethylbutyryl chloride (6.3 µL, 46 µmol) was added. The mixture was stirred for 30 minutes. Thereafter, Compound 113 (11 mg, 7.8 µmol) was added, and the mixture was stirred for 2 hours and 15 minutes. 2,2-Dimethylbutyryl chloride (21 µL, 0.15 mmol) was added, and the mixture was stirred for 1 hour and 10 minutes. The reaction mixture was analyzed by LC-MS, and Compound 114 was identified as the main product.

MS (ESI$^+$): [M+H]$^+$ 1480.0474.

Example 121 (Deprotection of 3'-Position of Adenosine Having Pseudo Solid Phase-Protecting Group): Synthesis of Compound 115

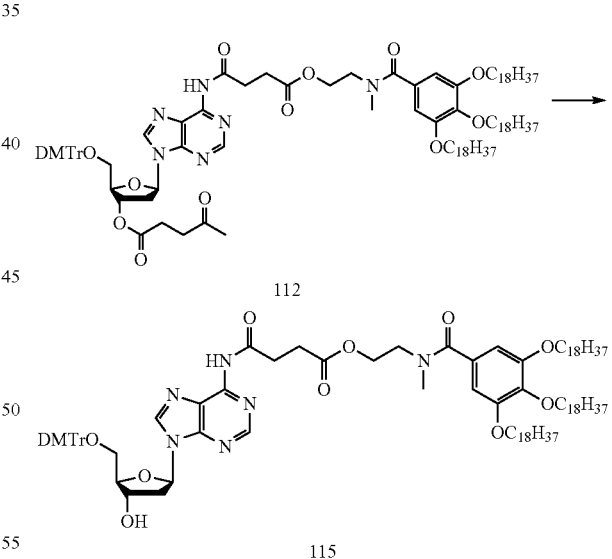

In a nitrogen atmosphere, acetic acid (0.20 mL) was added to a methylene chloride (0.13 g) solution of Compound 112 (33 mg, 19 µmol) at room temperature. Thereafter, the mixture was cooled to 0° C., and hydrazine monohydrate (1.9 µL, 39 µmol) was added. The mixture was stirred for 4 hours and 30 minutes. The reaction mixture was analyzed by LC-MS, and Compound 115 was identified as the main product.

MS (ESI$^+$): [M+H]$^+$ 1620.1626.

Example 122 (Synthesis of Novel Pseudo Solid Phase-Protecting Group, and Transformation of 5'-Functional Group of Adenosine): Synthesis of Compound 120

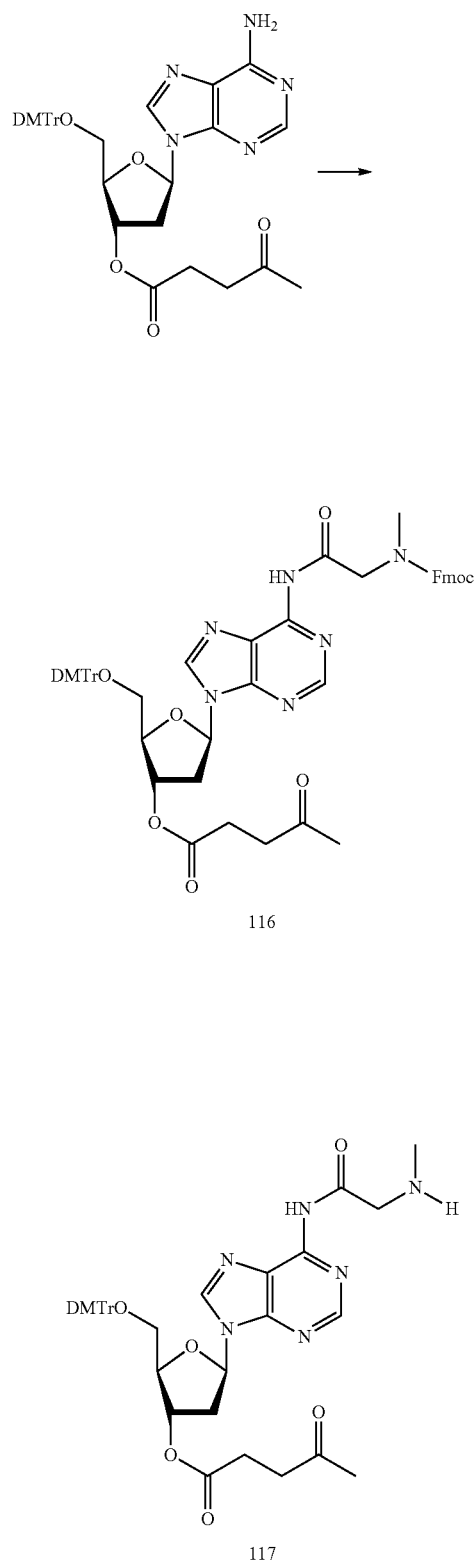

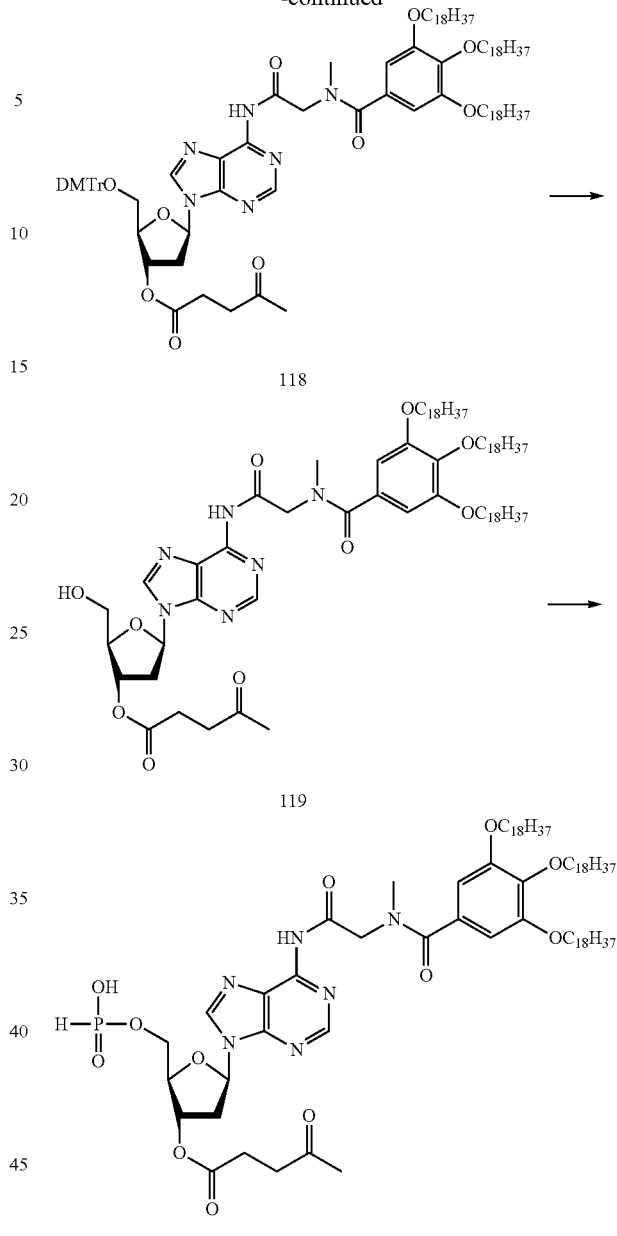

Step 1: Synthesis of Compound 116

In a nitrogen atmosphere, a methylene chloride (10 mL) solution of 5'-O-(4,4'-dimethoxytrityl)-3'-O-levulinyl-2'-deoxyadenosine (2.0 g, 3.1 mmol) and DMAP (0.78 g, 6.4 mmol) was heated to 40° C., and N-α-(9-fluorenylmethoxycarbonyl)-N-α-methylglycine (2.0 g, 6.3 mmol) and WSC.HCl (1.2 g, 6.3 mmol) were added in this order. The mixture was stirred at 40° C. for 3 hours, cooled to room temperature, and washed with a 5% aqueous sodium hydrogen carbonate solution two times. The organic phase thus obtained was washed with water one time. The organic phase was vacuum concentrated, and the residue was purified by silica gel chromatography (chloroform-methanol). Consequently, Compound 116 (1.3 g) was obtained.

$^1$H-NMR: (300 MHz; CDCl$_3$) δ2.21 (s, 3H), 2.42-2.81 (m, 5H), 3.05-3.14 (m, 4H), 3.45 (brs, 2H), 3.77 (s, 6H), 4.00-4.69 (m, 6H), 5.55 (brs, 1H), 6.50 (brs, 1H), 6.77-6.91 (m, 4H), 7.19-7.78 (m, 17H), 8.14 (d, 1H), 8.52-8.90 (m, 2H).
MS (ESI+): [M+H]+ 945.3776.

Step 2: Synthesis of Compound 117

In a nitrogen atmosphere, piperidine (32 µL, 0.32 mmol) was added to an acetonitrile (2.1 g) solution of Compound 116 (0.10 g, 0.11 mmol) at room temperature, and the mixture was stirred for 2 hours and 39 minutes. Heptane was added, and the liquids were separated. The acetonitrile phase was washed with heptane three times. The organic phase obtained was vacuum concentrated. Consequently, Compound 117 (61 mg) was obtained.
MS (ESI+): [M+H]+ 723.3209.

Step 3: Synthesis of Compound 118

In a nitrogen atmosphere, HOBt (anhydride) (12 mg, 90 µmol) was added to a methylene chloride (2.5 g) solution of 3,4,5-tris(octadecyloxy)benzoic acid (synthesized in accordance with the method described in WO 2014/077292) (51 mg, 55 µmol) and Compound 117 (61 mg, 85 µmol). Subsequently, WSC.HCl (18 mg, 92 µmol) was added, and the mixture was stirred for 4 hours and 39 minutes. The reaction mixture was added to methanol (31 g) to precipitate a solid, which was then recovered by filtration. Consequently, Compound 118 (65 mg) was obtained as a white solid.

1H-NMR: (300 MHz; CDCl3) δ0.88 (t, 9H), 1.26-1.77 (m, 96H), 2.21 (s, 3H), 2.58-2.81 (m, 5H), 3.01-3.16 (m, 4H), 3.78 (s, 6H), 3.96 (s, 6H), 4.81 (s, 2H), 5.53 (d, 1H), 6.48 (q, 1H), 6.70 (s, 2H), 6.77-7.39 (m, 14H), 8.11 (s, 1H), 8.58 (brs, 1H).
MS (ESI+): [M+H]+ 1632.1611.

Step 4: Synthesis of Compound 120

In a nitrogen atmosphere, a methylene chloride (0.20 mL) solution of Compound 118 (11 mg, 6.9 µmol) and indole (2.1 mg, 18 µmol) was cooled to 10° C., and phosphonic acid (14 mg, 0.17 mmol) was added. The mixture was stirred for 1 hour and 27 minutes. The reaction mixture was analyzed by LC-MS, and Compound 119 was identified as the main product.
MS (ESI+): [M+H]+ 1330.0382.

Thereafter, pyridine (0.050 mL) was added, and the mixture was brought to room temperature. 2,2-Dimethylbutyryl chloride (14 µL, 0.10 mmol) was added, and the mixture was stirred for 1 hour and 40 minutes. The reaction mixture was analyzed by LC-MS, and Compound 120 was identified as the main product.
MS (ESI+): [M+H]+ 1394.0054.

Example 123 (Comparison of Sulfurizing Agent): Synthesis of Compound 121

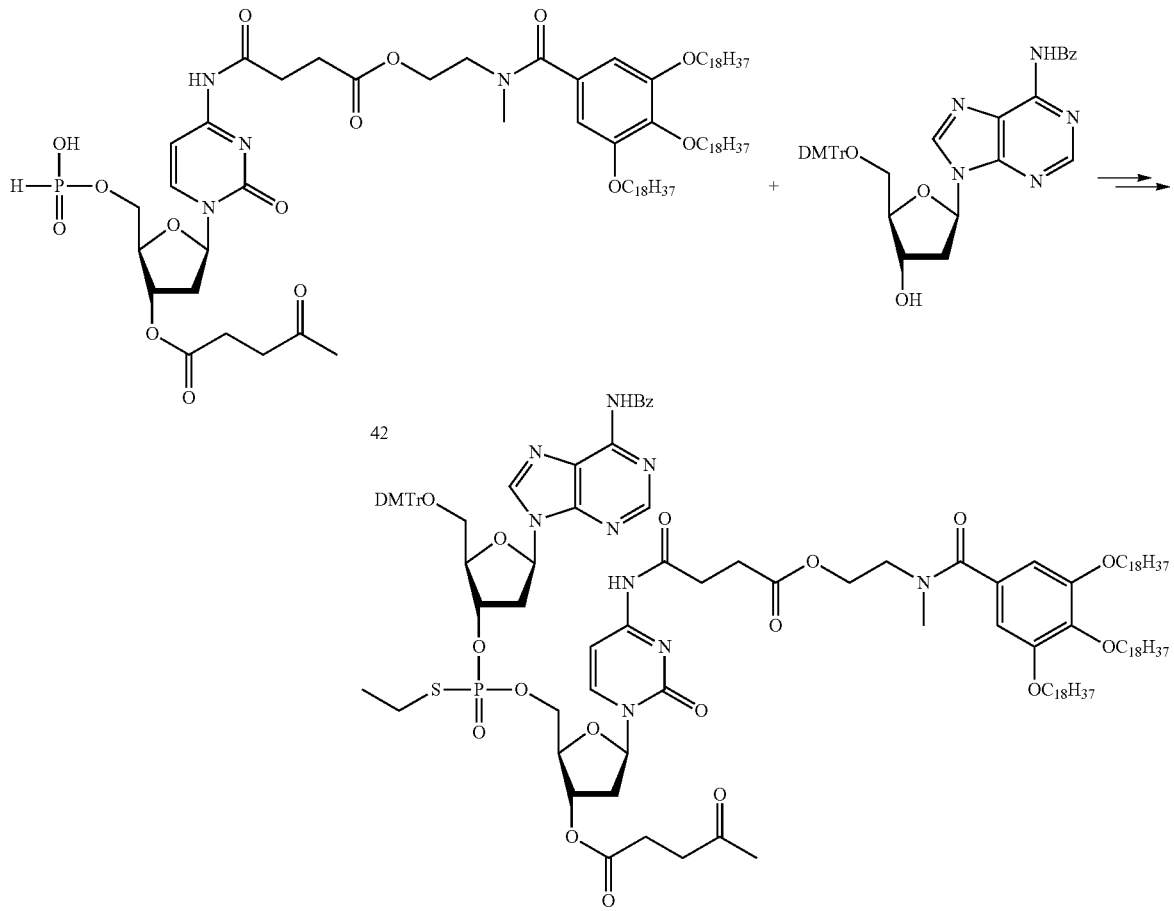

121

In a nitrogen atmosphere, bispentafluorophenyl carbonate (0.13 g, 0.32 mmol) as a condensing agent was added to a pyridine (3.0 mL) solution of Compound 42 (0.15 g) and $N^6$-benzoyl-5'-O-(4,4'-dimethoxytrityl)-2'-deoxyadenosine (manufactured by Tokyo Chemical Industry Co., Ltd.) (0.10 g, 0.16 mmol) at 25° C., and the mixture was stirred for 20 minutes, thereby performing the coupling reaction. N-(ethylthio)phthalimide (synthesized in accordance with the method described in Synlett, 2009, No. 1, pp. 112-116) (4.5 mg, 22 μmol) as a sulfurizing agent was added to a 0.47 g portion of the reaction mixture (3.53 g), and the mixture was stirred at room temperature for 1 hour. The reaction mixture was analyzed by LC-MS, and Compound 121 was identified as the main product.

MS (ESI$^+$): [M+H]$^+$ 2155.2871.

Example 124 (Comparison of Sulfurizing Agent): Synthesis of Compound 122

N-(n-propylthio)phthalimide (synthesized in accordance with the method described in Bioorganic & Medicinal Chemistry, 2006, vol. 14, No. 11, pp. 3775-3784) (5.7 mg, 26 μmol) as a sulfurizing agent was added to the reaction mixture (0.46 g) after the coupling reaction obtained in Example 123, and the mixture was stirred at room temperature for 1 hour. The reaction mixture was analyzed by LC-MS, and Compound 122 was identified as the main product.

MS (ESI$^+$): [M+H]$^+$ 2169.3107.

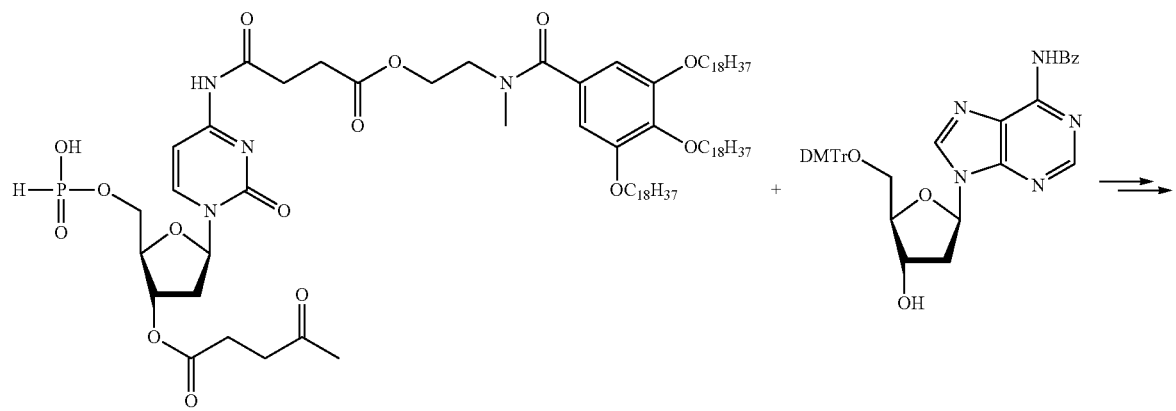

42

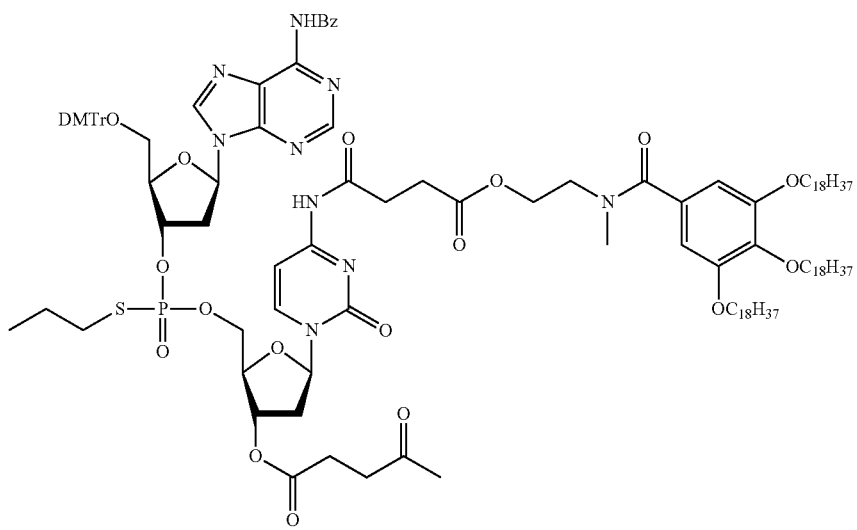

122

Example 125 (Comparison of Sulfurizing Agent):
Synthesis of Compound 123

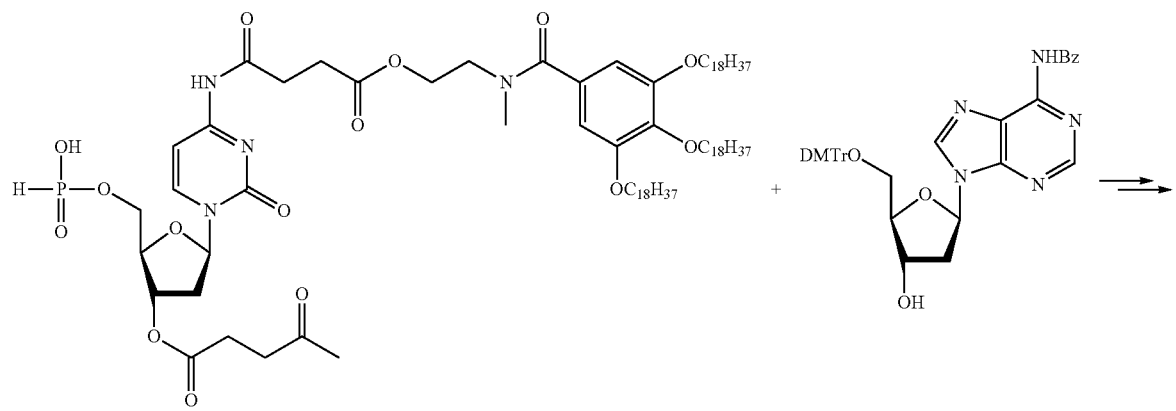

42

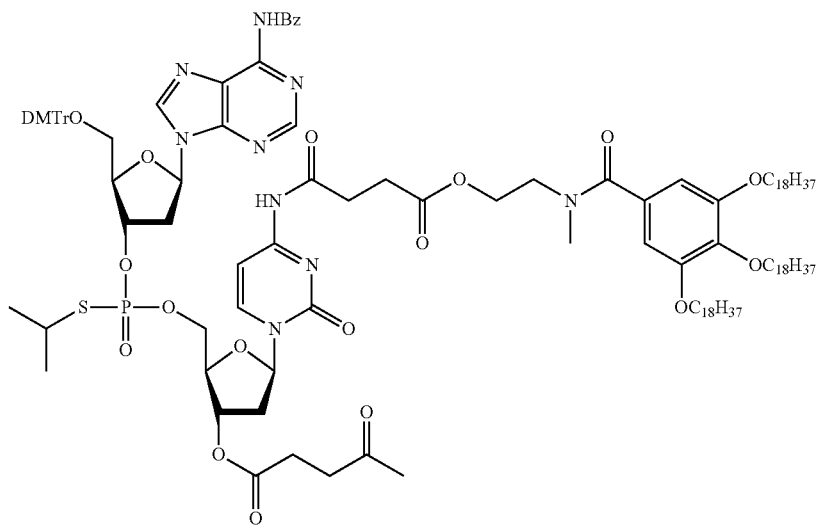

123

N-(isopropylthio)phthalimide (synthesized in accordance with the method described in Bioorganic & Medicinal Chemistry, 2006, vol. 14, No. 11, pp. 3775-3784) (5.6 mg, 25 μmol) as a sulfurizing agent was added to the reaction mixture (0.48 g) after the coupling reaction obtained in Example 123, and the mixture was stirred at room temperature for 3 hours and 30 minutes. Thereafter, N-(isopropylthio)phthalimide (32 mg, 0.15 mmol) was added, and the mixture was stirred for 1 hour. The reaction mixture was analyzed by LC-MS, and Compound 123 was identified as the main product.

MS (ESI$^+$): [M+H]$^+$ 2169.2959.

Example 126 (Comparison of Sulfurizing Agent):
Synthesis of Compound 124

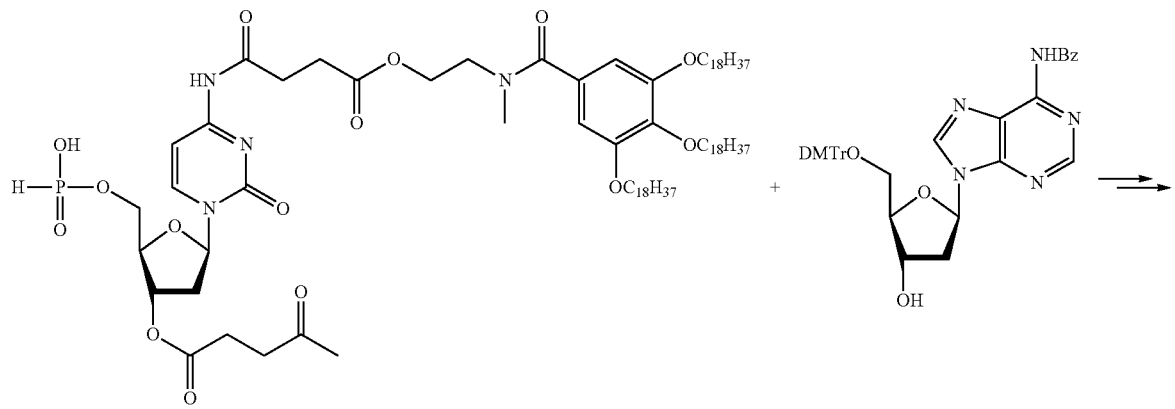

42

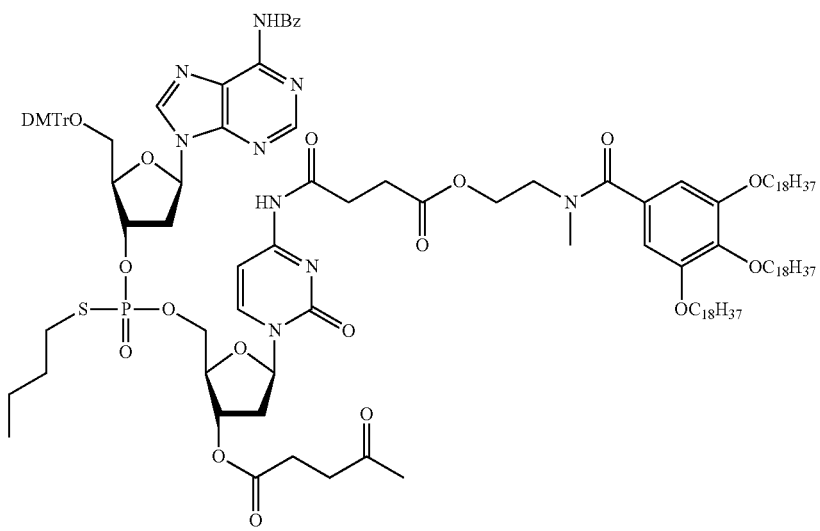

124

N-(n-butylthio)phthalimide (synthesized in accordance with the method described in Bioorganic & Medicinal Chemistry, 2006, vol. 14, No. 11, pp. 3775-3784) (6.6 mg, 28 μmol) as a sulfurizing agent was added to the reaction mixture (0.48 g) after the coupling reaction obtained in Example 123, and the mixture was stirred at room temperature for 1 hour. The reaction mixture was analyzed by LC-MS, and Compound 124 was identified as the main product.

MS (ESI$^+$): [M+H]$^+$ 2183.3273.

Example 127 (Comparison of Sulfurizing Agent):
Synthesis of Compound 125

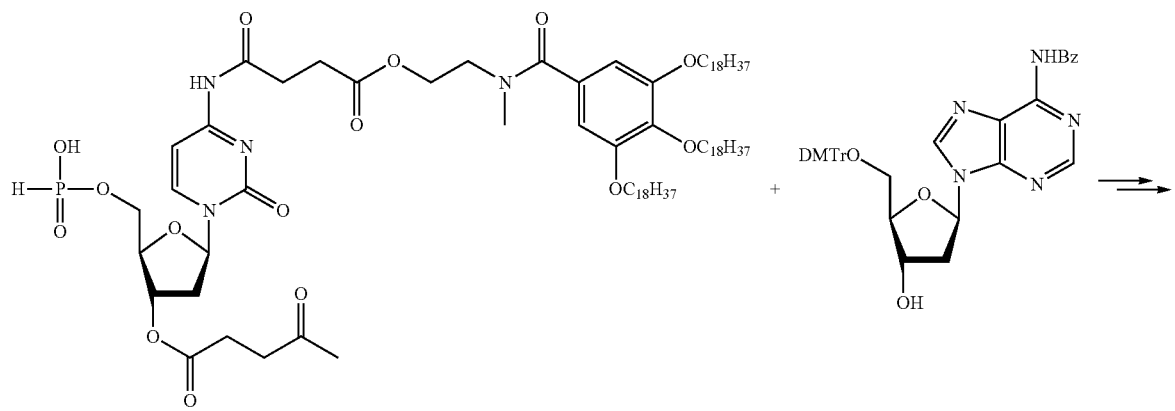

42

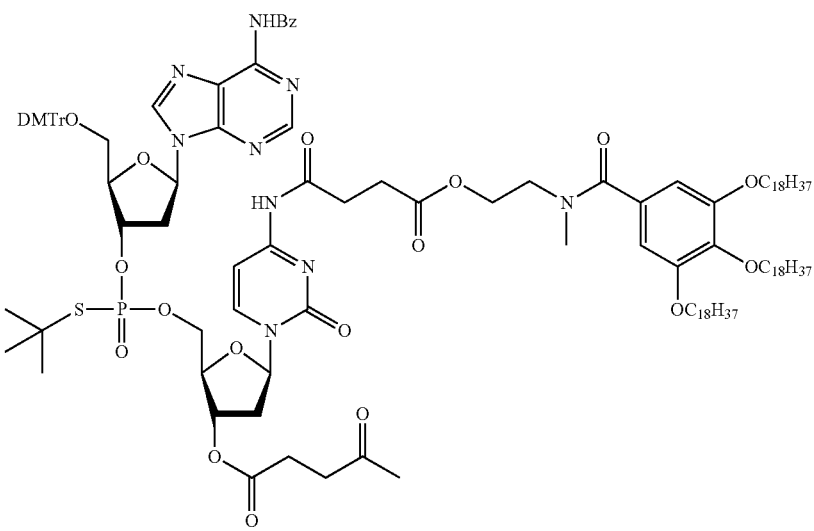

125

N-(tert-butylthio)phthalimide (synthesized in accordance with the method described in Synlett, 2009, No. 1, pp. 112-116) (6.4 mg, 27 μmol) as a sulfurizing agent was added to the reaction mixture (0.47 g) after the coupling reaction obtained in Example 123, and the mixture was stirred at room temperature for 3 hours and 30 minutes. Thereafter, N-(tert-butylthio)phthalimide (0.11 g, 0.47 mmol) was added, and the mixture was stirred for 1 hour. The reaction mixture was analyzed by LC-MS, and Compound 125 was identified as the main product.

MS (ESI$^+$): [M+H]$^+$ 2183.3326.

Example 128 (Comparison of Sulfurizing Agent):
Synthesis of Compound 126

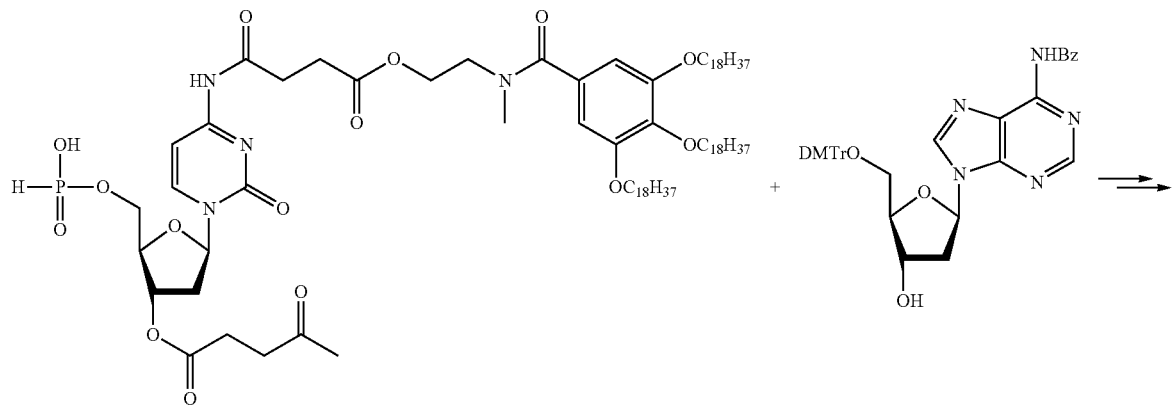

42

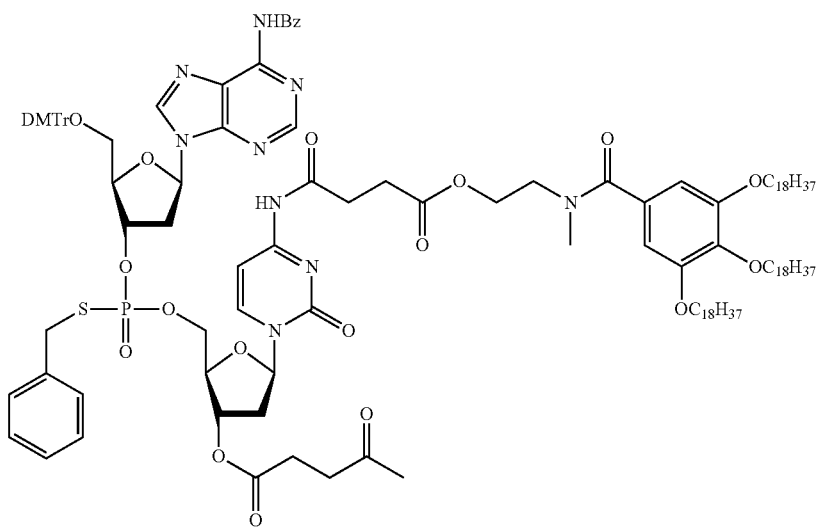

126

N-(benzylthio)phthalimide (synthesized in accordance with the method described in Bioorganic & Medicinal Chemistry, 2006, vol. 14, No. 11, pp. 3775-3784) (5.7 mg, 21 μmol) as a sulfurizing agent was added to the reaction mixture (0.48 g) after the coupling reaction obtained in Example 123, and the mixture was stirred at room temperature for 1 hour. The reaction mixture was analyzed by LC-MS, and Compound 126 was identified as the main product.

MS (ESI$^+$): [M+H]$^+$ 2217.3232

Reference Synthetic Example 8 (Synthesis of 5-mer): Synthesis of Compound 134
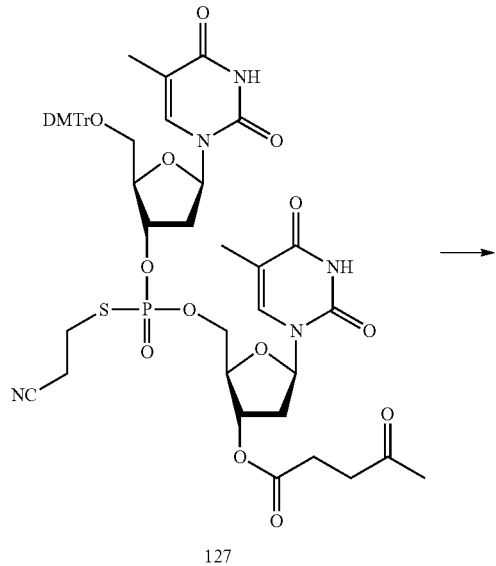
127
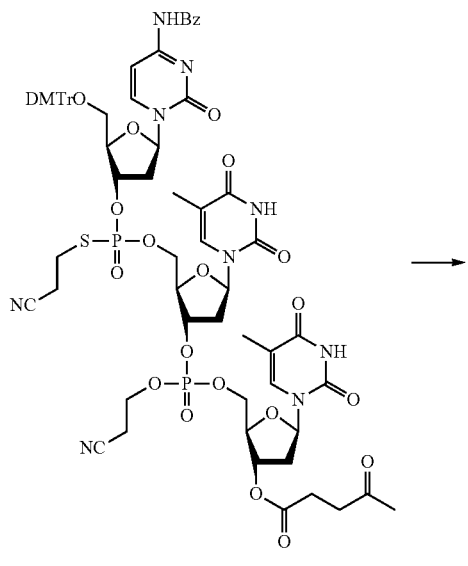
129
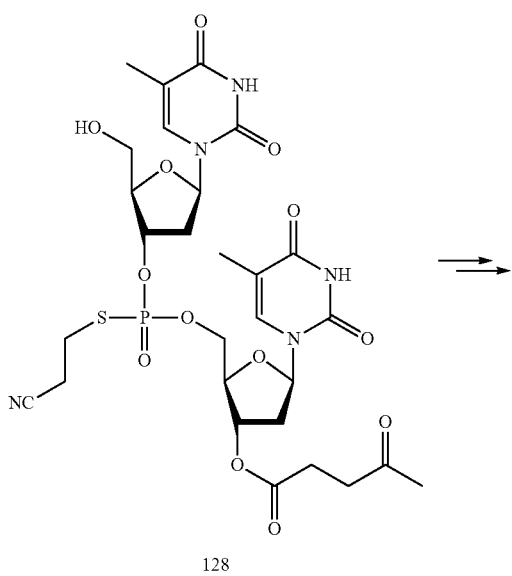
128
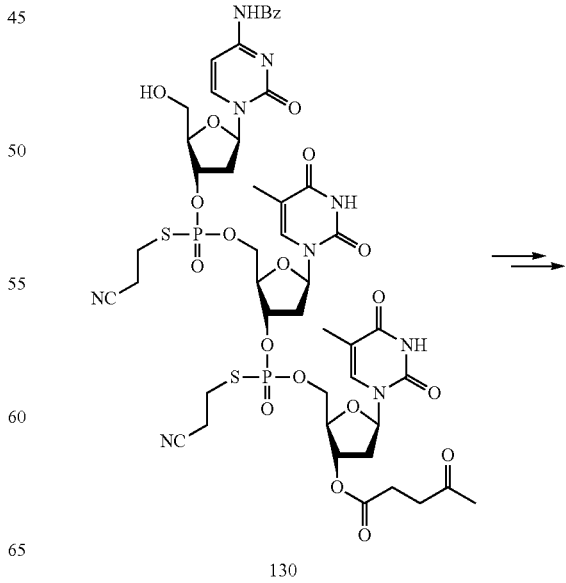
130

299
-continued

131

132

300
-continued

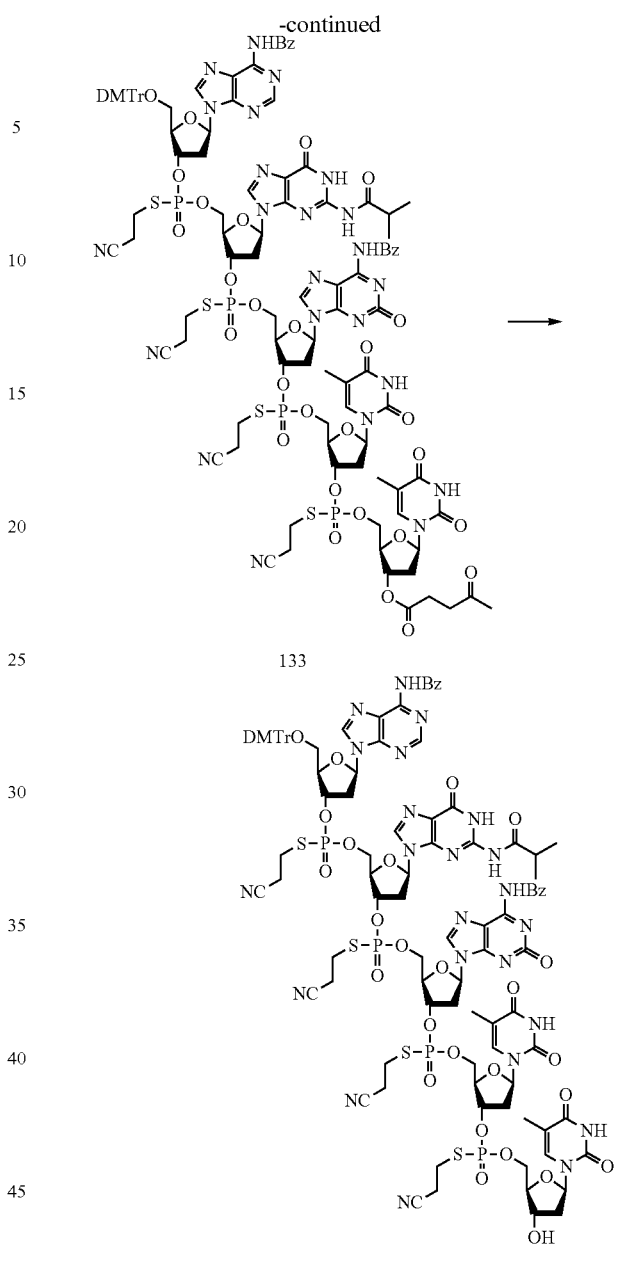

133

134

Step 1: Synthesis of Compound 128

Indole (0.78 g, 6.6 mmol) was added to a methylene chloride (26 g) solution which contained Compound 127 synthesized in accordance with the method described in Japanese Patent Kohyo Publication 2003-525305 using 3'-O-levulinylthymidine (synthesized in accordance with the method described in Bioorganic & Medicinal Chemistry, 2013, vol. 21, pp. 8013-8018) (0.75 g, 2.2 mmol). The mixture was cooled to 10° C., and dichloroacetic acid (0.90 mL, 11 mmol) was added. The mixture was stirred for 1 hour and 17 minutes. Further, dichloroacetic acid (0.90 mL, 11 mmol) was added, and the mixture was stirred for 40 minutes. The reaction mixture was added to a 5% aqueous sodium hydrogen carbonate solution, and the liquids were separated. Methylene chloride was added to the aqueous phase and the liquids were separated, this reextraction operation being performed 11 times. The organic phases obtained were combined. The solvent was distilled away under vacuum to give a crude product. The crude product was purified by silica gel chromatography (chloroform-methanol). Consequently, Compound 128 (0.65 g) was obtained.

MS (ESI$^+$): [M+H]$^+$ 714.1865.

Step 2: Synthesis of Compound 130

In a nitrogen atmosphere, bispentafluorophenyl carbonate (1.3 g, 3.2 mmol) was added to a pyridine (8 mL) solution of Compound 128 (0.65 g, 0.91 mmol) and N$^4$-benzoyl-5'-O-(4,4'-dimethoxytrityl)-3'-O-hydroxyphosphynyl-2'-deoxycytidine triethylamine salt (manufactured by ChemGenes Corporation) (1.0 g, 1.3 mmol) at room temperature, and the mixture was stirred for 15 minutes. Thereafter, N-[(2-cyanoethyl)thio]phthalimide (0.43 g, 1.9 mmol) as a sulfurizing agent was added, and the mixture was stirred for 1 hour and 57 minutes. Methylene chloride and a 5% aqueous sodium hydrogen carbonate solution were added, and the liquids were separated. The aqueous phase obtained was washed with methylene chloride two times. The organic phases obtained were combined. The solvent was distilled away under vacuum. Consequently, a reaction mixture (13 g) containing Compound 129 was obtained. A 12 g portion of the mixture was vacuum concentrated. Toluene was added and the mixture was vacuum concentrated, these operations being repeated three times. Thereafter, methylene chloride (16 g) and indole (0.30 g, 2.6 mmol) were added, and the mixture was cooled to 10° C. Dichloroacetic acid (0.69 mL, 8.4 mmol) was added. The mixture was stirred for 1 hour and 40 minutes. The reaction mixture was added to a 5% aqueous sodium hydrogen carbonate solution, and the liquids were separated. Methylene chloride was added to the aqueous phase and the liquids were separated, this reextraction operation being performed two times. The organic phases obtained were combined. The solvent was distilled away under vacuum to give a crude product. The crude product was purified by silica gel chromatography (chloroform-methanol). Consequently, Compound 130 (0.30 g) was obtained.

MS(ESI$^+$): [M+H]$^+$ 1176.2650.

Step 3: Synthesis of Compound 132

In a nitrogen atmosphere, bispentafluorophenyl carbonate (0.43 g, 1.1 mmol) was added to a pyridine (6 mL) solution of Compound 130 (0.24 g, 0.20 mmol) and N$^2$-isobutyryl-5'-O-(4,4'-dimethoxytrityl)-3'-O-hydroxyphosphynyl-2'-deoxyguanosine triethylamine salt (manufactured by ChemGenes Corporation) (0.23 g, 0.29 mmol) at room temperature, and the mixture was stirred for 27 minutes. Thereafter, N-[(2-cyanoethyl)thio]phthalimide (0.10 g, 0.43 mmol) as a sulfurizing agent was added. The mixture was stirred for 1 hour and 34 minutes. Methylene chloride and a 5% aqueous sodium hydrogen carbonate solution were added, and the liquids were separated. The aqueous phase obtained was washed with methylene chloride two times. The organic phases obtained were combined. The solvent was distilled away under vacuum. Consequently, a reaction mixture containing Compound 131 was obtained. Toluene was added and the mixture was vacuum concentrated, these operations being repeated three times. Thereafter, methylene chloride (8.0 g) and indole (77 mg, 0.66 mmol) were added, and the mixture was cooled to 10° C. Dichloroacetic acid (0.17 mL, 2.0 mmol) was added, and the mixture was stirred for 2 hours and 8 minutes. The reaction mixture was added to a 5% aqueous sodium hydrogen carbonate solution, and the liquids were separated. Methylene chloride was added to the aqueous phase and the liquids were separated, this reextraction operation being performed two times. The organic phases obtained were combined. The solvent was distilled away under vacuum to give a crude product. The crude product was purified by silica gel chromatography (chloroform-methanol). Consequently, Compound 132 (0.12 g) was obtained.

MS (ESI$^+$): [M+H]$^+$ 1644.3648.

Step 4: Synthesis of Compound 134

In a nitrogen atmosphere, bispentafluorophenyl carbonate (0.28 g, 0.71 mmol) was added to a pyridine (5 mL) solution of Compound 132 (0.12 g, 74 µmol) and N$^6$-benzoyl-5'-O-(4,4'-dimethoxytrityl)-3'-O-hydroxyphosphynyl-2'-deoxyadenosine triethylamine salt (manufactured by ChemGenes Corporation) (90 mg, 0.11 mmol) at room temperature, and the mixture was stirred for 1 hour and 2 minutes. Thereafter, N-[(2-cyanoethyl)thio]phthalimide (37 mg, 0.16 mmol) as a sulfurizing agent was added, and the mixture was stirred for 2 hours and 8 minutes. Methylene chloride, acetonitrile and a 5% aqueous sodium hydrogen carbonate solution were added, and the liquids were separated. The aqueous phase obtained was washed with a mixed solvent of methylene chloride and acetonitrile two times. The organic phases obtained were combined. The solvent was distilled away under vacuum. Consequently, a reaction mixture containing Compound 133 was obtained. Methylene chloride (3.1 g) was added to the reaction mixture, and the resultant mixture was cooled to 0° C. Acetic acid (0.15 mL) was added. Thereafter, hydrazine monohydrate (36 µL, 0.74 mmol) was added, and the mixture was stirred for 1 hour and 26 minutes. Acetylacetone (0.30 mL) was added to the reaction mixture, and the resultant mixture was brought to room temperature. A 5% aqueous sodium hydrogen carbonate solution was added, and the liquids were separated. Methylene chloride was added to the aqueous phase and the liquids were separated, this reextraction operation being performed two times. The organic phases obtained were combined. The solvent was distilled away under vacuum to give a crude product. The crude product was purified by silica gel chromatography (chloroform-methanol). Consequently, Compound 134 (55 mg) was obtained.

MS (ESI$^+$): [M+H]$^+$ 2334.5224.

Example 129 (Synthesis of 15-mer): Synthesis of Compound 136
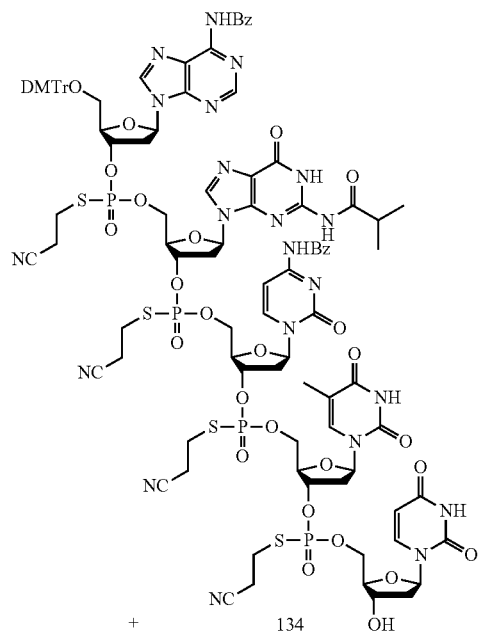
134
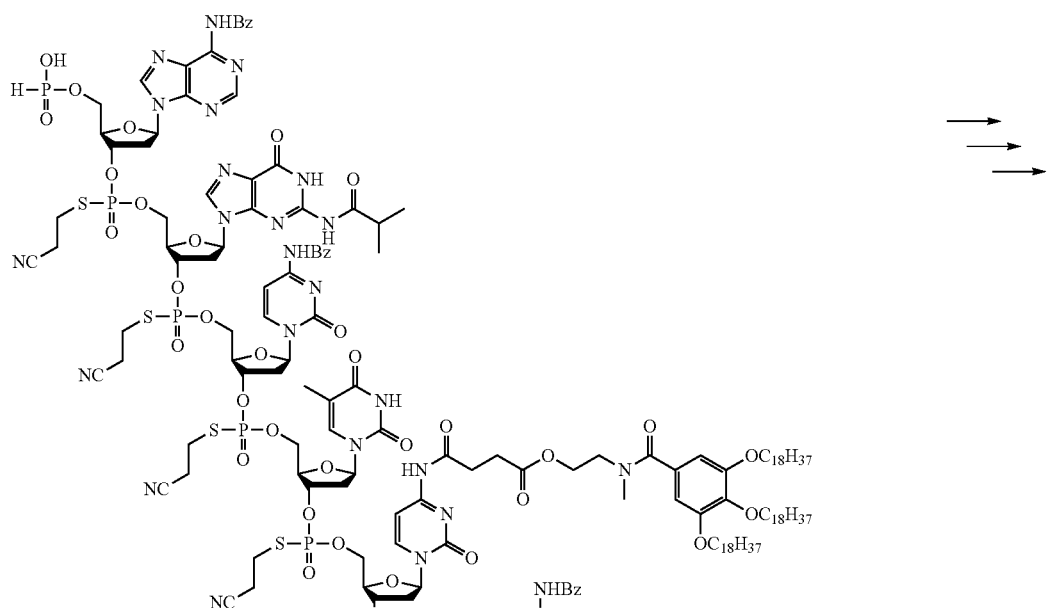

-continued
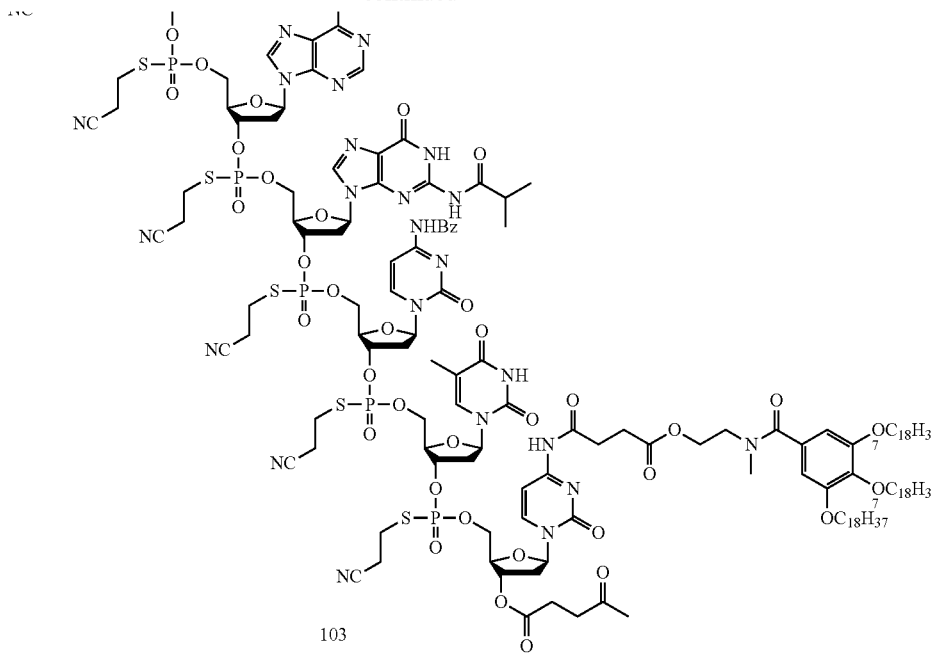
103
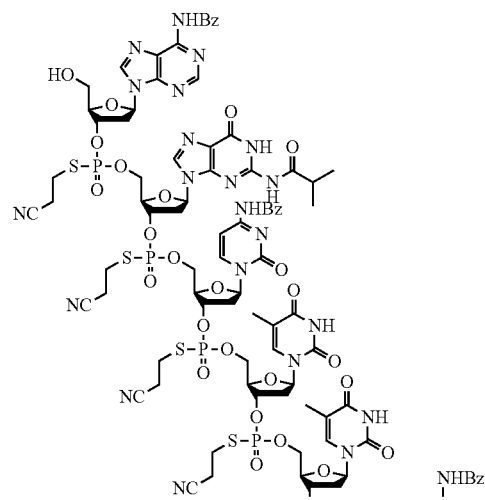
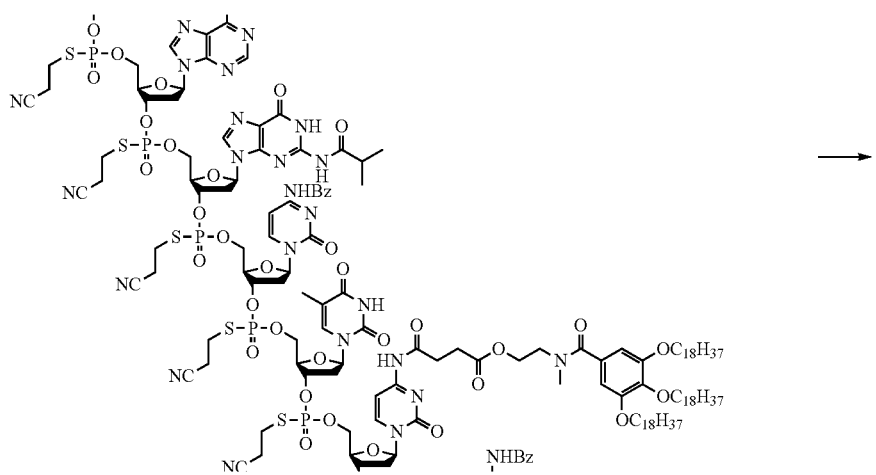

-continued
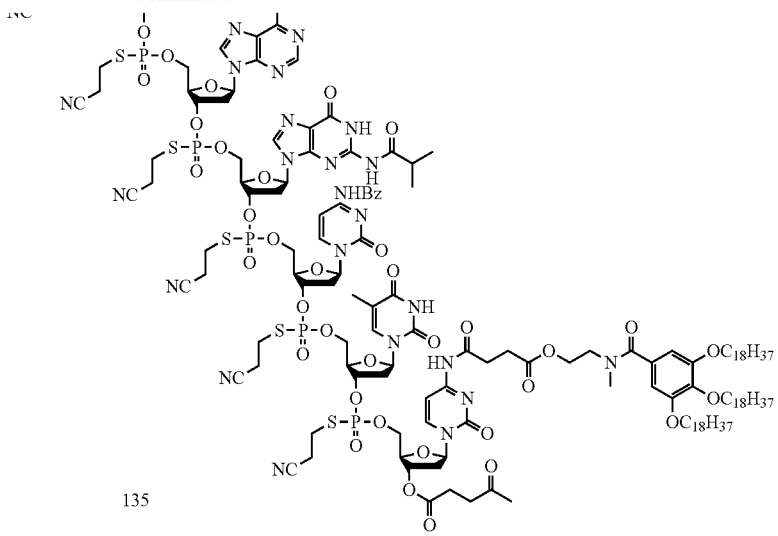
135
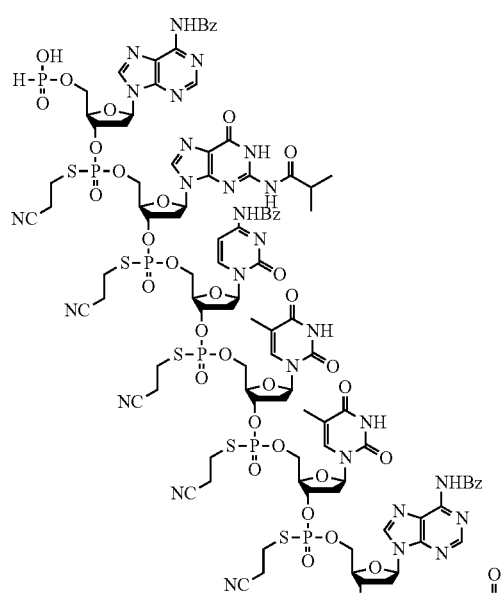
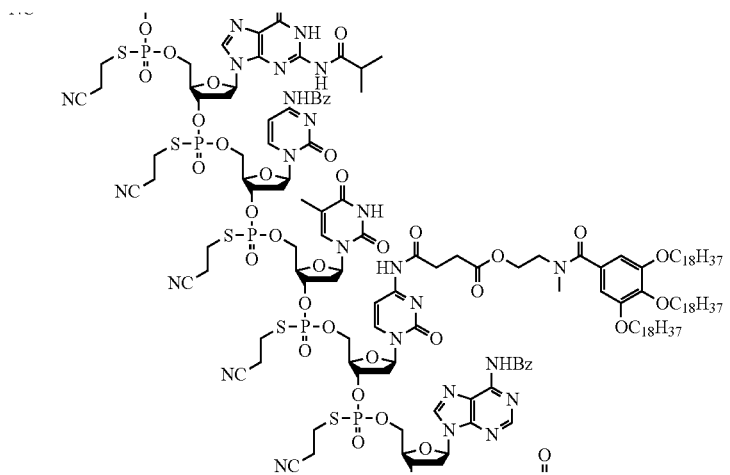

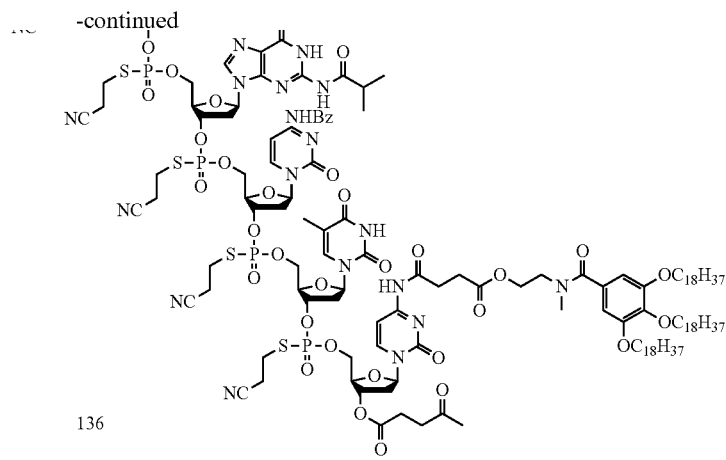

136

Step 1: Synthesis of Compound 135

In a nitrogen atmosphere, bispentafluorophenyl carbonate (59 mg, 0.15 mmol) was added to a pyridine (1.4 mL) solution of Compound 103 (43 mg) and Compound 134 (19 mg, 8.3 µmol) at room temperature, and the mixture was stirred for 58 minutes. Thereafter, N-[(2-cyanoethyl)thio]phthalimide (10 mg, 44 µmol) as a sulfurizing agent was added, and the mixture was stirred for 40 minutes. Thereafter, the reaction mixture was vacuum concentrated. Toluene (2 g) was added and the mixture was vacuum concentrated, these operations being repeated three times. Thereafter, methylene chloride (1.2 mL) was added. Indole (2.5 mg, 21 µmol) and dichloroacetic acid (6.2 µL, 76 µmol) were added at 10° C., and the mixture was stirred for 1 hour and 51 minutes. Thereafter, dichloroacetic acid (6.2 µL, 76 µmol) was added, and the mixture was stirred for 2 hours and 41 minutes. Further, dichloroacetic acid (6.2 µL, 76 µmol) was added, and the mixture was stirred for 1 hour and 38 minutes. Pyridine (0.20 mL) was added, and the mixture was brought to room temperature. The reaction mixture was added to acetonitrile (38 g), and the resultant solid was recovered by precipitation filtration. Consequently, Compound 135 (51 mg) was obtained as a light skin color solid.

MS (ESI$^+$): [M+4H]$^{4+}$ 2140.0080.

Step 2: Synthesis of Compound 136

In a nitrogen atmosphere, phosphonic acid (19 mg, 0.23 mmol) was added to a solution of Compound 135 (50 mg, 5.8 µmol) in a mixed solvent of methylene chloride (2.0 mL) and pyridine (0.12 mL) at 40° C., and 2,2-dimethylbutyryl chloride (25 µL, 0.18 mmol) was added in 5 portions. The mixture was stirred for 1 hour and 12 minutes. Thereafter, the reaction mixture was added to acetonitrile (39 g), and the resultant solid was recovered by filtration. Consequently, Compound 136 (44 mg) was obtained as a light skin color solid.

MS (ESI$^+$): [M+4H]$^{4+}$ 2155.9794.

Example 130 (Synthesis of 20-mer): Synthesis of Compound 137

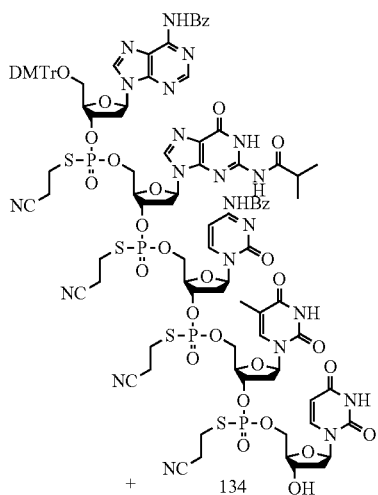

134

311
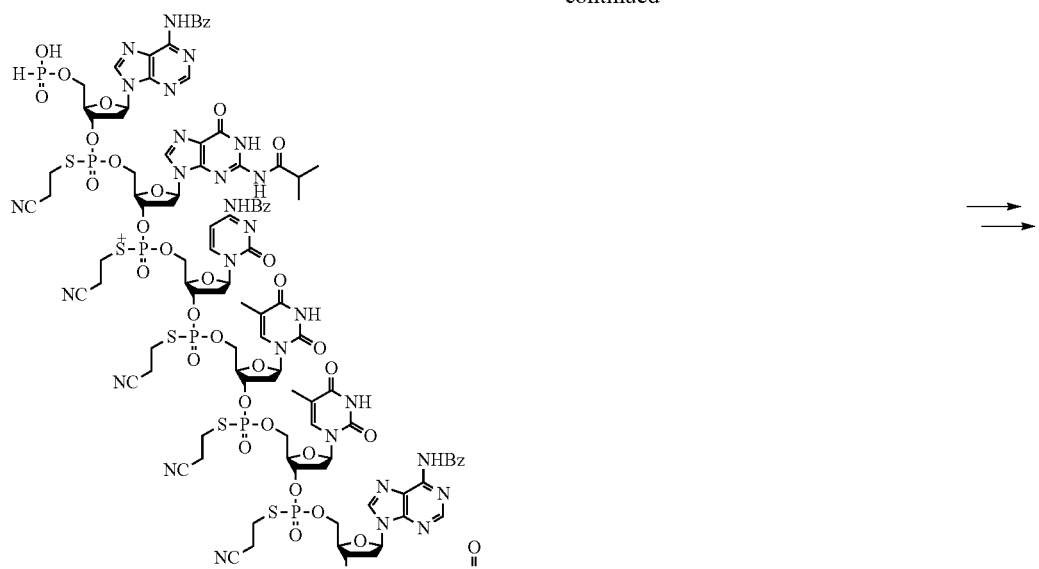
-continued
312
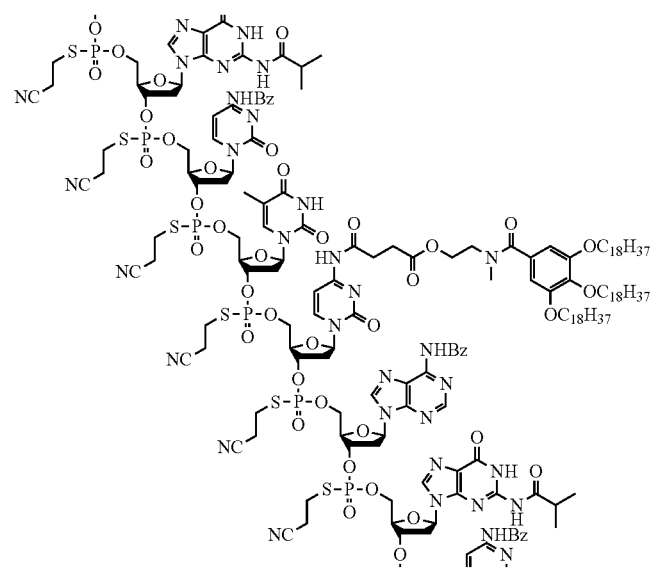
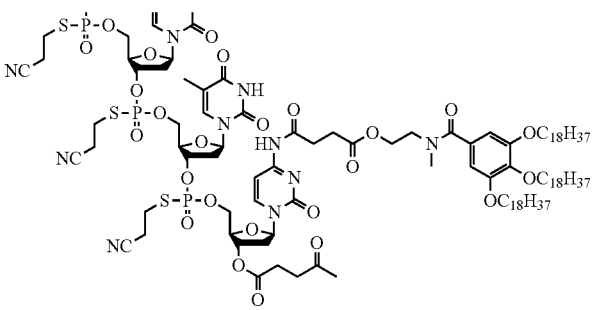
136

-continued
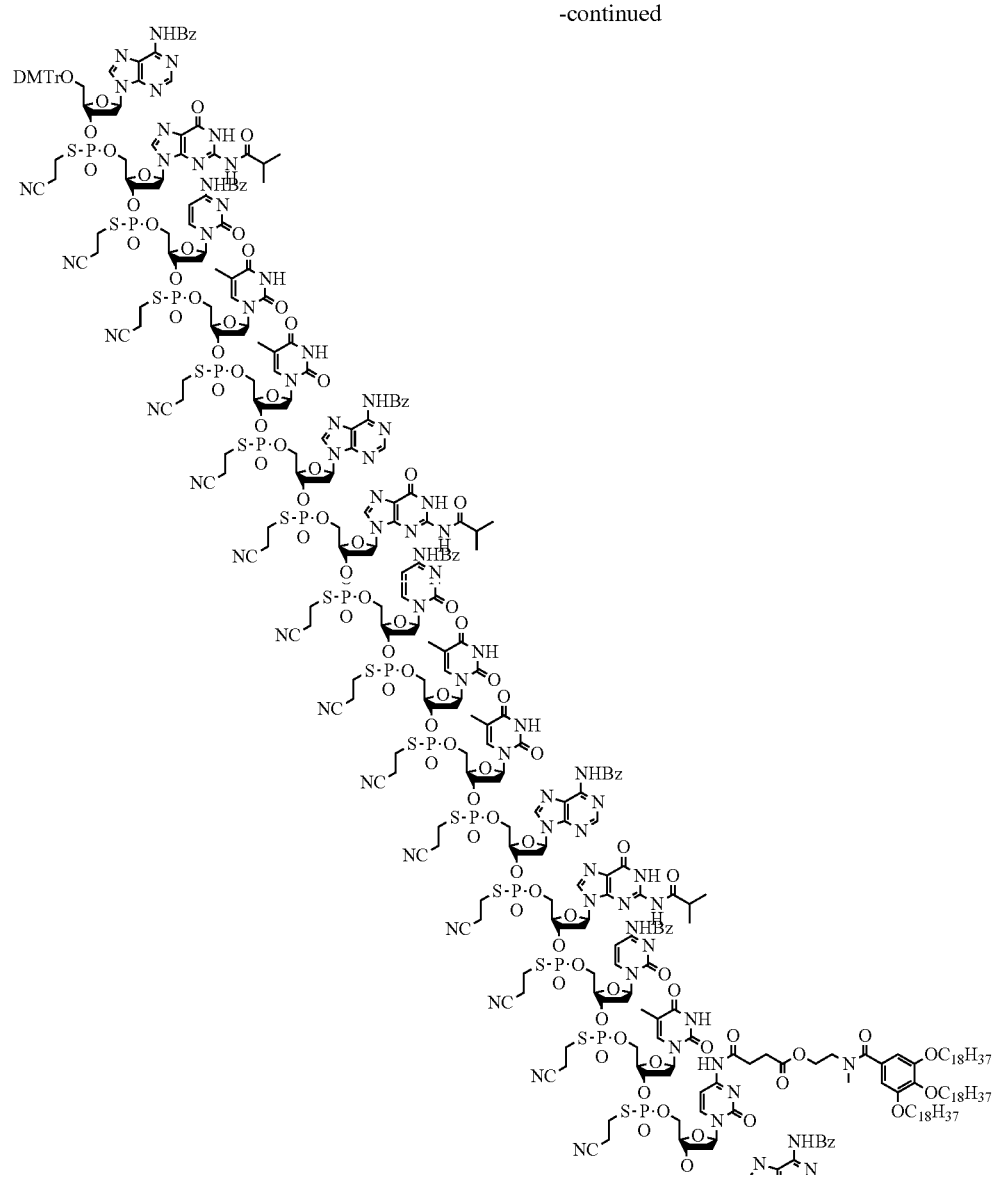
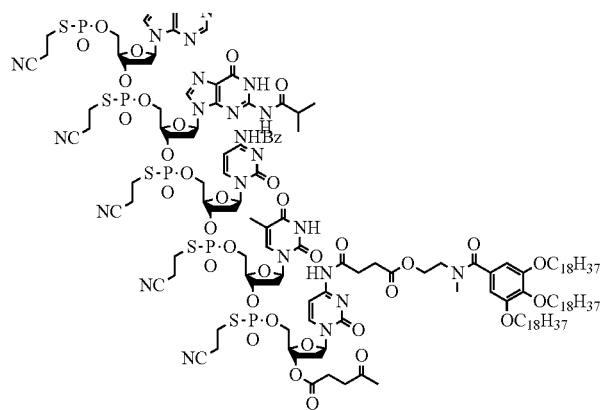

In a nitrogen atmosphere, bispentafluorophenyl carbonate (274 mg, 0.69 mmol) was added to a pyridine (1.2 mL) solution of Compound 134 (19 mg, 8.1 μmol) and Compound 136 (44 mg) at room temperature, and the mixture was stirred for 1 hour. Thereafter, N-[(2-cyanoethyl)thio] phthalimide (5.1 mg, 22 μmol) as a sulfurizing agent was added, and the mixture was stirred for 1 hour. The reaction mixture was added to methanol (30 g), and the resultant solid was recovered by filtration. Consequently, Compound 137 (46 mg) was obtained as a white solid.

MS (ESI$^+$): [M+5H]$^{5+}$ 2205.1210.

Example 131 (Deprotection of 20-mer): Synthesis of Compound 138

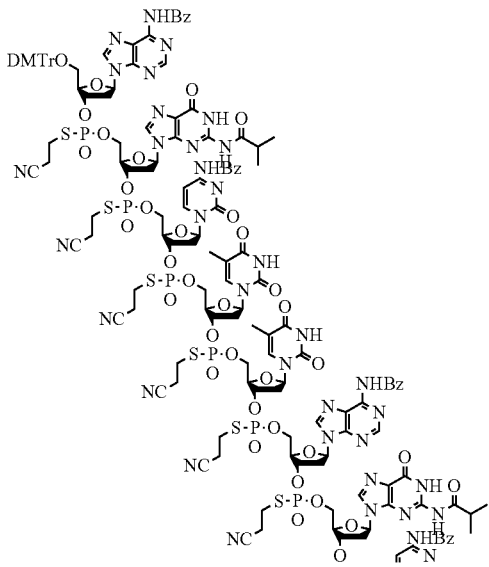

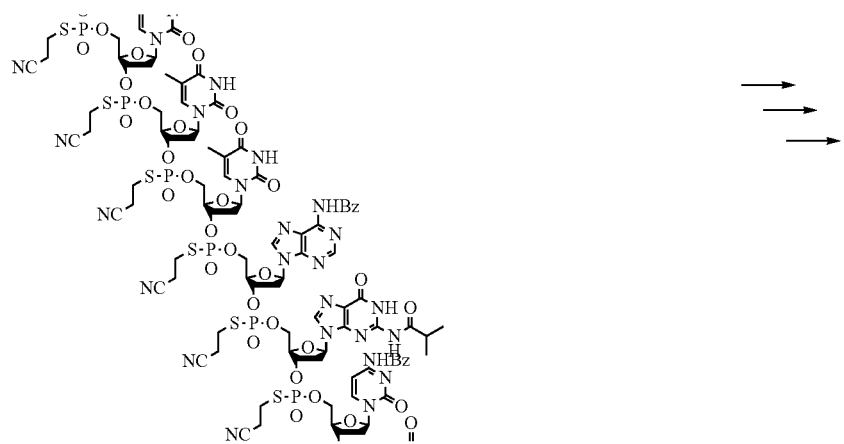

-continued
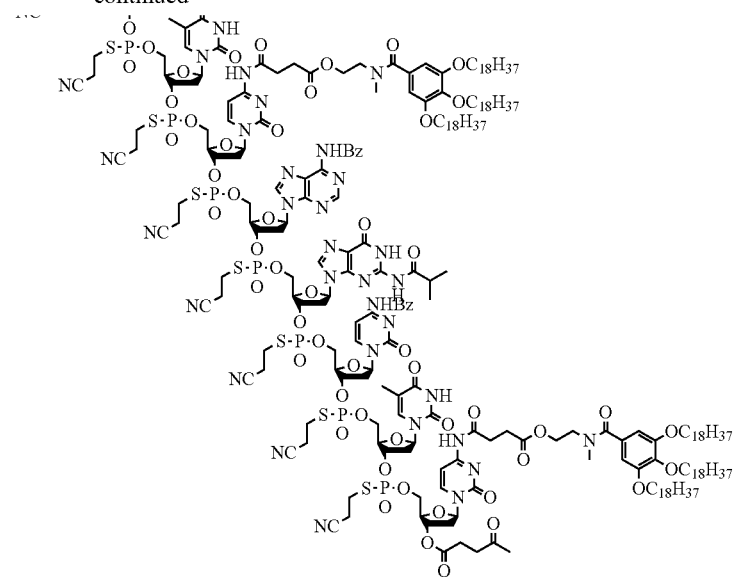
137
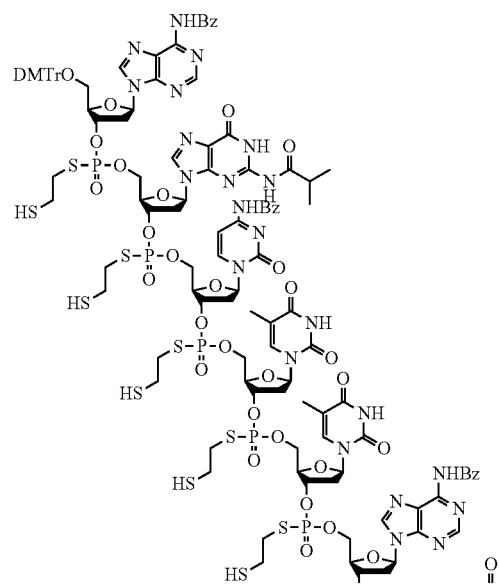

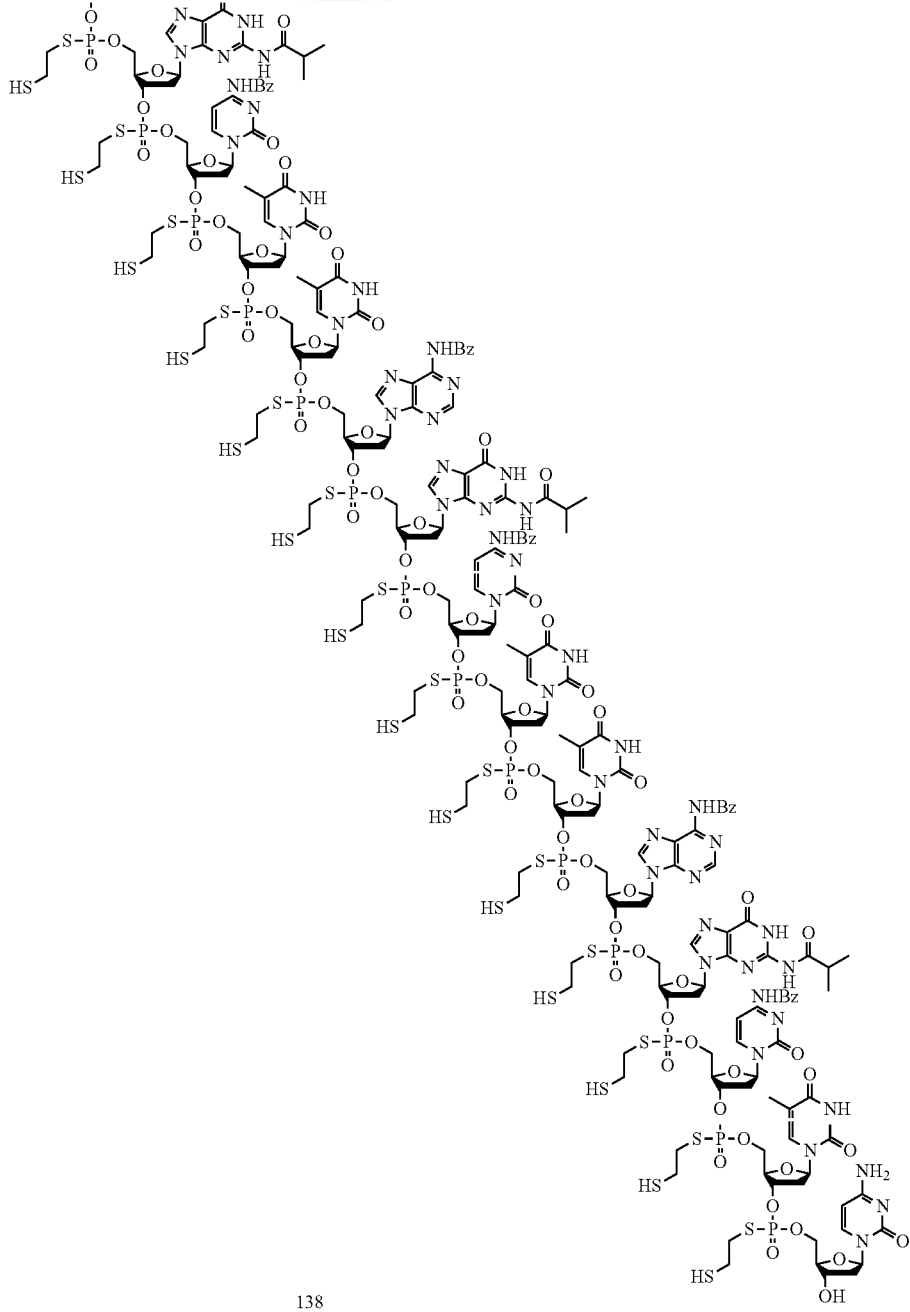

138

In a nitrogen atmosphere, 1,8-diazabicyclo[5.4.0]-7-undecene [DBU] (3.5 μL, 23 μmol) and TMSCl (0.70 μL, 5.5 μmol) were added to a methylene chloride (0.38 g) solution of Compound 137 (2.6 mg, 0.24 μmol) at room temperature, and the mixture was stirred for 30 minutes. The reaction mixture (1.6 g) was vacuum concentrated, and 28% ammonia water (1.0 mL) and ethylenediaminetetraacetic acid (3.1 mg, 11 μmol) were added. The mixture was stirred at 80° C. for 2 hours and 6 minutes. The reaction mixture was analyzed by LC-MS, and Compound 138 was identified.

MS (ESI$^+$): [M+3H]$^{3+}$ 2123.8976.

INDUSTRIAL APPLICABILITY

The production method differs from a usual production method including a coupling step, a phosphorus atom modification step such as oxidation reaction or sulfurization reaction, and a deprotection step, and includes a step of subjecting to H-phosphonation a 5'-hydroxyl group or a 3'-hydroxyl group of a nucleoside or oligonucleotide having a pseudo solid phase-protecting group. It is now possible to provide a novel production method adaptable to mass synthesis of an oligonucleotide using a nucleoside or oligonucleotide that is easy to isolate and has high storage stability. Thus, the present invention can be applied to the production of oligonucleotides such as siRNA, antisense nucleic acids and vaccine adjuvants, and is highly useful in fields such as genome-based drug discovery, and gene diagnosis and treatment.

The invention claimed is:

1. A production method of an oligonucleotide comprising at least one elongation reaction cycle, wherein the elongation reaction cycle comprises a first step of deprotecting a first nucleoside or first oligonucleotide having a pseudo solid phase-protecting group in at least one location selected from the group consisting of 2'-position, 3'-position and a nucleobase moiety, having a 3'-hydroxyl group protected with a basic protecting group or a pseudo solid phase-protecting group, and having a 5'-hydroxyl group protected with a temporary protecting group, to remove the temporary protecting group to form a 5'-hydroxyl group, a second step of converting the resultant 5'-hydroxyl group into an H-phosphonated form using an H-phosphonate reagent, wherein the H-phosphonated form is of the formula

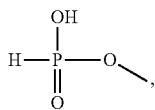

a third step of forming an oligomer of the first nucleoside or first oligonucleotide with a second nucleoside or second oligonucleotide having a 3'-hydroxyl group and having a 5'-hydroxyl group protected with a temporary protecting group, by forming a phosphite diester bond from the 5'-hydroxyl group, now converted to the H-phosphonated form, of the first nucleoside or first oligonucleotide and the 3'-hydroxyl group of the second nucleoside or second oligonucleotide, a fourth step of converting the phosphite diester bond of the oligomer into a phosphodiester bond, a thiophosphodiester bond, a boranophosphodiester bond, an aminophosphodiester bond, a phosphodiester bond protected with a basic protecting group, or a thiophosphodiester bond protected with a basic protecting group, and a fifth step of adding a polar solvent to a reaction mixture obtained from at least one step selected from the group consisting of the first step to the fourth step to form a precipitate, and collecting the precipitate by solid liquid separation, wherein the pseudo solid phase-protecting group is of formula (I):

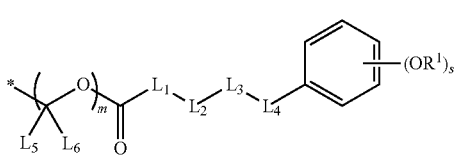

wherein
* indicates a bond to a group protected by the pseudo solid phase-protecting group,
$R^1$ is a C10-30 alkyl group or a C10-30 alkenyl group,
s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^5$ is a hydrogen atom, a C1-6 alkyl group, a C1-6 haloalkyl group, a C2-6 alkenyl group or a C2-6 haloalkenyl group, $L^6$ is a hydrogen atom, a C1-6 alkyl group, a C1-6 haloalkyl group, a C2-6 alkenyl group or a C2-6 haloalkenyl group, m is 0 or 1, and when the pseudo solid phase-protecting group is present in the nucleobase moiety and when m in the pseudo solid phase-protecting group is 0, the number of single bonds represented by $L^1$, $L^2$, $L^3$ and $L^4$ in the pseudo solid phase-protecting group is 0 to 3.

2. The production method according to claim 1, wherein the fourth step converts the phosphite diester bond of the oligomer into a phosphodiester bond, a thiophosphodiester bond, a boranophosphodiester bond or an aminophosphodiester bond.

3. The production method according to claim 1, wherein the polar solvent is an alcohol solvent with 1 to 6 carbon atoms or a nitrile solvent with 1 to 6 carbon atoms.

4. The production method according to claim 1, further comprising a sixth step of removing all of the basic protecting group, the temporary protecting group and the pseudo solid phase-protecting group.

5. The production method according to claim 1 wherein the first nucleoside or the first oligonucleotide has a hydroxyl group protected with a pseudo solid phase-protecting group at 3'-position.

6. The production method according to claim 1, wherein the third step uses the second nucleoside.

7. The production method according to claim 1, wherein the pseudo solid phase-protecting group is represented by the following formula (II):

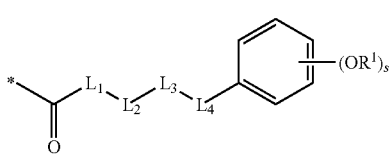

wherein
* indicates a bond to a group protected by the pseudo solid phase-protecting group,
$R^1$ is a C10-30 alkyl group or a C10-30 alkenyl group,
s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group) or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group) or —O—, and when the pseudo solid phase-protecting group is present in the nucleobase moiety, the number of single bonds represented by $L^1$, $L^2$, $L^3$ and $L^4$ in the pseudo solid phase-protecting group is 0 to 3.

8. The production method according to claim 1, wherein the temporary protecting group is a tert-butyldimethylsilyl group, a 4,4'-dimethoxytrityl group or a levulinyl group.

9. The production method according to claim 1, wherein the H-phosphonation step uses at least one H-phosphonate reagent selected from the group consisting of phosphorous acid, diphenyl phosphite, phenyl-H-phosphonate triethylammonium salt, p-toluyl-H-phosphonate triethylammonium salt, 2-chloro-4H-1,3,2-benzodioxaphosphorin-4-one and phosphorus trichloride.

10. The production method according to claim 1, wherein the nucleobases present in the first to the fourth nucleosides and the first to the fourth oligonucleotides are each independently at least one selected from the group consisting of 6-aminopurin-9-yl group (adenine residue), 2-amino-6-hydroxypurin-9-yl group (guanine residue), 2-oxo-4-amino-1,2-dihydropyrimidin-1-yl group (cytosine residue), 2-oxo-4-amino-5-methyl-1,2-dihydropyrimidin-1-yl group (5-methylcytosine residue), 2-oxo-4-hydroxy-1,2-dihydropyrimidin-1-yl group (uracil residue) and 2-oxo-4-hydroxy-5-methyl-1,2-dihydropyrimidin-1-yl group (thymine residue).

11. The production method according to claim 1, wherein the H-phosphonate reagent is selected from the group consisting of phosphorous acid, a diaryl phosphite, an aryl-H-phosphonate ammonium salt, and a phosphorus halide.

12. A production method of an oligonucleotide comprising at least one elongation reaction cycle, wherein the elongation reaction cycle comprises:

a first step of deprotecting a third nucleoside or third oligonucleotide having a pseudo solid phase-protecting group in at least one location selected from the group consisting of 2'-position, 5'-position and a nucleobase moiety, having a 5'-hydroxyl group protected with a basic protecting group or a pseudo solid phase-protecting group, and having a 3'-hydroxyl group protected with a temporary protecting group, to remove the temporary protecting group to form a 3'-hydroxyl group, a second step of converting the resultant 3'-hydroxyl group into an H-phosphonated form using an H-phosphonate reagent, wherein the H-phosphonated form is of the formula

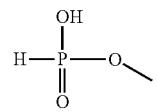

a third step of forming an oligomer of the third nucleoside or third oligonucleotide with a fourth nucleoside or fourth oligonucleotide having a 5'-hydroxyl group and having a 3'-hydroxyl group protected with a temporary protecting group, by forming a phosphite diester bond from the 3'-hydroxyl group, now converted to the H-phosphonated form, of the third nucleoside or third oligonucleotide and the 5'-hydroxyl group of the fourth nucleoside or fourth oligonucleotide, a fourth step of converting the phosphite diester bond of the oligomer into a phosphodiester bond, a thiophosphodiester bond, a boranophosphodiester bond, or an aminophosphodiester bond, a phosphodiester bond protected with a basic protecting group, or a thiophosphodiester bond protected with a basic protecting group, and a fifth step of adding a polar solvent to a reaction mixture obtained from any of the first step to the fourth step to form a precipitate, and collecting the precipitate by solid liquid separation, wherein the pseudo solid phase-protecting group is of formula (I):

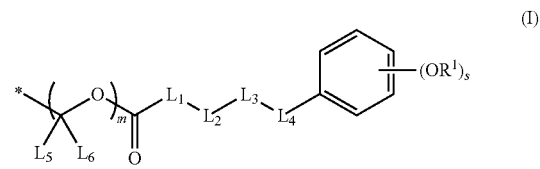

(I)

wherein

* indicates a bond to a group protected by the pseudo solid phase-protecting group, $R^1$ is a C10-30 alkyl group or a C10-30 alkenyl group, s is an integer of 1 to 5, $L^1$ is a single bond, a C1-6 alkylene group, a C2-6 alkenylene group or a C2-6 alkynylene group, $L^2$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^3$ is a single bond, a C1-6 alkylene group, a C2-6 alkenylene group or a C2-6 alkynylene group, $L^4$ is a single bond, —COO—, —CON($R^2$)— (wherein $R^2$ is a hydrogen atom, a C1-6 alkyl group, a C1-6 haloalkyl group, a C2-6 alkenyl group or a C2-6 haloalkenyl group), —OCO—, —N($R^2$)CO— (wherein $R^2$ is a hydrogen atom, a C1-6 alkyl group, a C1-6 haloalkyl group, a C2-6 alkenyl group or a C2-6 haloalkenyl group), —C(O)— or —O—, $L^5$ is a hydrogen atom, a C1-6 alkyl group, a C1-6 haloalkyl group, a C2-6 alkenyl group or a C2-6 haloalkenyl group, $L^6$ is a hydrogen atom, a C1-6 alkyl group, a C1-6 haloalkyl group, a C2-6 alkenyl group or a C2-6 haloalkenyl group, m is 0 or 1, and when the pseudo solid phase-protecting group is present in the nucleobase moiety and when m in the pseudo solid phase-protecting group is 0, the number of single bonds represented by $L^1$, $L^2$, $L^3$ and $L^4$ in the pseudo solid phase-protecting group is 0 to 3.

13. The production method according to claim 12, wherein the fourth step converts the phosphite diester bond of the oligomer into a phosphodiester bond, a thiophosphodiester bond, a boranophosphodiester bond or an aminophosphodiester bond.

14. The production method according to claim 12, wherein the polar solvent is an alcohol solvent with 1 to 6 carbon atoms or a nitrile solvent with 1 to 6 carbon atoms.

15. The production method according to claim 12, further comprising a sixth step of removing all of the basic protecting group, the temporary protecting group and the pseudo solid phase-protecting group.

16. The production method according to claim 12, wherein the third nucleoside or the third oligonucleotide has a hydroxyl group protected with a pseudo solid phase-protecting group at 5'-position.

17. The production method according to claim 12, wherein the third step uses the fourth nucleoside.

\* \* \* \* \*

UNITED STATES PATENT AND TRADEMARK OFFICE
CERTIFICATE OF CORRECTION

| | | |
|---|---|---|
| PATENT NO. | : 11,548,910 B2 | Page 1 of 1 |
| APPLICATION NO. | : 15/776709 | |
| DATED | : January 10, 2023 | |
| INVENTOR(S) | : Sugawara | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 670 days.

Signed and Sealed this
Twenty-sixth Day of November, 2024

Katherine Kelly Vidal
*Director of the United States Patent and Trademark Office*